United States Patent
Gray et al.

(10) Patent No.: US 9,908,884 B2
(45) Date of Patent: Mar. 6, 2018

(54) EGFR INHIBITORS AND METHODS OF TREATING DISORDERS

(75) Inventors: Nathanael S. Gray, Boston, MA (US); Pasi Janne, Newton, MA (US); Michael J. Eck, Boston, MA (US); Wenjun Zhou, Brighton, MA (US)

(73) Assignee: DANA-FARBER CANCER INSTITUTE, INC., Boston, MA (US)

( * ) Notice: Subject to any disclaimer, the term of this patent is extended or adjusted under 35 U.S.C. 154(b) by 0 days.

(21) Appl. No.: 13/319,079

(22) PCT Filed: May 5, 2010

(86) PCT No.: PCT/US2010/001341
§ 371 (c)(1),
(2), (4) Date: Dec. 22, 2011

(87) PCT Pub. No.: WO2010/129053
PCT Pub. Date: Nov. 11, 2010

(65) Prior Publication Data
US 2012/0094999 A1   Apr. 19, 2012

Related U.S. Application Data

(60) Provisional application No. 61/215,419, filed on May 5, 2009.

(51) Int. Cl.
*C07D 403/12* (2006.01)
*C07D 473/16* (2006.01)
*C07D 403/14* (2006.01)

(52) U.S. Cl.
CPC ......... *C07D 473/16* (2013.01); *C07D 403/14* (2013.01)

(58) Field of Classification Search
None
See application file for complete search history.

(56) References Cited

U.S. PATENT DOCUMENTS

| | | | |
|---|---|---|---|
| 5,958,935 | A | 9/1999 | Davis et al. |
| 6,093,716 | A | 7/2000 | Davis et al. |
| 6,114,333 | A | 9/2000 | Davis et al. |
| 6,127,376 | A | 10/2000 | Davey et al. |

(Continued)

FOREIGN PATENT DOCUMENTS

| | | |
|---|---|---|
| EP | 1054004 A1 | 11/2000 |
| EP | 2172461 A1 | 4/2010 |

(Continued)

OTHER PUBLICATIONS

Slichenmeyer et al. "CI-1033, a Pan-erbB Tyrosine Kinase Inhibitor" Semin Oncol. 2001; 28(Suppl 16):80-85.*

(Continued)

*Primary Examiner* — Marcos Sznaidman
*Assistant Examiner* — Rayna B Rodriguez
(74) *Attorney, Agent, or Firm* — Swanson & Bratschun, L.L.C.

(57) ABSTRACT

The present invention relates to novel pyrimidine, pyrrolo-pyrimidine, pyrrolo-pyridine, pyridine, purine and triazine compounds which are able to modulate epidermal growth factor receptor (EGFR), including Her-kinases, and the use of such compounds in the treatment of various diseases, disorders or conditions.

5 Claims, 13 Drawing Sheets

WZ-3146 X=O, Y= H
WZ-4002 X=O, Y= OMe
WZ-8040 X=S, Y= H

(56) References Cited

U.S. PATENT DOCUMENTS

| | | | |
|---|---|---|---|
| 6,160,010 A | 12/2000 | Uckun et al. | |
| 6,262,088 B1 | 7/2001 | Phillips | |
| 6,579,983 B1 | 6/2003 | Batchelor et al. | |
| 6,593,326 B1 | 7/2003 | Bradbury et al. | |
| 6,649,608 B2 * | 11/2003 | Pease et al. | 514/227.8 |
| 6,838,464 B2 | 1/2005 | Pease et al. | |
| 6,939,874 B2 | 9/2005 | Harmange et al. | |
| 7,060,827 B2 | 6/2006 | Singh et al. | |
| 7,122,542 B2 | 10/2006 | Singh et al. | |
| 7,125,879 B2 | 10/2006 | Guillemont et al. | |
| 7,176,212 B2 | 2/2007 | Breault et al. | |
| 7,202,033 B2 | 4/2007 | Prescott et al. | |
| 7,241,769 B2 | 7/2007 | Stadtmueller et al. | |
| 7,282,504 B2 | 10/2007 | Armistead et al. | |
| 7,329,671 B2 | 2/2008 | Singh et al. | |
| 7,329,672 B2 | 2/2008 | Singh et al. | |
| 7,332,484 B2 | 2/2008 | Singh et al. | |
| 7,435,814 B2 | 10/2008 | Singh et al. | |
| 7,452,879 B2 | 11/2008 | Singh et al. | |
| 7,485,724 B2 | 2/2009 | Singh et al. | |
| 7,491,732 B2 | 2/2009 | Li et al. | |
| 7,498,435 B2 | 3/2009 | Singh et al. | |
| 7,504,396 B2 | 3/2009 | Nunes et al. | |
| 7,514,444 B2 | 4/2009 | Honigberg et al. | |
| 7,514,446 B2 | 4/2009 | Davis-Ward et al. | |
| 7,517,886 B2 | 4/2009 | Singh et al. | |
| 7,528,143 B2 | 5/2009 | Noronha et al. | |
| 7,531,548 B2 | 5/2009 | Guillemont et al. | |
| 7,550,460 B2 | 6/2009 | Singh et al. | |
| 7,557,210 B2 | 7/2009 | Singh et al. | |
| 7,582,648 B2 | 9/2009 | Singh et al. | |
| 7,589,200 B2 | 9/2009 | Singh et al. | |
| 7,642,351 B2 | 1/2010 | Singh et al. | |
| 7,655,797 B2 | 2/2010 | Singh et al. | |
| 7,718,662 B1 | 5/2010 | Chen et al. | |
| 7,741,330 B1 | 6/2010 | Chen et al. | |
| 7,803,939 B2 | 9/2010 | Singh et al. | |
| 7,812,029 B1 | 10/2010 | Singh et al. | |
| 7,820,819 B2 | 10/2010 | Singh et al. | |
| 7,825,116 B2 | 11/2010 | Singh et al. | |
| 7,858,633 B2 | 12/2010 | Li et al. | |
| 7,884,111 B2 | 2/2011 | Argade et al. | |
| 7,906,644 B2 | 3/2011 | Singh et al. | |
| 7,989,465 B2 | 8/2011 | Singh et al. | |
| 8,088,781 B2 | 1/2012 | Honigberg et al. | |
| 8,148,525 B2 | 4/2012 | Singh et al. | |
| 8,158,621 B2 | 4/2012 | Singh et al. | |
| 8,188,276 B2 | 5/2012 | Singh et al. | |
| 8,334,296 B2 | 12/2012 | Singh et al. | |
| 8,338,439 B2 | 12/2012 | Singh et al. | |
| 8,501,413 B2 | 8/2013 | Varmus et al. | |
| 8,557,806 B2 | 10/2013 | Singh et al. | |
| 8,735,404 B2 | 5/2014 | Honigberg et al. | |
| 8,748,438 B2 | 6/2014 | Honigberg et al. | |
| 8,748,597 B2 | 6/2014 | Singh et al. | |
| 8,822,685 B2 | 9/2014 | Singh et al. | |
| 8,835,430 B2 | 9/2014 | Singh et al. | |
| 8,853,397 B2 | 10/2014 | Singh et al. | |
| 8,883,435 B2 | 11/2014 | Honigberg et al. | |
| 8,883,803 B2 | 11/2014 | Honigberg et al. | |
| 8,975,249 B2 | 3/2015 | Lee et al. | |
| 9,375,431 B2 | 6/2016 | Lee et al. | |
| 9,409,887 B2 | 8/2016 | Lee et al. | |
| 9,409,921 B2 | 8/2016 | Singh et al. | |
| 2004/0002395 A1 | 1/2004 | Poynor | |
| 2004/0019067 A1 | 1/2004 | Armistead et al. | |
| 2004/0023957 A1 | 2/2004 | Wang et al. | |
| 2004/0077661 A1 | 4/2004 | Arbiser | |
| 2005/0004125 A1 | 1/2005 | Freyne et al. | |
| 2005/0014753 A1 | 1/2005 | Ding et al. | |
| 2005/0085637 A1 | 4/2005 | Cheung et al. | |
| 2005/0209221 A1 | 9/2005 | Nunes et al. | |
| 2005/0272083 A1 | 12/2005 | Seshagiri | |
| 2006/0030018 A1 | 2/2006 | Zuccola et al. | |
| 2006/0079543 A1 | 4/2006 | Sum et al. | |
| 2006/0084644 A1 | 4/2006 | Pal et al. |
| 2006/0084645 A1 | 4/2006 | Pal et al. |
| 2006/0100227 A1 | 5/2006 | Baenteli et al. |
| 2006/0160803 A1 | 7/2006 | Adams et al. |
| 2006/0247241 A1 | 11/2006 | Garcia-Echeverria et al. |
| 2006/0247262 A1 | 11/2006 | Baenteli et al. |
| 2006/0270694 A1 | 11/2006 | Wong |
| 2006/0293311 A1 | 12/2006 | Li et al. |
| 2007/0010668 A1 | 1/2007 | Davis-Ward et al. |
| 2007/0032493 A1 | 2/2007 | Foley et al. |
| 2007/0066658 A1 | 3/2007 | Chappell |
| 2007/0203161 A1 | 8/2007 | Argade et al. |
| 2007/0203162 A1 | 8/2007 | Li et al. |
| 2007/0259904 A1 | 11/2007 | Noronha et al. |
| 2008/0009484 A1 | 1/2008 | Argade et al. |
| 2008/0009494 A1 | 1/2008 | Li et al. |
| 2008/0021020 A1 | 1/2008 | Argade et al. |
| 2008/0027045 A1 | 1/2008 | Argade et al. |
| 2008/0039622 A1 | 2/2008 | Singh et al. |
| 2008/0058358 A1 | 3/2008 | Luecking et al. |
| 2008/0076921 A1 | 3/2008 | Honigberg et al. |
| 2008/0132504 A1 | 6/2008 | Garcia-Echeverria et al. |
| 2008/0139582 A1 | 6/2008 | Honigberg et al. |
| 2008/0182852 A1 | 7/2008 | Johnson et al. |
| 2008/0194603 A1 | 8/2008 | Li et al. |
| 2008/0207613 A1 | 8/2008 | Styles et al. |
| 2008/0214501 A1 | 9/2008 | Pan et al. |
| 2008/0260754 A1 | 10/2008 | Li et al. |
| 2008/0279867 A1 | 11/2008 | Atuegbu et al. |
| 2008/0300268 A1 | 12/2008 | Singh et al. |
| 2008/0312438 A1 | 12/2008 | Singh et al. |
| 2009/0131436 A1 | 5/2009 | Imbach et al. |
| 2009/0137588 A1 | 5/2009 | Singh et al. |
| 2009/0156622 A1 | 6/2009 | Singh et al. |
| 2009/0171086 A1 | 7/2009 | Singh et al. |
| 2009/0181987 A1 | 7/2009 | Honigberg et al. |
| 2009/0215803 A1 | 8/2009 | Rice et al. |
| 2009/0286778 A1 | 11/2009 | Combs et al. |
| 2009/0298830 A1 | 12/2009 | Mann et al. |
| 2009/0318407 A1 | 12/2009 | Bauer et al. |
| 2010/0004270 A1 | 1/2010 | Honigberg et al. |
| 2010/0016296 A1 | 1/2010 | Singh et al. |
| 2010/0022561 A1 | 1/2010 | Honigberg et al. |
| 2010/0029610 A1 | 2/2010 | Singh et al. |
| 2010/0041677 A1 | 2/2010 | Honigberg et al. |
| 2010/0087482 A1 | 4/2010 | Haber et al. |
| 2010/0088912 A1 | 4/2010 | Higgs et al. |
| 2010/0173285 A1 | 7/2010 | Varmus et al. |
| 2010/0197918 A1 | 8/2010 | Singh et al. |
| 2010/0249092 A1 | 9/2010 | Singh et al. |
| 2011/0039868 A1 | 2/2011 | Honigberg et al. |
| 2011/0144330 A1 | 6/2011 | Singh et al. |
| 2011/0207736 A1 | 8/2011 | Gray et al. |
| 2011/0224235 A1 | 9/2011 | Honigberg et al. |
| 2011/0245284 A1 | 10/2011 | Greul et al. |
| 2011/0281322 A1 | 11/2011 | Honigberg et al. |
| 2011/0281850 A1 | 11/2011 | Flynn et al. |
| 2012/0088912 A1 | 4/2012 | Honigberg et al. |
| 2012/0149687 A1 | 6/2012 | Lee et al. |
| 2012/0149722 A1 | 6/2012 | Lee et al. |
| 2012/0157426 A1 | 6/2012 | Lee et al. |
| 2013/0035334 A1 | 2/2013 | Honigberg et al. |
| 2013/0065879 A1 | 3/2013 | Singh et al. |
| 2013/0065899 A1 | 3/2013 | Singh et al. |
| 2013/0072469 A1 | 3/2013 | Singh et al. |
| 2013/0165462 A1 | 6/2013 | Singh et al. |
| 2014/0163027 A1 | 6/2014 | Verner et al. |
| 2014/0303154 A1 | 10/2014 | Singh et al. |
| 2014/0303191 A1 | 10/2014 | Buggy et al. |
| 2014/0330007 A1 | 11/2014 | Singh et al. |
| 2014/0371241 A1 | 12/2014 | Buggy et al. |
| 2015/0005297 A1 | 1/2015 | Singh et al. |
| 2015/0025055 A1 | 1/2015 | Lee et al. |
| 2015/0038518 A1 | 2/2015 | Balasubramanian |
| 2015/0126504 A1 | 5/2015 | Singh et al. |
| 2015/0158823 A1 | 6/2015 | Singh et al. |
| 2015/0246040 A1 | 9/2015 | Lee et al. |
| 2017/0027937 A1 | 2/2017 | Lee et al. |

(56) References Cited

U.S. PATENT DOCUMENTS

FOREIGN PATENT DOCUMENTS

| | | |
|---|---|---|
| JP | 07041461 A | 2/1995 |
| JP | H0741461 A | 2/1995 |
| WO | WO-96/28427 A1 | 9/1996 |
| WO | WO-97/19065 A1 | 5/1997 |
| WO | WO-00/27825 A1 | 5/2000 |
| WO | WO-00/46203 A2 | 8/2000 |
| WO | WO-01/47897 A1 | 7/2001 |
| WO | WO-01/64654 A1 | 9/2001 |
| WO | WO-01/64655 A1 | 9/2001 |
| WO | WO-01/85699 A2 | 11/2001 |
| WO | WO-02/083653 A1 | 10/2002 |
| WO | WO-03/016306 A1 | 2/2003 |
| WO | 03-026664 A1 | 4/2003 |
| WO | WO-03/030909 A1 | 4/2003 |
| WO | WO-03/066601 A1 | 8/2003 |
| WO | WO-2004/014382 A1 | 2/2004 |
| WO | WO-2004/031232 A1 | 4/2004 |
| WO | WO-2004/056786 A2 | 7/2004 |
| WO | WO-2004/069812 A1 | 8/2004 |
| WO | WO-2004/080980 A1 | 9/2004 |
| WO | WO-2005/013996 A2 | 2/2005 |
| WO | WO-2005/016893 A2 | 2/2005 |
| WO | WO 2005/016894 A1 | 2/2005 |
| WO | WO-2005/016894 A1 | 2/2005 |
| WO | WO-2005/026130 A2 | 3/2005 |
| WO | WO-2005/026158 A1 | 3/2005 |
| WO | WO-2006/021457 A2 | 3/2006 |
| WO | WO-2006/021544 A1 | 3/2006 |
| WO | WO-2006/045066 A2 | 4/2006 |
| WO | WO-2006/053109 A1 | 5/2006 |
| WO | WO-2006/074057 A2 | 7/2006 |
| WO | WO-2006/101977 A2 | 9/2006 |
| WO | WO-2006/108487 A1 | 10/2006 |
| WO | WO-2006/124874 A2 | 11/2006 |
| WO | WO-2006/128129 A1 | 11/2006 |
| WO | WO-2006/129100 A1 | 12/2006 |
| WO | WO-2006/133426 A2 | 12/2006 |
| WO | WO-2007/027238 A2 | 3/2007 |
| WO | WO-2007/048064 A2 | 4/2007 |
| WO | WO-2007/053452 A1 | 5/2007 |
| WO | WO-2007/056151 A2 | 5/2007 |
| WO | WO-2007/085833 A2 | 8/2007 |
| WO | WO-2007/089768 A2 | 8/2007 |
| WO | WO-2007/113254 A1 | 10/2007 |
| WO | WO-2007/113256 A1 | 10/2007 |
| WO | WO-2007/120339 A1 | 10/2007 |
| WO | WO-2007/125351 A1 | 11/2007 |
| WO | WO-2008/005538 A2 | 1/2008 |
| WO | WO-2008/009458 A1 | 1/2008 |
| WO | WO-2008/025556 A1 | 3/2008 |
| WO | WO-2008/049123 A2 | 4/2008 |
| WO | WO-2008/073687 A2 | 6/2008 |
| WO | WO-2008/074515 A1 | 6/2008 |
| WO | WO-2008/079719 A1 | 7/2008 |
| WO | WO-2008/079907 A1 | 7/2008 |
| WO | WO-2008/080964 A1 | 7/2008 |
| WO | WO-2008/080965 A2 | 7/2008 |
| WO | 2008-094737 A2 | 8/2008 |
| WO | WO-2008/092199 A1 | 8/2008 |
| WO | WO-2008/104754 A1 | 9/2008 |
| WO | WO-2008/107096 A1 | 9/2008 |
| WO | WO-2008/115738 A1 | 9/2008 |
| WO | WO-2008/115742 A1 | 9/2008 |
| WO | WO-2008/118822 A1 | 10/2008 |
| WO | WO-2008/132505 A1 | 11/2008 |
| WO | WO-2008/150118 | 12/2008 |
| WO | WO-2009/008371 A1 | 1/2009 |
| WO | WO-2009/012421 A1 | 1/2009 |
| WO | 2009-017838 A2 | 2/2009 |
| WO | 2009-017838 A2 † | 2/2009 |
| WO | WO-2009/032668 A2 | 3/2009 |
| WO | WO-2009/032694 A1 | 3/2009 |
| WO | WO-2009/032703 A1 | 3/2009 |
| WO | 2009/051822 A1 † | 4/2009 |
| WO | WO-2009/051822 A1 | 4/2009 |
| WO | WO-2009/080638 A2 | 7/2009 |
| WO | WO-2009/112490 A1 | 9/2009 |
| WO | WO-2009/115267 A2 | 9/2009 |
| WO | WO-2009/127642 A2 | 10/2009 |
| WO | WO-2009/136995 A2 | 11/2009 |
| WO | WO-2009/143389 A1 | 11/2009 |
| WO | 2009/158571 A1 † | 12/2009 |
| WO | WO-2009/158571 A1 | 12/2009 |
| WO | WO-2010/025833 A1 | 3/2010 |
| WO | 2010-080712 | 7/2010 |
| WO | WO-2010/129053 A2 | 11/2010 |
| WO | WO-2011/079231 A1 | 6/2011 |
| WO | WO-2011/090760 A1 | 7/2011 |
| WO | 2011-115725 | 9/2011 |
| WO | WO-2011/140338 A1 | 11/2011 |
| WO | WO-2011/153514 A2 | 12/2011 |

OTHER PUBLICATIONS

Gura et. al. (Science, 1997, 278:1041-1042).*
Johnson et. al. (British Journal of Cancer, 2001, 84:1424-1431).*
U.S. Appl. No. 61/076,450, filed Jun. 27, 2008, Singh et al.
Aliagas-Martin, I. et al., A class of 2,4-bisanilinopyrimidine Aurora A inhibitors with unusually high selectivity against Aurora B, J. Med. Chem. 52:3300-3307 (2009).
Andrulis, I. et al., Neu/ErbB-2 amplification identifies a poor-prognosis group of women with node-negative breast cancer, J Clin Oncol 16(4):1340-1349 (Apr. 1998).
Bamborough, P. et al., N-4-Pyrimidinyl-1H-indazol-4-amine inhibitors of Lck: Indazoles as phenol isosteres with improved pharmacokinetics, Bioorg. & Med. Chem. Lett. 17:4363-4368 (2007).
Carter, T. et al, Inhibition of drug-resistant mutants of ABL, KIT, and EGF receptor kinases, Proc. Natl. Acad. Sci. USA 102(31):11011-11016 (Aug. 2005).
Cohen, M. et al., Structural bioinformatics-based design of selective, irreversible inhibitors, Science 308:1318-1321 (May 2005).
Curto, M. et al., Contact-dependent inhibition of EGFR signaling by Nf2/Merlin, J Cell Biol 177(5):893-903 (Jun. 2007).
Ding, K. et al., Design, Synthesis and Biological Evaluation of Novel Conformationally Constrained Inhibitors Targeting Epidermal Growth Factor Receptor $T^{790}$Methionine$^{790}$ mutant, J. Med. Chem. Feb. 16, 2012, DOI: 10.1021/jm201591k.
Fallon, K. et al., Constitutive activation of the neuregulin-1/erbB signaling pathway promotes the proliferation of a human peripheral neuroepithelioma cell line, J Neuro Oncol 66:273-284 (2004).
Frank, D., STAT signaling in the pathogenesis and treatment of cancer, Mol. Med. 5:432-456 (1999).
Fry, D. et al., Specific, irreversible inactivation of the epidermal growth factor receptor and erbB2, by a new class of tyrosine kinase inhibitor, Proc. Natl. Acad. Sci. USA 95:12022-12027 (Sep. 1998).
Ghoneim, K., Synthesis and evaluation of some 2-, 4-, di-substituted-6-methylpyrimidine derivatives for antimicrobial activity, J. Indian Chem. Soc. 63(10):914-917 (Oct. 1986).
Ghosh, D., 2-4-bis (arylamino)-5-methylpyrimidines as antimicrobial agents, J. Med. Chem. 10(5):974-975 (1967).
Ghosh, D., 2-4-bis (arylamino)-6-methylpyrimidines as antimicrobial agents, J. Indian Chem. Soc. 58(5):512-513 (May 1981).
Gonzales, A. et al, Antitumor activity and pharmacokinetic properties of PF-00299804, a second-generation, irreversible pan-erbB receptor tyrosine kinase inhibitor, Mol. Cancer Ther. 7(7):1880-1889 (Jul. 2008).
Hur, W. et al., Clinical stage EGFR inhibitors irreversibly alkylate Bmx kinase, Bioorg. Med. Chem. Lett. 18:5916-5919 (2008).
Kirken, R., Targeting Jak3 for immune suppression and allograft acceptance, Transplant. Proc. 33:3268-3270 (2001).
Kwak, E. et al., Irreversible inhibitors of the EGF receptor may circumvent acquired resistance to gefitinib, Proc. Natl. Acad. Sci. USA 102(21):7665-7670 (May 2005).
Lajeunesse, D. et al., A systematic screen for dominant second-site modifiers of Merlin/NF2 phenotypes reveals an interaction with blistered/DSRF and scribbler, Genetics 158:667-679 (Jun. 2001).

(56) References Cited

OTHER PUBLICATIONS

Li, D. et al., BIBW2992, an irreversible EGFR/HER2 inhibitor highly effective in preclinical lung cancer models, Oncogene 27(34):4702-4711 (Aug. 2008).

Lin, N. and Winer, E., New targets for therapy in breast cancer: Small molecule tyrosine kinase inhibitors, Breast Cancer Res 6(5):204-210 (2004).

Malaviya, R. et al., Targeting Janus Kinase 3 in Mast Cells Prevents Immediate Hypersensitivity Reactions and Anaphylaxis, J. Biol. Chem. 274(38):27028-27038 (Sep. 1999).

McClatchey, A. and Giovannini, M., Membrane organization and tumorigenesis—the NF2 tumor suppressor, Merlin, Genes Dev 19:2265-2277 (2005).

Minkovsky, N. and Berezov, A., BIBW-2992, a dual receptor tyrosine kinase inhibitor for the treatment of solid tumors, Curr Opin Invest Drugs 9(12):1336-1346 (2008).

Pelton, P. et al., Ruffling membrane, stress fiber, cell spreading and proliferation abnormalities in human Schwann cells, Oncogene 17:2195-2209 (1998).

PubChem CID 44594695. Feb. 1, 2010. [Retrieved from the Internet May 14, 2011: http://pubchem.ncbi.nlm.nih.gov/summary.cgi?cid=44594695&loc=ec_rcs].

Readinger, J. et al., Selective Targeting of ITK Blocks Multiple Steps of HIV Replication, Proc. Natl. Acad. Sci. USA 105(18): 6684-6689 (May 2008).

Seidel, H. et al., Pharmaceutical intervention in the JAK/STAT signaling pathway, Oncogene 19: 2645-2656 (2000).

Sequist, L., Second-Generation Epidermal Growth Factor Receptor Tyrosine Kinase Inhibitors in Non-Small Cell Lung Cancer, The Oncologist 12(3):325-330 (2007).

Singh, J. et al, Structure-based design of a potent, selective, and irreversible inhibitor of the catalytic domain of the erbB receptor subfamily of protein tyrosine kinases, J. Med. Chem. 40:1130-1135 (1997).

Stonecypher, M. et al., Activation of the neuregulin-1/ErbB signaling pathway promotes the proliferation of neoplastic Schwann cells in human malignant peripheral nerve sheath tumors, Oncogene 24:5589-5605 (2005).

Sudbeck, E. et al., Structure-based Design of Specific Inhibitors of Janus Kinase 3 as Apoptosis-inducing Antileukemic Agents, Clin. Cancer Res. 5:1569-1582 (Jun. 1999).

Trieu, V. et al., A specific inhibitor of janus kinase-3 increases survival in a transgenic mouse model of amyotrophic lateral sclerosis, Biochem. Biophys. Res. Commun. 267:22-25 (2000).

Wong, K. et al, A phase I study with neratinib (HKI-272), an irreversible pan Erb B receptor tyrosine kinase inhibitor, in patients with solid tumors, Clin. Cancer Res. 15(7):2552-2558 (Apr. 2009).

Zhang, J. et al., Targeting Cancer with Small Molecule Kinase Inhibitors, Nature Rev. Cancer 9:28-39 (Jan. 2009).

Zhang, Y. et al., Antitumor Activity of Epidermal Growth Factor Receptor-Related Protein Is Mediated by Inactivation of ErbB Receptors and Nuclear Factor-kB in Pancreatic Cancer, Cancer Res 66(2)1025-1032 (Jan. 2006).

Zhou, W. et al. Novel mutant-selective EGFR kinase inhibitors against EGFR T790M, Nature. Dec. 24/31, 2009; 462(7276):1070-1074.

Kumar et al. (Apr. 2008) "Structure and Clinical Relevance of the Epidermal Growth Factor Receptor in Human Cancer", Journal of Clinical Oncology 26(10):1742-1751.

Form PCT/ISA/210, Published on Jan. 24, 2011.

Form PCT/ISA/237, Published on Jan. 24, 2011.

Third Party Submission filed Jul. 31, 2013 in EP application serial No. 10772385.0.

Stevens et al. Synthesis and stereochemical effects of pyrrolidinyl-acetylenic thieno[3,2-d]pyrimidines as EGFR and ErbB-2 inhibitors, Bioorganic and Medicinal Chemistry Letters 19:21-26 (2009).

Blair, et al., "Structure-guided development of affinity probes for tyrosine kinases using chemical genetics", Nature Chemical Biology, vol. 3(4), pp. 229-238 (Apr. 2007).

Yun et al., "The T790M mutation in EGFR kinase causes drug resistance by increasing the affinity for ATP" PNAS, 2008, vol. 105(6), pp. 2070-2075 (Feb. 2008).

Third Party Submission filed in EP10772385.0 on Apr. 9, 2015.

Third Party Submission filed in JP2012-509790 on Mar. 2, 2015.

European Search Report for EP11816874.9, 5 pages (dated Dec. 12, 2013).

Itai, A. and Tomioka, N., Lead generation wo shikou sita computer graphics (Computer graphics directed to lead generation), Shinyaku no lead generation (Lead generation of new drug)—Saishin drug design (Latest drug design), Tokyo Kagaku Dojin, 57-72 (1987). Japanese and English Translation.

Pearlstein, R. et al., Understanding the structure-activity relationship of the human ether-a-go-go-related gene cardiac K+ channel. A model for bad behavior, Journal of Medicinal Chemistry, 46(11):2017-2022 (2003).

Sawanishi, H. et al., Drug Design of Condensed Purines for PDE4 Isoenzyme Inhibitors—Transformation from Xanthines to Imidazo [2,1-i] purines-, Bulletin of Hokuriku University, 28: 1-15 (2004). Japanese and English Translation.

Sjin, R. et al., In vitro and in vivo characterization of irreversible mutant-selective EGFR inhibitors that are wild-type sparing, Molecular Cancer Therapeutics, 13(6):1468-1479 (2014).

\* cited by examiner
† cited by third party

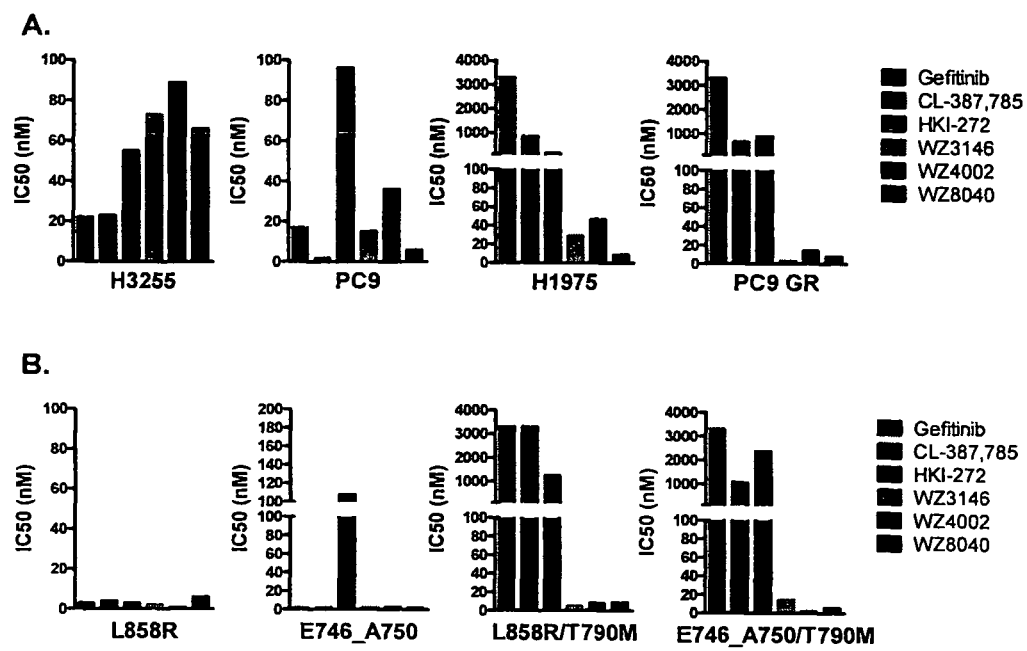
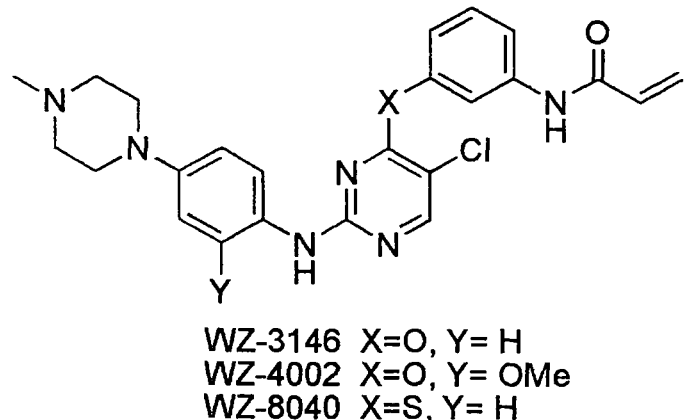
WZ-3146 X=O, Y= H
WZ-4002 X=O, Y= OMe
WZ-8040 X=S, Y= H
Figure 1

H1975 (L858R/T790M)

PC9GR (Del E746_A750/T790M)

WT EGFR

EGFR L858R/T790M

Del E746_A750/T790M  L858R/T790M

| Cell Line | EGFR or ERBB2 Mutation | Gefitinib | CL-387,785 | HKI-272 | WZ3146 | WZ4002 | WZ8040 |
|---|---|---|---|---|---|---|---|
| HCC827 | EGFR Del E746_A750 | 8 nM | 2 nM | 94 nM | 3 nM | 5 nM | 1 nM |
| PC9 | EGFR Del E746_A750 | 17 nM | 2 nM | 96 nM | 15 nM | 36 nM | 6 nM |
| H3255 | EGFR L858R | 22 nM | 23 nM | 55 nM | 73 nM | 89 nM | 66 nM |
| H1975 | EGFR L858R/T790M | > 3.3 µM | 850 nM | 153 nM | 29 nM | 47 nM | 9 nM |
| PC9 GR | EGFR Del E746_A750/T790M | > 3.3 µM | 660 nM | 876 nM | 3 nM | 14 nM | 8 nM |
| HCC827 GR | EGFR E746_A750/MET amp | > 3.3 µM | > 3.3 µM | > 3.3 µM | > 3.3 µM | > 3.3 µM | > 3.3 µM |
| H1819 | ERBB2 amp | 307 nM | 116 nM | 12 nM | 429 nM | 924 nM | 738 nM |
| Calu-3 | ERBB2 amp | 2.7 µM | 54 nM | 54 nM | 743 nM | 1.96 µM | 915 nM |
| H1781 | ERBB2 Ins G776V, C | > 3.3 µM | 88 nM | 84 nM | 736 nM | 1.51 µM | 744 nM |
| HN11 | EGFR & ERBB2 WT | 244 nM | 217 nM | 33 nM | 750 nM | 2.13 µM | 1.82 µM |

Figure 8. Efficacy in cell lines with different *EGFR* and *ERBB2* genotypes

| Ba/F3 cell line | Gefitinib | CL-387,785 | HKI-272 | WZ3146 | WZ4002 | WZ8040 |
|---|---|---|---|---|---|---|
| *EGFR* | | | | | | |
| L858R | 3 nM | 4 nM | 3 nM | 2 nM | 2 nM | 6 nM |
| L858R/T790M | > 3.3 µM | 3.3 µM | 1.25 µM | 5 nM | 8 nM | 9 nM |
| L858R/T790M/C797S | > 3.3 µM | 2.69 µM | 2.17 µM | 2.74 µM | > 3.3 µM | 2.01 µM |
| E746_A750 | 2 nM | 2 nM | 108 nM | 2 nM | 3 nM | 2 nM |
| E746_A750/T790M | > 3.3 µM | 1.06 µM | 2.37 µM | 14 nM | 2 nM | 6 nM |
| E746_A750/T790M/C797S | > 3.3 µM | 3.17 µM | 2.27 µM | 2.55 µM | > 3.3 µM | 2.54 µM |
| vIII | 454 nM | 2 nM | 16 nM | 66 nM | 157 nM | 48 nM |
| vIII/T790M | | | | | | |
| A767_V769dupASV | > 3.3 µM | 2.81 µM | 265 nM | 632 nM | 1.86 µM | 306 nM |
| *ERBB2* | | | | | | |
| WT | 760 nM | 26 nM | <1 nM | 24 nM | 113 nM | 32 nM |
| WT/T798I | | | | | | |
| Ins G776V, C | 1.9 µM | 8 nM | <1 nM | 10 nM | 35 nM | 20 nM |
| Ins 774YVMA | 2.3 µM | 75 nM | <1 nM | 248 nM | 619 nM | 374 nM |

Figure 9. Efficacy if Ba/F3 cells with different genotypes

|  | Drug | | | | |
| --- | --- | --- | --- | --- | --- |
|  | 4002 | | | 3146 | |
|  | Ambit Score | | | Ambit Score | |
| Concentration | 0.1 μM | 10 μM | | 0.1 μM | 10 μM |
|  | | | Kd | | |
| Gene | | | | | |
| ALK | NB | 0.7 | 300 | NB | NB |
| ARK5 | 18 | 0.65 | 91 | 5.4 | 0 |
| BLK | NB | 0.75 | 220 | 2 | 0 |
| BMX | NB | 8.6 | NB | 6.8 | NB |
| BTK | 17 | 0.1 | 36 | 0.45 | 0.2 |
| DCAMKL3 | NB | 0.35 | 910 | 0.35 | NB |
| EGFR | 19 | 0.1 | 46 | 6.5 | 0 |
| EGFR del E746_A750 | 12 | 0.2 | 12 | 4.5 | 0 |
| EGFR del L747_E749, A750P | 6.5 | 0.05 | 14 | 2.4 | 0 |
| EGFR del L747_S752,P753S | 10 | 0.4 | NB | 6.6 | 0.15 |
| EGFR del L747_T751, Sins | 13 | 0 | NB | 7 | 0 |
| EGFR del S752_I759 | 12 | 0.25 | 28 | 5.8 | 0.05 |
| EGFR G719S | NB | 0.35 | NB | 34 | 0.05 |
| EGFR G719C | NB | 0.3 | NB | NB | 0.2 |
| EGFR L858R | 10 | 0.1 | 29 | 3.9 | 0.05 |
| EGFR L861Q | 12 | 0.05 | NB | 4.8 | 0 |
| ERBB4 | 23 | 0.25 | 28 | 4 | 0.03 |
| FLT3 D835Y | NB | 0.8 | 33 | NB | 0.8 |
| GCN2 | NB | 0.35 | 140 | NB | 0.3 |
| GAK | NB | 0.45 | 91 | NB | 0.45 |
| ITK | 21 | 0.55 | 43 | 0.55 | 0.2 |
| JAK3 | NB | 0.4 | 150 | NB | 0.05 |
| PLK4 | NB | 0.2 | 100 | NB | 0.1 |
| FAK | 33 | 0.1 | 78 | NB | 0.35 |
| SNARK | 28 | 0.3 | 10 | NB | 0 |

Figure 10. Summary of Ambit binding data for WZ-4002 and WZ-3146. The Kds for selected kinases are also shown for WZ-4002.

| | IC$_{50}$ (μM) | | | | |
|---|---|---|---|---|---|
| Compound | Wild type | TEL-BMX | TEL-BLK | TEL-JAK2 | TEL-JAK3 |
| WZ-4002 | 7.56 | 0.048 | 0.756 | 3.76 | 2.82 |
| WZ-3146 | 1.82 | 0.0004 | 0.02 | 1.98 | 0.035 |

Figure 11. Summary of inhibitory activity of WZ-4002 and WZ-3146 against Ba/F3 cells expressing fusion kinases.

| | |
|---|---|
| Formulation | PEG 300/D5W 3:1 |
| Dose | 20 mg/kg |
| Route | Oral gavage |
| | |
| Cmax (nM) | 866.72 |
| Tmax (hrs) | 0.5 |
| AUC$_{0-5}$ (hrs*nM) | 2592 |
| Clast (nM) | 296.76 |
| Tlast (hrs) | 5 |
| AUC$_{0-5}$ hrs/dose[(min*μg/ml)/(mg/kg)] | 3.85 |

Figure 12. Pharmacokinetic parameters of WZ4002

| Time (hrs) | Plasma Concentration (nM) |
|---|---|
| 0.5 | 866.72 |
| 1.0 | 689.13 |
| 3.0 | 500.23 |
| 5.0 | 296.79 |

Figure 13. Mean plasma concentration of WZ4002 over time following single oral administration at 20 mg/kg. All PK studies are from a mean of two animals

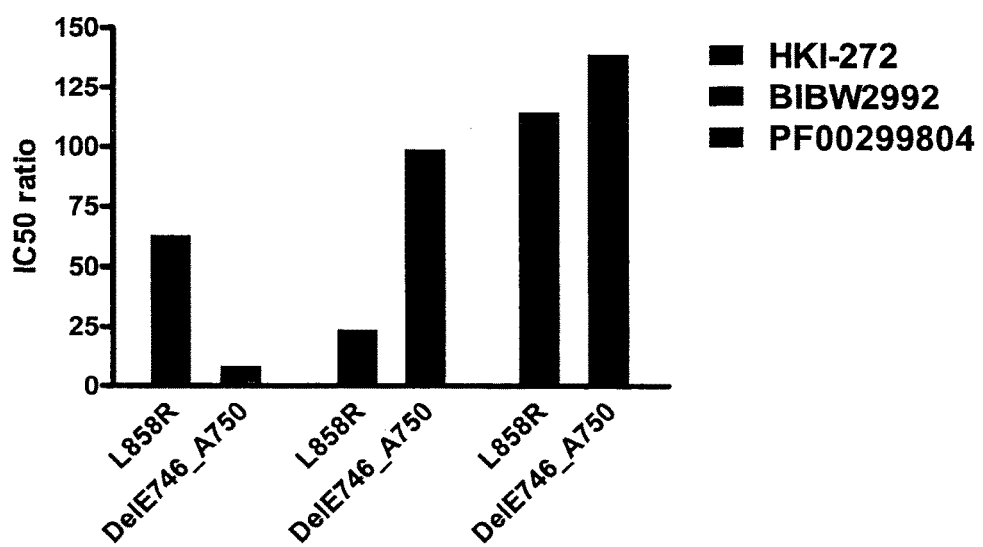
Figure 14. $IC_{50}$ ratios of irreversible EGFR inhibitors currently under clinical development. For each drug, the $IC_{50}$ ratio in Ba/F3 cells with and without T790M for a given genotype (e.g. (L858R/T790M)/L858R)) is shown.

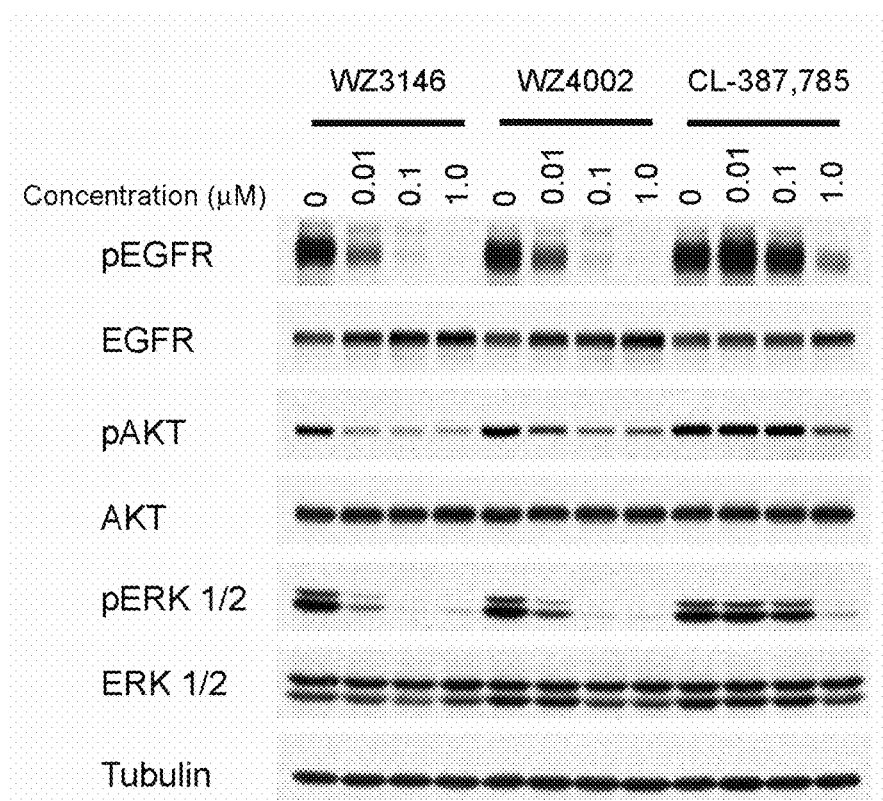
Figure 16. Comparison of WZ-3146, WZ-4002 and CL-387,785 on EGFR signaling in H1975 cells. The cells were treated with the indicated concentrations of each drug for hours. Cell extracts were immunoblotted to detect the indicated proteins.

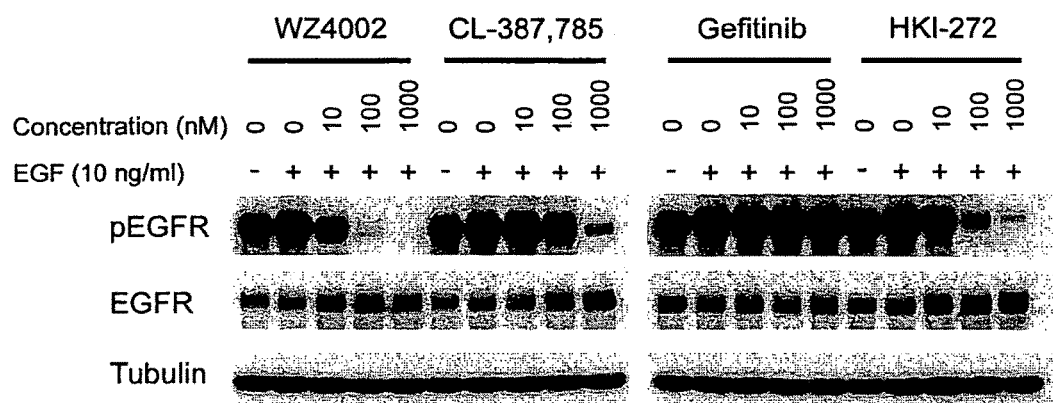
Figure 17. Comparison of EGFR inhibitors on ability to inhibit EGFR phosphorylation in 3T3 cells expressing L858R/T90M. The cells were treated with indicated concentrations of each drug for 16 hours and stimulated with EGF (10 ng/ml) 15 minutes prior to lysis. Cell extracts were immunoblotted to detect the indicated proteins.

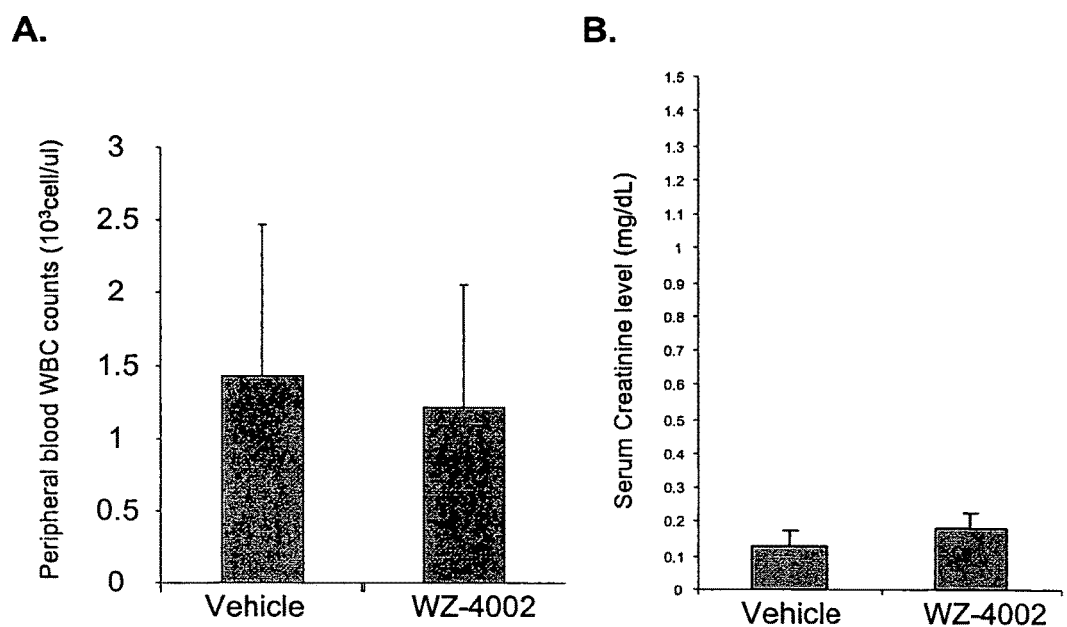
Figure 18. Evaluation of WBC (A.) and serum creatinine (B.) in vehicle and WZ-4002 treated del E746_A750/T790M mice following 2 weeks of continuous treatment. The data obtained from mice in each cohort. The mean and standard deviation are plotted.

US 9,908,884 B2

EGFR INHIBITORS AND METHODS OF TREATING DISORDERS

RELATED APPLICATIONS

This application is the U.S. national phase, pursuant to 35 U.S.C. § 371, of PCT international application PCT/US2010/001341, filed May 5, 2010, designating the United States and published on Mar. 24, 2011 as publication WO 2010/129053, which claims priority to U.S. provisional application Ser. No. 61/215,419, filed May 5, 2009. The entire content of the aforementioned patent applications are incorporated herein by this reference.

This invention was made with government support under grant numbers R01 CA080942, R01 CA116020, and P50 CA090578 awarded by The National Institutes of Health and grant number 0744413 awarded by The National Science Foundation. The government has certain rights in the invention.

TECHNICAL FIELD

The present invention relates to novel pyrimidine, pyrrolo-pyrimidine, pyrrolo-pyridine, pyridine, purine and triazine compounds which are able to modulate epidermal growth factor receptor (EGFR), including Her-kinases, and the use of such compounds in the treatment of various diseases, disorders or conditions.

BACKGROUND OF THE INVENTION

The epidermal growth factor receptor (EGFR, Erb-B1) belongs to a family of proteins, involved in the proliferation of normal and malignant cells (Artega, C. L., J. Clin Oncol 19, 2001, 32-40). Overexpression of Epidermal Growth Factor Receptor (EGFR) is present in at least 70% of human cancers (Seymour, L. K., Curr Drug Targets 2, 2001, 117-133) such as, non-small cell lung carcinomas (NSCLC), breast cancers, gliomas, squamous cell carcinoma of the head and neck, and prostate cancer (Raymond et al., Drugs 60 Suppl 1, 2000, discussion 41-2; Salomon et al., Crit. Rev Oncol Hematol 19, 1995, 183-232; Voldborg et al., Ann Oncol 8, 1997, 1197-1206). The EGFR-TK is therefore widely recognized as an attractive target for the design and development of compounds that can specifically bind and inhibit the tyrosine kinase activity and its signal transduction pathway in cancer cells, and thus can serve as either diagnostic or therapeutic agents. For example, the EGFR tyrosine kinase (EGFR-TK) reversible inhibitor, TARCEVA®, is approved by the FDA for treatment of NSCLC and advanced pancreatic cancer. Other anti-EGFR targeted molecules have also been approved including LAPATINIB® and IRESSA®.

The efficacy of erlotinib and gefitinib is limited when administered to all lung cancer patients. When erlotinib or gefitinib are used in the treatment of all lung cancer patients (not selected for presence/absence of activated (mutant) EGFR), the likelihood of tumor shrinkage (response rate) is 8-10% and the median time to tumor progression is approximately 2 months {Shepherd et al NEJM 2004, Thatcher et al. Lancet 2005}. In 2004 it was discovered that lung cancers with somatic mutations in EGFR were associated with dramatic clinical responses following treatment with gefitinib and erlotinib {Paez et al. Science 20004; Lynch et al. NEJM 2004; Pao et al PNAS 2004}. Somatic mutations identified to date include point mutations in which a single aminoacid residue is altered in the expressed protein (e.g. L858R, G719S, G719C, G719A, L861Q), as well as small in frame deletions in Exon19 or insetions in Exon20. Somatic mutations in EGFR are found in 10-15% of Caucasian and in 30-40% of Asian NSCLC patients. EGFR mutations are present more frequently in never-smokers, females, those with adenocarcinoma and in patients of East Asian ethnicity {Shigematsu et at JNCI-2005}. These are the same groups of patients previously clinically identified as most likely to benefit from gefitinib or erlotinib {Fukuoka et al. JCO 2003; Kris et at JAMA 2003 and Shepherd et at NEJM 2004}. Six prospective clinical trials treating chemotherapy naïve patients with EGFR mutations with gefitinib or erlotinib have been reported to date {Inoue et at JCO 2006, Tamura et al Br. J. Cancer 2008; Asahina et al., Br. J. Cancer 2006; Sequist et al., JCO 2008}. Cumulatively, these studies have prospectively identified and treated over 200 patients with EGFR mutations. Together they demonstrate radiographic response rates ranging from 60-82% and median times to progression of 9.4 to 13.3 months in the patients treated with gefitinib and erlotinib. These outcomes are 3 to 4 folder greater than that observed with platin-based chemotherapy (20-30% and 3-4 months, respectively) for advanced NSCLC {Schiller, et al JCO 2002}. In a recently completed phase III clinical trial, EGFR mutant chemotherapy naïve NSCLC patients had a significantly longer (hazard ratio=0.48 (95% CI; 0.36-0.64); p<0.0001) progression free survival (PFS) and tumor response rate (71.3 vs. 47.2%; p=0.0001) when treated with gefitinib compared with conventional chemotherapy {Mok et al. ESMO meeting 2008}. Conversely, NSCLC patients that were EGFR wild type had a worse outcome when they received gefitinib compared to chemotherapy as their initial treatment for advanced NSCLC {Mok et at ESMO meeting 2008}. Thus EGFR mutations provide an important selection method for NSCLC patients for a therapy (EGFR TKIs) that is more effective than conventional systemic chemotherapy. EGFR mutations are routinely being evaluated in NSCLC patients in many clinical centers.

Despite the initial clinical benefits of gefitinib/erlotinib in NSCLC patients harboring EGFR mutations, most if not all patients ultimately develop progressive cancer while receiving therapy on these agents. Initial studies of relapsed specimens identified a secondary EGFR mutation, T790M, that renders gefitinib and erlotinib ineffective inhibitors of EGFR kinase activity {Kobayashi et al NEJM 2005 and Pao et al PLOS Medicien 2005}. Subsequent studies have demonstrated that the EGFR T790M mutation is found in approximately 50% of tumors (24/48) from patients that have developed acquired resistance to gefitinib or erlotinib {Kosaka et al CCR 2006; Balak et al CCR 2006 and Engelman et al Science 2007}. This secondary genetic alteration occurs in the 'gatekeeper' residue and in an analogous position to other secondary resistance alleles in diseases treated with kinase inhibitors (for example T315I in ABL in imatinib resistant CML).

The initial identification of EGFR T790M also determined that an irreversible EGFR inhibitor, CL-387,785, could still inhibit EGFR even when it possessed the T790M mutation. Subsequent studies demonstrated that other irreversible EGFR inhibitors, EKB-569 and HKI-272, could also inhibit phosphorylation of EGFR T790M and the growth of EGFR mutant NSCLC cell lines harboring the T790M mutation {Kwak et al PNAS 2005; Kobayashi et al NEJM 2005}. These irreversible EGFR inhibitors are structurally similar to reversible inhibitors gefitinib and erlotinib, but differ in that they contain a Michael-acceptor that allows them to covalently bind EGFR at Cys 797. The T790M mutation does not preclude binding of irreversible inhibitors; instead, it confers resistance to reversible inhibitors in part by increasing the affinity of the enzyme for ATP, at least in the L858R/T790M mutant EGFR {Yun et al., PNAS 2008}. Irreversible inhibitors overcome this mechanism of resistance because once they are covalently bound, they are no longer in competition with ATP. These observations have led to clinical development of irreversible EGFR inhibitors for patients developing acquired resistance to gefitinib or erlotinib. Three such agents (HKI-272, BIBW2992 and PF00299804) are currently under clinical development. However, the preclinical studies to date would suggest that these agents are not optimal at inhibiting EGFR variants bearing the T790M mutation.

Recent studies in a mouse model of EGFR L858R/T790M mediated lung cancer demonstrate that a subset of cancers in these mice (bronchial tumors) were insensitive to HKI-272 alone {Li et al Cancer Cell 2007}. Thus even in this solely EGFR-driven model, HKI-272 alone is unable to cause tumor regression. This is in sharp contrast to the dramatic effects of erlotinib alone in mouse lung cancer models that contain only EGFR activating mutations {Ji et al Cancer Cell 2006} and suggests that HKI-272 may also be ineffective in some NSCLC patients with EGFR T790M. Similar findings have been reported for BIBW 2992 (Li et al. Oncogene 2008) Furthermore, the $IC_{50}$ of HKI-272 required to inhibit the growth of Ba/F3 cells harboring EGFR T790M in conjunction with different exon 19 deletion mutations ranges from 200-800 nM while the mean Cmax in the Phase I trial was only about 200 nM {Yuza et al Cancer Biol Ther 2007; Wong et al CCR 2009 in press}. Thus there continues to be a need to develop more effective EGFR targeted agents capable of inhibiting EGFR T790M.

A major limitation of all current EGFR inhibitors is the development of toxicity in normal tissues. Since ATP affinity of EGFR T790M is similar to WT EGFR, the concentration of an irreversible EGFR inhibitor required to inhibit EGFR T790M will also effectively inhibit WT EGFR. The class-specific toxicities of current EGFR kinase inhibitors, skin rash and diarrhea, are a result of inhibiting WT EGFR in non-cancer tissues. This toxicity, as a result of inhibiting WT EGFR, precludes dose escalation of current agents to plasma levels that would effectively inhibit EGFR T790M. A major advance would be the identification of a mutant specific EGFR inhibitor that was less effective against wild type EGFR. Such an agent would likely be clinically more effective and also potentially more tolerable as a therapeutic agent in patients with cancer.

SUMMARY OF THE INVENTION

The current invention provides a compound that exhibits greater inhibition of L858R/T790M or Del/T790M EGFR relative to wild-type EGFR. In certain embodiments, the current invention is directed towards a compound that exhibits at least 2-fold, 3-fold, 5-fold, 10-fold, 25-fold, 50-fold or 100-fold greater inhibition of L858R/T790M or Del/T790M EGFR relative to wild-type EGFR. In various embodiments, the current invention is directed towards a compound that exhibits up to 1000-fold greater inhibition of L858R/T790M or Del/T790M EGFR relative to wild-type EGFR. In various embodiments, the current invention is directed towards a compound that exhibits up to 10000-fold greater inhibition of L858R/T790M or Del/T790M EGFR relative to wild-type EGFR.

In various embodiments, the current invention is directed towards a compound that exhibits from about 2-fold to about 10-fold greater inhibition of L858R/T790M or Del/T790M EGFR relative to wild-type EGFR. In various embodiments, the current invention is directed towards a compound that exhibits from about 10-fold to about 100-fold greater inhibition of L858R/T790M or Del/T790M EGFR relative to wild-type EGFR. In various embodiments, the current invention is directed towards a compound that exhibits from about 100-fold to about 1000-fold greater inhibition of L858R/T790M or Del/T790M EGFR relative to wild-type EGFR. In various embodiments, the current invention is directed towards a compound that exhibits from about 1000-fold to about 10000-fold greater inhibition of L858R/T790M or Del/T790M EGFR relative to wild-type EGFR.

In certain embodiments, the current invention is directed towards a compound that exhibits at least 2-fold greater inhibition of L858R/T790M or Del/T790M EGFR relative to wild-type EGFR. In certain embodiments, the current invention is directed towards a compound that exhibits at least 3-fold greater inhibition of L858R/T790M or Del/T790M EGFR relative to wild-type EGFR. In certain embodiments, the current invention is directed towards a compound that exhibits at least 5-fold greater inhibition of L858R/T790M or Del/T790M EGFR relative to wild-type EGFR. In certain embodiments, the current invention is directed towards a compound that exhibits at least 10-fold greater inhibition of L858R/T790M or Del/T790M EGFR relative to wild-type EGFR. In certain embodiments, the current invention is directed towards a compound that exhibits at least 25-fold greater inhibition of L858R/T790M or Del/T790M EGFR relative to wild-type EGFR. In certain embodiments, the current invention is directed towards a compound that exhibits at least 50-fold greater inhibition of L858R/T790M or Del/T790M EGFR relative to wild-type EGFR. In certain embodiments, the current invention is directed towards a compound that exhibits greater than 100-fold inhibition of L858R/T790M or Del/T790M EGFR relative to wild-type EGFR.

In some embodiments, the compound covalently modifies Cysteine 797 in EGFR.

In one aspect, the invention provides a compound comprising an irreversible kinase inhibitor, wherein the compound is a more potent inhibitor of a drug-resistant epidermal growth factor receptor (EGFR) mutant relative to a wild type EGFR. For example, the compound can be at least about 2-fold, 3-fold, 5-fold, 10-fold, 25-fold, 50-fold or about 100-fold more potent at inhibiting the kinase activity of the drug-resistant EGFR mutant relative to the compound's inhibition of wild type EGFR kinase activity. In some embodiments, the drug-resistant EGFR mutant is resistant to one or more of gefitinib, erlotinib and lapatinib. In some embodiments, the drug-resistant EGFR mutant comprises an activating mutation.

In another aspect, the invention provides a compound comprising an irreversible kinase inhibitor, wherein the compound inhibits kinase activity of a drug-resistant EGFR mutant harboring an activating mutation and a drug-resistance mutation with less than a 10-fold difference in potency relative to an EGFR mutant harboring the activating mutation but not the drug-resistance mutation. In some embodiments, the difference in potency is less than about 9-fold, 8-fold, 7-fold, 6-fold, 5-fold, 4-fold, 3-fold or 2-fold.

In yet another aspect, the invention provides a compound comprising an irreversible kinase inhibitor, wherein the compound is more potent than gefitinib, HKI-272 and CL-387,785 at inhibiting EGFR T790M kinase activity. For example, the compound can be at least about 2-fold, 3-fold, 5-fold, 10-fold, 25-fold, 50-fold or about 100-fold more potent than gefitinib, HKI-272 and CL-387,785 at inhibiting the kinase activity of the EGFR T790M mutant. In some embodiments, the compound is also less potent than gefitinib, HKI-272 and CL-387,785 at inhibiting a kinase activity of a wild type EGFR. For example, the compound can be at least about 2-fold, 3-fold, 5-fold, 10-fold, 25-fold, 50-fold or about 100-fold less potent than gefitinib, HKI-272 or CL-387,785 at inhibiting the kinase activity of the wild type EGFR.

Potency of the inhibitor can be determined by IC50 value. A compound with a lower IC50 value, as determined under substantially similar conditions, is a more potent inhibitor relative to a compound with a higher IC50 value. In some embodiments, the substantially similar conditions comprise determining an EGFR-dependent phosphorylation level in 3T3 cells expressing a wild type EGFR, a mutant EGFR, or a fragment of any thereof.

Activating mutation comprise without limitation L858R, G719S, G719C, G719A, L861Q, a deletion in exon 19 and/or an insertion in exon 20. Drug-resistant EGFR mutants can have without limitation a drug resistance mutation comprising T790M, T854A or D761Y.

The selectivity between wild-type EGFR and the L858R/T790M or Exon19 deletion/T790M EGFR mutants can be measured using cellular proliferation assays where cell proliferation is completely dependent on kinase activity. For example, murine Ba/F3 cells transfected with a suitable version of wild-type EGFR (such as VIII; containing a WT EGFR kinase domain), or Ba/F3 cells transfected with L858R/T790M or Exon19 deletion/T790M can be used. Proliferation assays are preformed at a range of inhibitor concentrations (10 uM, 3 uM, 1.1 uM, 330 nM, 110 nM, 33 nM, 11 nM, 3 nM, 1 nM) and an EC50 is calculated.

An alternative method is to measure effects on EGFR activity is to assay EGFR phosphorylation. Wild type or mutant (L858R/T790M or Del19/T790M) EGFR can be transfected into NIH-3T3 cells (which do not normally express endogenous EGFR) and the ability of the inhibitor (using concentrations as above) to inhibit EGFR phosphorylation can be assayed. Cells are exposed to increasing concentrations of inhibitor for 6 hours and stimulated with EGF for 10 minutes. The effects on EGFR phosphorylation are assayed by Western Blotting using phospho-specific (Y1068) EGFR antibodies.

In certain aspects, the compound described above is a compound of formula I.

In one aspect, the invention provides a compound of formula I:

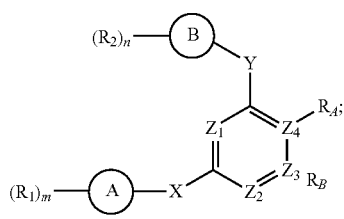

(I)

or a pharmaceutically acceptable salt, ester or prodrug thereof,
wherein,
$Z_1$ and $Z_2$ are each independently N or $CR_5$; $Z_3$ and $Z_4$ are each independently N or C, wherein $R_A$ and $R_B$ are absent when $Z_3$ or $Z_4$ is N; wherein at least one of $Z_1$, $Z_2$, $Z_3$ or $Z_4$ is N;

X is O, S, or $NR_6$;
Y is absent, CO, O, S, or $NR_6$;
each $R_6$ is independently H or alkyl;
ring A is aryl, heteroaryl, carbocyclic or heterocyclic; or a fused 8-14 membered bicyclic aryl, heteroaryl, carbocyclic or heterocyclic;
ring B is aryl, heteroaryl, carbocyclic or heterocyclic; or a fused 8-14 membered bicyclic aryl, heteroaryl, carbocyclic or heterocyclic;
$R_A$ is H, hal, OH, $NH_2$, $NHR_3$, $NR_3R_4$, $SR_3$, haloalkyl, CN, $N_3$, $NO_2$; alkyl, alkoxy, alkenyl, alkynyl, aryl, arylalkyl, heteroaryl, heterocyclic, or carbocyclic, each of which may be optionally substituted;
$R_B$ is H, hal, OH, $NH_2$, $NHR_3$, $NR_3R_4$, $SR_3$, haloalkyl, CN, $N_3$, $NO_2$; alkyl, alkoxy, alkenyl, alkynyl, aryl, arylalkyl, heteroaryl, heterocyclic, or carbocyclic, each of which may be optionally substituted;
or $R_A$ and $R_B$, together with the atoms to which each is attached, form a fused aryl, heteroaryl, carbocyclic or heterocyclic, each of which may be optionally substituted;
each $R_1$ is independently $NH(R_3)$, $N(R_3)(R_4)$, $N(R_3)CO(R_4)$, $N(R_3)SO_2(R_4)$, $N(R_3)SO(R_4)$, $N(R_3)SO(R_4)$, $CO_2H$, $C(O)R_3$, $C(O)OR_3$, $C(O)NH_2$, $C(O)NH(R_3)$, $C(O)N(R_3)(R_4)$, $SO_2R_3$, $SOR_3$, $SR_3$, $SO_2NR_3R_4$, $SONR_3R_4$, $OR_3$, cyano, nitro, hal, alkyl, alkenyl, alkynyl, haloalkyl, aryl, arylalkyl, alkoxy, heteroaryl, heterocyclic, or carbocyclic, each of which may be optionally substituted;
or if m is 2 or 3, then at least two of $R_1$ may together with the atoms to which each is attached, form a 5 or 6 membered carbocyclic, heterocyclic, aryl, or heteroaryl, each of which may be optionally substituted;
each $R_2$ is independently an optionally substituted alkyl, hal,

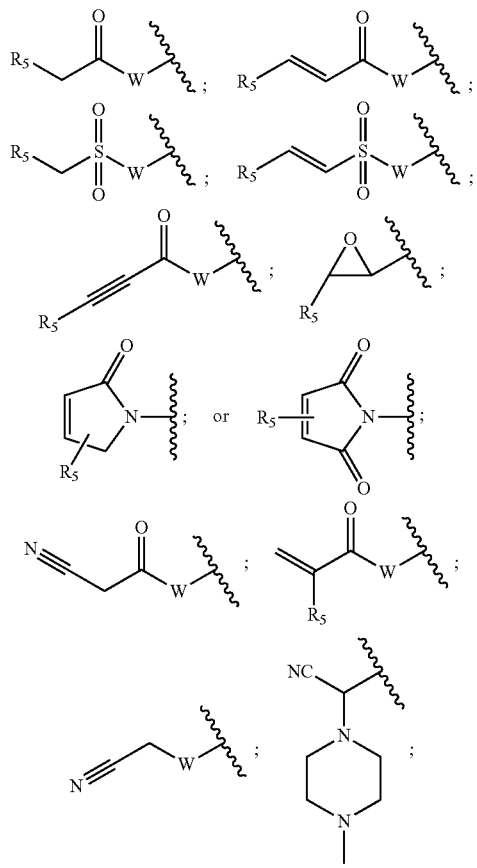

-continued

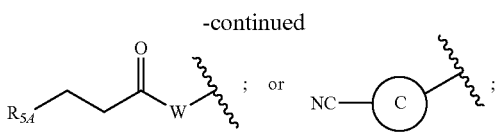

each $R_3$ and $R_4$ is independently H, alkyl, alkenyl, vinyl, heterocyclic, or carbocyclic, each of which may be optionally substituted;

each $R_5$ is independently H, alkyl, hal, or haloalkyl, each of which may be optionally substituted;

each $R_{5A}$ is independently hal or $OS(O)_pR'$, wherein p is 0, 1 or 2 and R' is alkyl or aryl;

each W is independently absent, $CH_2$, $CH_2CH_2$, $(CH_2)_3$, $(CH_2)_4$, O, S, or $NR_3$;

ring C is a 5-6 membered heterocyclic or heteroaryl having 1, 2, or 3 nitrogens;

m is 1, 2, or 3; and n is 0, 1 or 2;

wherein if X is S, $Z_2$ is $CR_5$, and $R_5$ is hal, then ring A is not phenyl para-substituted with $R_1$; or if Y is S, and $R_4$ is hal, then ring B is not phenyl para-substituted with $R_2$;

wherein if $R_A$ and $R_B$ together with the atoms to which each is attached, form a fused aryl, heteroaryl, carbocyclic or heterocyclic, then one of

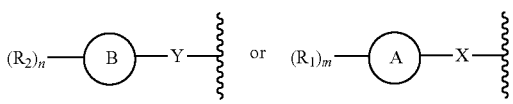

may be absent.

In another aspect, the invention provides a pharmaceutical composition comprising a compound of formula I, or a pharmaceutically acceptable ester, salt, or prodrug thereof, together with a pharmaceutically acceptable carrier.

DESCRIPTION OF THE DRAWINGS

FIG. 1—Growth assays in NSCLC cells and Ba/F3 cells A. NSCLC cell lines were treated with increasing concentrations of indicated drugs (range 1 nM to 3.3 µM), and viable cells were measured after 72 hours of treatment. The $IC_{50}$ values for each cell is represented as a bar graph. B. Ba/F3 cells with different EGFR genotypes were treated with increasing concentrations of indicated drugs (range 1 nM to 3.3 µM), and viable cells were measured after 72 hours of treatment. The $IC_{50}$ values for each cell is represented as a bar graph. The EGFR genotypes of the Ba/F3 cells correspond to those in the NSCLC indicated in A.

A. PC9 GR cells were treated different drugs at the indicated concentrations, and viable cells were measured after 72 hours of treatment. The percentage of viable cells is shown relative to untreated controls. B. PC9 GR cells were treated for 16 hours with increasing concentrations of WZ3146, WZ4002 or CL-287,785. Cell extracts were immunoblotted to detect the indicated proteins. WZ3146 and WZ4002 inhibited EGFR and consequently Akt and ERK 1/2 phosphorylation at significantly lower concentrations compared with CL-387,785.

Figures 2A, 2B:
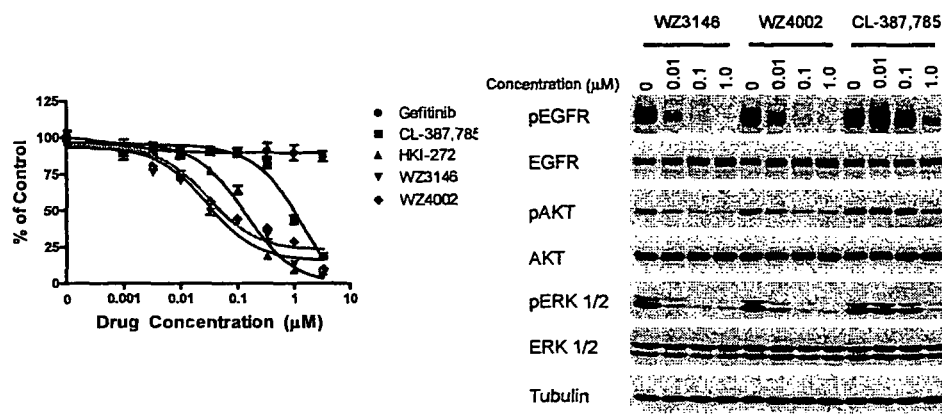
FIG. 2—Examination of growth and EGFR signaling in H1975 (L858R/T790M) cells
A. H1975 cells were treated different drugs at the indicated concentrations, and viable cells were measured after 72 hours of treatment. The percentage of viable cells is shown relative to untreated controls B. H1975 cells were treated for 16 hours with increasing concentrations of WZ3146, WZ4002 or CL-287,785. Cell extracts were immunoblotted to detect the indicated proteins. WZ3146 and WZ4002 inhibited EGFR and consequently Akt and ERK 1/2 phosphorylation at significantly lower concentrations compared with CL-387,785.
Figures 3A, 3B:
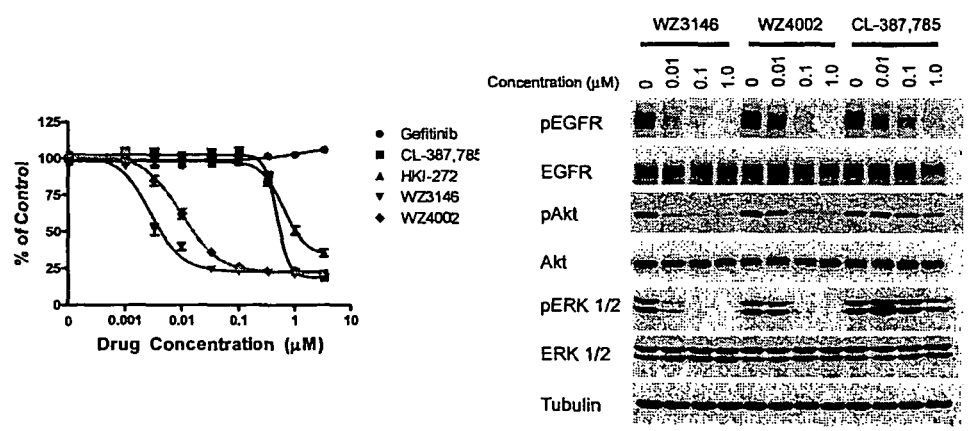
FIG. 3—Examination of growth and EGFR signaling in PC9 GR (E746_A750/T790M) cells.
Figure 4:
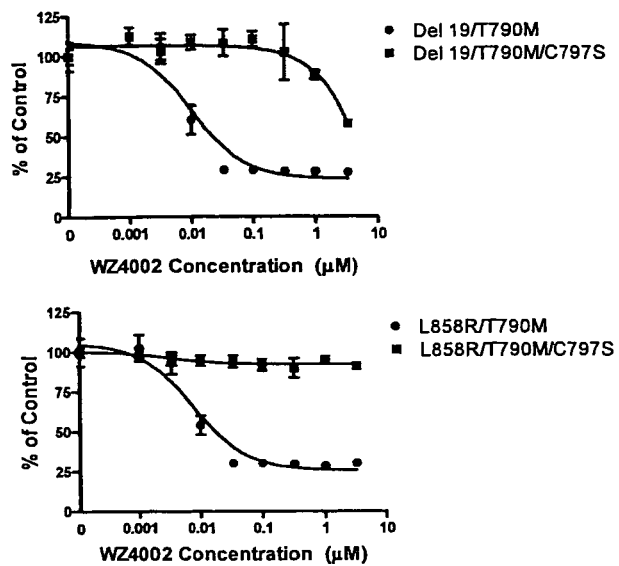

FIG. 4—Impact of C797S mutation on the efficacy of WZ4002

C797S mutation was introduced into L858R/T790M (top) or Del E746_A750/T790M Ba/F3 cells using site directed mutagenesis. The indicated Ba/F3 cells were treated different drugs at the indicated concentrations, and viable cells were measured after 72 hours of treatment. The percentage of viable cells is shown relative to untreated controls. The introduction of the C797S mutation significantly impairs the efficacy of WZ4002.

Figure 5:
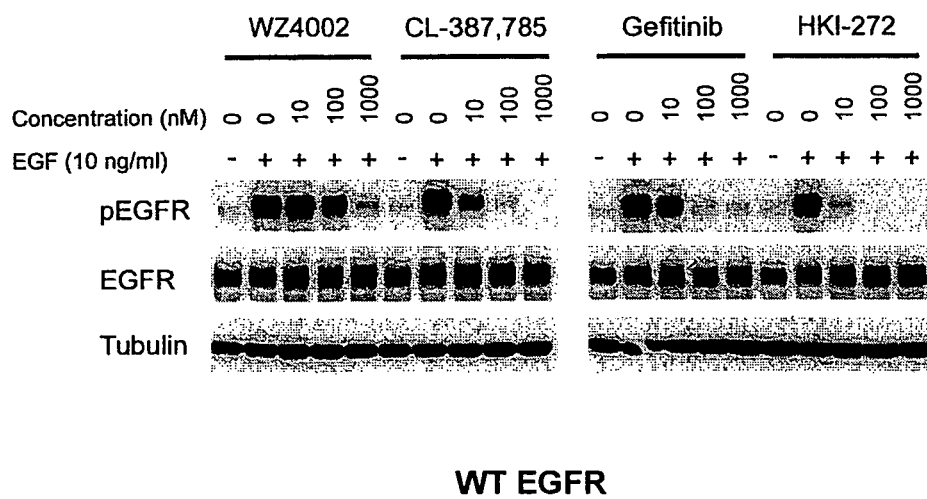

FIG. 5—WZ4002 is less effective at inhibiting WT EGFR than currently available EGFR inhibitors. NIH3T3 cells expressing wild type EGFR were exposed to increasing concentrations of WZ4002, CL-387,785, gefitinib or HKI-272 for 16 hours. The cells were subsequently stimulated with EGF (10 ng/ml) for 15 minutes prior to lysis. Cell extracts were immunoblotted to detect the indicated proteins. The concentration of WZ4002 required to inhibit EGFR phosphorylation is significantly higher than for CL-387,785, gefitinib or HKI-272.

Figure 6:
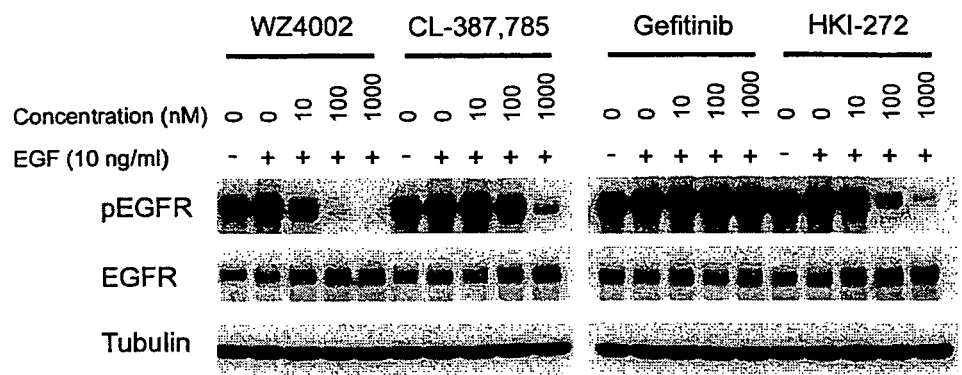

FIG. 6—inhibition of EGFR phosphorylation in L858R/T790M NIH-3T3 cells NIH3T3 cells expressing EGFR L858R/T790M were exposed to increasing concentrations of WZ4002, CL-387,785, gefitinib or HKI-272 for 16 hours. The cells were subsequently stimulated with EGF (10 ng/ml) for 15 minutes prior to lysis. Cell extracts were immunoblotted to detect the indicated proteins. The concentration of WZ4002 required to inhibit EGFR phosphorylation are substantially lower than for CL-387,785 or gefitinib and somewhat lower than for HKI-272.

Figure 7:
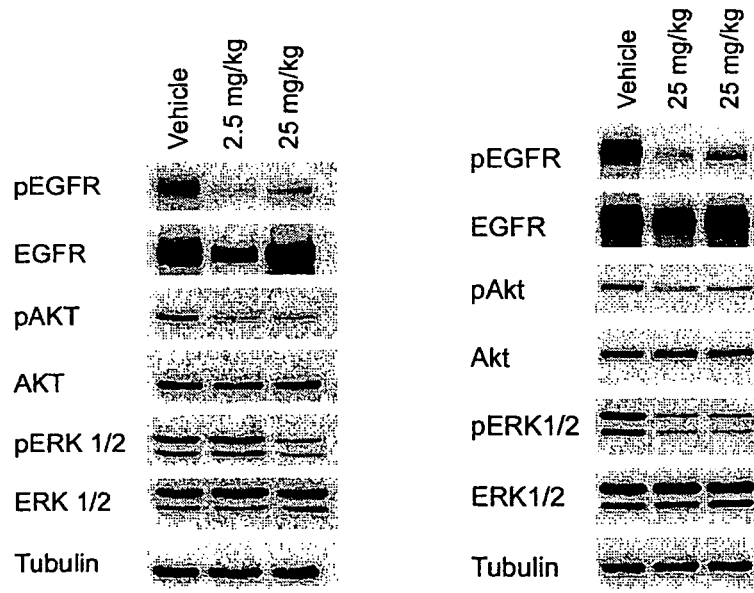

FIG. 7—Pharmacodynamic assessment of WZ4002 in transgenic mice harboring EGFR T790M. Transgenic mice with MRI confirmed lung tumors with the indicated EGFR genotypes were treated with vehicle alone or with two doses of WZ4002 (24 hrs apart) at the indicated concentrations by oral gavage. Six hours after the second dose, the mice were sacrificed, the lungs grossly dissected and lysed. The cell extracts were immunoblotted to detect the indicated proteins. In both genotypes, treatment with the 25 mg/kg dose leads to substantial inhibition of EGFR, Akt and ERK 1/2 phosphorylation.

FIG. 8—Efficacy in cell lines with different EGFR and ERBB2 genotypes.

FIG. 9—Efficacy if Ba/F3 cells with different genotypes.

FIG. 10—Summary of Ambit binding data for WZ-4002 and WZ-3146. The Kds for selected kinases are also shown for WZ-4002.

FIG. 11—Summary of inhibitory activity of WZ-4002 and WZ-3146 against Ba/F3 cells expressing fusion kinases.

FIG. 12—Pharmacokinetic parameters of WZ4002.

FIG. 13—Mean plasma concentration of WZ4002 over time following single oral administration at 20 mg/kg. All PK studies are from a mean of two animals.

FIG. 14—$IC_{50}$ ratios of irreversible EGFR inhibitors currently under clinical development. For each drug, the $IC_{50}$ ratio in Ba/F3 cells with and without T790M for a given genotype (e.g. (L858R/T790M)/L858R)) is shown.

Figure 15:
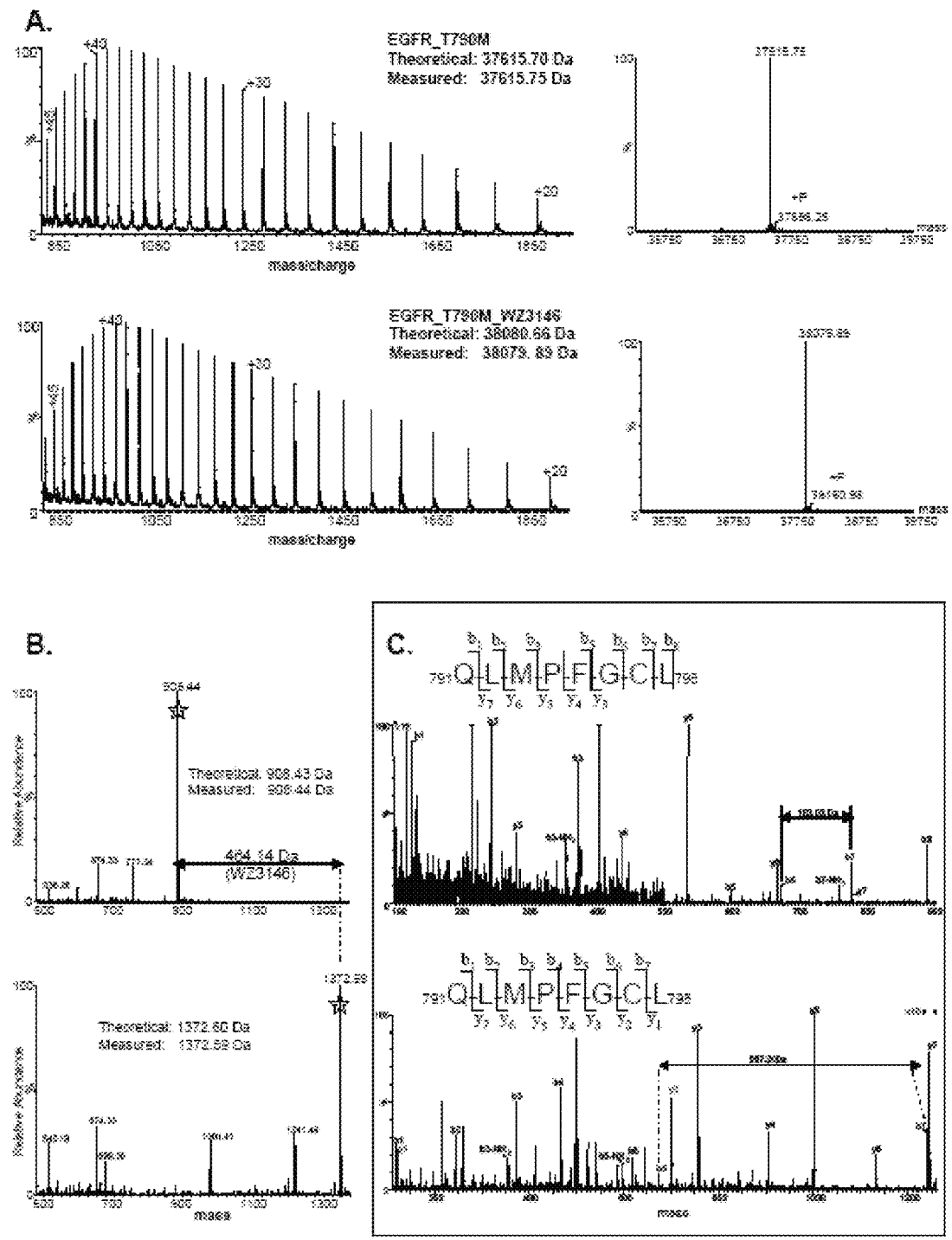

FIG. 15—Mass spectrometric analysis of T790M EGFR modification by WZ3146. (A) Intact ESI mass spectra of the free and inhibitor bound. The raw m/z data are shown on the left and the transformed, mass only spectra shown on the right. The measured and theoretical molecular weights of the unmodified as well as modified version of each protein are indicated. In the transformed mass spectra, peaks corresponding to a phosphorylation are indicated. (B) Transformed ESI-MS spectra of pepsin digested peptides from T790M unmodified (upper panel) and WZ3146 modified (lower panel). Peaks at 908.44 and 1372.59 Da were assigned to peptic peptide 791-798 in which the Cys797 was covalently modified by WZ3416 compound (lower panel). All the ions in these mass spectra have been converted to a single charge state. The other peaks that appear in the mass spectra correspond to other peptic peptides that are not significant to be discussed in this paragraph. (C) MS/MS spectra of the peptic peptide 791-798 alone (upper panel) and covalently modified (lower panel). The mass differences between fragment ions $b_6$ and $b_7$ (blue color) and $y_1$ and $y_2$ (green color) indicate that Cys797 was the site of covalent attachment by WZ3146 in T790M.

FIG. 16—Comparison of WZ-3146, WZ-4002 and CL-387,785 on EGFR signaling in H1975 cells. The cells were treated with the indicated concentrations of each drug for 6 hours. Cell extracts were immunoblotted to detect the indicated proteins.

FIG. 17—Comparison of EGFR inhibitors on ability to inhibit EGFR phosphorylation in 3T3 cells expressing L858R/T90M. The cells were treated with indicated concentrations of each drug for 16 hours and stimulated with EGF (10 ng/ml) 15 minutes prior to lysis. Cell extracts were immunoblotted to detect the indicated proteins.

FIG. 18—Evaluation of WBC (A.) and serum creatinine (B.) in vehicle and WZ-4002 treated del E746_A750/T790M mice following 2 weeks of continuous treatment. The data obtained from 6 mice in each cohort. The mean and standard deviation are plotted.

DETAILED DESCRIPTION OF THE INVENTION

Definitions

Listed below are definitions of various terms used to describe this invention. These definitions apply to the terms as they are used throughout this specification and claims, unless otherwise limited in specific instances, either individually or as part of a larger group.

The term "alkyl," as used herein, refers to saturated, straight- or branched-chain hydrocarbon radicals containing, in certain embodiments, between one and six, or one and eight carbon atoms, respectively. Examples of $C_1$-$C_6$ alkyl radicals include, but are not limited to, methyl, ethyl, propyl, isopropyl, n-butyl, tert-butyl, neopentyl, n-hexyl radicals; and examples of $C_1$-$C_8$ alkyl radicals include, but are not limited to, methyl, ethyl, propyl, isopropyl, n-butyl, tert-butyl, neopentyl, n-hexyl, heptyl, octyl radicals.

The term "alkenyl," as used herein, denotes a monovalent group derived from a hydrocarbon moiety containing, in certain embodiments, from two to six, or two to eight carbon atoms having at least one carbon-carbon double bond. The double bond may or may not be the point of attachment to another group. Alkenyl groups include, but are not limited to, for example, ethenyl, propenyl, butenyl, 1-methyl-2-buten-1-yl, heptenyl, octenyl and the like.

The term "alkynyl," as used herein, denotes a monovalent group derived from a hydrocarbon moiety containing, in certain embodiments, from two to six, or two to eight carbon atoms having at least one carbon-carbon triple bond. The alkynyl group may or may not be the point of attachment to another group. Representative alkynyl groups include, but are not limited to, for example, ethynyl, 1-propynyl, 1-butynyl, heptynyl, octynyl and the like.

The term "alkoxy" refers to an —O-alkyl radical.

The term "aryl," as used herein, refers to a mono- or poly-cyclic carbocyclic ring system having one or more aromatic rings, fused or non-fused, including, but not limited to, phenyl, naphthyl, tetrahydronaphthyl, indanyl, idenyl and the like.

The term "aralkyl," as used herein, refers to an alkyl residue attached to an aryl ring. Examples include, but are not limited to, benzyl, phenethyl and the like.

The term "cycloalkyl," as used herein, denotes a monovalent group derived from a monocyclic or polycyclic saturated or partially unsaturated carbocyclic ring compound. Examples of $C_3$-$C_8$-cycloalkyl include, but not limited to, cyclopropyl, cyclobutyl, cyclopentyl, cyclohexyl, cyclopentyl and cyclooctyl; and examples of $C_3$-$C_{12}$-cycloalkyl include, but not limited to, cyclopropyl, cyclobutyl, cyclopentyl, cyclohexyl, bicyclo[2.2.1]heptyl, and bicyclo[2.2.2]octyl. Also contemplated are a monovalent group derived from a monocyclic or polycyclic carbocyclic ring compound having at least one carbon-carbon double bond by the removal of a single hydrogen atom. Examples of such groups include, but are not limited to, cyclopropenyl, cyclobutenyl, cyclopentenyl, cyclohexenyl, cycloheptenyl, cyclooctenyl, and the like.

The term "heteroaryl," as used herein, refers to a mono- or poly-cyclic (e.g., bi-, or tri-cyclic or more) fused or non-fused, radical or ring system having at least one aromatic ring, having from five to ten ring atoms of which one ring atoms is selected from S, O and N; zero, one or two ring atoms are additional heteroatoms independently selected from S, O and N; and the remaining ring atoms are carbon. Heteroaryl includes, but is not limited to, pyridinyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, benzimidazolyl, benzoxazolyl, quinoxalinyl, and the like.

The term "heteroaralkyl," as used herein, refers to an alkyl residue residue attached to a heteroaryl ring. Examples include, but are not limited to, pyridinylmethyl, pyrimidinylethyl and the like.

The term "heterocycloalkyl," as used herein, refers to a non-aromatic 3-, 4-, 5-, 6- or 7-membered ring or a bi- or tri-cyclic group fused of non-fused system, where (i) each ring contains between one and three heteroatoms independently selected from oxygen, sulfur and nitrogen, (ii) each 5-membered ring has 0 to 1 double bonds and each 6-membered ring has 0 to 2 double bonds, (iii) the nitrogen and sulfur heteroatoms may optionally be oxidized, (iv) the nitrogen heteroatom may optionally be quaternized, and (iv) any of the above rings may be fused to a benzene ring. Representative heterocycloalkyl groups include, but are not limited to, [1,3]dioxolane, pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, isothiazolidinyl, and tetrahydrofuryl.

The term "alkylamino" refers to a group having the structure —NH($C_1$-$C_{12}$ alkyl) where $C_1$-$C_{12}$ alkyl is as previously defined.

The term "acyl" includes residues derived from acids, including but not limited to carboxylic acids, carbamic acids, carbonic acids, sulfonic acids, and phosphorous acids. Examples include aliphatic carbonyls, aromatic carbonyls, aliphatic sulfonyls, aromatic sulfinyls, aliphatic sulfinyls, aromatic phosphates and aliphatic phosphates. Examples of aliphatic carbonyls include, but are not limited to, acetyl, propionyl, 2-fluoroacetyl, butyryl, 2-hydroxy acetyl, and the like.

In accordance with the invention, any of the aryls, substituted aryls, heteroaryls and substituted heteroaryls described herein, can be any aromatic group. Aromatic groups can be substituted or unsubstituted.

The terms "hal," "halo," and "halogen," as used herein, refer to an atom selected from fluorine, chlorine, bromine and iodine.

As described herein, compounds of the invention may optionally be substituted with one or more substituents, such as are illustrated generally above, or as exemplified by particular classes, subclasses, and species of the invention. It will be appreciated that the phrase "optionally substituted" is used interchangeably with the phrase "substituted or unsubstituted." In general, the term "substituted", whether preceded by the term "optionally" or not, refers to the replacement of hydrogen radicals in a given structure with the radical of a specified substituent. Unless otherwise indicated, an optionally substituted group may have a substituent at each substitutable position of the group, and when more than one position in any given structure may be substituted with more than one substituent selected from a specified group, the substituent may be either the same or different at every position. The terms "optionally substituted", "optionally substituted alkyl," "optionally substituted "optionally substituted alkenyl," "optionally substituted alkynyl", "optionally substituted cycloalkyl," "optionally substituted cycloalkenyl," "optionally substituted aryl", "optionally substituted heteroaryl," "optionally substituted aralkyl", "optionally substituted heteroaralkyl," "optionally substituted heterocycloalkyl," and any other optionally substituted group as used herein, refer to groups that are substituted or unsubstituted by independent replacement of one, two, or three or more of the hydrogen atoms thereon with substituents including, but not limited to:

—F, —Cl, —Br, —I,
—OH, protected hydroxy,
—NO$_2$, —CN,
—NH$_2$, protected amino, —NH—C$_1$-C$_{12}$-alkyl, —NH—C$_2$-C$_{12}$-alkenyl, —NH—C$_2$-C$_{12}$-alkenyl, —NH—C$_3$-C$_{12}$-cycloalkyl, —NH-aryl, —NH-heteroaryl, —NH-heterocycloalkyl, -dialkylamino, -diarylamino, -diheteroarylamino,
—O—C$_1$-C$_{12}$-alkyl, —O—C$_2$-C$_{12}$-alkenyl, —O—C$_2$-C$_{12}$-alkenyl, —O—C$_3$-C$_{12}$-cycloalkyl, —O-aryl, —O-heteroaryl, —O-heterocycloalkyl,
—C(O)—C$_1$-C$_{12}$-alkyl, —C(O)—C$_2$-C$_{12}$-alkenyl, —C(O)—C$_2$-C$_{12}$-alkenyl, —C(O)—C$_3$-C$_{12}$-cycloalkyl, —C(O)-aryl, —C(O)-heteroaryl, —C(O)-heterocycloalkyl,
—CONH$_2$, —CONH—C$_1$-C$_{12}$-alkyl, —CONH—C$_2$-C$_{12}$-alkenyl, —CONH—C$_2$-C$_{12}$-alkenyl, —CONH—C$_3$-C$_{12}$-cycloalkyl, —CONH-heteroaryl, —CONH-heterocycloalkyl,
—OCO$_2$—C$_1$-C$_{12}$-alkyl, —OCO$_2$—C$_2$-C$_{12}$-alkenyl, —OCO$_2$—C$_2$-C$_{12}$-alkenyl, —OCO$_2$—C$_3$-C$_{12}$-cycloalkyl, —OCO$_2$-aryl, —OCO$_2$-heteroaryl, —OCO$_2$-heterocycloalkyl, —OCONH$_2$, —OCONH—C$_1$-C$_{12}$-alkyl, —OCONH—C$_2$-C$_{12}$-alkenyl, —OCONH—C$_2$-C$_{12}$-alkenyl, —OCONH—C$_3$-C$_{12}$-cycloalkyl, —OCONH— aryl, —OCONH— heteroaryl, —OCONH— heterocycloalkyl,
—NHC(O)—C$_1$-C$_{12}$-alkyl, —NHC(O)—C$_2$-C$_{12}$-alkenyl, —NHC(O)—C$_2$-C$_{12}$-alkenyl, —NHC(O)—C$_3$-C$_{12}$-cycloalkyl, —NHC(O)-aryl, —NHC(O)-heteroaryl, —NHC(O)-heterocycloalkyl, —NHCO$_2$—C$_1$-C$_{12}$-alkyl, —NHCO$_2$—C$_2$-C$_{12}$-alkenyl, —NHCO$_2$—C$_2$-C$_{12}$-alkenyl, —NHCO$_2$—C$_3$-C$_{12}$-cycloalkyl, —NHCO$_2$— aryl, —NHCO$_2$— heteroaryl, —NHCO$_2$— heterocycloalkyl, —NHC(O)NH$_2$, —NHC(O)NH—C$_1$-C$_{12}$-alkyl, —NHC(O)NH—C$_2$-C$_{12}$-alkenyl, —NHC(O)NH—C$_2$-C$_{12}$-alkenyl, —NHC(O)NH—C$_3$-C$_{12}$-cycloalkyl, —NHC(O)NH-aryl, —NHC(O)NH-heteroaryl, —NHC(O)NH-heterocycloalkyl, NHC(S)NH$_2$, —NHC(S)NH—C$_1$-C$_{12}$-alkyl, —NHC(S)NH—C$_2$-C$_{12}$-alkenyl, —NHC(S)NH—C$_2$-C$_{12}$-alkenyl, —NHC(S)NH—C$_3$-C$_{12}$-cycloalkyl, —NHC(S)NH-aryl, —NHC(S)NH-heteroaryl, —NHC(S)NH-heterocycloalkyl, —NHC(NH)NH$_2$, —NHC(NH)NH—C$_1$-C$_{12}$-alkyl, —NHC(NH)NH—C$_2$-C$_{12}$-alkenyl, —NHC(NH)NH—C$_2$-C$_{12}$-alkenyl, —NHC(NH)NH—C$_3$-C$_{12}$-cycloalkyl, —NHC(NH)NH-aryl, —NHC(NH)NH-heteroaryl, —NHC(NH)NH-heterocycloalkyl, —NHC(NH)—C$_1$-C$_{12}$-alkyl, —NHC(NH)—C$_2$-C$_{12}$-alkenyl, —NHC(NH)—C$_2$-C$_{12}$-alkenyl, —NHC(NH)—C$_3$-C$_{12}$-cycloalkyl, —NHC(NH)-aryl, —NHC(NH)-heteroaryl, —NHC(NH)-heterocycloalkyl,
—C(NH)NH—C$_1$-C$_{12}$-alkyl, —C(NH)NH—C$_2$-C$_{12}$-alkenyl, —C(NH)NH—C$_2$-C$_{12}$-alkenyl, —C(NH)NH—C$_3$-C$_{12}$-cycloalkyl, —C(NH)NH-aryl, —C(NH)NH-heteroaryl, —C(NH)NH-heterocycloalkyl,
—S(O)—C$_1$-C$_{12}$-alkyl, —S(O)—C$_2$-C$_{12}$-alkenyl, —S(O)—C$_2$-C$_{12}$-alkenyl, —S(O)—C$_3$-C$_{12}$-cycloalkyl, —S(O)-aryl, —S(O)-heteroaryl, —S(O)-heterocycloalkyl —SO$_2$NH$_2$, —SO$_2$NH—C$_1$-C$_{12}$-alkyl, —SO$_2$NH—C$_2$-C$_{12}$-alkenyl, —SO$_2$NH—C$_2$-C$_{12}$-alkenyl, —SO$_2$NH—C$_3$-C$_{12}$-cycloalkyl, —SO$_2$NH-aryl, —SO$_2$NH— heteroaryl, —SO$_2$NH— heterocycloalkyl,
—NHSO$_2$—C$_1$-C$_{12}$-alkyl, —NHSO$_2$—C$_2$-C$_{12}$-alkenyl, —NHSO$_2$—C$_2$-C$_{12}$-alkenyl, —NHSO$_2$—C$_3$-C$_{12}$-cycloalkyl, —NHSO$_2$-aryl, —NHSO$_2$-heteroaryl, —NHSO$_2$-heterocycloalkyl,
—CH$_2$NH$_2$, —CH$_2$SO$_2$CH$_3$, -aryl, -arylalkyl, -heteroaryl, -heteroarylalkyl, -heterocycloalkyl, —C$_3$-C$_{12}$-cycloalkyl, polyalkoxyalkyl, polyalkoxy, -methoxymethoxy, -methoxyethoxy, —SH, —S—C$_1$-C$_{12}$-alkyl, —S—C$_2$-C$_{12}$-alkenyl, —S—C$_2$-C$_{12}$-alkenyl, —S—C$_3$-C$_{12}$-cycloalkyl, —S-aryl, —S-heteroaryl, —S-heterocycloalkyl, or methylthiomethyl.

It is understood that the aryls, heteroaryls, alkyls, and the like can be further substituted.

The term "cancer" includes, but is not limited to, the following cancers: epidermoid Oral: buccal cavity, lip, tongue, mouth, pharynx; Cardiac: sarcoma (angiosarcoma, fibrosarcoma, rhabdomyosarcoma, liposarcoma), myxoma, rhabdomyoma, fibroma, lipoma and teratoma; Lung: bronchogenic carcinoma (squamous cell or epidermoid, undifferentiated small cell, undifferentiated large cell, adenocarcinoma), alveolar (bronchiolar) carcinoma, bronchial adenoma, sarcoma, lymphoma, chondromatous hamartoma, mesothelioma; Gastrointestinal: esophagus (squamous cell carcinoma, larynx, adenocarcinoma, leiomyosarcoma, lymphoma), stomach (carcinoma, lymphoma, leiomyosarcoma), pancreas (ductal adenocarcinoma, insulinoma, glucagonoma, gastrinoma, carcinoid tumors, vipoma), small bowel or small intestines (adenocarcinoma, lymphoma, carcinoid tumors, Karposi's sarcoma, leiomyoma, hemangioma, lipoma, neurofibroma, fibroma), large bowel or large intestines (adenocarcinoma, tubular adenoma, villous adenoma, hamartoma, leiomyoma), colon, colon-rectum, colorectal, rectum; Genitourinary tract: kidney (adenocarcinoma, Wilm's tumor (nephroblastoma), lymphoma, leukemia), bladder and urethra (squamous cell carcinoma, transitional cell carcinoma, adenocarcinoma), prostate (adenocarcinoma, sarcoma), testis (seminoma, teratoma, embryonal carcinoma, teratocarcinoma, choriocarcinoma, sarcoma, interstitial cell carcinoma, fibroma, fibroadenoma, adenomatoid tumors, lipoma); Liver: hepatoma (hepatocellular carcinoma), cholangiocarcinoma, hepatoblastoma, angiosarcoma, hepatocellular adenoma, hemangioma, biliary passages; Bone: osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma and giant cell tumors; Nervous system: skull (osteoma, hemangioma, granuloma, xanthoma, osteitis deformans), meninges (meningioma, meningiosarcoma, gliomatosis), brain (astrocytoma, medulloblastoma, glioma, ependymoma, germinoma (pinealoma), glioblastoma multiform, oligodendroglioma, schwannoma, retinoblastoma, congenital tumors), spinal cord neurofibroma, meningioma, glioma, sarcoma); Gynecological: uterus (endometrial carcinoma), cervix (cervical carcinoma, pre-tumor cervical dysplasia), ovaries (ovarian carcinoma (serous cystadenocarcinoma, mucinous cystadenocarcinoma, unclassified carcinoma), granulosa-thecal cell tumors, Sertoli-Leydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma), fallopian tubes (carcinoma), breast; Hematologic: blood (myeloid leukemia (acute and chronic), acute lymphoblastic leukemia, chronic lymphocytic leukemia, myeloproliferative diseases, multiple myeloma, myelodysplastic syndrome), Hodgkin's disease, non-Hodgkin's lymphoma (malignant lymphoma) hairy cell; lymphoid disorders; Skin: malignant melanoma, basal cell carcinoma, squamous cell carcinoma, Karposi's sarcoma, keratoacanthoma, moles dysplastic nevi, lipoma, angioma, dermatofibroma, keloids, psoriasis, Thyroid gland: papillary thyroid carcinoma, follicular thyroid carcinoma; medullary thyroid carcinoma, undifferentiated thyroid cancer, multiple endocrine neoplasia type 2A, multiple endocrine neoplasia type 2B, familial medullary thyroid cancer, pheochromocytoma, paraganglioma; and Adrenal glands: neuroblastoma. Thus, the term "cancerous cell" as provided herein, includes a cell afflicted by any one of the above-identified conditions.

The term "EGFR kinase" herein refers to epidermal growth factor receptor kinase.

The term "HER" or "Her", herein refers to human epidermal growth factor receptor kinase.

The term "subject" as used herein refers to a mammal. A subject therefore refers to, for example, dogs, cats, horses, cows, pigs, guinea pigs, and the like. Preferably the subject is a human. When the subject is a human, the subject may be referred to herein as a patient.

Treat", "treating" and "treatment" refer to a method of alleviating or abating a disease and/or its attendant symptoms.

As used herein, the term "pharmaceutically acceptable salt" refers to those salts of the compounds formed by the process of the present invention which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge, et al. describes pharmaceutically acceptable salts in detail in J. Pharmaceutical Sciences, 66: 1-19 (1977). The salts can be prepared in situ during the final isolation and purification of the compounds of the invention, or separately by reacting the free base function with a suitable organic acid. Examples of pharmaceutically acceptable include, but are not limited to, nontoxic acid addition salts are salts of an amino group formed with inorganic acids such as hydrochloric acid, hydrobromic acid, phosphoric acid, sulfuric acid and perchloric acid or with organic acids such as acetic acid, maleic acid, tartaric acid, citric acid, succinic acid or malonic acid or by using other methods used in the art such as ion exchange. Other pharmaceutically acceptable salts include, but are not limited to, adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, alkyl having from 1 to 6 carbon atoms, sulfonate and aryl sulfonate.

As used herein, the term "pharmaceutically acceptable ester" refers to esters of the compounds formed by the process of the present invention which hydrolyze in vivo and include those that break down readily in the human body to leave the parent compound or a salt thereof. Suitable ester groups include, for example, those derived from pharmaceutically acceptable aliphatic carboxylic acids, particularly alkanoic, alkenoic, cycloalkanoic and alkanedioic acids, in which each alkyl or alkenyl moiety advantageously has not more than 6 carbon atoms. Examples of particular esters include, but are not limited to, formates, acetates, propionates, butyrates, acrylates and ethylsuccinates.

The term "pharmaceutically acceptable prodrugs" as used herein refers to those prodrugs of the compounds formed by the process of the present invention which are, within the scope of sound medical judgment, suitable for use in contact with the tissues of humans and lower animals with undue toxicity, irritation, allergic response, and the like, commensurate with a reasonable benefit/risk ratio, and effective for their intended use, as well as the zwitterionic forms, where possible, of the compounds of the present invention. "Prodrug", as used herein means a compound which is convertible in vivo by metabolic means (e.g. by hydrolysis) to afford any compound delineated by the formulae of the instant invention. Various forms of prodrugs are known in the art, for example, as discussed in Bundgaard, (ed.), Design of Prodrugs, Elsevier (1985); Widder, et al. (ed.), Methods in Enzymology, vol. 4, Academic Press (1985); Krogsgaard-Larsen, et al., (ed). "Design and Application of Prodrugs, Textbook of Drug Design and Development, Chapter 5, 113-191 (1991); Bundgaard, et al., Journal of Drug Deliver Reviews, 8:1-38 (1992); Bundgaard, J. of Pharmaceutical Sciences, 77:285 et seq. (1988); Higuchi and Stella (eds.) Prodrugs as Novel Drug Delivery Systems, American Chemical Society (1975); and Bernard Testa & Joachim Mayer, "Hydrolysis In Drug And Prodrug Metabolism: Chemistry, Biochemistry And Enzymology," John Wiley and Sons, Ltd. (2002).

This invention also encompasses pharmaceutical compositions containing, and methods of treating disorders through administering, pharmaceutically acceptable prodrugs of compounds of the invention. For example, compounds of the invention having free amino, amido, hydroxy or carboxylic groups can be converted into prodrugs. Prodrugs include compounds wherein an amino acid residue, or a polypeptide chain of two or more (e.g., two, three or four) amino acid residues is covalently joined through an amide or ester bond to a free amino, hydroxy or carboxylic acid group of compounds of the invention. The amino acid residues include but are not limited to the 20 naturally occurring amino acids commonly designated by three letter symbols and also includes 4-hydroxyproline, hydroxyysine, demosine, isodemosine, 3-methylhistidine, norvalin, beta-alanine, gamma-aminobutyric acid, citrulline, homocysteine, homoserine, ornithine and methionine sulfone. Additional types of prodrugs are also encompassed. For instance, free carboxyl groups can be derivatized as amides or alkyl esters. Free hydroxy groups may be derivatized using groups including but not limited to hemisuccinates, phosphate esters, dimethylaminoacetates, and phosphoryloxymethyloxy carbonyls, as outlined in Advanced Drug Delivery Reviews, 1996, 19, 1 15. Carbamate prodrugs of hydroxy and amino groups are also included, as are carbonate prodrugs, sulfonate esters and sulfate esters of hydroxy groups. Derivatization of hydroxy groups as (acyloxy)methyl and (acyloxy)ethyl ethers wherein the acyl group may be an alkyl ester, optionally substituted with groups including but not limited to ether, amine and carboxylic acid functionalities, or where the acyl group is an amino acid ester as described above, are also encompassed. Prodrugs of this type are described in J. Med. Chem. 1996, 39, 10. Free amines can also be derivatized as amides, sulfonamides or phosphonamides. All of these prodrug moieties may incorporate groups including but not limited to ether, amine and carboxylic acid functionalities Combinations of substituents and variables envisioned by this invention are only those that result in the formation of stable compounds. The term "stable", as used herein, refers to compounds which possess stability sufficient to allow manufacture and which maintains the integrity of the compound for a sufficient period of time to be useful for the purposes detailed herein (e.g., therapeutic or prophylactic administration to a subject).

Compounds of the Invention

In one aspect, the invention provides a compound of formula I:

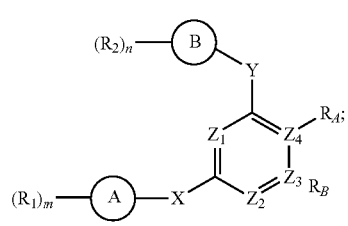

(I)

or a pharmaceutically acceptable salt, ester or prodrug thereof, wherein, $Z_1$ and $Z_2$ are each independently N or $CR_5$; $Z_3$ and $Z_4$ are each independently N or C, wherein $R_A$ and $R_B$ are absent when $Z_3$ or $Z_4$ is N; wherein at least one of $Z_1$, $Z_2$, $Z_3$ or $Z_4$ is N;

X is O, S, or $NR_6$;

Y is absent, CO, O, S, or $NR_6$;

each $R_6$ is independently H or alkyl;

ring A is aryl, heteroaryl, carbocyclic or heterocyclic; or a fused 8-14 membered bicyclic aryl, heteroaryl, carbocyclic or heterocyclic;

ring B is aryl, heteroaryl, carbocyclic or heterocyclic; or a fused 8-14 membered bicyclic aryl, heteroaryl, carbocyclic or heterocyclic;

$R_A$ is H, hal, OH, $NH_2$, $NHR_3$, $NR_3R_4$, $SR_3$, haloalkyl, CN, $N_3$, $NO_2$; alkyl, alkoxy, alkenyl, alkynyl, aryl, arylalkyl, heteroaryl, heterocyclic, or carbocyclic, each of which may be optionally substituted;

$R_B$ is H, hal, OH, $NH_2$, $NHR_3$, $NR_3R_4$, $SR_3$, haloalkyl, CN, $N_3$, $NO_2$; alkyl, alkoxy, alkenyl, alkynyl, aryl, arylalkyl, heteroaryl, heterocyclic, or carbocyclic, each of which may be optionally substituted;

or $R_A$ and $R_B$, together with the atoms to which each is attached, form a fused aryl, heteroaryl, carbocyclic or heterocyclic, each of which may be optionally substituted;

each $R_1$ is independently $NH(R_3)$, $N(R_3)(R_4)$, $N(R_3)CO(R_4)$, $N(R_3)SO_2(R_4)$, $N(R_3)SO(R_4)$, $N(R_3)SO(R_4)$, $CO_2H$, $C(O)R_3$, $C(O)OR_3$, $C(O)NH_2$, $C(O)NH(R_3)$, $C(O)N(R_3)(R_4)$, $SO_2R_3$, $SOR_3$, $SR_3$, $SO_2NR_3R_4$, $SONR_3R_4$, $OR_3$, cyano, nitro, hal, alkyl, alkenyl, alkynyl, haloalkyl, aryl, arylalkyl, alkoxy, heteroaryl, heterocyclic, or carbocyclic, each of which may be optionally substituted;

or if m is 2 or 3, then at least two of $R_1$ may together with the atoms to which each is attached, form a 5 or 6 membered carbocyclic, heterocyclic, aryl, or heteroaryl, each of which may be optionally substituted;

each $R_2$ is independently an optionally substituted alkyl, hal,

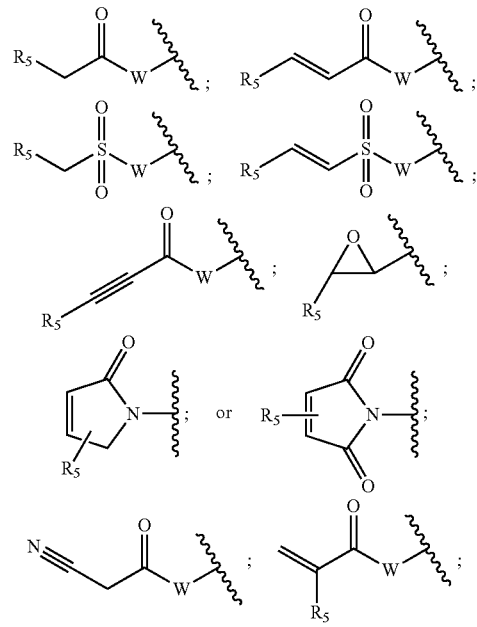

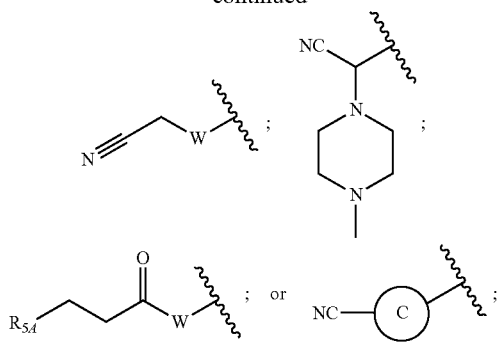

each $R_3$ and $R_4$ is independently H, alkyl, alkenyl, vinyl, heterocyclic, or carbocyclic, each of which may be optionally substituted;

each $R_5$ is independently H, alkyl, hal, or haloalkyl, each of which may be optionally substituted;

each $R_{5A}$ is independently hal or $OS(O)_pR'$, wherein p is 0, 1 or 2 and R' is alkyl or aryl;

each W is independently absent, $CH_2$, $CH_2CH_2$, $(CH_2)_3$, $(CH_2)_4$, O, S, or $NR_3$;

ring C is a 5-6 membered heterocyclic or heteroaryl having 1, 2, or 3 nitrogens;

m is 1, 2, or 3; and n is 0, 1 or 2;

wherein if X is S, $Z_2$ is $CR_5$, and $R_5$ is hal, then ring A is not phenyl para-substituted with $R_1$; or if Y is S, and $R_A$ is hal, then ring B is not phenyl para-substituted with $R_2$;

wherein if $R_A$ and $R_B$ together with the atoms to which each is attached, form a fused aryl, heteroaryl, carbocyclic or heterocyclic, then one of

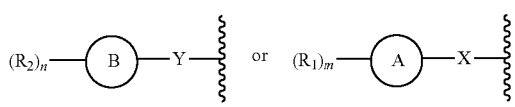

may be absent.

In one embodiment, $Z_1$ and $Z_2$ are N, and $Z_3$ and $Z_4$ are C.

In another embodiment, $Z_1$, $Z_2$ and $Z_4$ are N, and $Z_3$ is C.

In certain embodiments, $R_A$ is H, hal, OH, $NH_2$, $NHR_3$, haloalkyl, CN, $N_3$, or $NO_2$; and $R_B$ is H, hal, OH, $NH_2$, $NHR_3$, haloalkyl, CN, $N_3$, or $NO_2$.

In various embodiments, $R_A$ and $R_B$, together with the atoms to which each is attached, form a fused aryl, heteroaryl, carbocyclic or heterocyclic, each of which may be optionally substituted.

In certain embodiments, the invention provides a compound of formula I:

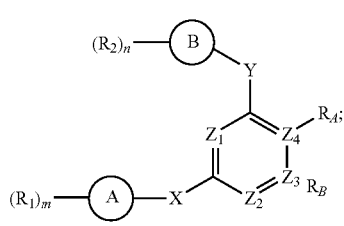

(I)

or a pharmaceutically acceptable salt, ester or prodrug thereof, wherein, $Z_1$ and $Z_2$ are each independently N or CH; $Z_3$ and $Z_4$ are each independently N or C, wherein $R_A$ and $R_B$ are absent when $Z_3$ or $Z_4$ is N; wherein at least two of $Z_1$, $Z_2$, $Z_3$ or $Z_4$ are N;

X is O, S, or $NR_6$;

Y is absent, CO, O, S, or $NR_6$;

each $R_6$ is independently H or alkyl;

ring A is aryl, heteroaryl, or heterocyclic;

ring B is aryl, heteroaryl, or heterocyclic;

$R_A$ is H, hal, OH, $NH_2$, $NHR_3$, haloalkyl, CN, $N_3$, or $NO_2$;

$R_B$ is H, hal, OH, $NH_2$, $NHR_3$, haloalkyl, CN, $N_3$, or $NO_2$;

each $R_1$ is independently $NH(R_3)$, $N(R_3)CO(R_4)$, $C(O)R_3$, $C(O)NH(R_3)$, $SO_2R_3$, alkyl, haloalkyl, alkoxy, heteroaryl, carbocyclic or heterocyclic, each of which may be optionally substituted;

each $R_2$ is independently hal,

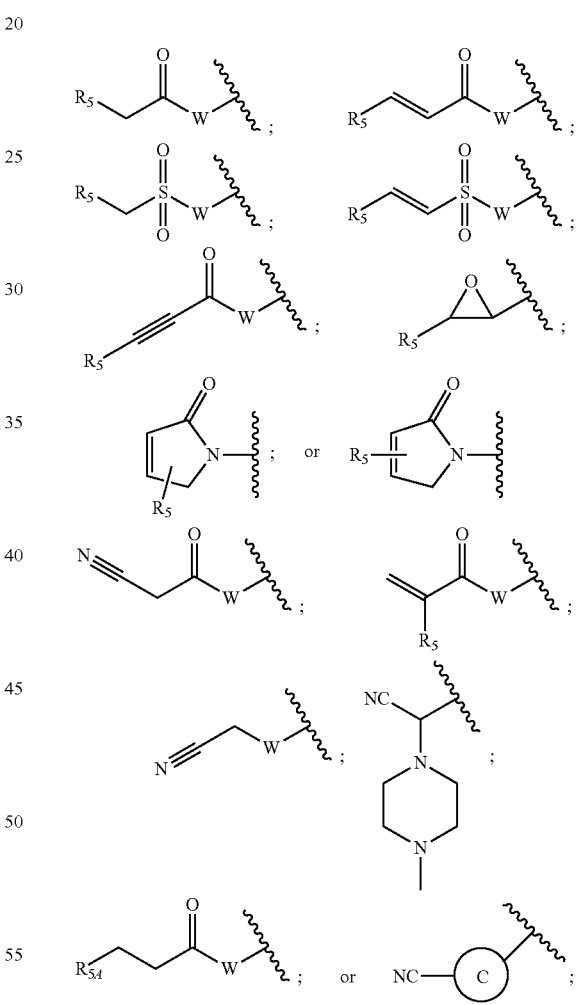

each $R_3$ and $R_4$ is independently H, alkyl, alkenyl, vinyl, heterocyclic, or carbocyclic, each of which may be optionally substituted;

each $R_5$ is independently H, alkyl, hal, or haloalkyl, each of which may be optionally substituted;

each $R_{5A}$ is independently hal or $OS(O)_pR'$, wherein p is 0, 1 or 2 and R' is alkyl or aryl;

each W is independently absent, $CH_2$, $CH_2CH_2$, $(CH_2)_3$, $(CH_2)_4$, O, S, or $NR_3$;

ring C is a 5-6 membered heterocyclic or heteroaryl having 1, 2, or 3 nitrogens;

m is 1, 2, or 3; and n is 0, 1 or 2.

In various embodiments, $Z_1$ and $Z_2$ are N and $Z_3$ and $Z_4$ are C.

In a further embodiment, $R_A$ is H, Cl, Br, or $CF_3$, and $R_B$ is H.

In another further embodiment, X is NH.

In another embodiment, Y is O, S, NH, or NMe.

In certain embodiments, ring A and ring B are each independently phenyl or pyridyl.

In a first embodiment, the invention provides a compound formula II-a:

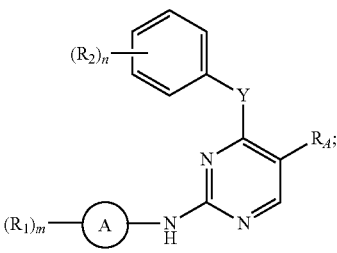

(II-a)

or a pharmaceutically acceptable salt, ester or prodrug thereof, wherein,

Y is absent, CO, O, S, or $NR_6$;

$R_6$ is H or alkyl;

ring A is phenyl or pyridyl;

$R_A$ is H, Cl, Br, or $CF_3$;

each $R_1$ is independently $NH(R_3)$, $N(R_3)CO(R_4)$, $C(O)R_3$, $C(O)NH(R_3)$, $SO_2R_3$, alkyl, haloalkyl, alkoxy, heteroaryl, carbocyclic, or, heterocyclic, each of which may be optionally substituted;

each $R_2$ is independently alkyl, hal,

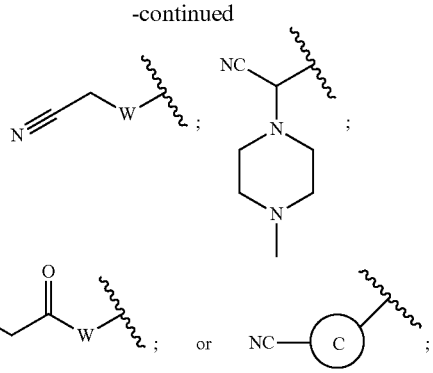

each $R_3$ and $R_4$ is independently H, alkyl, alkenyl, vinyl, heterocyclic, or carbocyclic, each of which may be optionally substituted;

$R_5$, for each instance, is independently H, alkyl, hal, or haloalkyl, each of which may be optionally substituted;

$R_{5A}$, for each instance, is independently hal or $OS(O)_pR'$, wherein p is 0, 1 or 2 and R' is alkyl or aryl;

W, for each instance, is independently absent, $CH_2$, $CH_2CH_2$, $(CH_2)_3$, $(CH_2)_4$, O, S, or $NR_3$;

ring C is a 5-6 membered heterocyclic or heteroaryl having 1, 2, or 3 nitrogens;

m is 1, 2, or 3; and n is 1 or 2.

In one embodiment, each $R_1$ is independently $N(R_3)CO(R_4)$, $C(O)R_3$, $C(O)NH(R_3)$, alkyl, haloalkyl, alkoxy, heteroaryl, carbocyclic, or heterocyclic, each of which may be optionally substituted; and m is 1 or 2.

In another embodiment, each $R_1$ is independently $N(R_3)CO(R_4)$, $C(O)R_3$, $C(O)NH(R_3)$, methyl, trifluoromethyl, fluoromethyl, methoxy, ethoxy, cyclohexyl, pyridinyl, pyrrolidinyl, morpholinyl, piperidinyl, piperazinyl, or imidazolyl, each of which may be optionally substituted.

In another embodiment, each $R_1$ is independently methyl, fluoromethyl, methoxy,

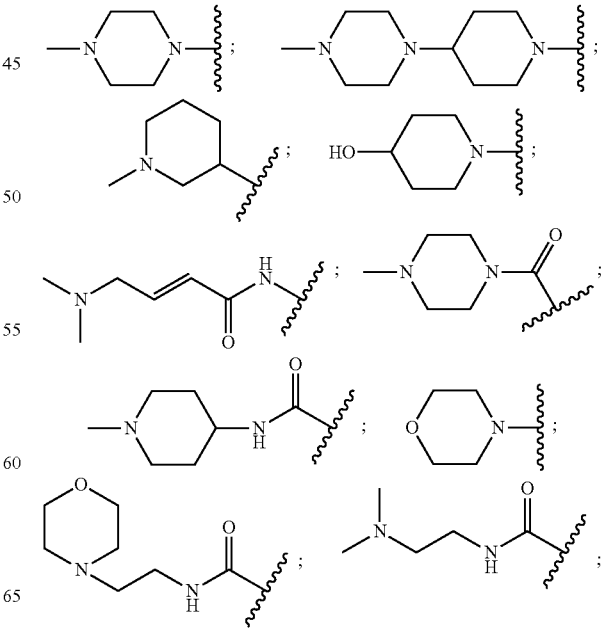

-continued

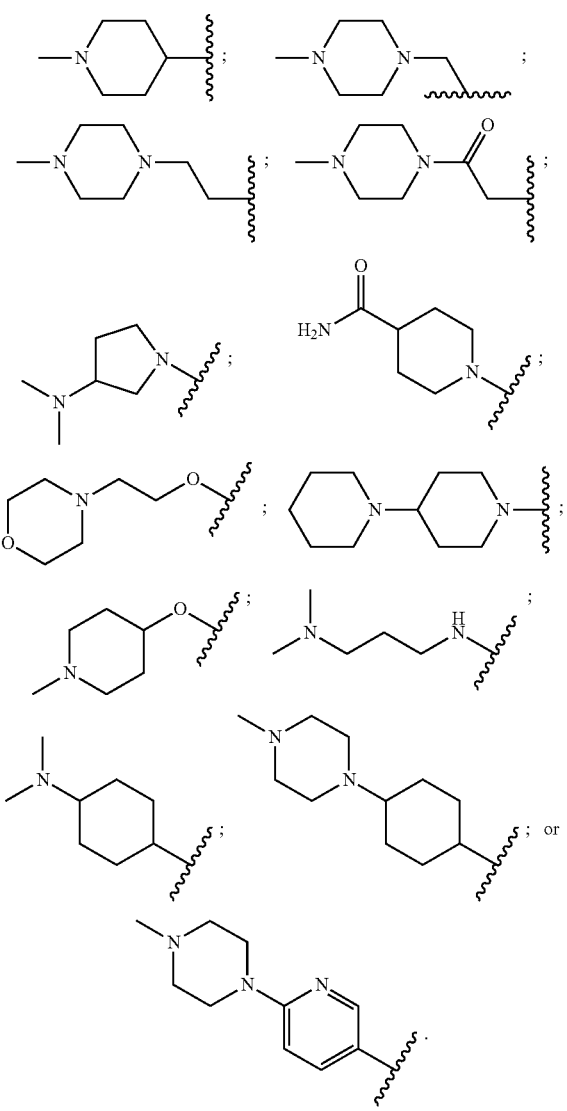

In certain embodiments, each $R_2$ is independently methyl, F, Cl,

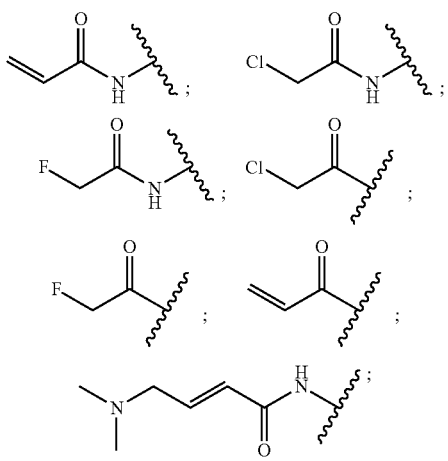

-continued

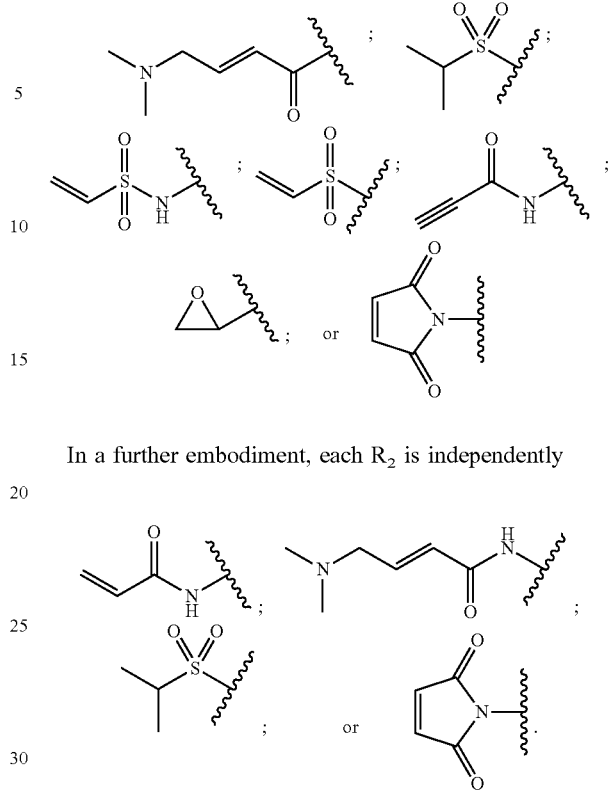

In a further embodiment, each $R_2$ is independently

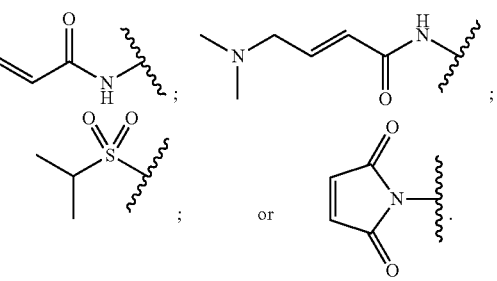

In a second embodiment, the invention provides a compound of formula II-b:

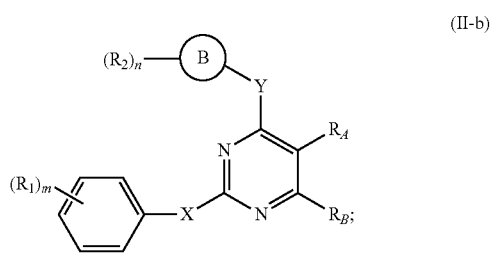

or a pharmaceutically acceptable salt, ester or prodrug thereof,
wherein,
X is O, S, or $NR_6$;
Y is absent, O, S, or $NR_6$;
each $R_6$ is independently H or alkyl;
ring B is heterocyclic;
$R_A$ is H, Cl, Br, or $CF_3$;
$R_B$ is H, hal, OH, $NH_2$, $NHR_3$, haloalkyl, CN, $N_3$, or $NO_2$;
each $R_1$ is independently $NH(R_3)$, $N(R_3)CO(R_4)$, $C(O)R_3$, $C(O)NH(R_3)$, $SO_2R_3$, alkyl, haloalkyl, alkoxy, or heterocyclic, each of which may be optionally substituted;
each $R_2$ is independently hal,

-continued

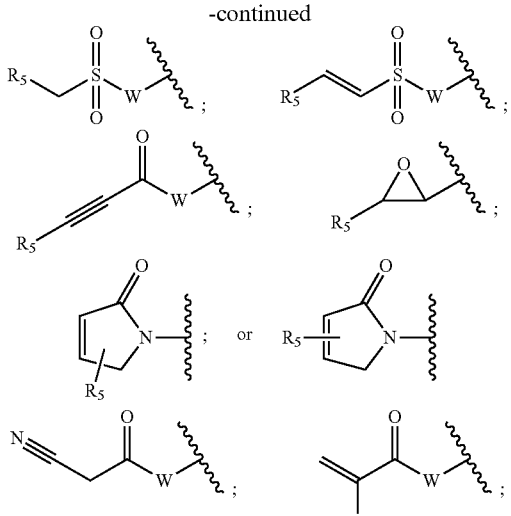

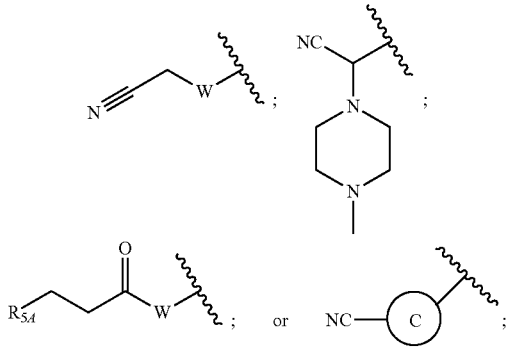

each $R_3$ and $R_4$ is independently H, alkyl, alkenyl, vinyl, heterocyclic, or carbocyclic, each of which may be optionally substituted;
each $R_5$ is independently H, alkyl, hal, or haloalkyl, each of which may be optionally substituted;
each $R_{5A}$ is independently hal or $OS(O)_pR'$, wherein p is 0, 1 or 2 and R' is alkyl or aryl;
each W is independently absent, $CH_2$, $CH_2CH_2$, $(CH_2)_3$, $(CH_2)_4$, O, S, or $NR_3$;
ring C is a 5-6 membered heterocyclic or heteroaryl having 1, 2, or 3 nitrogens;
m is 1, 2, or 3; and
n is 1 or 2.
In one embodiment, ring B is indolinyl, pyrrolidinyl, morpholinyl, piperidinyl, piperazinyl, or imidazolyl.
In another embodiment, each $R_1$ is independently $N(R_3)(R_4)$, $N(R_3)CO(R_4)$, $C(O)R_3$, $C(O)NH(R_3)$, alky, haloalky, alkoxy, or heterocyclic; and each $R_3$ and $R_4$ is independently H or alkyl, each of which may be optionally substituted.
In other embodiments, each $R_1$ is independently methyl, fluoromethyl, methoxy,

-continued

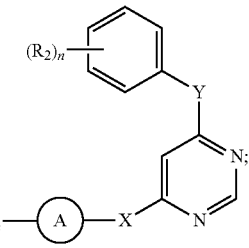

In certain embodiments, $R_2$ is independently

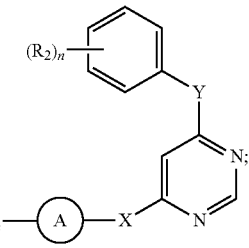

In a third embodiment, the invention provides a compound of formula II-c:

(II-c)

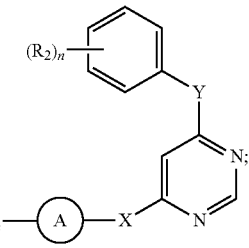

or a pharmaceutically acceptable salt, ester or prodrug thereof,
wherein,
ring A is aryl or heteroaryl;
X is O, S, or $NR_6$;
Y is absent, O, S, or $NR_6$;
each $R_6$ is independently H or alkyl;
each $R_1$ is independently $NH(R_3)$, $N(R_3)CO(R_4)$, $C(O)R_3$, $C(O)NH(R_3)$, $SO_2R_3$, alkyl, haloalkyl, alkoxy, or heterocyclic, each of which may be optionally substituted;
each $R_2$ is independently

-continued

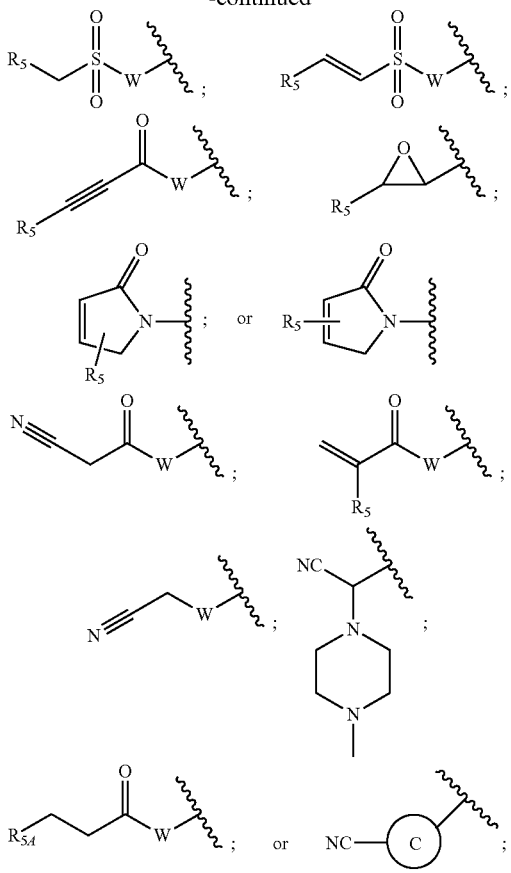

each R₃ and R₄ is independently H, alkyl, alkenyl, vinyl, heterocyclic, or carbocyclic, each of which may be further substituted;
each R₅ is independently H, alkyl, hal, or haloalkyl, each of which may be optionally substituted;
each $R_{5A}$ is independently hal or $OS(O)_pR'$, wherein p is 0, 1 or 2 and R' is alkyl or aryl;
each W is independently absent, $CH_2$, $CH_2CH_2$, $(CH_2)_3$, $(CH_2)_4$, O, S, or $NR_3$;
ring C is a 5-6 membered heterocyclic or heteroaryl having 1, 2, or 3 nitrogens;
m is 1, 2, or 3; and
n is 1 or 2.
In certain embodiments, each R₁ is independently methyl, fluoromethyl, methoxy,

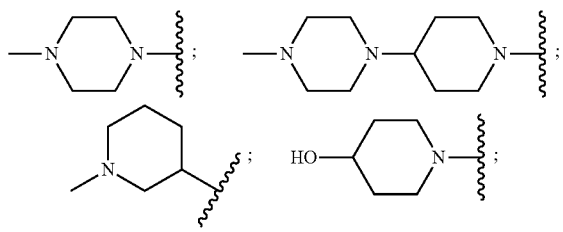

-continued

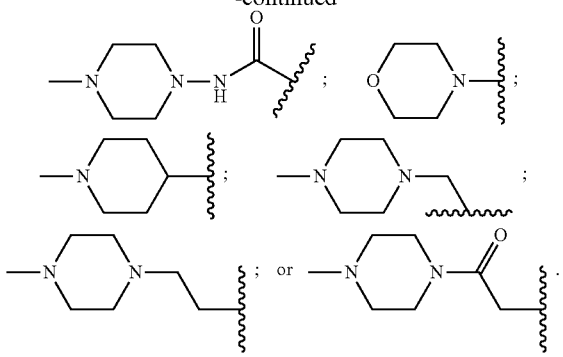

In various embodiments, each R₂ is independently

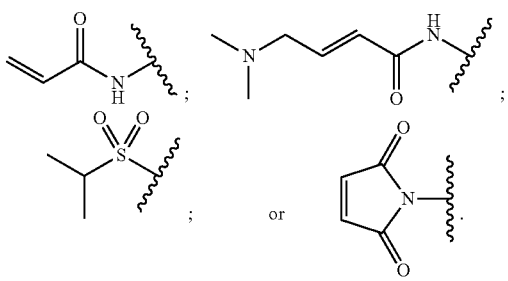

In a fourth embodiment, the invention provides a compound of formula III:

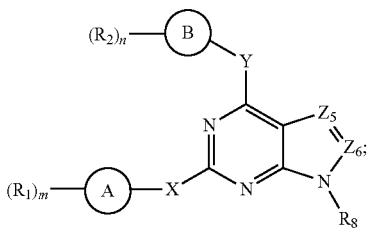

(III)

or a pharmaceutically acceptable salt, ester or prodrug thereof,
wherein,
Z₅ is N or CH;
Z₆ is N or CH, wherein one of Z₅ or Z₆ is N;
X is O, S, or NR₆;
Y is absent, O, S, or NR₆;
each R₆ is independently H or alkyl;
ring A is aryl, heteroaryl, carbocyclic, or heterocyclic;
ring B is aryl, heteroaryl, carbocyclic, or heterocyclic;
each R₁ is independently N(R₃)(R₄), N(R₃)CO(R₄), C(O)R₃, alkyl, alkoxy, or heterocyclic, each of which may be optionally substituted;
each R₂ is independently

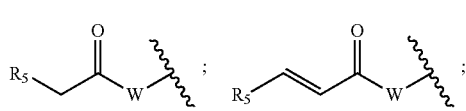

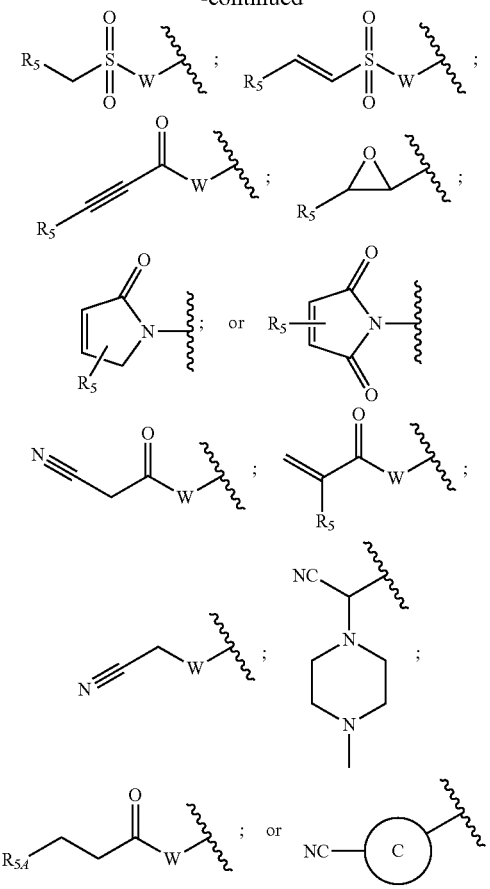

each R₃ and R₄ is independently H, alkyl, alkenyl, vinyl, heterocyclic, or carbocyclic, each of which may be optionally substituted;

each R₅ is independently H, alkyl, hal, or haloalkyl, each of which may be optionally substituted;

each $R_{5A}$ is independently hal or $OS(O)_pR'$, wherein p is 0, 1 or 2 and R' is alkyl or aryl;

each W is independently absent, $CH_2$, $CH_2CH_2$, $(CH_2)_3$, $(CH_2)_4$, O, S, or $NR_3$; ring C is a 5-6 membered heterocyclic or heteroaryl having 1, 2, or 3 nitrogens;

$R_8$ is H, alky, or aryl, each of which may be optionally substituted;

m is 1, 2, or 3; and n is 1 or 2.

In certain embodiments, $Z_5$ is N and $Z_6$ is CH.

In a further embodiment, X is $NR_6$; and Y is O, $NR_6$, or absent.

In other embodiments, ring A is aryl, carbocyclic or heterocyclic. In a further embodiment, ring A is phenyl, naphthyl, piperidinyl, cyclopropyl, cyclobutyl, cyclopentyl, cyclohexyl, or cycloheptyl, each of which may be optionally substituted.

In another embodiment, ring B is aryl or heterocyclic. In a further embodiment, ring B is phenyl, naphthyl, piperidinyl, pyrrolidinyl, morpholinyl, piperazinyl, or imidazolyl, each of which may be optionally r substituted.

In other embodiments, each $R_1$ is independently methyl, methoxy,

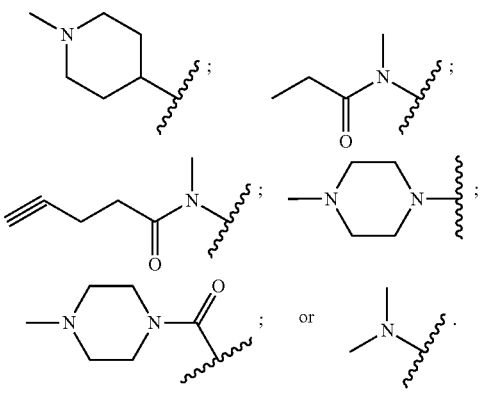

In still other embodiments, each $R_2$ is independently

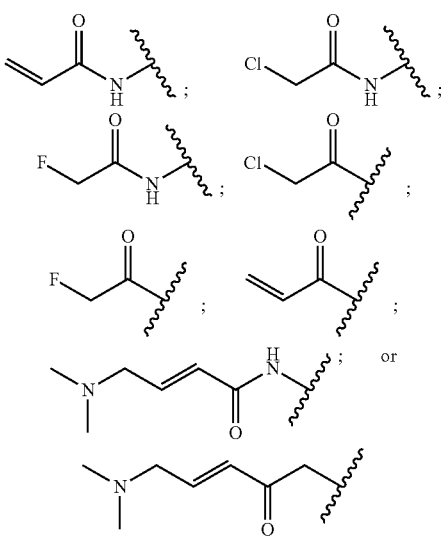

In yet other embodiments, $R_8$ is H, methyl, isopropyl, or phenyl, each of which may be optionally substituted.

In certain embodiments, $Z_5$ is CH and $Z_6$ is N.

In another embodiment, X is $NR_5$; and Y is O, S, $NR_6$, or absent.

In other embodiments, ring A is aryl or heterocyclic. In a further embodiment, ring A is phenyl, naphthyl, or piperidinyl, each of which may be optionally substituted.

In still other embodiments, ring B is aryl or heterocyclic. In a further embodiment, ring B is phenyl, naphthyl, piperidinyl, pyrrolidinyl, morpholinyl, piperazinyl, or imidazolyl, each of which may be optionally substituted.

In other embodiments, $R_1$ is $N(R_3)(R_4)$, $N(R_3)CO(R_4)$, $C(O)R_3$, alkyl, alkoxy or heterocyclic, each of which may be optionally substituted.

In a further embodiment, each $R_1$ is independently methyl, methoxy,

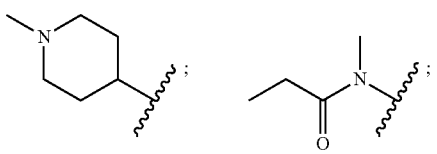

-continued

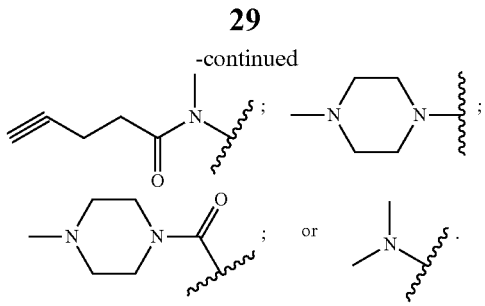

In another embodiment, each $R_2$ is independently hal,

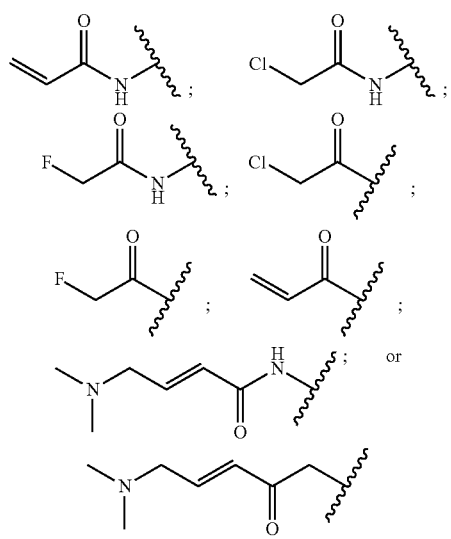

In various embodiments, $R_8$ is H, methyl, isopropyl, or phenyl, each of which may be optionally substituted.

In a fifth embodiment, the invention provides a compound of formula IV:

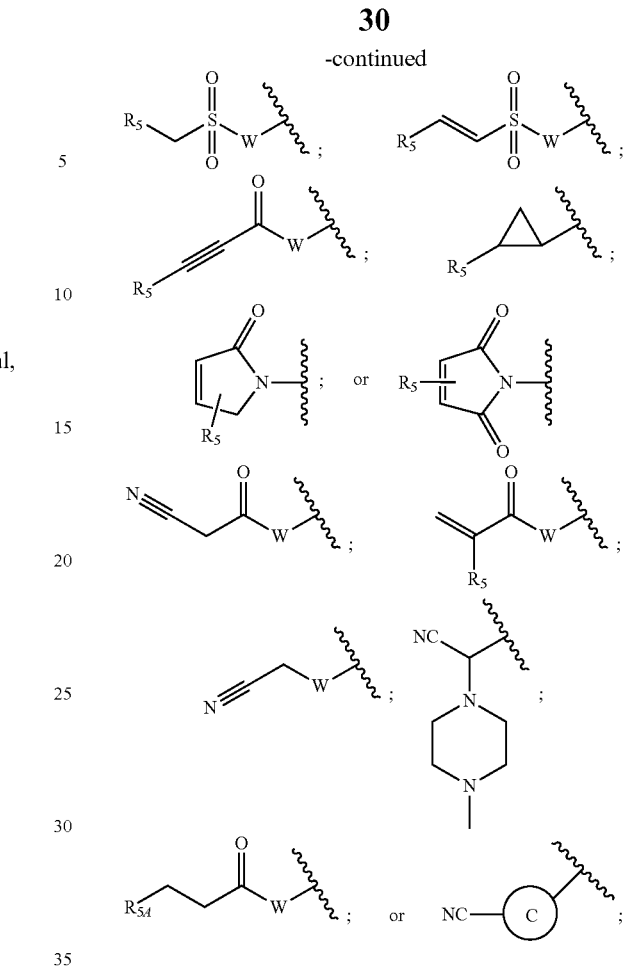

(IV)

or a pharmaceutically acceptable salt, ester or prodrug thereof,
wherein,
Y is O, S, or $NR_6$;
each $R_6$ is independently H or alkyl;
ring B is aryl, heteroaryl, carbocyclic, or heterocyclic;
ring D is aryl, heteroaryl, carbocyclic, or heterocyclic;
each $R_2$ is independently

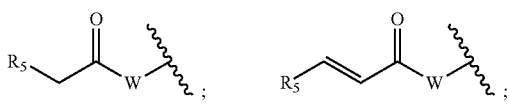

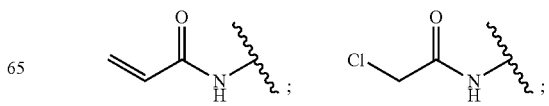

each $R_7$ is independently $NH(R_3)$, $N(R_3)(R_4)$, $N(R_3)CO(R_4)$, $CO_2H$, $C(O)R_3$, $C(O)OR_3$, $C(O)NH_2$, $C(O)NH(R_3)$, $C(O)N(R_3)(R_4)$, $SO_2R_3$, $SOR_3$, $SR_3$, alkyl, aryl, arylalkyl, alkoxy, heteroaryl, heterocyclic, and carbocyclic, each of which may be optionally substituted;

each $R_3$ and $R_4$ is independently H, alkyl, alkenyl, vinyl, heterocyclic, or carbocyclic, each of which may be further substituted;

each $R_5$ is independently H, alkyl, hal, or haloalkyl, each of which may be further substituted;

each $R_{5A}$ is independently hal or $OS(O)_pR'$, wherein p is 0, 1 or 2 and R' is alkyl or aryl;

each W is independently absent, $CH_2$, $CH_2CH_2$, $(CH_2)_3$, $(CH_2)_4$, O, S, or $NR_3$;

ring C is a 5-6 membered heterocyclic or heteroaryl having 1, 2, or 3 nitrogens;

n is 1 or 2; and
q is 0, 1 or 2.

In certain embodiments, Y is O.

In another embodiment, ring B is aryl. In a further embodiment, ring B is phenyl or naphthyl, each of which may be optionally substituted.

In other embodiments, ring D is aryl or heteroaryl. In a further embodiment, ring D is phenyl, naphthyl, pyridinyl, or quinolynyl, each of which may be optionally substituted.

In certain embodiments, each $R_2$ is independently

-continued

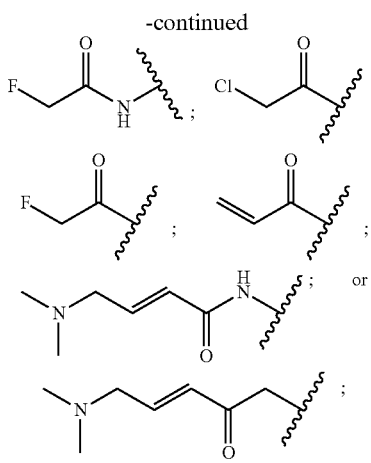

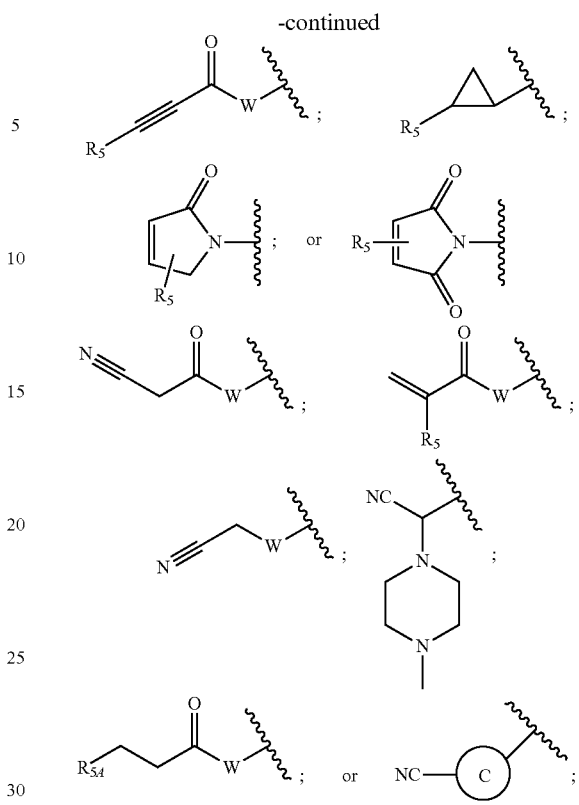

preferably

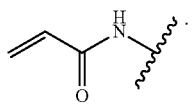

In other embodiments, $R_2$ is alkyl or alkoxy.

In a sixth embodiment, the invention provides a compound of formula V:

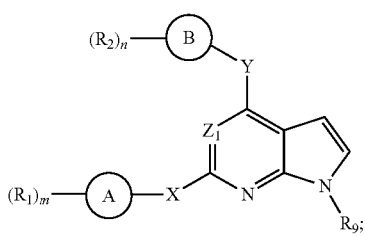

(V)

or a pharmaceutically acceptable salt, ester or prodrug thereof,
wherein,
$Z_1$ is N or $CR_6$;
X is O, S, or $NR_6$;
Y is O, S, or $NR_6$;
each $R_6$ is independently H or alkyl which may be optionally substituted;
ring A is aryl, heteroaryl, carbocyclic, or heterocyclic;
ring B is aryl, heteroaryl, carbocyclic, or heterocyclic;
each $R_1$ is independently $N(R_3)(R_4)$, $N(R_3)CO(R_4)$, $C(O)R_3$, alkyl, alkoxy, or heterocyclic, each of which may be optionally substituted;
each $R_2$ is independently hal,

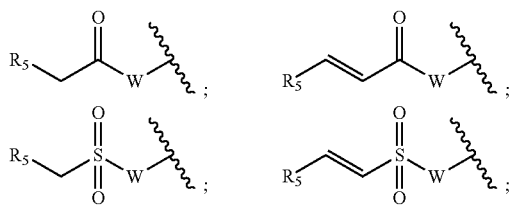

each $R_3$ and $R_4$ is independently H, alkyl, alkenyl, vinyl, heterocyclic, or carbocyclic, each of which may be optionally substituted;
each $R_5$ is independently H, alkyl, hal, or haloalkyl, each of which may be further substituted;
each $R_{5A}$ is independently hal or $OS(O)_pR'$, wherein p is 0, 1 or 2 and R' is alkyl or aryl;
each W is independently absent, $CH_2$, $CH_2CH_2$, $(CH_2)_3$, $(CH_2)_4$, O, S, or $NR_3$;
ring C is a 5-6 membered heterocyclic or heteroaryl having 1, 2, or 3 nitrogens;
$R_9$ is H or aryl which may be optionally substituted;
m is 1, 2, or 3; and
n is 1 or 2;
wherein one of

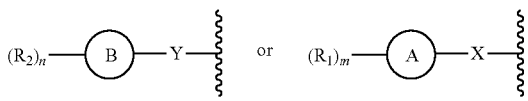

may be absent.

In certain embodiments, ring A is aryl or carbocyclic. In a further embodiment, ring A is phenyl, naphthyl, cyclopropyl, cyclobutyl, cyclopentyl, cyclohexyl, or cycloheptyl, each of which may be optionally substituted.

In another embodiment, ring B is aryl or heterocyclic. In a further embodiment, ring B is phenyl, naphthyl, piperidinyl, pyrrolidinyl, morpholinyl, piperazinyl, or imidazolyl, each of which may be optionally substituted.

In other embodiments, each $R_1$ is independently $N(R_3)(R_4)$, $N(R_3)CO(R_4)$, $C(O)R_3$, alkyl, alkoxy, or heterocyclic, each of which may be optionally substituted. In a further embodiment, each $R_1$ is independently methyl, methoxy,

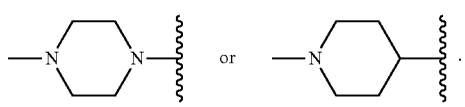

In certain embodiments, each $R_2$ is independently

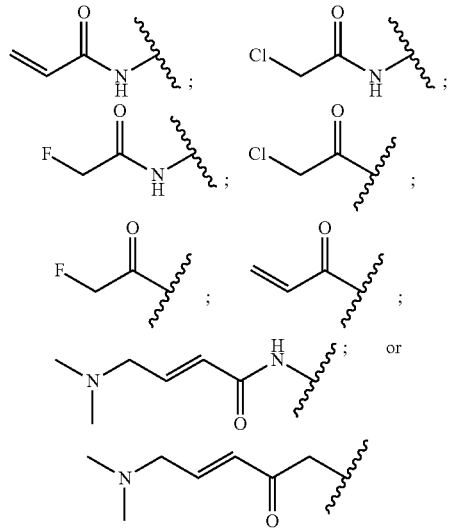

In a seventh embodiment, the invention provides a compound of formula VI:

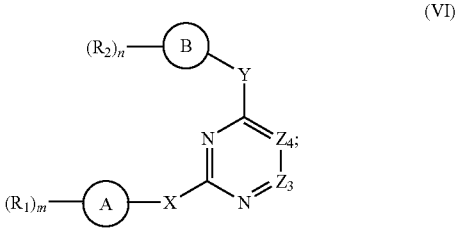

(VI)

or a pharmaceutically acceptable salt, ester or prodrug thereof, wherein, $Z_3$ is N or $CR_B$;

$Z_4$ is N or $CR_A$; wherein one of $Z_3$ or $Z_4$ is N;

X is O, S, or $NR_6$;

Y is O, S, or $NR_6$;

each $R_6$ is independently H or alkyl;

$R_A$ is H, Cl, Br, or $CF_3$;

$R_B$ is H, hal, OH, $NH_2$, $NHR_3$, haloalkyl, CN, $N_3$, or $NO_2$;

ring A is aryl, heteroaryl, carbocyclic, or heterocyclic;

ring B is aryl, heteroaryl, carbocyclic, or heterocyclic;

each $R_1$ is independently $NH(R_3)$, $N(R_3)(R_4)$, $N(R_3)CO(R_4)$, $CO_2H$, $C(O)R_3$, $C(O)OR_3$, $C(O)NH_2$, $C(O)NH(R_3)$, $C(O)N(R_3)(R_4)$, $SO_2R_3$, $SOR_3$, $SR_3$, alkyl, aryl, arylalkyl, alkoxy, heteroaryl, heterocyclic, and carbocyclic, each of which may be optionally substituted;

each $R_2$ is independently hal,

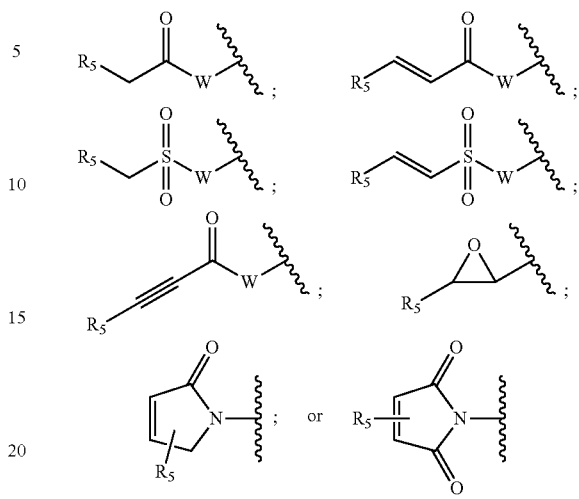

each $R_3$ and $R_4$ is independently H, alkyl, alkenyl, vinyl, heterocyclic, or carbocyclic, each of which may be further substituted;

each $R_5$ is independently H, alkyl, hal, or haloalkyl, each of which may be optionally substituted;

each $R_{5A}$ is independently hal or $OS(O)_pR'$, wherein p is 0, 1 or 2 and R' is alkyl or aryl;

each W is independently absent, $CH_2$, $CH_2CH_2$, $(CH_2)_3$, $(CH_2)_4$, O, S, or $NR_3$;

ring C is a 5-6 membered heterocyclic or heteroaryl having 1, 2, or 3 nitrogens;

m is 1, 2, or 3; and n is 1 or 2.

In certain embodiments, X is O or $NR_6$; and Y is O or $NR_6$.

In various embodiments, ring A is aryl or heterocyclic. In a further embodiment, ring A is phenyl, naphthyl, piperidinyl, pyrrolidinyl, morpholinyl, piperazinyl, or imidazolyl, each of which may be further substituted, each of which may be further substituted.

In other embodiments, ring B is aryl or heterocyclic. In a further embodiment, ring B is phenyl, naphthyl, piperidinyl, pyrrolidinyl, morpholinyl, piperazinyl, or imidazolyl, each of which may be further substituted.

In other embodiments, each $R_1$ is independently $N(R_3)(R_4)$, $N(R_3)CO(R_4)$, $C(O)R_3$, alkyl, alkoxy, or heterocyclic, each of which may be further substituted. In a further embodiment, each $R_1$ is independently methyl, methoxy,

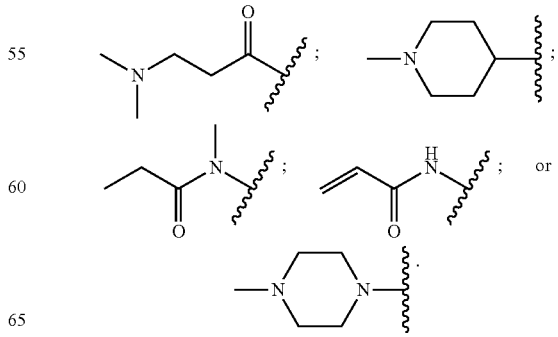

In various embodiments, each $R_2$ is independently hal,

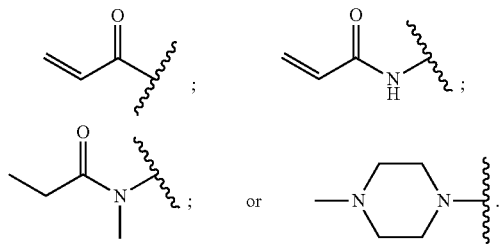

In certain embodiments, $R_B$ is H, hal, OH, $NH_2$, $NHR_3$, or haloalkyl.

In still other embodiments, $R_A$ is H or Cl.

In an eighth embodiment, the invention provides a compound of formula VII:

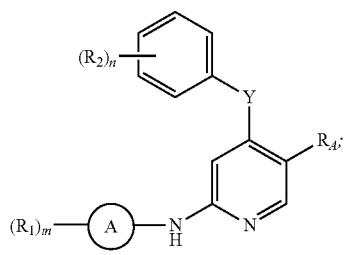

(VII)

or a pharmaceutically acceptable salt, ester or prodrug thereof, wherein,

Y is O or $NR_6$;

$R_6$ is H or alkyl;

ring A is phenyl or pyridyl;

$R_A$ is H, Cl, Br, or $CF_3$;

each $R_1$ is independently $N(R_3)CO(R_4)$, $C(O)NH(R_3)$, alkyl, haloalkyl, alkoxy, heteroaryl, carbocyclic, or heterocyclic, each of which may be optionally substituted;

each $R_2$ is independently alkyl, hal,

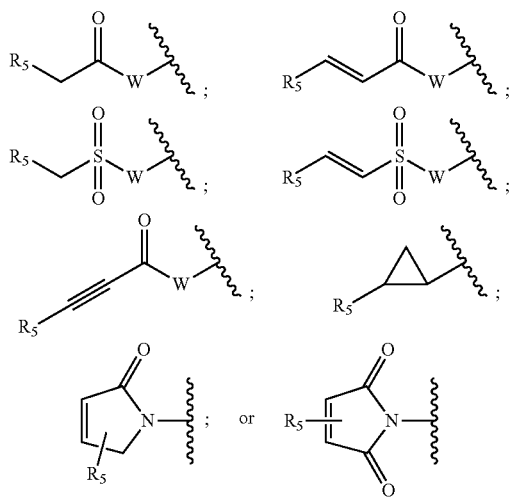

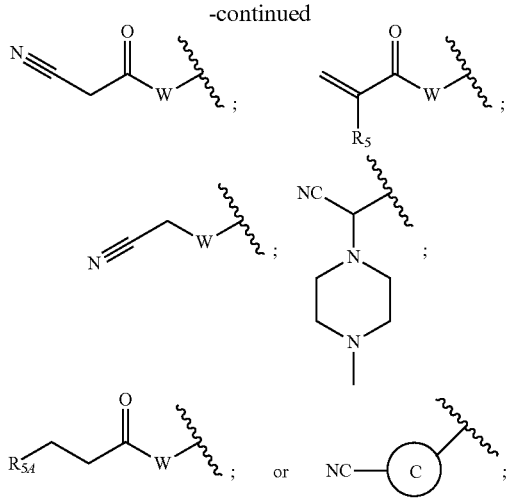

each $R_3$ and $R_4$ is independently H, alkyl, alkenyl, vinyl, heterocyclic, or carbocyclic, each of which may be optionally substituted;

$R_5$, for each instance, is independently H, alkyl, hal, or haloalkyl, each of which may be optionally substituted;

$R_{5A}$, for each instance, is independently hal or $OS(O)_pR'$, wherein p is 0, 1 or 2 and R' is alkyl or aryl;

W, for each instance, is independently absent, $CH_2$, $CH_2CH_2$, $(CH_2)_3$, $(CH_2)_4$, O, S, or $NR_3$;

ring C is a 5-6 membered heterocyclic or heteroaryl having 1, 2, or 3 nitrogens;

m is 1, 2, or 3; and n is 1 or 2.

In certain embodiments, each $R_1$ is independently methyl, trifluoromethyl, fluoromethyl, methoxy, ethoxy, cyclohexyl, pyridinyl, pyrrolidinyl, morpholinyl, piperidinyl, piperazinyl, or imidazolyl, each of which may be optionally substituted.

In various embodiments, each $R_1$ is independently methyl, fluoromethyl, methoxy,

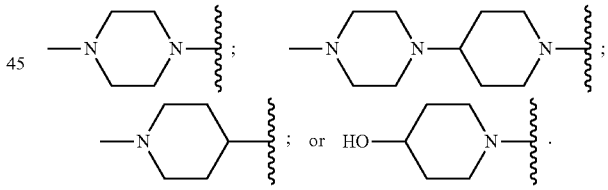

In other embodiments, each $R_2$ is independently

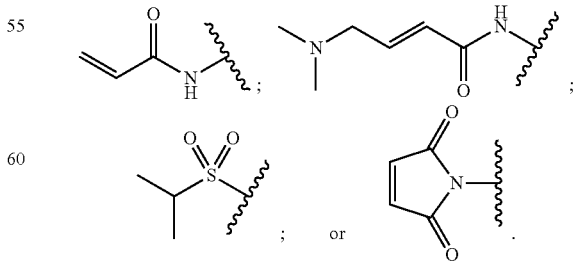

In another aspect, the invention provides a compound that covalently modifies Cysteine 797 in EGFR, wherein the compound exhibits greater inhibition of L858R/T790M or Del/T790M EGFR relative to wild-type EGFR. In certain embodiments, the current invention is directed towards a compound that exhibits at least 2-fold, 3-fold, 5-fold, 10-fold, 25-fold, 50-fold or 100-fold greater inhibition of L858R/T790M or Del/T790M EGFR relative to wild-type EGFR. In certain embodiments, the current invention is directed towards a compound that exhibits at least 100-fold greater inhibition of L858R/T790M or Del/T790M EGFR relative to wild-type EGFR.

In certain embodiments, the compound is a compound of formula I.

In certain embodiments, the invention provides a compound selected from Table 1, Table 2, Table 3, Table 4 Table 5 or Table 6. Representative compounds of the invention include, but are not limited to, the following compounds of Tables 1-6 below.

TABLE 1

| Compound Number | Structure | Physical Data $^1$H NMR 600 MHz and/or MS (m/z) |
|---|---|---|
| 1-1 | 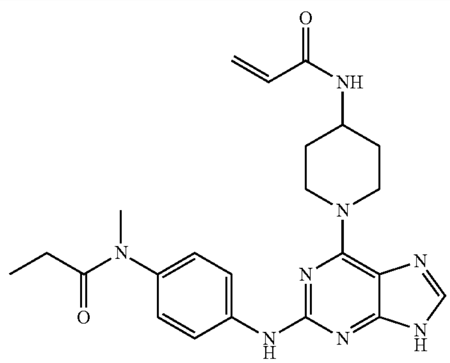 [SMILES: C=CC(=O)NC1CCN(c2nc(Nc3ccc(N(C)C(=O)CC)cc3)nc3[nH]cnc23)CC1] | MS m/z: 449.52 (M + 1). |
| 1-2 | 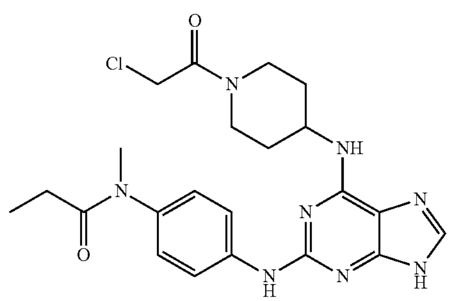 [SMILES: CCC(=O)N(C)c1ccc(Nc2nc(NC3CCN(C(=O)CCl)CC3)c3nc[nH]c3n2)cc1] | MS m/z: 471.96 (M + 1). |
| 1-3 | 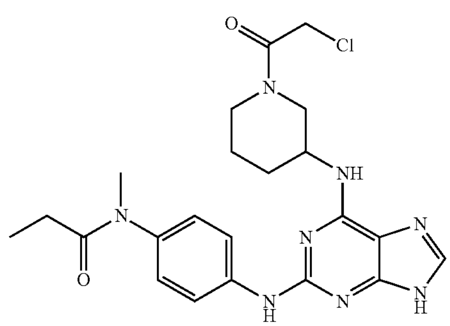 [SMILES: CCC(=O)N(C)c1ccc(Nc2nc(NC3CCCN(C(=O)CCl)C3)c3nc[nH]c3n2)cc1] | MS m/z: 471.96 (M + 1). |
| 1-4 | 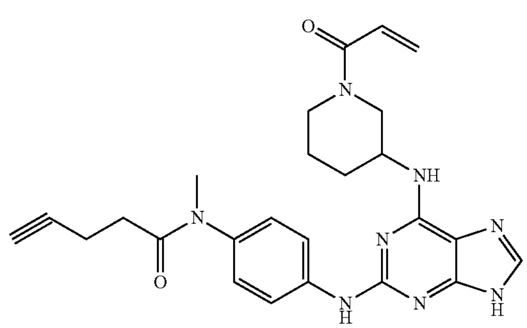 [SMILES: C#CCCC(=O)N(C)c1ccc(Nc2nc(NC3CCCN(C(=O)C=C)C3)c3nc[nH]c3n2)cc1] | MS m/z: 473.54 (M + 1). |

TABLE 1-continued

| Compound Number | Structure | Physical Data<br>¹H NMR 600 MHz and/or MS (m/z) |
|---|---|---|
| 1-5 | 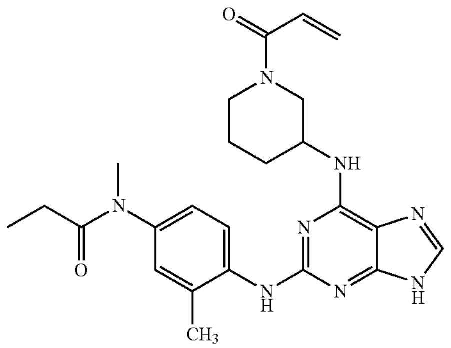 [SMILES: C=CC(=O)N1CCCC(Nc2nc(Nc3ccc(N(C)C(=O)CC)cc3C)nc3[nH]cnc23)C1] | MS m/z: 463.55 (M + 1). |
| 1-6 | 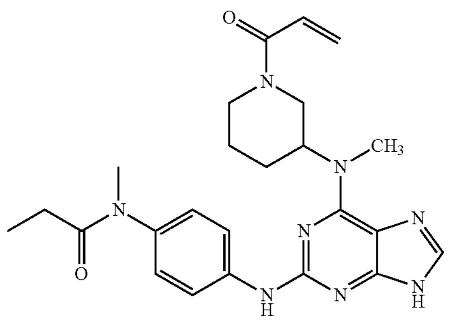 [SMILES: C=CC(=O)N1CCCC(N(C)c2nc(Nc3ccc(N(C)C(=O)CC)cc3)nc3[nH]cnc23)C1] | MS m/z: 463.55 (M + 1). |
| 1-7 | 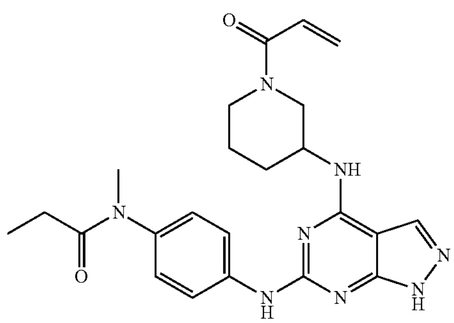 [SMILES: C=CC(=O)N1CCCC(Nc2nc(Nc3ccc(N(C)C(=O)CC)cc3)nc3[nH]ncc23)C1] | MS m/z: 449.52 (M + 1). |
| 1-8 | 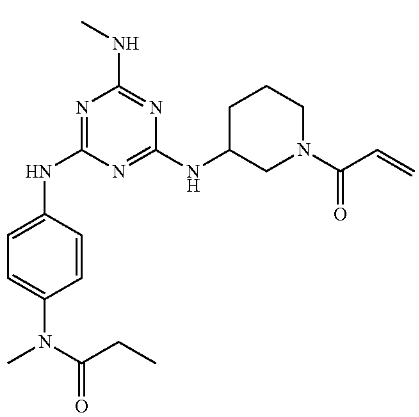 [SMILES: C=CC(=O)N1CCCC(Nc2nc(NC)nc(Nc3ccc(N(C)C(=O)CC)cc3)n2)C1] | MS m/z: 439.53 (M + 1). |

TABLE 1-continued

| Compound Number | Structure | Physical Data<br>¹H NMR 600 MHz and/or MS (m/z) |
|---|---|---|
| 1-9 | 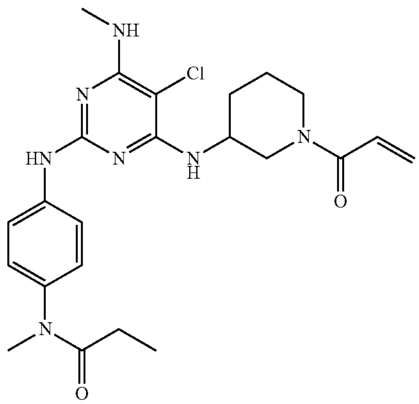 [SMILES: C=CC(=O)N1CCCC(Nc2nc(Nc3ccc(N(C)C(=O)CC)cc3)nc(NC)c2Cl)C1] | MS m/z: 472.98 (M + 1). |
| 1-10 | 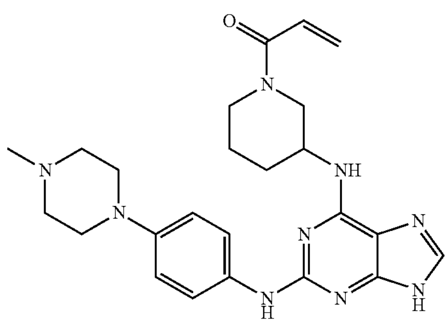 [SMILES: C=CC(=O)N1CCCC(Nc2nc(Nc3ccc(N4CCN(C)CC4)cc3)nc3[nH]cnc23)C1] | MS m/z: 462.56 (M + 1). |
| 1-11 | 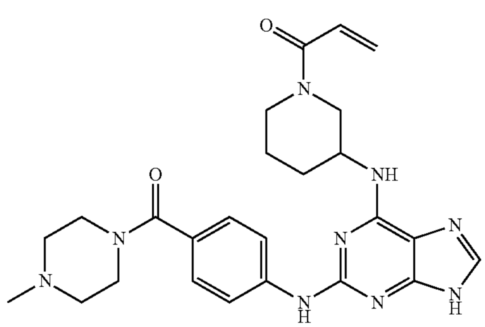 [SMILES: C=CC(=O)N1CCCC(Nc2nc(Nc3ccc(C(=O)N4CCN(C)CC4)cc3)nc3[nH]cnc23)C1] | MS m/z: 490.57 (M + 1). |
| 1-12 | 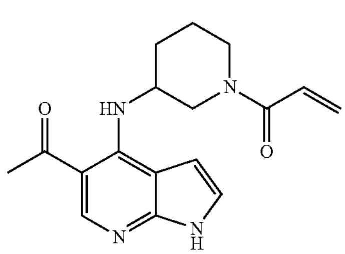 [SMILES: C=CC(=O)N1CCCC(Nc2c(C(C)=O)cnc3[nH]ccc23)C1] | MS m/z: 313.37 (M + 1). |

TABLE 1-continued

| Compound Number | Structure | Physical Data<br>¹H NMR 600 MHz and/or MS (m/z) |
|---|---|---|
| 1-13 | 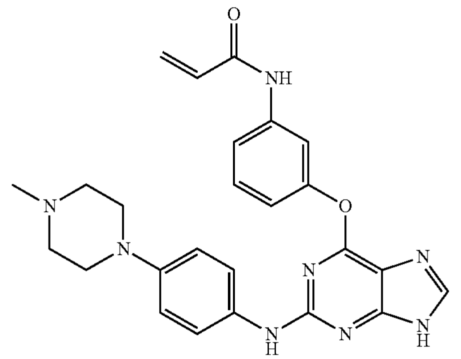 [SMILES: C=CC(=O)Nc1cccc(Oc2nc(Nc3ccc(N4CCN(C)CC4)cc3)nc3[nH]cnc23)c1] | MS m/z: 471.53 (M + 1). |
| 1-14 | 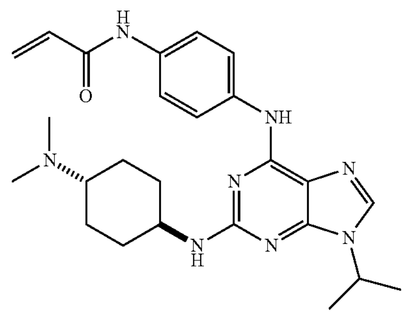 | MS m/z: 463.59 (M + 1). |
| 1-15 | 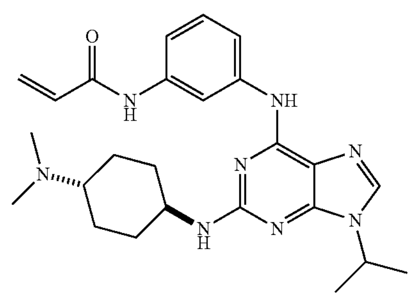 | MS m/z: 463.59 (M + 1). |
| 1-16 | 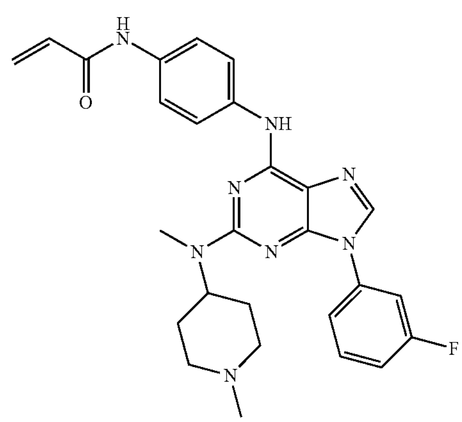 [SMILES: C=CC(=O)Nc1ccc(Nc2nc(N(C)C3CCN(C)CC3)nc3c2ncn3-c2cccc(F)c2)cc1] | MS m/z: 501.57 (M + 1). |

TABLE 1-continued

| Compound Number | Structure | Physical Data $^1$H NMR 600 MHz and/or MS (m/z) |
|---|---|---|
| 1-17 | 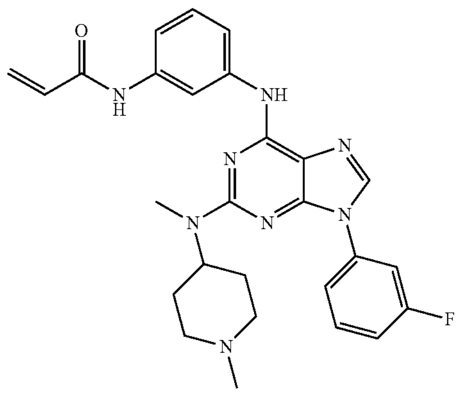 [SMILES: C=CC(=O)Nc1cccc(Nc2nc(N(C)C3CCN(C)CC3)nc3c2ncn3-c2cccc(F)c2)c1] | MS m/z: 501.57 (M + 1). |
| 1-18 | 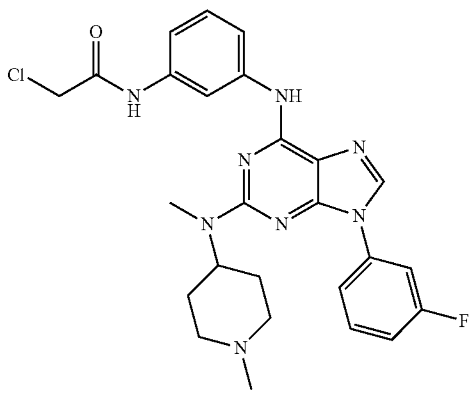 [SMILES: CN1CCC(N(C)c2nc(Nc3cccc(NC(=O)CCl)c3)c3ncn(-c4cccc(F)c4)c3n2)CC1] | MS m/z: 524 (M + 1). |

TABLE 2

| Compound Number | Structure | Physical Data $^1$H NMR 600 MHz and/or MS (m/z) |
|---|---|---|
| 2-1 | 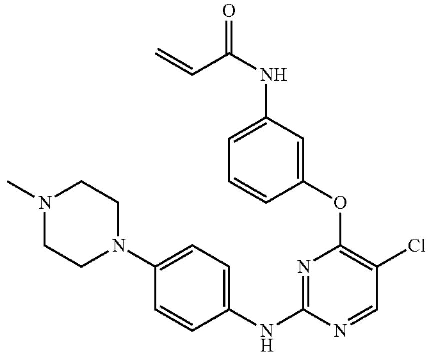 [SMILES: C=CC(=O)Nc1cccc(Oc2nc(Nc3ccc(N4CCN(C)CC4)cc3)ncc2Cl)c1] | MS m/z: 465.95 (M + 1). |

TABLE 2-continued

| Compound Number | Structure | Physical Data<br>¹H NMR 600 MHz and/or MS (m/z) |
|---|---|---|
| 2-2 | (structure) | MS m/z: 495.97 (M + 1). |
| 2-3 | (structure) | MS m/z: 495.97 (M + 1). |
| 2-4 | (structure) | MS m/z: 431.5 (M + 1). |
| 2-5 | (structure) | MS m/z: 430.52 (M + 1). |

TABLE 2-continued

| Compound Number | Structure | Physical Data<br>$^1$H NMR 600 MHz and/or MS (m/z) |
|---|---|---|
| 2-6 | 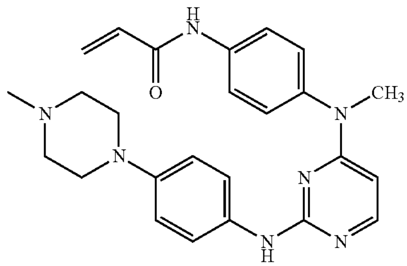 | MS m/z: 444.54 (M + 1). |
| 2-7 | 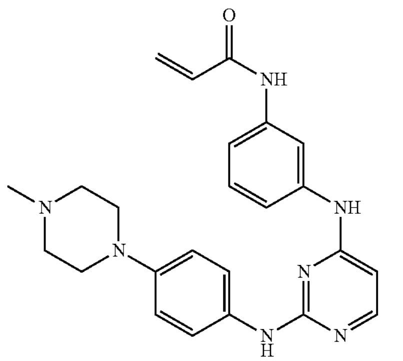 [SMILES: C=CC(=O)Nc1cccc(Nc2ccnc(Nc3ccc(N4CCN(C)CC4)cc3)n2)c1] | MS m/z: 430.52 (M + 1). |
| 2-8 | 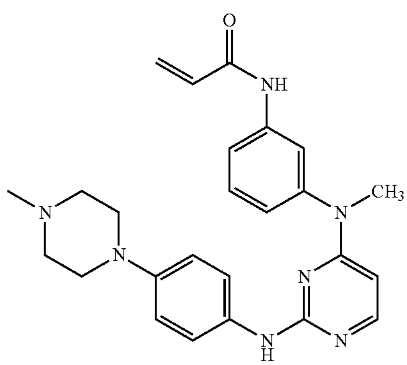 | MS m/z: 444.54 (M + 1). |
| 2-9 | 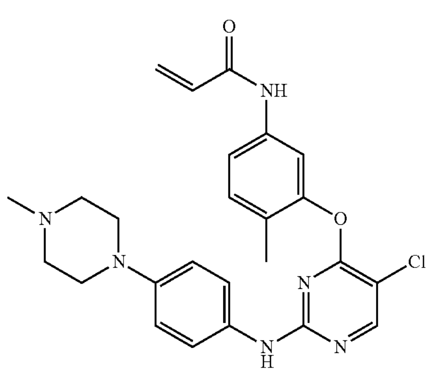 | MS m/z: 479.97 (M + 1). |

TABLE 2-continued

| Compound Number | Structure | Physical Data<br>¹H NMR 600 MHz and/or MS (m/z) |
|---|---|---|
| 2-10 | 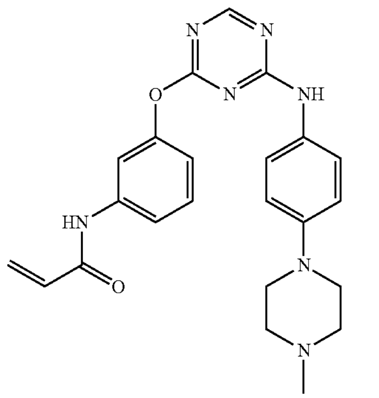 [SMILES: C=CC(=O)Nc1cccc(Oc2ncnc(Nc3ccc(N4CCN(C)CC4)cc3)n2)c1] | MS m/z: 432.49 (M + 1). |
| 2-11 | 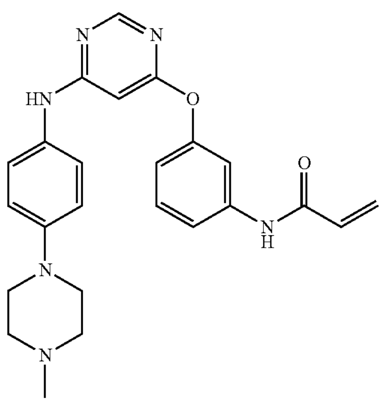 [SMILES: C=CC(=O)Nc1cccc(Oc2cc(Nc3ccc(N4CCN(C)CC4)cc3)ncn2)c1] | MS m/z: 431.50 (M + 1). |
| 2-12 | 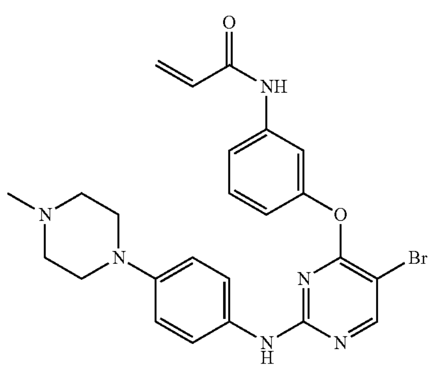 [SMILES: C=CC(=O)Nc1cccc(Oc2nc(Nc3ccc(N4CCN(C)CC4)cc3)ncc2Br)c1] | MS m/z: 510.39 (M + 1). |
| 2-13 | 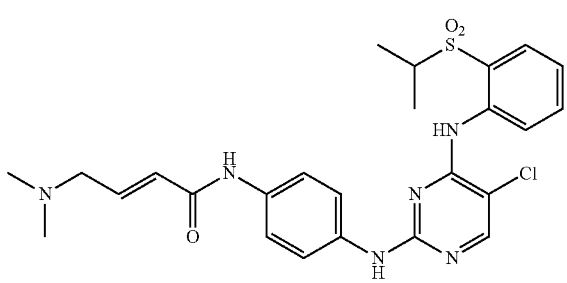 [SMILES: CC(C)S(=O)(=O)c1ccccc1Nc1nc(Nc2ccc(NC(=O)/C=C/CN(C)C)cc2)ncc1Cl] | MS m/z: 530.05 (M + 1). |

TABLE 2-continued

| Compound Number | Structure | Physical Data $^1$H NMR 600 MHz and/or MS (m/z) |
|---|---|---|
| 2-14 | 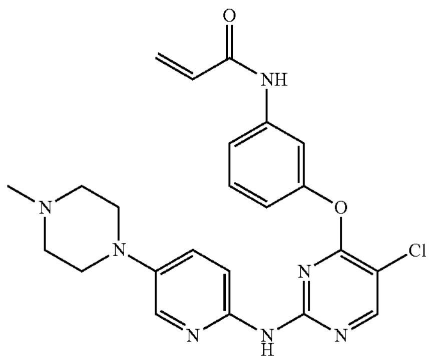 [SMILES: C=CC(=O)Nc1cccc(Oc2nc(Nc3ccc(N4CCN(C)CC4)cn3)ncc2Cl)c1] | MS m/z: 466.93 (M + 1). |
| 2-15 | 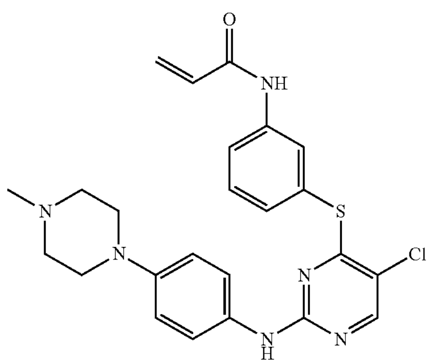 | MS m/z: 482.01 (M + 1). |
| 2-16 | 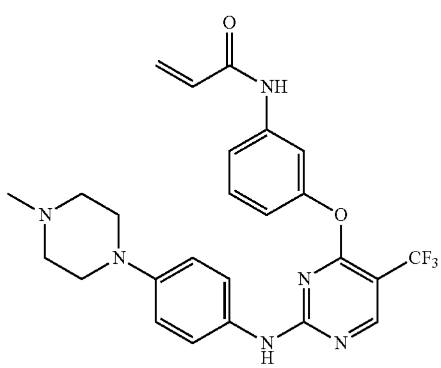 [SMILES: C=CC(=O)Nc1cccc(Oc2nc(Nc3ccc(N4CCN(C)CC4)cc3)ncc2C(F)(F)F)c1] | MS m/z: 499.50 (M + 1). |
| 2-17 | 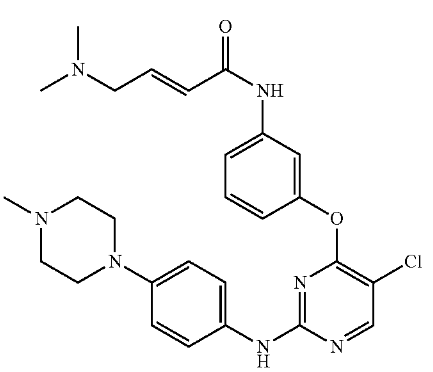 [SMILES: CN(C)C/C=C/C(=O)Nc1cccc(Oc2nc(Nc3ccc(N4CCN(C)CC4)cc3)ncc2Cl)c1] | MS m/z: 523.04 (M + 1). |

TABLE 2-continued

| Compound Number | Structure | Physical Data<br>¹H NMR 600 MHz and/or MS (m/z) |
|---|---|---|
| 2-18 | 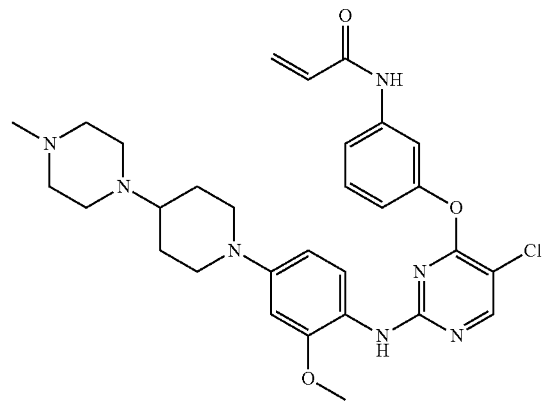 [SMILES: C=CC(=O)Nc1cccc(Oc2nc(Nc3ccc(N4CCC(N5CCN(C)CC5)CC4)cc3OC)ncc2Cl)c1] | MS m/z: 579.10 (M + 1). |
| 2-19 | 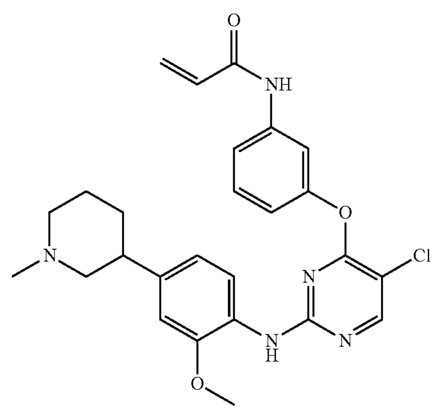 | MS m/z: 494.98 (M + 1). |
| 2-20 | 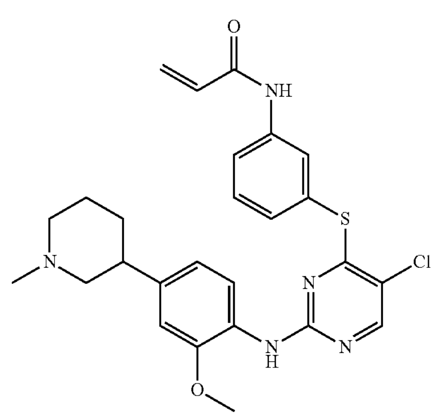 [SMILES: C=CC(=O)Nc1cccc(Sc2nc(Nc3ccc(C4CCCN(C)C4)cc3OC)ncc2Cl)c1] | MS m/z: 511.05 (M + 1). |

TABLE 2-continued

| Compound Number | Structure | Physical Data<br>¹H NMR 600 MHz and/or MS (m/z) |
|---|---|---|
| 2-21 | 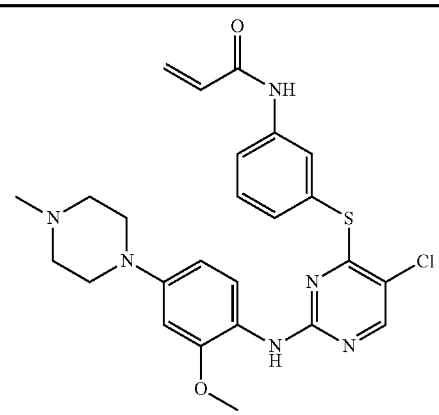 | MS m/z: 512.04 (M + 1). |
| 2-22 | 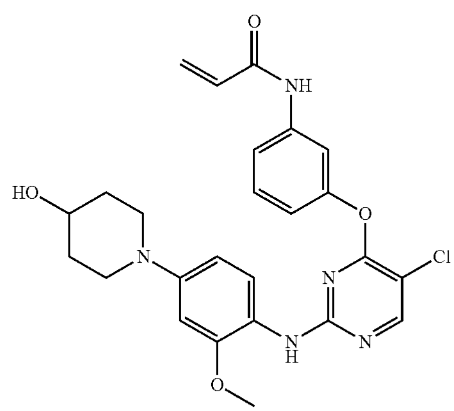 [SMILES: C=CC(=O)Nc1cccc(Oc2nc(Nc3ccc(N4CCC(O)CC4)cc3OC)ncc2Cl)c1] | MS m/z: 496.96 (M + 1). |
| 2-23 | 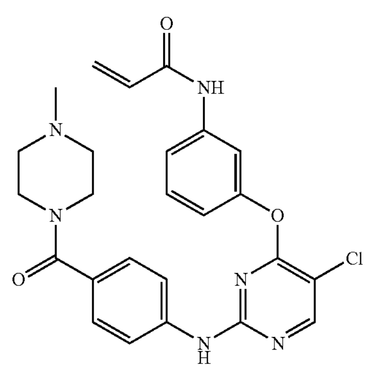 [SMILES: C=CC(=O)Nc1cccc(Oc2nc(Nc3ccc(C(=O)N4CCN(C)CC4)cc3)ncc2Cl)c1] | MS m/z: 493.96 (M + 1). |
| 2-24 | 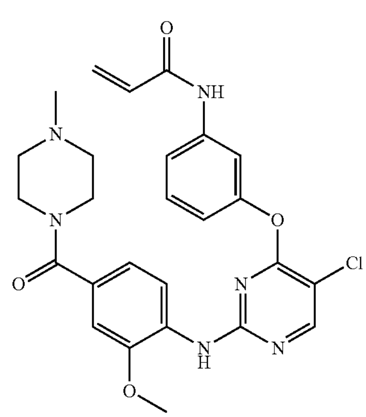 [SMILES: C=CC(=O)Nc1cccc(Oc2nc(Nc3ccc(C(=O)N4CCN(C)CC4)cc3OC)ncc2Cl)c1] | MS m/z: 523.98 (M + 1). |

TABLE 2-continued

| Compound Number | Structure | Physical Data<br>¹H NMR 600 MHz and/or MS (m/z) |
|---|---|---|
| 2-25 | 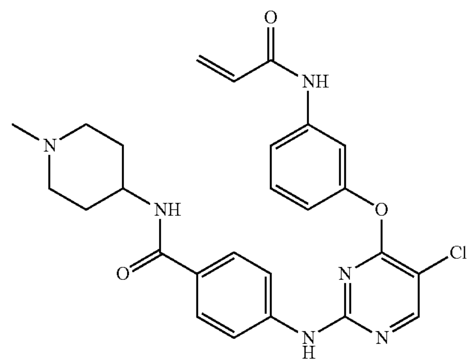 [SMILES: C=CC(=O)Nc1cccc(Oc2nc(Nc3ccc(C(=O)NC4CCN(C)CC4)cc3)ncc2Cl)c1] | MS m/z: 507.98 (M + 1). |
| 2-26 | 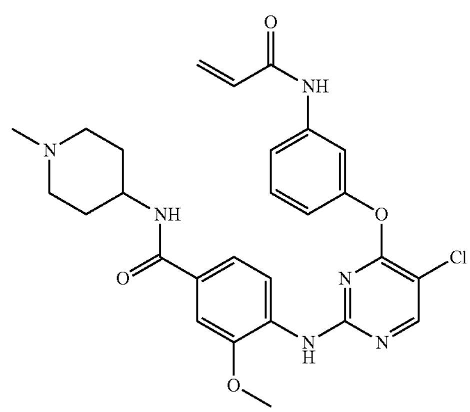 [SMILES: C=CC(=O)Nc1cccc(Oc2nc(Nc3ccc(C(=O)NC4CCN(C)CC4)cc3OC)ncc2Cl)c1] | MS m/z: 538.01 (M + 1). |
| 2-27 | 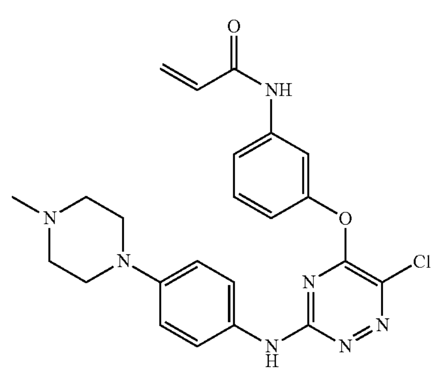 | MS m/z: 466.94 (M + 1). |

TABLE 2-continued

| Compound Number | Structure | Physical Data<br>¹H NMR 600 MHz and/or MS (m/z) |
|---|---|---|
| 2-28 | 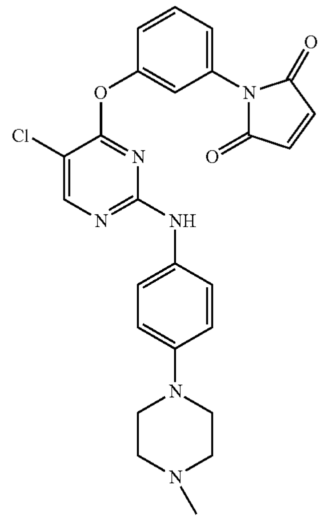 | MS m/z: 505.97 (M + 1). |
| 2-29 | 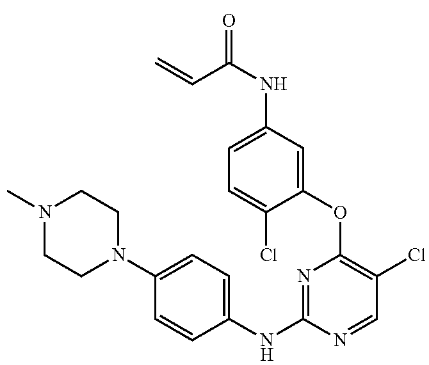 | MS m/z: 500.39 (M + 1). |
| 2-30 | 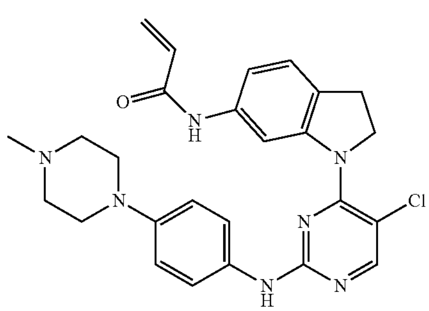 [SMILES: C=CC(=O)Nc1ccc2c(c1)N(c1nc(Nc3ccc(N4CCN(C)CC4)cc3)ncc1Cl)CC2] | MS m/z: 490.99 (M + 1). |

TABLE 3

| Compound Number | Structure | Physical Data ¹H NMR 600 MHz and/or MS (m/z) |
|---|---|---|
| 3-1 | 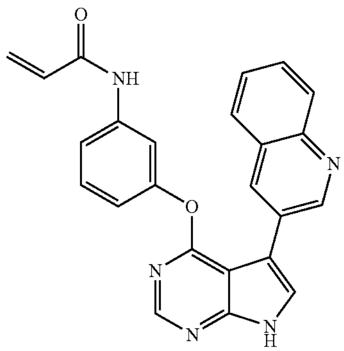 [SMILES: C=CC(=O)Nc1cccc(Oc2ncnc3[nH]cc(-c4cnc5ccccc5c4)c23)c1] | MS m/z: 407.42 (M + 1). |
| 3-2 | 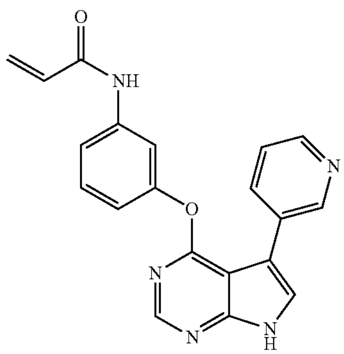 [SMILES: C=CC(=O)Nc1cccc(Oc2ncnc3[nH]cc(-c4cccnc4)c23)c1] | MS m/z: 357.36 (M + 1). |
| 3-3 | 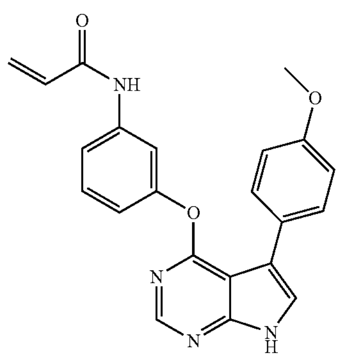 [SMILES: C=CC(=O)Nc1cccc(Oc2ncnc3[nH]cc(-c4ccc(OC)cc4)c23)c1] | MS m/z: 386.40 (M + 1). |
| 3-4 | 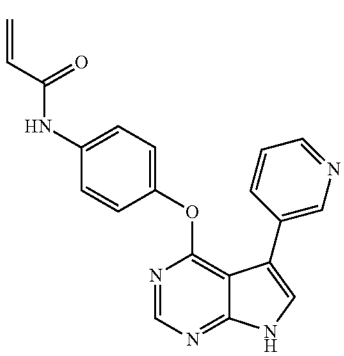 [SMILES: C=CC(=O)Nc1ccc(Oc2ncnc3[nH]cc(-c4cccnc4)c23)cc1] | MS m/z: 357.36 (M + 1). |

TABLE 3-continued

| Compound Number | Structure | Physical Data ¹H NMR 600 MHz and/or MS (m/z) |
|---|---|---|
| 3-5 | 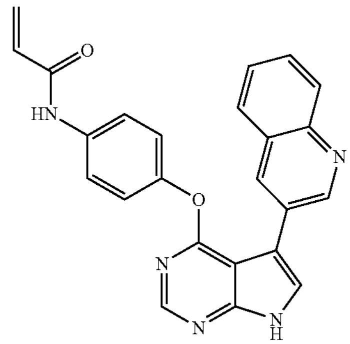 [SMILES: C=CC(=O)Nc1ccc(Oc2ncnc3[nH]cc(-c4cnc5ccccc5c4)c23)cc1] | MS m/z: 407.42 (M + 1). |

TABLE 4

| | | |
|---|---|---|
| 4-1 | | MS m/z: 449.96 (M + 1). |
| 4-2 | | MS m/z: 494.99 (M + 1). |
| 4-3 | | MS m/z: 538.01 (M + 1). |

TABLE 5

| Compound Number | Structure | Physical Data ¹H NMR 600 MHz and/or MS (m/z) |
|---|---|---|
| 5-1 | | MS m/z: 482.93 (M + 1). |
| 5-2 | | MS m/z: 540.02 (M + 1). |
| 5-3 | | MS m/z: 509.01 (M + 1). |
| 5-4 | 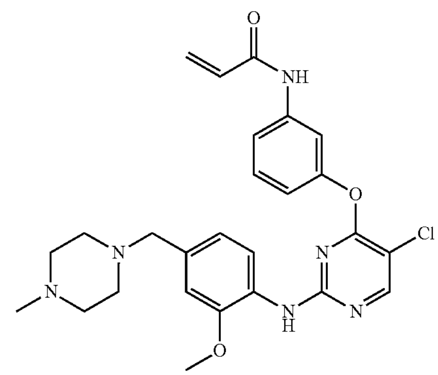 [SMILES: C=CC(=O)Nc1cccc(Oc2nc(Nc3ccc(CN4CCN(C)CC4)cc3OC)ncc2Cl)c1] | MS m/z: 510.0 (M + 1). |
| 5-5 | 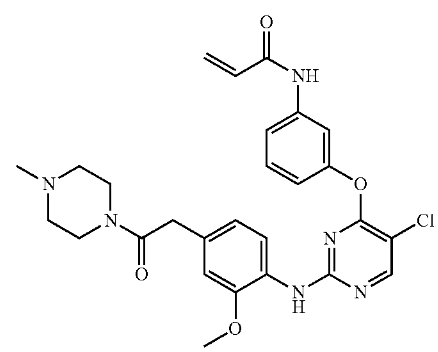 [SMILES: C=CC(=O)Nc1cccc(Oc2nc(Nc3ccc(CC(=O)N4CCN(C)CC4)cc3OC)ncc2Cl)c1] | MS m/z: 538.01 (M + 1). |
| 5-6 | 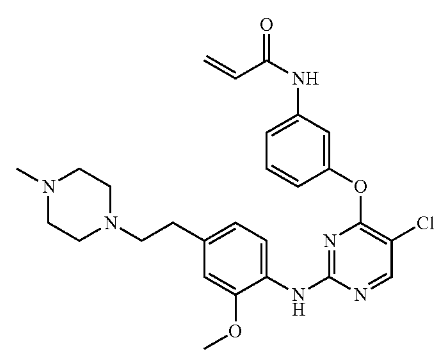 [SMILES: C=CC(=O)Nc1cccc(Oc2nc(Nc3ccc(CCN4CCN(C)CC4)cc3OC)ncc2Cl)c1] | MS m/z: 524.02 (M + 1). |
| 5-7 | 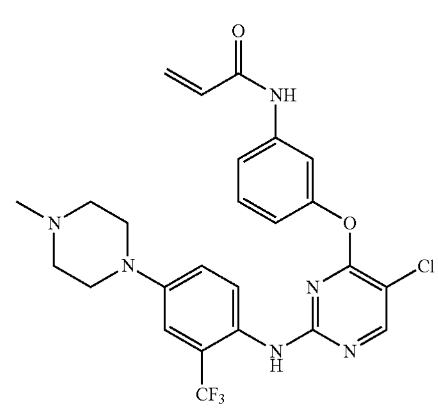 [SMILES: C=CC(=O)Nc1cccc(Oc2nc(Nc3ccc(N4CCN(C)CC4)cc3C(F)(F)F)ncc2Cl)c1] | MS m/z: 533.94 (M + 1). |

TABLE 5-continued

| Compound Number | Structure | Physical Data ¹H NMR 600 MHz and/or MS (m/z) |
|---|---|---|
| 5-8 | 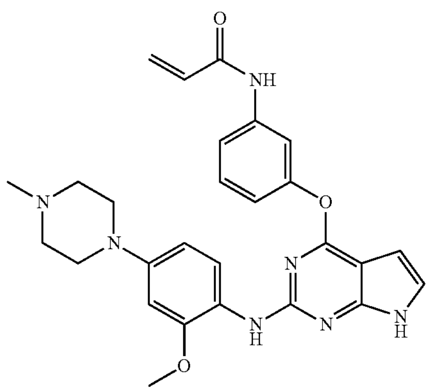 [SMILES: C=CC(=O)Nc1cccc(Oc2nc(Nc3ccc(N4CCN(C)CC4)cc3OC)nc3[nH]ccc23)c1] | MS m/z: 499.56 (M + 1). |
| 5-9 | 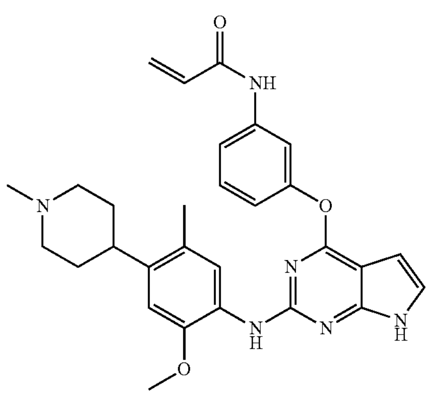 [SMILES: C=CC(=O)Nc1cccc(Oc2nc(Nc3cc(C)c(C4CCN(C)CC4)cc3OC)nc3[nH]ccc23)c1] | MS m/z: 513.60 (M + 1). |
| 5-10 | 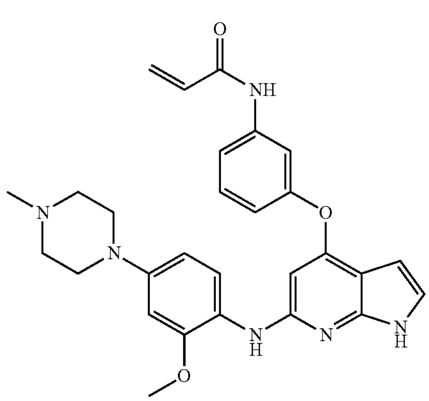 [SMILES: C=CC(=O)Nc1cccc(Oc2cc(Nc3ccc(N4CCN(C)CC4)cc3OC)nc3[nH]ccc23)c1] | MS m/z: 499.58 (M + 1). |
| 5-11 | | MS m/z: 513.60 (M + 1). |
| 5-12 | | MS m/z: 494.98 (M + 1). |
| 5-13 | | MS m/z: 512.97 (M + 1). |

TABLE 5-continued

| Compound Number | Structure | Physical Data ¹H NMR 600 MHz and/or MS (m/z) |
|---|---|---|
| 5-14 | 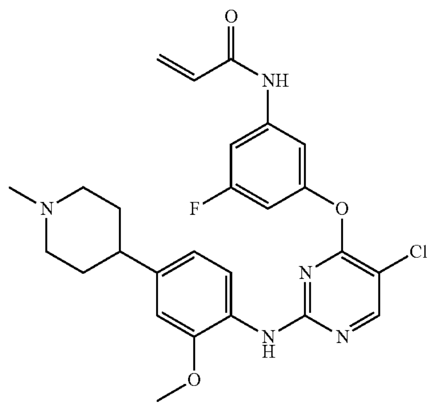 | MS m/z: 512.97 (M + 1). |
| 5-15 | 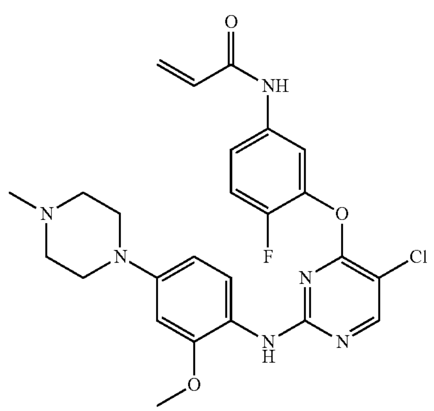 [SMILES: C=CC(=O)Nc1ccc(F)c(Oc2nc(Nc3ccc(C4CCN(C)CC4)cc3OC)ncc2Cl)c1] | MS m/z: 513.96 (M + 1). |
| 5-16 | 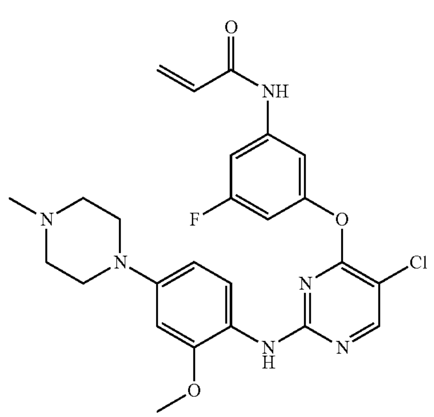 [SMILES: C=CC(=O)Nc1cc(F)cc(Oc2nc(Nc3ccc(N4CCN(C)CC4)cc3OC)ncc2Cl)c1] | MS m/z: 513.96 (M + 1). |
| 5-17 | | MS m/z: 494.99 (M + 1). |
| 5-18 | | MS m/z: 494.00 (M + 1). |
| 5-19 | | MS m/z: 508.03 (M + 1). |

TABLE 5-continued
| Compound Number | Structure | Physical Data $^1$H NMR 600 MHz and/or MS (m/z) |
|---|---|---|
| 5-20 | 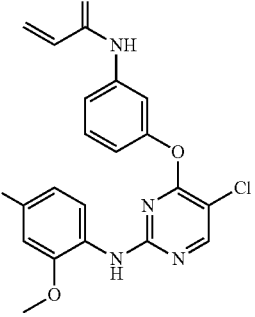 | MS m/z: 527.99 (M + 1). |
TABLE 6
| 6-1 | 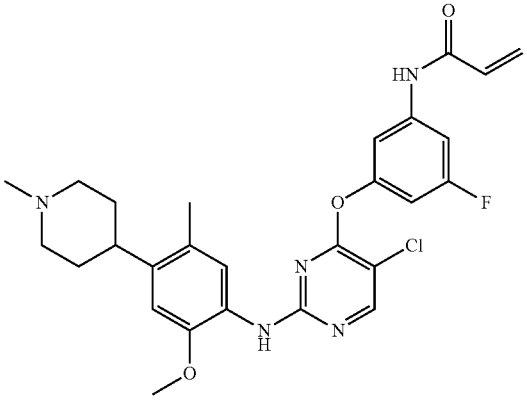 | MS m/z: 527.00 (M + 1). |
| 6-2 | 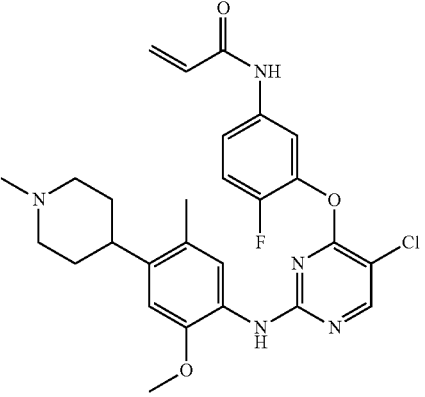 [SMILES: C=CC(=O)Nc1ccc(F)c(Oc2nc(Nc3cc(C)c(C4CCN(C)CC4)cc3OC)ncc2Cl)c1] | MS m/z: 527.00 (M + 1). |

TABLE 6-continued
| | | |
|---|---|---|
| 6-3 | 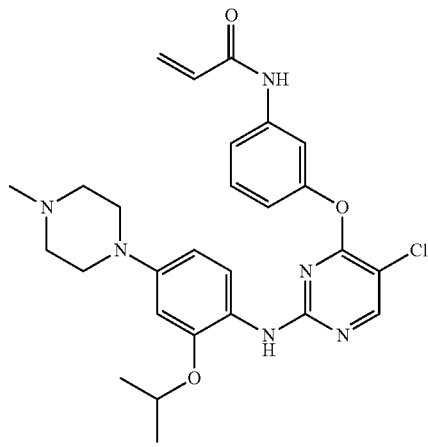 [SMILES: C=CC(=O)Nc1cccc(Oc2nc(Nc3ccc(N4CCN(C)CC4)cc3OC(C)C)ncc2Cl)c1] | MS m/z: 524.0 (M + 1). |
| 6-4 | 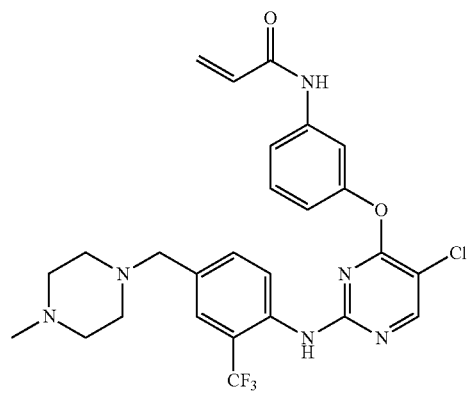 [SMILES: C=CC(=O)Nc1cccc(Oc2nc(Nc3ccc(CN4CCN(C)CC4)cc3C(F)(F)F)ncc2Cl)c1] | MS m/z: 547.9 (M + 1). |
| 6-5 | 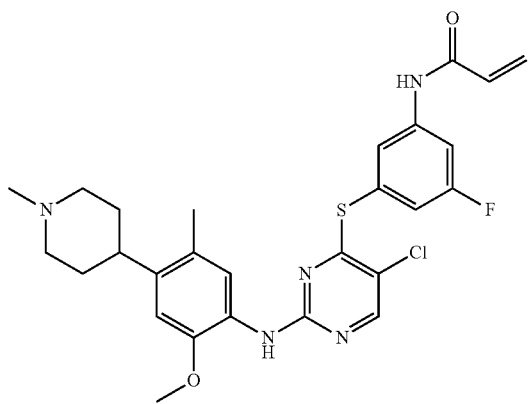 | MS m/z: 543.0 (M + 1). |
| 6-6 | 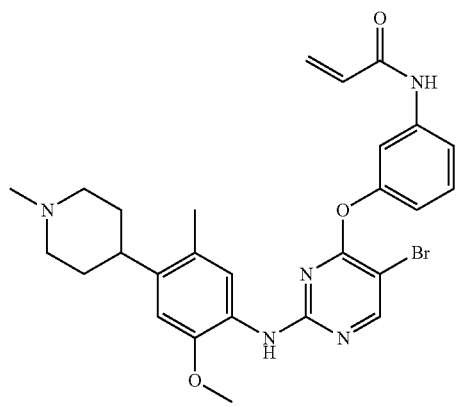 [SMILES: C=CC(=O)Nc1cccc(Oc2nc(Nc3cc(C)c(C4CCN(C)CC4)cc3OC)ncc2Br)c1] | MS m/z: 553.4 (M + 1). |

TABLE 6-continued
| | | |
|---|---|---|
| 6-7 | 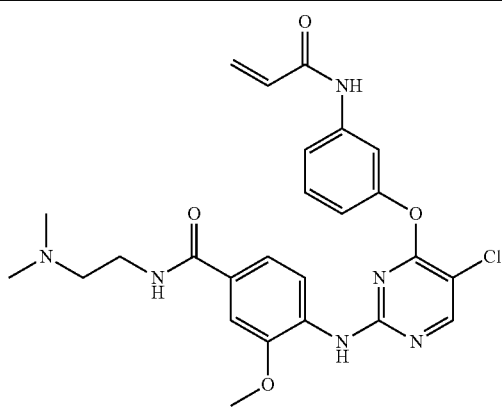 | MS m/z: 511.9 (M + 1). |
| 6-8 | 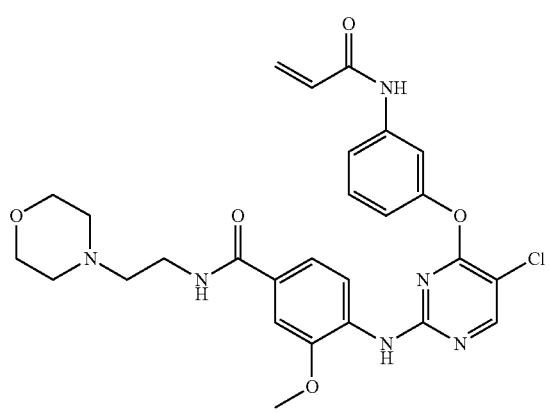 [SMILES: C=CC(=O)Nc1cccc(Oc2nc(Nc3ccc(C(=O)NCCN4CCOCC4)cc3OC)ncc2Cl)c1] | MS m/z: 554.0 (M + 1). |
| 6-9 | 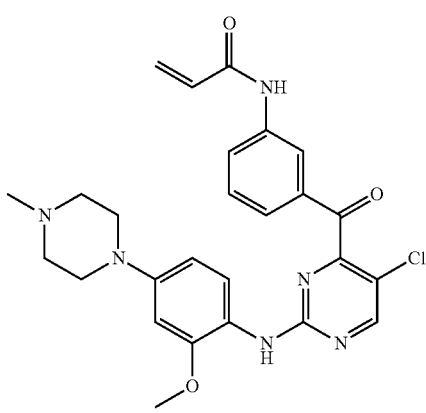 [SMILES: C=CC(=O)Nc1cccc(C(=O)c2nc(Nc3ccc(N4CCN(C)CC4)cc3OC)ncc2Cl)c1] | MS m/z: 507.98 (M + 1). |
| 6-10 | 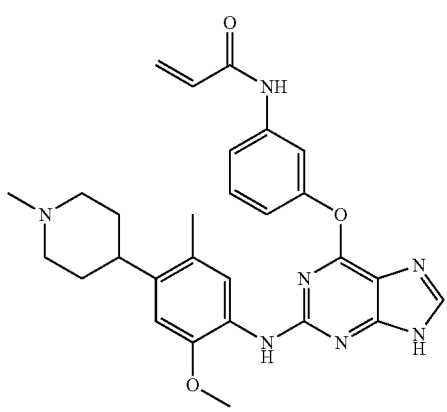 [SMILES: C=CC(=O)Nc1cccc(Oc2nc(Nc3cc(C)c(C4CCN(C)CC4)cc3OC)nc3[nH]cnc23)c1] | MS m/z: 514.6 (M + 1). |

TABLE 6-continued
| | | |
|---|---|---|
| 6-11 | 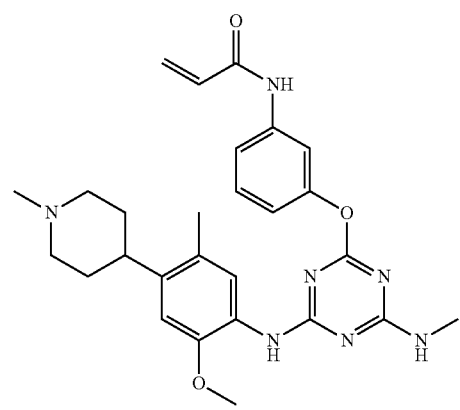 | MS m/z: 504.6 (M + 1). |
| 6-12 | 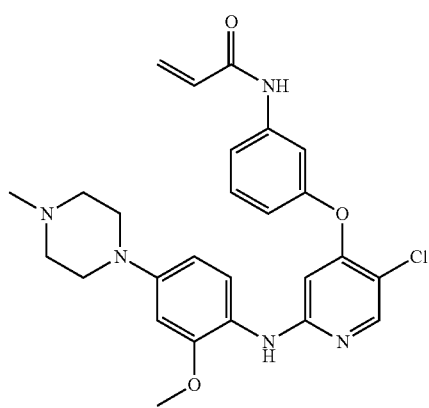 [SMILES: C=CC(=O)Nc1cccc(Oc2cc(Nc3ccc(N4CCN(C)CC4)cc3OC)ncc2Cl)c1] | MS m/z: 494.9 (M + 1). |
| 6-13 | 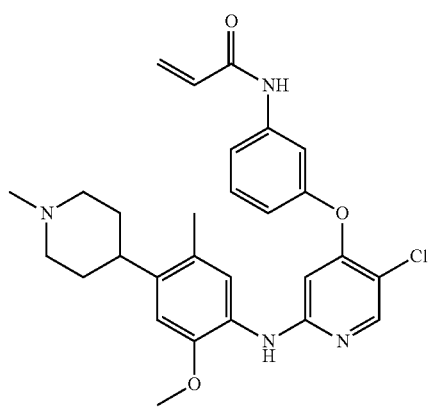 [SMILES: C=CC(=O)Nc1cccc(Oc2cc(Nc3cc(C)c(C4CCN(C)CC4)cc3OC)ncc2Cl)c1] | MS m/z: 508.02 (M + 1). |
| 6-14 | 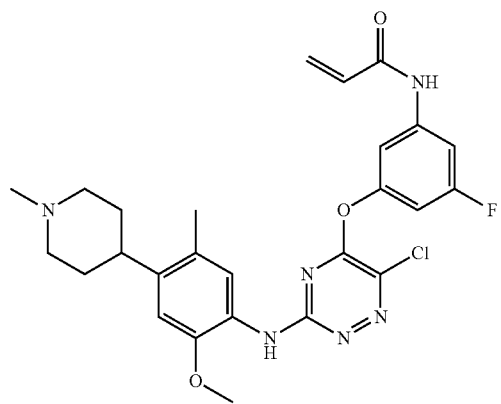 [SMILES: C=CC(=O)Nc1cc(F)cc(Oc2nc(Nc3cc(C)c(C4CCN(C)CC4)cc3OC)nnc2Cl)c1] | MS m/z: 527.9 (M + 1). |

TABLE 6-continued
| 6-15 | 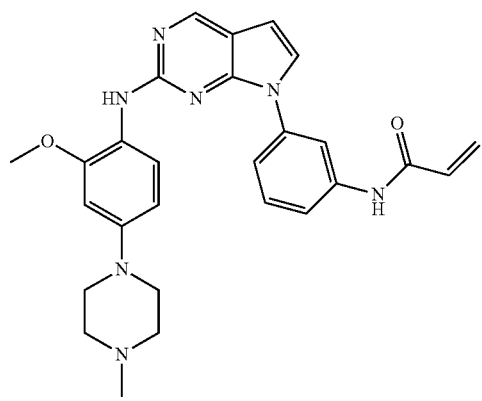 [SMILES: C=CC(=O)Nc1cccc(-n2ccc3cnc(Nc4ccc(N5CCN(C)CC5)cc4OC)nc32)c1] | MS m/z: 484.5 (M + 1). |
| 6-16 | 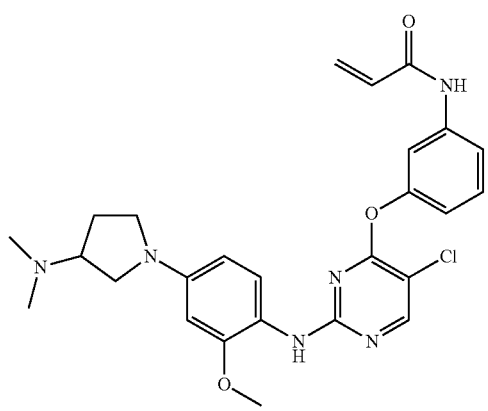 [SMILES: C=CC(=O)Nc1cccc(Oc2nc(Nc3ccc(N4CCC(N(C)C)C4)cc3OC)ncc2Cl)c1] | MS m/z: 510.0 (M + 1). |
| 6-17 | 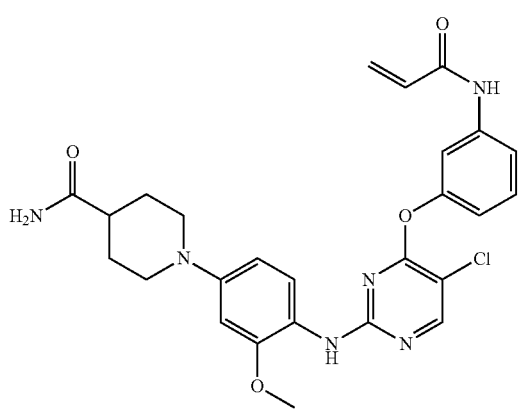 [SMILES: C=CC(=O)Nc1cccc(Oc2nc(Nc3ccc(N4CCC(C(N)=O)CC4)cc3OC)ncc2Cl)c1] | MS m/z: 523.9 (M + 1). |
| 6-18 | 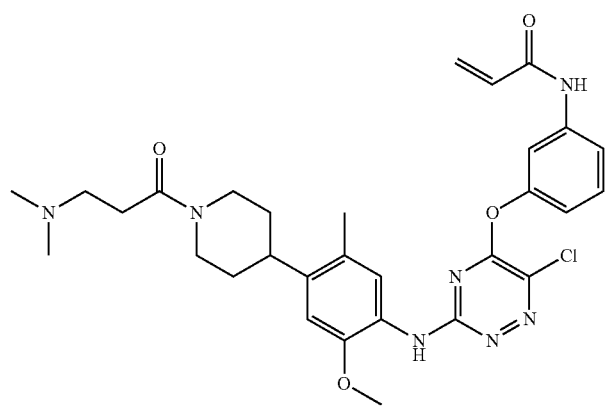 [SMILES: C=CC(=O)Nc1cccc(Oc2nc(Nc3cc(C)c(C4CCN(C(=O)CCN(C)C)CC4)cc3OC)nnc2Cl)c1] | MS m/z: 595.1 (M + 1). |

TABLE 6-continued
| | | |
|---|---|---|
| 6-19 | 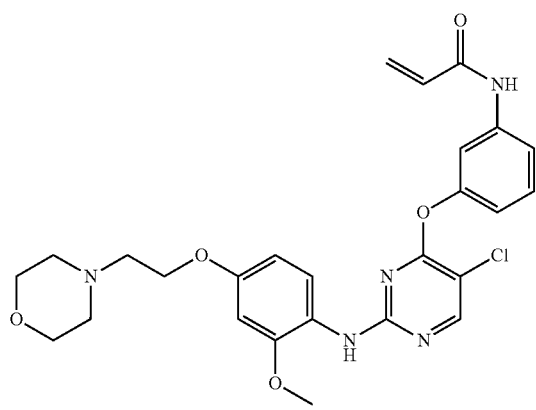 [SMILES: C=CC(=O)Nc1cccc(Oc2nc(Nc3ccc(OCCN4CCOCC4)cc3OC)ncc2Cl)c1] | MS m/z: 526.9 (M + 1). |
| 6-20 | 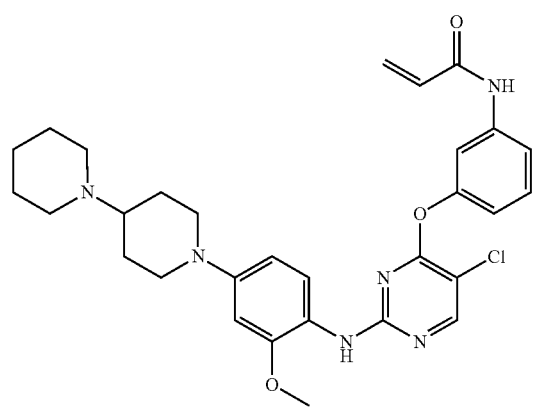 [SMILES: C=CC(=O)Nc1cccc(Oc2nc(Nc3ccc(N4CCC(N5CCCCC5)CC4)cc3OC)ncc2Cl)c1] | MS m/z: 564.1 (M + 1). |
| 6-21 | 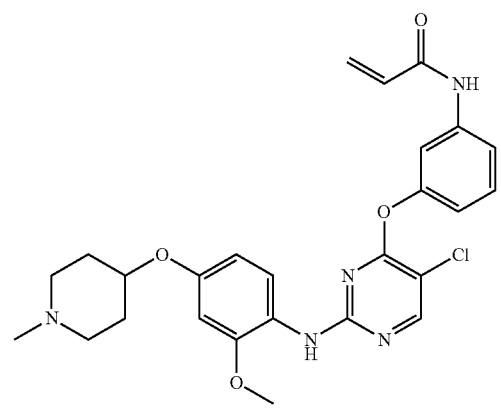 [SMILES: C=CC(=O)Nc1cccc(Oc2nc(Nc3ccc(OC4CCN(C)CC4)cc3OC)ncc2Cl)c1] | MS m/z: 510.9 (M + 1). |
| 6-22 | 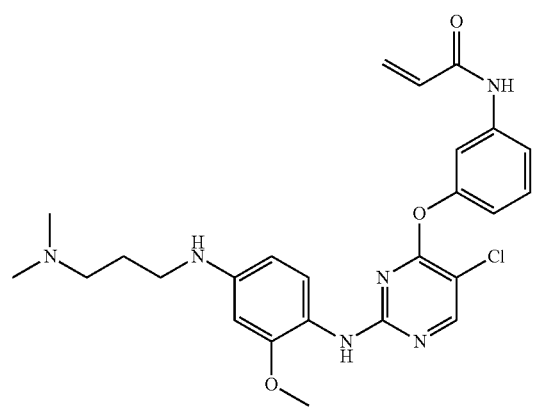 [SMILES: C=CC(=O)Nc1cccc(Oc2nc(Nc3ccc(NCCCN(C)C)cc3OC)ncc2Cl)c1] | MS m/z: 497.9 (M + 1). |

TABLE 6-continued
| | | |
|---|---|---|
| 6-23 | 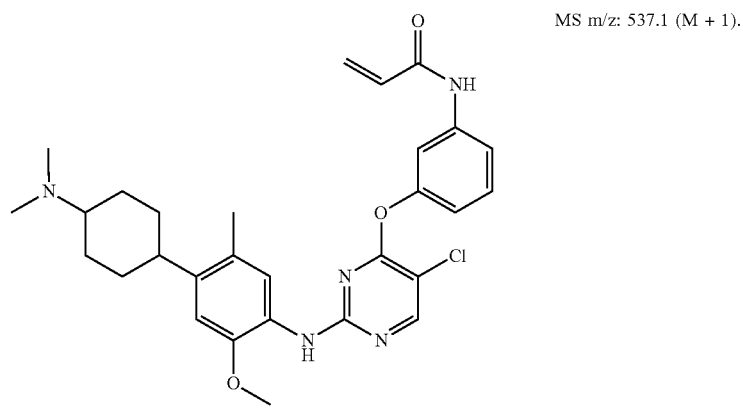 | MS m/z: 537.1 (M + 1). |
| 6-24 | 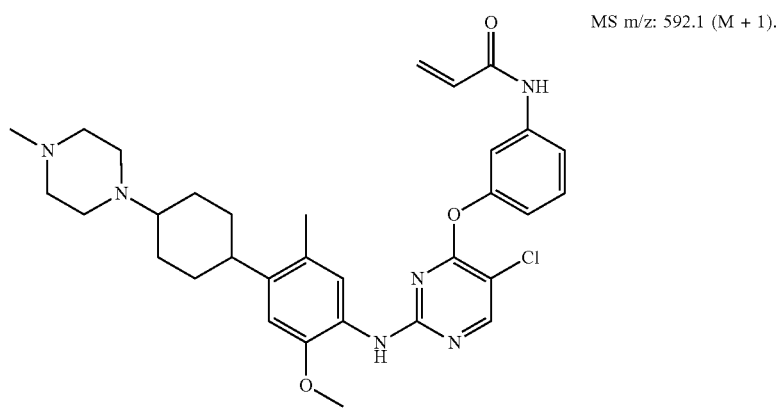 | MS m/z: 592.1 (M + 1). |
| 6-25 | 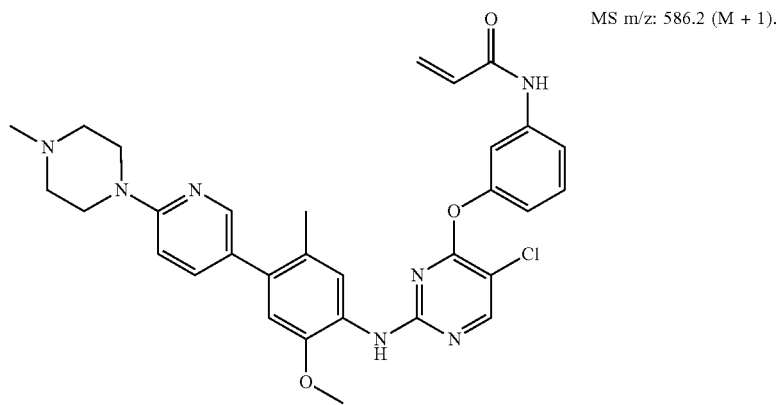 | MS m/z: 586.2 (M + 1). |
| 6-26 | 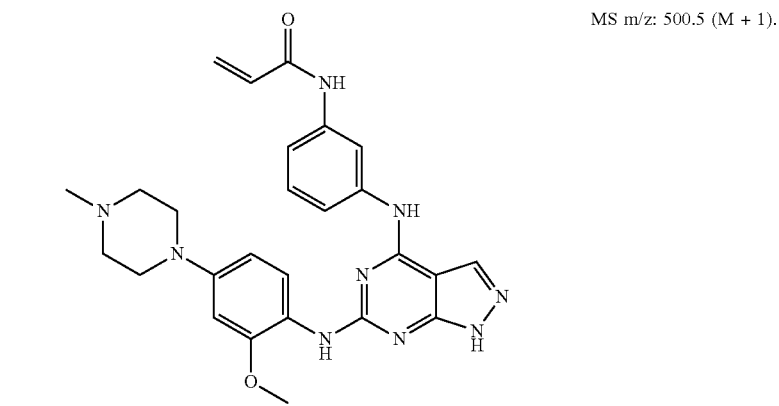 | MS m/z: 500.5 (M + 1). |

TABLE 6-continued
| | | |
|---|---|---|
| 6-27 | 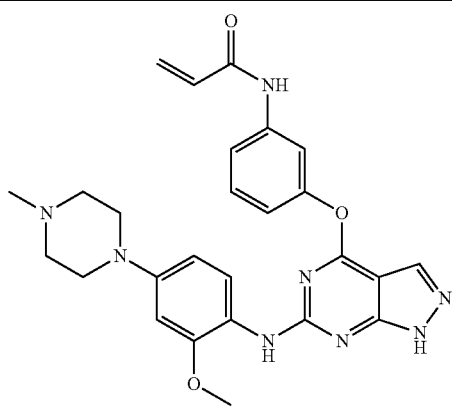 | MS m/z: 501.5 (M + 1). |
| 6-28 | 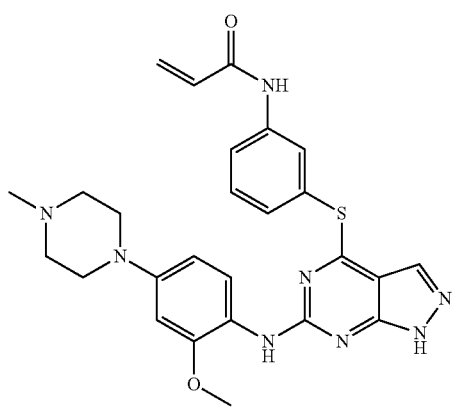 [SMILES: C=CC(=O)Nc1cccc(Oc2nc(Nc3ccc(N4CCN(C)CC4)cc3OC)nc3[nH]ncc23)c1] | MS m/z: 517.6 (M + 1). |
| 6-29 | 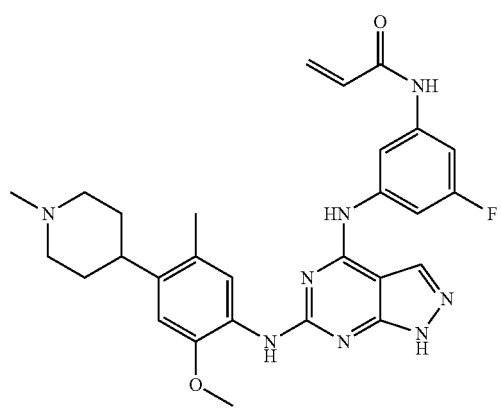 [SMILES: C=CC(=O)Nc1cc(F)cc(Nc2nc(Nc3cc(C)c(C4CCN(C)CC4)cc3OC)nc3[nH]ncc23)c1] | MS m/z: 531.6 (M + 1). |
| 6-30 | 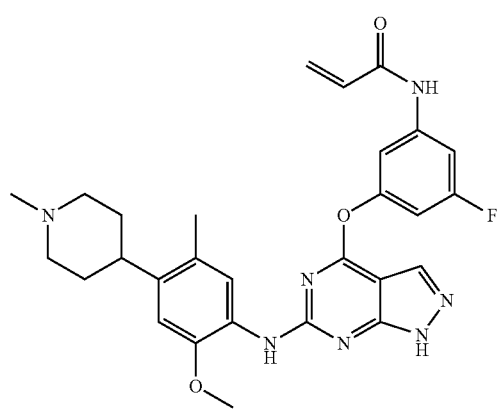 [SMILES: C=CC(=O)Nc1cc(F)cc(Oc2nc(Nc3cc(C)c(C4CCN(C)CC4)cc3OC)nc3[nH]ncc23)c1] | MS m/z: 532.6 (M + 1). |

TABLE 6-continued

| | | |
|---|---|---|
| 6-31 | 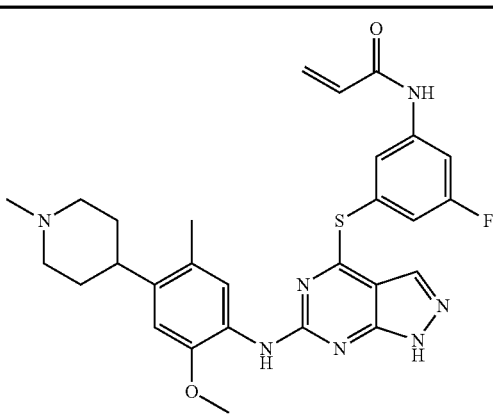 | MS m/z: 548.6 (M + 1). |
| 6-32 | 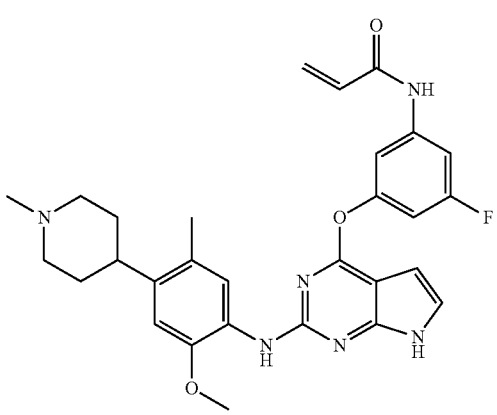 [SMILES: C=CC(=O)Nc1cc(F)cc(Oc2nc(Nc3cc(C)c(C4CCN(C)CC4)cc3OC)nc3[nH]ccc23)c1] | MS m/z: 531.6 (M + 1). |
| 6-33 | 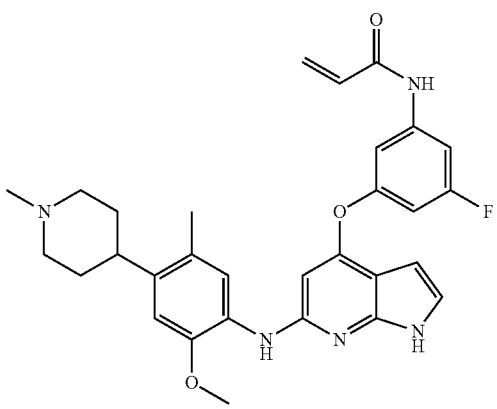 [SMILES: C=CC(=O)Nc1cc(F)cc(Oc2cc(Nc3cc(C)c(C4CCN(C)CC4)cc3OC)nc3[nH]ccc23)c1] | MS m/z: 530.6 (M + 1). |

The invention also provides for a pharmaceutical composition comprising a compound of formula I, or a pharmaceutically acceptable ester, salt, or prodrug thereof, together with a pharmaceutically acceptable carrier.

In another aspect, the invention provides a kit comprising a compound capable of inhibiting EGFR activity selected from one or more compounds of formula I, and instructions for use in treating cancer.

In another aspect, the invention provides a method of method of synthesizing a compound of formula I.

The synthesis of the compounds of the invention can be found in the Examples below.

Another embodiment is a method of making a compound of any of the formulae herein using any one, or combination of, reactions delineated herein. The method can include the use of one or more intermediates or chemical reagents delineated herein.

Another aspect is an isotopically labeled compound of any of the formulae delineated herein. Such compounds have one or more isotope atoms which may or may not be radioactive (e.g., $^{3}H$, $^{2}H$, $^{14}C$, $^{13}C$, $^{18}F$, $^{35}S$, $^{32}P$, $^{125}I$, and $^{131}I$) introduced into the compound. Such compounds are useful for drug metabolism studies and diagnostics, as well as therapeutic applications.

A compound of the invention can be prepared as a pharmaceutically acceptable acid addition salt by reacting the free base form of the compound with a pharmaceutically acceptable inorganic or organic acid. Alternatively, a pharmaceutically acceptable base addition salt of a compound of the invention can be prepared by reacting the free acid form of the compound with a pharmaceutically acceptable inorganic or organic base.

Alternatively, the salt forms of the compounds of the invention can be prepared using salts of the starting materials or intermediates.

The free acid or free base forms of the compounds of the invention can be prepared from the corresponding base addition salt or acid addition salt from, respectively. For example a compound of the invention in an acid addition salt form can be converted to the corresponding free base by treating with a suitable base (e.g., ammonium hydroxide solution, sodium hydroxide, and the like). A compound of the invention in a base addition salt form can be converted to the corresponding free acid by treating with a suitable acid (e.g., hydrochloric acid, etc.).

Prodrug derivatives of the compounds of the invention can be prepared by methods known to those of ordinary skill in the art (e.g., for further details see Saulnier et al., (1994), Bioorganic and Medicinal Chemistry Letters, Vol. 4, p. 1985). For example, appropriate prodrugs can be prepared by reacting a non-derivatized compound of the invention with a suitable carbamylating agent (e.g., 1,1-acyloxyalkylcarbanochloridate, para-nitrophenyl carbonate, or the like).

Protected derivatives of the compounds of the invention can be made by means known to those of ordinary skill in the art. A detailed description of techniques applicable to the creation of protecting groups and their removal can be found in T. W. Greene, "Protecting Groups in Organic Chemistry", 3.sup.rd edition, John Wiley and Sons, Inc., 1999.

Compounds of the present invention can be conveniently prepared, or formed during the process of the invention, as solvates (e.g., hydrates). Hydrates of compounds of the present invention can be conveniently prepared by recrystallization from an aqueous/organic solvent mixture, using organic solvents such as dioxin, tetrahydrofuran or methanol.

Acids and bases useful in the methods herein are known in the art. Acid catalysts are any acidic chemical, which can be inorganic (e.g., hydrochloric, sulfuric, nitric acids, aluminum trichloride) or organic (e.g., camphorsulfonic acid, p-toluenesulfonic acid, acetic acid, ytterbium triflate) in nature. Acids are useful in either catalytic or stoichiometric amounts to facilitate chemical reactions. Bases are any basic chemical, which can be inorganic (e.g., sodium bicarbonate, potassium hydroxide) or organic (e.g., triethylamine, pyridine) in nature. Bases are useful in either catalytic or stoichiometric amounts to facilitate chemical reactions.

In addition, some of the compounds of this invention have one or more double bonds, or one or more asymmetric centers. Such compounds can occur as racemates, racemic mixtures, single enantiomers, individual diastereomers, diastereomeric mixtures, and cis- or trans- or E- or Z-double isomeric forms, and other stereoisomeric forms that may be defined, in terms of absolute stereochemistry, as (R)- or (S)-, or as (D)- or (L)- for amino acids. All such isomeric forms of these compounds are expressly included in the present invention. Optical isomers may be prepared from their respective optically active precursors by the procedures described above, or by resolving the racemic mixtures. The resolution can be carried out in the presence of a resolving agent, by chromatography or by repeated crystallization or by some combination of these techniques which are known to those skilled in the art. Further details regarding resolutions can be found in Jacques, et al., *Enantiomers, Racemates, and Resolutions* (John Wiley & Sons, 1981). The compounds of this invention may also be represented in multiple tautomeric forms, in such instances, the invention expressly includes all tautomeric forms of the compounds described herein (e.g., alkylation of a ring system may result in alkylation at multiple sites, the invention expressly includes all such reaction products). When the compounds described herein contain olefinic double bonds or other centers of geometric asymmetry, and unless specified otherwise, it is intended that the compounds include both E and Z geometric isomers. Likewise, all tautomeric forms are also intended to be included. The configuration of any carbon-carbon double bond appearing herein is selected for convenience only and is not intended to designate a particular configuration unless the text so states; thus a carbon-carbon double bond depicted arbitrarily herein as trans may be cis, trans, or a mixture of the two in any proportion. All such isomeric forms of such compounds are expressly included in the present invention. All crystal forms of the compounds described herein are expressly included in the present invention.

The synthesized compounds can be separated from a reaction mixture and further purified by a method such as column chromatography, high pressure liquid chromatography, or recrystallization. As can be appreciated by the skilled artisan, further methods of synthesizing the compounds of the formulae herein will be evident to those of ordinary skill in the art. Additionally, the various synthetic steps may be performed in an alternate sequence or order to give the desired compounds. In addition, the solvents, temperatures, reaction durations, etc. delineated herein are for purposes of illustration only and one of ordinary skill in the art will recognize that variation of the reaction conditions can produce the desired bridged macrocyclic products of the present invention. Synthetic chemistry transformations and protecting group methodologies (protection and deprotection) useful in synthesizing the compounds described herein are known in the art and include, for example, those such as described in R. Larock, *Comprehensive Organic Transformations*, VCH Publishers (1989); T. W. Greene and P. G. M. Wuts, *Protective Groups in Organic Synthesis*, 2d. Ed., John Wiley and Sons (1991); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995), and subsequent editions thereof.

The compounds of this invention may be modified by appending various functionalities via any synthetic means delineated herein to enhance selective biological properties. Such modifications are known in the art and include those which increase biological penetration into a given biological system (e.g., blood, lymphatic system, central nervous system), increase oral availability, increase solubility to allow administration by injection, alter metabolism and alter rate of excretion.

The compounds of the invention are defined herein by their chemical structures and/or chemical names. Where a compound is referred to by both a chemical structure and a chemical name, and the chemical structure and chemical name conflict, the chemical structure is determinative of the compound's identity.

The recitation of a listing of chemical groups in any definition of a variable herein includes definitions of that variable as any single group or combination of listed groups. The recitation of an embodiment for a variable herein includes that embodiment as any single embodiment or in combination with any other embodiments or portions thereof.

Methods of the Invention

In another aspect, the invention provides a method of inhibiting a kinase, comprising contacting the kinase with a compound of formula I

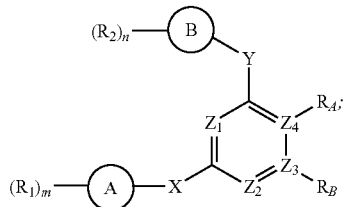

(I)

or a pharmaceutically acceptable salt, ester or prodrug thereof, wherein, $Z_1$ and $Z_2$ are each independently N or $CR_5$; $Z_3$ and $Z_4$ are each independently N or C, wherein $R_A$ and $R_B$ are absent when $Z_3$ or $Z_4$ is N; wherein at least one of $Z_1$, $Z_2$, $Z_3$ or $Z_4$ is N;

X is O, S, or $NR_6$;

Y is absent, CO, O, S, or $NR_6$;

each $R_6$ is independently H or alkyl;

ring A is aryl, heteroaryl, carbocyclic or heterocyclic; or a fused 8-14 membered bicyclic aryl, heteroaryl, carbocyclic or heterocyclic;

ring B is aryl, heteroaryl, carbocyclic or heterocyclic; or a fused 8-14 membered bicyclic aryl, heteroaryl, carbocyclic or heterocyclic;

$R_A$ is H, hal, OH, $NH_2$, $NHR_3$, $NR_3R_4$, $SR_3$, haloalkyl, CN, $N_3$, $NO_2$; alkyl, alkoxy, alkenyl, alkynyl, aryl, arylalkyl, heteroaryl, heterocyclic, or carbocyclic, each of which may be optionally substituted;

$R_B$ is H, hal, OH, $NH_2$, $NHR_3$, $NR_3R_4$, $SR_3$, haloalkyl, CN, $N_3$, $NO_2$; alkyl, alkoxy, alkenyl, alkynyl, aryl, arylalkyl, heteroaryl, heterocyclic, or carbocyclic, each of which may be optionally substituted; or $R_A$ and $R_B$, together with the atoms to which each is attached, form a fused aryl, heteroaryl, carbocyclic or heterocyclic, each of which may be optionally substituted;

each $R_1$ is independently $NH(R_3)$, $N(R_3)(R_4)$, $N(R_3)CO(R_4)$, $N(R_3)SO_2(R_4)$, $N(R_3)SO(R_4)$, $N(R_3)SO(R_4)$, $CO_2H$, $C(O)R_3$, $C(O)OR_3$, $C(O)NH_2$, $C(O)NH(R_3)$, $C(O)N(R_3)(R_4)$, $SO_2R_3$, $SOR_3$, $SR_3$, $SO_2NR_3R_4$, $SONR_3R_4$, $OR_3$, cyano, nitro, hal, alkyl, alkenyl, alkynyl, haloalkyl, aryl, arylalkyl, alkoxy, heteroaryl, heterocyclic, or carbocyclic, each of which may be optionally substituted;

or if m is 2 or 3, then at least two of $R_1$ may together with the atoms to which each is attached, form a 5 or 6 membered carbocyclic, heterocyclic, aryl, or heteroaryl, each of which may be optionally substituted;

each $R_2$ is independently an optionally substituted alkyl, hal,

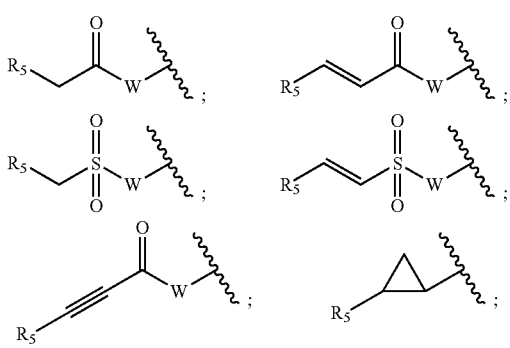

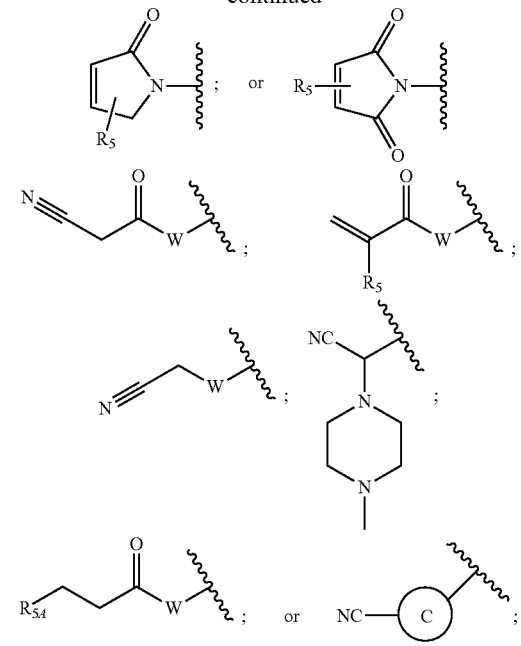

each $R_3$ and $R_4$ is independently H, alkyl, alkenyl, vinyl, heterocyclic, or carbocyclic, each of which may be optionally substituted;

each $R_5$ is independently H, alkyl, hal, or haloalkyl, each of which may be optionally substituted;

each $R_{5A}$ is independently hal or $OS(O)_pR'$, wherein p is 0, 1 or 2 and R' is alkyl or aryl;

each W is independently absent, $CH_2$, $CH_2CH_2$, $(CH_2)_3$, $(CH_2)_4$, O, S, or $NR_3$;

ring C is a 5-6 membered heterocyclic or heteroaryl having 1, 2, or 3 nitrogens;

m is 1, 2, or 3; and n is 0, 1 or 2;

wherein if $R_A$ and $R_B$ together with the atoms to which each is attached, form a fused aryl, heteroaryl, carbocyclic or heterocyclic, then one of

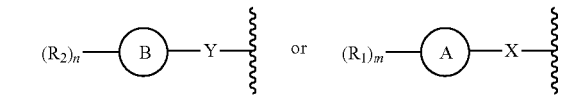

may be absent.

In certain embodiments, the invention provides a method as described above wherein the compound is a compound of formula II-a, II-b, II-c, III, IV, V, VI, or VII. In certain embodiments, the invention provides a method as described above wherein the compound is selected from the compounds in Tables 1-6. In certain embodiments, the invention provides a method as described above wherein the compound is WZ3146, WZ4002 or WZ8040.

In one embodiment, the kinase comprises a cysteine residue.

In a further embodiment, the cysteine residue is located in or near the position equivalent to Cys 797 in EGFR, including such position in Jak3, Blk, Bmx, Btk, HER2 (ErbB2), HER4 (ErbB4), Itk, Tec, and Txk.

In another aspect, the invention provides a method of inhibiting a kinase in a subject, comprising administering a compound of formula I

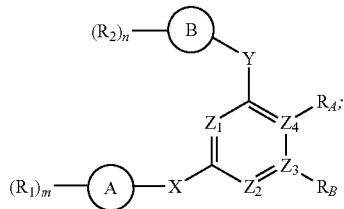

(I)

or a pharmaceutically acceptable salt, ester or prodrug thereof,
wherein, $Z_1$ and $Z_2$ are each independently N or $CR_5$; $Z_3$ and $Z_4$ are each independently N or C, wherein $R_A$ and $R_B$ are absent when $Z_3$ or $Z_4$ is N; wherein at least one of $Z_1$, $Z_2$, $Z_3$ or $Z_4$ is N;

X is O, S, or $NR_6$;
Y is absent, CO, O, S, or $NR_6$;
each $R_6$ is independently H or alkyl;
ring A is aryl, heteroaryl, carbocyclic or heterocyclic; or a fused 8-14 membered bicyclic aryl, heteroaryl, carbocyclic or heterocyclic;
ring B is aryl, heteroaryl, carbocyclic or heterocyclic; or a fused 8-14 membered bicyclic aryl, heteroaryl, carbocyclic or heterocyclic;

$R_A$ is H, hal, OH, $NH_2$, $NHR_3$, $NR_3R_4$, $SR_3$, haloalkyl, CN, $N_3$, $NO_2$; alkyl, alkoxy, alkenyl, alkynyl, aryl, arylalkyl, heteroaryl, heterocyclic, or carbocyclic, each of which may be optionally substituted;

$R_B$ is H, hal, OH, $NH_2$, $NHR_3$, $NR_3R_4$, $SR_3$, haloalkyl, CN, $N_3$, $NO_2$; alkyl, alkoxy, alkenyl, alkynyl, aryl, arylalkyl, heteroaryl, heterocyclic, or carbocyclic, each of which may be optionally substituted;

or $R_A$ and $R_B$, together with the atoms to which each is attached, form a fused aryl, heteroaryl, carbocyclic or heterocyclic, each of which may be optionally substituted;

each $R_1$ is independently $NH(R_3)$, $N(R_3)(R_4)$, $N(R_3)CO(R_4)$, $N(R_3)SO_2(R_4)$, $N(R_3)SO(R_4)$, $N(R_3)SO(R_4)$, $CO_2H$, $C(O)R_3$, $C(O)OR_3$, $C(O)NH_2$, $C(O)NH(R_3)$, $C(O)N(R_3)(R_4)$, $SO_2R_3$, $SOR_3$, $SR_3$, $SO_2NR_3R_4$, $SONR_3R_4$, $OR_3$, cyano, nitro, hal, alkyl, alkenyl, alkynyl, haloalkyl, aryl, arylalkyl, alkoxy, heteroaryl, heterocyclic, or carbocyclic, each of which may be optionally substituted;

or if m is 2 or 3, then at least two of $R_1$ may together with the atoms to which each is attached, form a 5 or 6 membered carbocyclic, heterocyclic, aryl, or heteroaryl, each of which may be optionally substituted;

each $R_2$ is independently an optionally substituted alkyl, hal,

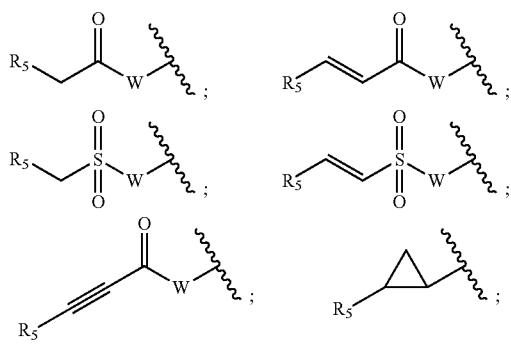

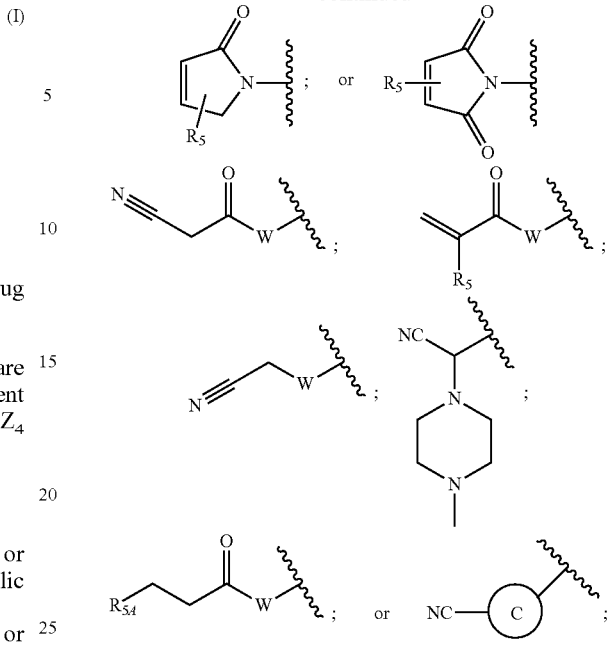

each $R_3$ and $R_4$ is independently H, alkyl, alkenyl, vinyl, heterocyclic, or carbocyclic, each of which may be optionally substituted;

each $R_5$ is independently H, alkyl, hal, or haloalkyl, each of which may be optionally substituted;

each $R_{5A}$ is independently hal or $OS(O)_pR'$, wherein p is 0, 1 or 2 and R' is alkyl or aryl;

each W is independently absent, $CH_2$, $CH_2CH_2$, $(CH_2)_3$, $(CH_2)_4$, O, S, or $NR_3$;

ring C is a 5-6 membered heterocyclic or heteroaryl having 1, 2, or 3 nitrogens;

m is 1, 2, or 3; and
n is 0, 1 or 2;

wherein if $R_A$ and $R_B$ together with the atoms to which each is attached, form a fused aryl, heteroaryl, carbocyclic or heterocyclic, then one of

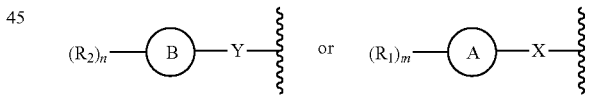

may be absent.

In certain embodiments, the invention provides a method as described above wherein the compound is a compound of formula II-a, II-b, II-c, III, IV, V, VI, or VII. In certain embodiments, the invention provides a method as described above wherein the compound is selected from the compounds in Tables 1-6. In certain embodiments, the invention provides a method as described above wherein the compound is WZ3146, WZ4002 or WZ8040.

In one embodiment, the kinase comprises a cysteine residue.

In a further embodiment, the cysteine residue is located in or near the position equivalent to Cys 797 in EGFR, including such positions in Jak3, Blk, Bmx, Btk, HER2 (ErbB2), HER4 (ErbB4), Itk, Tec, and Txk.

In another aspect, the invention provides a method of inhibiting epidermal growth factor receptor (EGFR) in a subject, comprising administering a compound of formula I

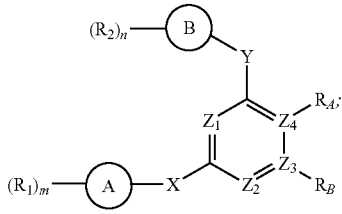

(I)

or a pharmaceutically acceptable salt, ester or prodrug thereof,
wherein, $Z_1$ and $Z_2$ are each independently N or $CR_5$; $Z_3$ and $Z_4$ are each independently N or C, wherein $R_A$ and $R_B$ are absent when $Z_3$ or $Z_4$ is N; wherein at least one of $Z_1$, $Z_2$, $Z_3$ or $Z_4$ is N;

X is O, S, or $NR_6$;

Y is absent, CO, O, S, or $NR_6$;

each $R_6$ is independently H or alkyl;

ring A is aryl, heteroaryl, carbocyclic or heterocyclic; or a fused 8-14 membered bicyclic aryl, heteroaryl, carbocyclic or heterocyclic;

ring B is aryl, heteroaryl, carbocyclic or heterocyclic; or a fused 8-14 membered bicyclic aryl, heteroaryl, carbocyclic or heterocyclic;

$R_A$ is H, hal, OH, $NH_2$, $NHR_3$, $NR_3R_4$, $SR_3$, haloalkyl, CN, $N_3$, $NO_2$; alkyl, alkoxy, alkenyl, alkynyl, aryl, arylalkyl, heteroaryl, heterocyclic, or carbocyclic, each of which may be optionally substituted;

$R_B$ is H, hal, OH, $NH_2$, $NHR_3$, $NR_3R_4$, $SR_3$, haloalkyl, CN, $N_3$, $NO_2$; alkyl, alkoxy, alkenyl, alkynyl, aryl, arylalkyl, heteroaryl, heterocyclic, or carbocyclic, each of which may be optionally substituted;

or $R_A$ and $R_B$, together with the atoms to which each is attached, form a fused aryl, heteroaryl, carbocyclic or heterocyclic, each of which may be optionally substituted;

each $R_1$ is independently $NH(R_3)$, $N(R_3)(R_4)$, $N(R_3)CO(R_4)$, $N(R_3)SO_2(R_4)$, $N(R_3)SO(R_4)$, $N(R_3)SO(R_4)$, $CO_2H$, $C(O)R_3$, $C(O)OR_3$, $C(O)NH_2$, $C(O)NH(R_3)$, $C(O)N(R_3)(R_4)$, $SO_2R_3$, $SOR_3$, $SR_3$, $SO_2NR_3R_4$, $SONR_3R_4$, $OR_3$, cyano, nitro, hal, alkyl, alkenyl, alkynyl, haloalkyl, aryl, arylalkyl, alkoxy, heteroaryl, heterocyclic, or carbocyclic, each of which may be optionally substituted;

or if m is 2 or 3, then at least two of $R_1$ may together with the atoms to which each is attached, form a 5 or 6 membered carbocyclic, heterocyclic, aryl, or heteroaryl, each of which may be optionally substituted;

each $R_2$ is independently an optionally substituted alkyl, hal,

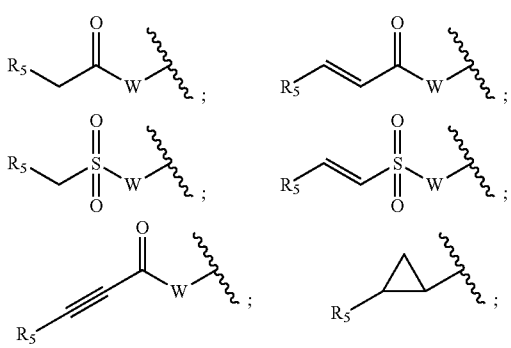

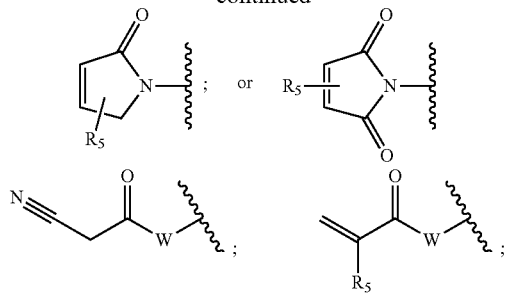

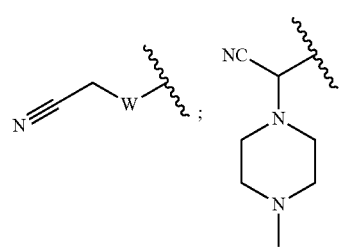

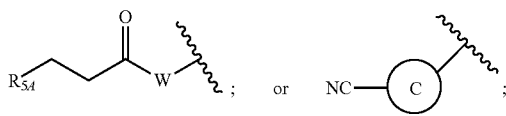

each $R_3$ and $R_4$ is independently H, alkyl, alkenyl, vinyl, heterocyclic, or carbocyclic, each of which may be optionally substituted;

each $R_5$ is independently H, alkyl, hal, or haloalkyl, each of which may be optionally substituted;

each $R_{5A}$ is independently hal or $OS(O)_pR'$, wherein p is 0, 1 or 2 and R' is alkyl or aryl;

each W is independently absent, $CH_2$, $CH_2CH_2$, $(CH_2)_3$, $(CH_2)_4$, O, S, or $NR_3$;

ring C is a 5-6 membered heterocyclic or heteroaryl having 1, 2, or 3 nitrogens;

m is 1, 2, or 3; and n is 0, 1 or 2;

wherein if $R_A$ and $R_B$ together with the atoms to which each is attached, form a fused aryl, heteroaryl, carbocyclic or heterocyclic, then one of

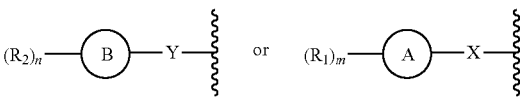

may be absent.

In certain embodiments, the invention provides a method as described above wherein the compound is a compound of formula II-a, II-b, II-c, III, IV, V, VI, or VII.

In one embodiment, the EGFR is a Her-kinase.

In still another aspect, the invention provides a method of treating a disease in a subject comprising administering to the subject a compound, pharmaceutically acceptable salt, ester or prodrug of formula I

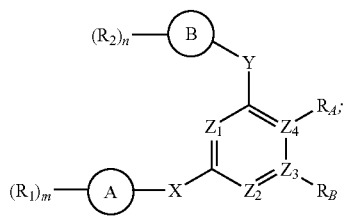

(I)

or a pharmaceutically acceptable salt, ester or prodrug thereof,
wherein,
$Z_1$ and $Z_2$ are each independently N or $CR_5$; $Z_3$ and $Z_4$ are each independently N or C, wherein $R_A$ and $R_B$ are absent when $Z_3$ or $Z_4$ is N; wherein at least one of $Z_1$, $Z_2$, $Z_3$ or $Z_4$ is N;
X is O, S, or $NR_6$;
Y is absent, CO, O, S, or $NR_5$;
each $R_6$ is independently H or alkyl;
ring A is aryl, heteroaryl, carbocyclic or heterocyclic; or a fused 8-14 membered bicyclic aryl, heteroaryl, carbocyclic or heterocyclic;
ring B is aryl, heteroaryl, carbocyclic or heterocyclic; or a fused 8-14 membered bicyclic aryl, heteroaryl, carbocyclic or heterocyclic;
$R_A$ is H, hal, OH, $NH_2$, $NHR_3$, $NR_3R_4$, $SR_3$, haloalkyl, CN, $N_3$, $NO_2$; alkyl, alkoxy, alkenyl, alkynyl, aryl, arylalkyl, heteroaryl, heterocyclic, or carbocyclic, each of which may be optionally substituted;
$R_B$ is H, hal, OH, $NH_2$, $NHR_3$, $NR_3R_4$, $SR_3$, haloalkyl, CN, $N_3$, $NO_2$; alkyl, alkoxy, alkenyl, alkynyl, aryl, arylalkyl, heteroaryl, heterocyclic, or carbocyclic, each of which may be optionally substituted;
or $R_A$ and $R_B$, together with the atoms to which each is attached, form a fused aryl, heteroaryl, carbocyclic or heterocyclic, each of which may be optionally substituted;
each $R_1$ is independently $NH(R_3)$, $N(R_3)(R_4)$, $N(R_3)CO(R_4)$, $N(R_3)SO_2(R_4)$, $N(R_3)SO(R_4)$, $N(R_3)SO(R_4)$, COAl, $C(O)R_3$, $C(O)OR_3$, $C(O)NH_2$, $C(O)NH(R_3)$, $C(O)N(R_3)(R_4)$, $SO_2R_3$, $SOR_3$, $SR_3$, $SO_2NR_3R_4$, $SONR_3R_4$, $OR_3$, cyano, nitro, hal, alkyl, alkenyl, alkynyl, haloalkyl, aryl, arylalkyl, alkoxy, heteroaryl, heterocyclic, or carbocyclic, each of which may be optionally substituted;
or if m is 2 or 3, then at least two of $R_1$ may together with the atoms to which each is attached, form a 5 or 6 membered carbocyclic, heterocyclic, aryl, or heteroaryl, each of which may be optionally substituted;
each $R_2$ is independently an optionally substituted alkyl, hal,

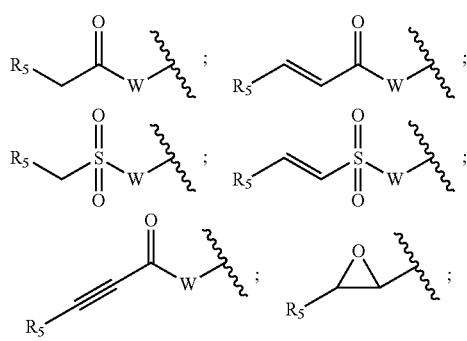

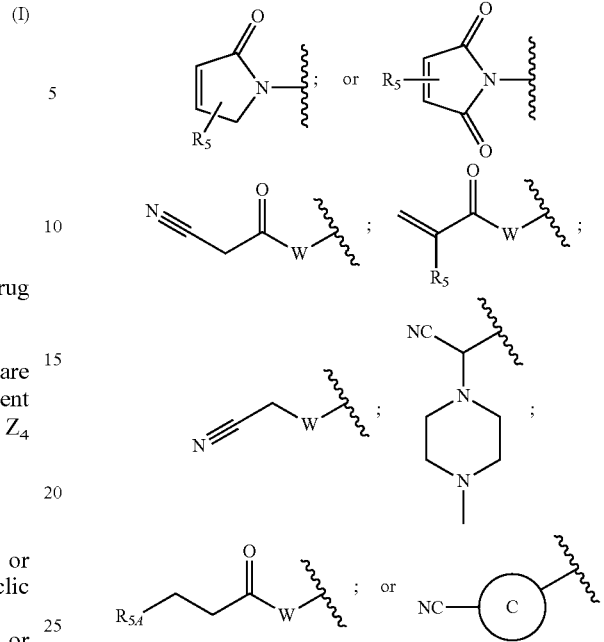

each $R_3$ and $R_4$ is independently H, alkyl, alkenyl, vinyl, heterocyclic, or carbocyclic, each of which may be optionally substituted;
each $R_5$ is independently H, alkyl, hal, or haloalkyl, each of which may be optionally substituted;
each $R_{5A}$ is independently hal or $OS(O)_pR'$, wherein p is 0, 1 or 2 and R' is alkyl or aryl;
each W is independently absent, $CH_2$, $CH_2CH_2$, $(CH_2)_3$, $(CH_2)_4$, O, S, or $NR_3$;
ring C is a 5-6 membered heterocyclic or heteroaryl having 1, 2, or 3 nitrogens;
m is 1, 2, or 3; and
n is 0, 1 or 2;
wherein if $R_A$ and $R_B$ together with the atoms to which each is attached, form a fused aryl, heteroaryl, carbocyclic or heterocyclic, then one of

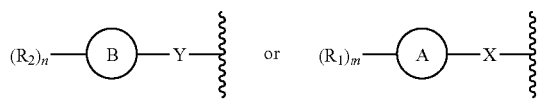

may be absent.

In certain embodiments, the invention provides a method as described above wherein the compound is a compound of formula II-a, II-b, II-c, III, IV, V, VI, or VII. In certain embodiments, the invention provides a method as described above wherein the compound is selected from the compounds in Tables 1-6. In certain embodiments, the invention provides a method as described above wherein the compound is WZ3146, WZ4002 or WZ8040.

In one embodiment, the disease is mediated by a kinase.
In a further embodiment, the kinase comprises a cysteine residue.
In still a further embodiment, the cysteine residue is located in or near the position equivalent to Cys 797 in EGFR, including Jak3, Blk, Bmx, Btk, HER2 (ErbB2), HER4 (ErbB4), Itk, Tec, and Txk.

In other embodiments, the disease is mediated by EGFR.

In a further embodiment, the EGFR is a Her-kinase. In a further embodiment, the disease is mediated by HER1, HER2, or HER4.

In certain embodiments, the disease is cancer or a proliferation disease.

In a further embodiment, the disease is lung cancer, colon cancer, breast cancer, prostate cancer, liver cancer, pancreas cancer, brai cancern, kidney cancer, ovarian cancer, stomach cancer, skin cancer, bone cancer, gastric cancer, breast cancer, pancreatic cancer, glioma, glioblastoma, hepatocellular carcinoma, papillary renal carcinoma, head and neck squamous cell carcinoma, leukemias, lymphomas, myelomas, and solid tumors.

In other embodiments, the disease is inflammation, arthritis, rheumatoid arthritis, spondylarthropathies, gouty arthritis, osteoarthritis, juvenile arthritis, and other arthritic conditions, systemic lupus erthematosus (SLE), skin-related conditions, psoriasis, eczema, burns, dermatitis, neuroinflammation, allergy, pain, neuropathic pain, fever, pulmonary disorders, lung inflammation, adult respiratory distress syndrome, pulmonary sarcoisosis, asthma, silicosis, chronic pulmonary inflammatory disease, and chronic obstructive pulmonary disease (COPD), cardiovascular disease, arteriosclerosis, myocardial infarction (including post-myocardial infarction indications), thrombosis, congestive heart failure, cardiac reperfusion injury, as well as complications associated with hypertension and/or heart failure such as vascular organ damage, restenosis, cardiomyopathy, stroke including ischemic and hemorrhagic stroke, reperfusion injury, renal reperfusion injury, ischemia including stroke and brain ischemia, and ischemia resulting from cardiac/coronary bypass, neurodegenerative disorders, liver disease and nephritis, gastrointestinal conditions, inflammatory bowel disease, Crohn's disease, gastritis, irritable bowel syndrome, ulcerative colitis, ulcerative diseases, gastric ulcers, viral and bacterial infections, sepsis, septic shock, gram negative sepsis, malaria, meningitis, HIV infection, opportunistic infections, cachexia secondary to infection or malignancy, cachexia secondary to acquired immune deficiency syndrome (AIDS), AIDS, ARC (AIDS related complex), pneumonia, herpes virus, myalgias due to infection, influenza, autoimmune disease, graft vs. host reaction and allograft rejections, treatment of bone resorption diseases, osteoporosis, multiple sclerosis, cancer, leukemia, lymphoma, colorectal cancer, brain cancer, bone cancer, epithelial call-derived neoplasia (epithelial carcinoma), basal cell carcinoma, adenocarcinoma, gastrointestinal cancer, lip cancer, mouth cancer, esophageal cancer, small bowel cancer, stomach cancer, colon cancer, liver cancer, bladder cancer, pancreas cancer, ovarian cancer, cervical cancer, lung cancer, breast cancer, skin cancer, squamus cell and/or basal cell cancers, prostate cancer, renal cell carcinoma, and other known cancers that affect epithelial cells throughout the body, chronic myelogenous leukemia (CML), acute myeloid leukemia (AML) and acute promyelocytic leukemia (APL), angiogenesis including neoplasia, metastasis, central nervous system disorders, central nervous system disorders having an inflammatory or apoptotic component, Alzheimer's disease, Parkinson's disease, Huntington's disease, amyotrophic lateral sclerosis, spinal cord injury, and peripheral neuropathy, Canine B-Cell Lymphoma.

In a further embodiment, the disease is inflammation, arthritis, rheumatoid arthritis, spondylarthropathies, gouty arthritis, osteoarthritis, juvenile arthritis, and other arthritic conditions, systemic lupus erthematosus (SLE), skin-related conditions, psoriasis, eczema, dermatitis, pain, pulmonary disorders, lung inflammation, adult respiratory distress syndrome, pulmonary sarcoisosis, asthma, chronic pulmonary inflammatory disease, and chronic obstructive pulmonary disease (COPD), cardiovascular disease, arteriosclerosis, myocardial infarction (including post-myocardial infarction indications), congestive heart failure, cardiac reperfusion injury, inflammatory bowel disease, Crohn's disease, gastritis, irritable bowel syndrome, leukemia, lymphoma.

In another aspect, the invention provides a method of treating a kinase mediated disorder in a subject comprising: administering to the subject identified as in need thereof a compound, pharmaceutically acceptable salt, ester or prodrug of formula I

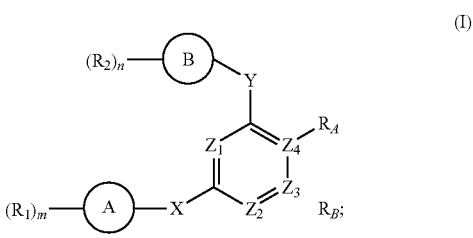

or a pharmaceutically acceptable salt, ester or prodrug thereof, wherein, $Z_1$ and $Z_2$ are each independently N or $CR_5$; $Z_3$ and $Z_4$ are each independently N or C, wherein $R_A$ and $R_B$ are absent when $Z_3$ or $Z_4$ is N; wherein at least one of $Z_1$, $Z_2$, $Z_3$ or $Z_4$ is N;

X is O, S, or $NR_6$;

Y is absent, CO, O, S, or $NR_6$;

each $R_6$ is independently H or alkyl;

ring A is aryl, heteroaryl, carbocyclic or heterocyclic; or a fused 8-14 membered bicyclic aryl, heteroaryl, carbocyclic or heterocyclic;

ring B is aryl, heteroaryl, carbocyclic or heterocyclic; or a fused 8-14 membered bicyclic aryl, heteroaryl, carbocyclic or heterocyclic;

$R_A$ is H, hal, OH, $NH_2$, $NHR_3$, $NR_3R_4$, $SR_3$, haloalkyl, CN, $N_3$, $NO_2$; alkyl, alkoxy, alkenyl, alkynyl, aryl, arylalkyl, heteroaryl, heterocyclic, or carbocyclic, each of which may be optionally substituted;

$R_B$ is H, hal, OH, $NH_2$, $NHR_3$, $NR_3R_4$, $SR_3$, haloalkyl, CN, $N_3$, $NO_2$; alkyl, alkoxy, alkenyl, alkynyl, aryl, arylalkyl, heteroaryl, heterocyclic, or carbocyclic, each of which may be optionally substituted;

or $R_A$ and $R_B$, together with the atoms to which each is attached, form a fused aryl, heteroaryl, carbocyclic or heterocyclic, each of which may be optionally substituted;

each $R_1$ is independently $NH(R_3)$, $N(R_3)(R_4)$, $N(R_3)CO(R_4)$, $N(R_3)SO_2(R_4)$, $N(R_3)SO(R_4)$, $N(R_3)SO(R_4)$, $CO_2H$, $C(O)R_3$, $C(O)OR_3$, $C(O)NH_2$, $C(O)NH(R_3)$, $C(O)N(R_3)(R_4)$, $SO_2R_3$, $SOR_3$, $SR_3$, $SO_2NR_3R_4$, $SONR_3R_4$, $OR_3$, cyano, nitro, hal, alkyl, alkenyl, alkynyl, haloalkyl, aryl, arylalkyl, alkoxy, heteroaryl, heterocyclic, or carbocyclic, each of which may be optionally substituted;

or if m is 2 or 3, then at least two of $R_1$ may together with the atoms to which each is attached, form a 5 or 6 membered carbocyclic, heterocyclic, aryl, or heteroaryl, each of which may be optionally substituted;

each $R_2$ is independently an optionally substituted alkyl, hal,

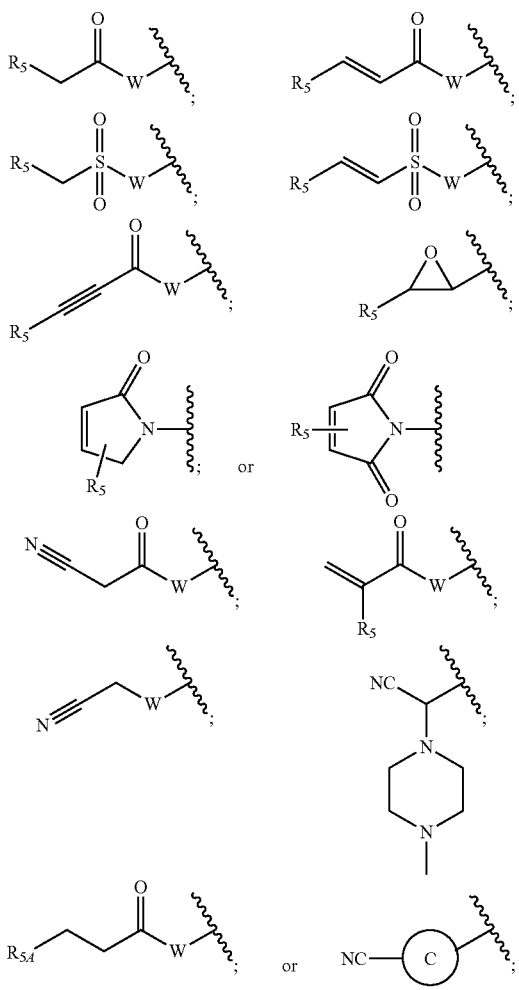

each $R_3$ and $R_4$ is independently H, alkyl, alkenyl, vinyl, heterocyclic, or carbocyclic, each of which may be optionally substituted;

each $R_5$ is independently H, alkyl, hal, or haloalkyl, each of which may be optionally substituted;

each $R_{5A}$ is independently hal or $OS(O)_pR'$, wherein p is 0, 1 or 2 and R' is alkyl or aryl;

each W is independently absent, $CH_2$, $CH_2CH_2$, $(CH_2)_3$, $(CH_2)_4$, O, S, or $NR_3$;

ring C is a 5-6 membered heterocyclic or heteroaryl having 1, 2, or 3 nitrogens;

m is 1, 2, or 3; and n is 0, 1 or 2;

wherein if $R_A$ and $R_B$ together with the atoms to which each is attached, form a fused aryl, heteroaryl, carbocyclic or heterocyclic, then one of

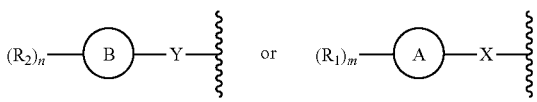

may be absent.

In certain embodiments, the invention provides a method as described above wherein the compound is a compound of formula II-a, II-b, II-c, III, IV, V, VI, or VII. In certain embodiments, the invention provides a method as described above wherein the compound is selected from the compounds in Tables 1-6. In certain embodiments, the invention provides a method as described above wherein the compound is WZ3146, WZ4002 or WZ8040.

In one embodiment the compound is an inhibitor of HER1, HER2, or HER4.

In another embodiment, the subject is administered an additional therapeutic agent.

In other embodiments, the compound and the additional therapeutic agent are administered simultaneously or sequentially.

In other aspects, the invention provides a method of treating a disease in a subject, wherein the disease is resistant to an EGFR targeted therapy, comprising administering to the subject a compound, pharmaceutically acceptable salt, ester or prodrug of formula I

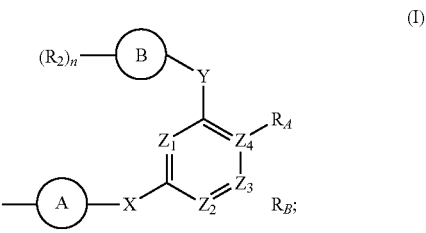

(I)

or a pharmaceutically acceptable salt, ester or prodrug thereof, wherein, $Z_1$ and $Z_2$ are each independently N or $CR_5$; $Z_3$ and $Z_4$ are each independently N or C, wherein $R_A$ and $R_B$ are absent when $Z_3$ or $Z_4$ is N; wherein at least one of $Z_1$, $Z_2$, $Z_3$ or $Z_4$ is N;

X is O, S, or $NR_6$;

Y is absent, CO, O, S, or $NR_6$;

each $R_6$ is independently H or alkyl;

ring A is aryl, heteroaryl, carbocyclic or heterocyclic; or a fused 8-14 membered bicyclic aryl, heteroaryl, carbocyclic or heterocyclic;

ring B is aryl, heteroaryl, carbocyclic or heterocyclic; or a fused 8-14 membered bicyclic aryl, heteroaryl, carbocyclic or heterocyclic;

$R_A$ is H, hal, OH, $NH_2$, $NHR_3$, $NR_3R_4$, $SR_3$, haloalkyl, CN, $N_3$, $NO_2$; alkyl, alkoxy, alkenyl, alkynyl, aryl, arylalkyl, heteroaryl, heterocyclic, or carbocyclic, each of which may be optionally substituted;

$R_B$ is H, hal, OH, $NH_2$, $NHR_3$, $NR_3R_4$, $SR_3$, haloalkyl, CN, $N_3$, $NO_2$; alkyl, alkoxy, alkenyl, alkynyl, aryl, arylalkyl, heteroaryl, heterocyclic, or carbocyclic, each of which may be optionally substituted;

or $R_A$ and $R_B$, together with the atoms to which each is attached, form a fused aryl, heteroaryl, carbocyclic or heterocyclic, each of which may be optionally substituted;

each $R_1$ is independently $NH(R_3)$, $N(R_3)(R_4)$, $N(R_3)CO(R_4)$, $N(R_3)SO_2(R_4)$, $N(R_3)SO(R_4)$, $N(R_3)SO(R_4)$, $CO_2H$, $C(O)R_3$, $C(O)OR_3$, $C(O)NH_2$, $C(O)NH(R_3)$, $C(O)N(R_3)(R_4)$, $SO_2R_3$, $SOR_3$, $SR_3$, $SO_2NR_3R_4$, $SONR_3R_4$, $OR_3$, cyano, nitro, hal, alkyl, alkenyl, alkynyl, haloalkyl, aryl, arylalkyl, alkoxy, heteroaryl, heterocyclic, or carbocyclic, each of which may be optionally substituted;

or if m is 2 or 3, then at least two of $R_1$ may together with the atoms to which each is attached, form a 5 or 6 membered carbocyclic, heterocyclic, aryl, or heteroaryl, each of which may be optionally substituted;

each $R_2$ is independently an optionally substituted alkyl, hal,

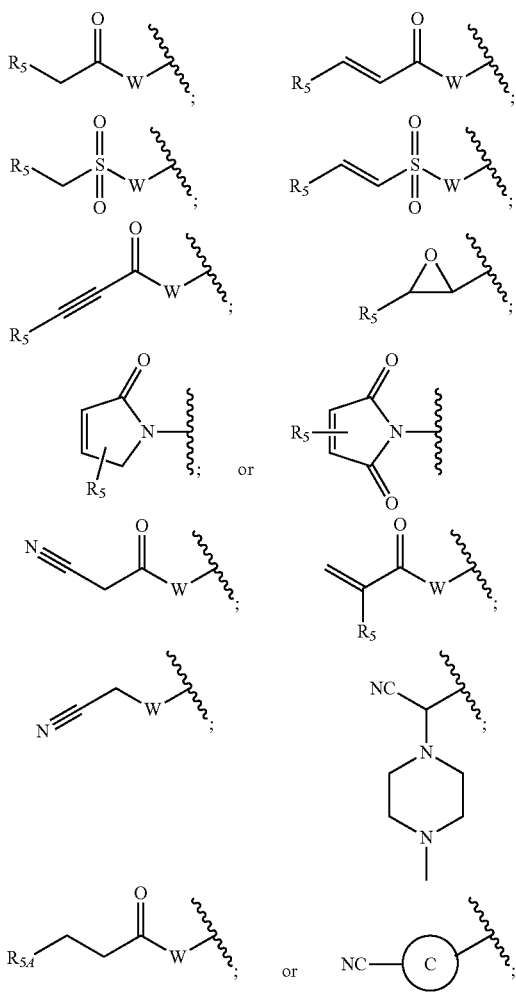

each $R_3$ and $R_4$ is independently H, alkyl, alkenyl, vinyl, heterocyclic, or carbocyclic, each of which may be optionally substituted;

each $R_5$ is independently H, alkyl, hal, or haloalkyl, each of which may be optionally substituted;

each $R_{5A}$ is independently hal or $OS(O)_pR'$, wherein p is 0, 1 or 2 and R' is alkyl or aryl;

each W is independently absent, $CH_2$, $CH_2CH_2$, $(CH_2)_3$, $(CH_2)_4$, O, S, or $NR_3$;

ring C is a 5-6 membered heterocyclic or heteroaryl having 1, 2, or 3 nitrogens;

m is 1, 2, or 3; and n is 0, 1 or 2;

wherein if $R_A$ and $R_B$ together with the atoms to which each is attached, form a fused aryl, heteroaryl, carbocyclic or heterocyclic, then one of

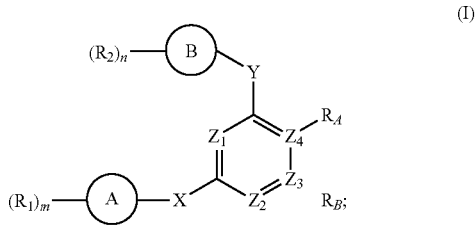

may be absent.

In certain embodiments, the invention provides a method as described above wherein the compound is a compound of formula II-a, II-b, II-c, III, IV, V, VI, or VII. In certain embodiments, the invention provides a method as described above wherein the compound is selected from the compounds in Tables 1-6. In certain embodiments, the invention provides a method as described above wherein the compound is WZ3146, WZ4002 or WZ8040.

In one embodiment, the EGFR targeted therapy comprises treatment with gefitinib, erlotinib, lapatinib, XL-647, HKI-272, BIBW2992, AV-412, CI-1033, PF00299804, BMS 690514, cetuximab, panitumumab, or matuzumab.

In another embodiment, the disease comprises an EGFR mutation.

In a further embodiment, the EGFR mutation is an EGFR T790M, T854A or D761Y resistance mutation.

In another embodiment the disease is cancer. In a further embodiment, the disease is lung cancer, colon cancer, breast cancer, prostate cancer, liver cancer, pancreas cancer, brain cancer, kidney cancer, ovarian cancer, stomach cancer, skin cancer, bone cancer, gastric cancer, breast cancer, pancreatic cancer, glioma, glioblastoma, hepatocellular carcinoma, papillary renal carcinoma, head and neck squamous cell carcinoma, leukemias, lymphomas, myelomas, or solid tumors.

In another aspect, the invention provides a method of treating cancer in a subject, wherein the cancer comprises EGFR activated tumors, comprising administering to the subject a compound, pharmaceutically acceptable salt, ester or prodrug of formula I (I)

or a pharmaceutically acceptable salt, ester or prodrug thereof, wherein, $Z_1$ and $Z_2$ are each independently N or $CR_5$; $Z_3$ and $Z_4$ are each independently N or C, wherein $R_A$ and $R_B$ are absent when $Z_3$ or $Z_4$ is N; wherein at least one of $Z_1$, $Z_2$, $Z_3$ or $Z_4$ is N;

X is O, S, or $NR_6$;

Y is absent, CO, O, S, or $NR_6$;

each $R_6$ is independently H or alkyl;

ring A is aryl, heteroaryl, carbocyclic or heterocyclic; or a fused 8-14 membered bicyclic aryl, heteroaryl, carbocyclic or heterocyclic;

ring B is aryl, heteroaryl, carbocyclic or heterocyclic; or a fused 8-14 membered bicyclic aryl, heteroaryl, carbocyclic or heterocyclic;

$R_A$ is H, hal, OH, $NH_2$, $NHR_3$, $NR_3R_4$, $SR_3$, haloalkyl, CN, $N_3$, $NO_2$; alkyl, alkoxy, alkenyl, alkynyl, aryl, arylalkyl, heteroaryl, heterocyclic, or carbocyclic, each of which may be optionally substituted;

$R_B$ is H, hal, OH, $NH_2$, $NHR_3$, $NR_3R_4$, $SR_3$, haloalkyl, CN, $N_3$, $NO_2$; alkyl, alkoxy, alkenyl, alkynyl, aryl, arylalkyl, heteroaryl, heterocyclic, or carbocyclic, each of which may be optionally substituted;

or $R_A$ and $R_B$, together with the atoms to which each is attached, form a fused aryl, heteroaryl, carbocyclic or heterocyclic, each of which may be optionally substituted;

each $R_1$ is independently $NH(R_3)$, $N(R_3)(R_4)$, $N(R_3)CO(R_4)$, $N(R_3)SO_2(R_4)$, $N(R_3)SO(R_4)$, $N(R_3)SO(R_4)$, $CO_2H$, $C(O)R_3$, $C(O)OR_3$, $C(O)NH_2$, $C(O)NH(R_3)$, $C(O)N(R_3)(R_4)$, $SO_2R_3$, $SOR_3$, $SR_3$, $SO_2NR_3R_4$, $SONR_3R_4$, $OR_3$, cyano, nitro, hal, alkyl, alkenyl, alkynyl, haloalkyl, aryl, arylalkyl, alkoxy, heteroaryl, heterocyclic, or carbocyclic, each of which may be optionally substituted;

or if m is 2 or 3, then at least two of $R_1$ may together with the atoms to which each is attached, form a 5 or 6 membered carbocyclic, heterocyclic, aryl, or heteroaryl, each of which may be optionally substituted;

each $R_2$ is independently an optionally substituted alkyl, hal,

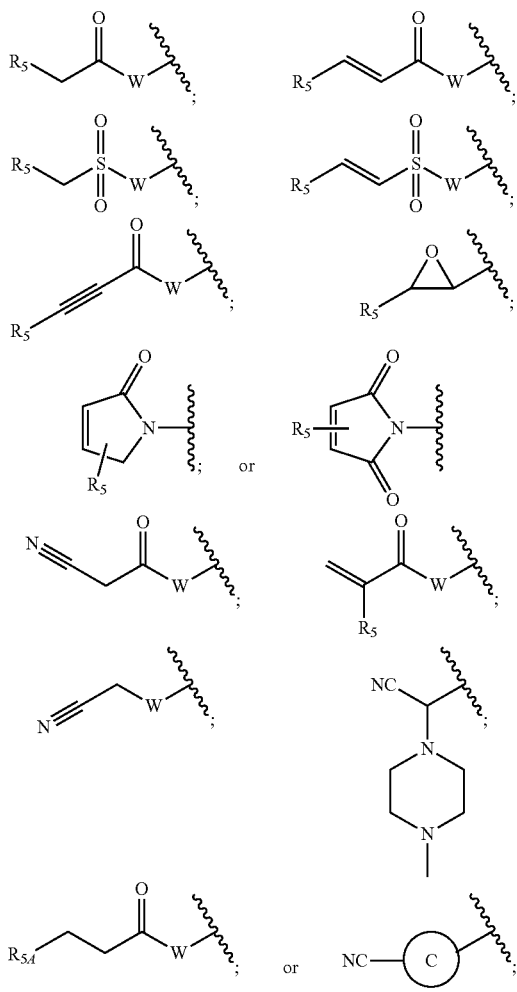

each $R_3$ and $R_4$ is independently H, alkyl, alkenyl, vinyl, heterocyclic, or carbocyclic, each of which may be optionally substituted;

each $R_5$ is independently H, alkyl, hal, or haloalkyl, each of which may be optionally substituted;

each $R_{5A}$ is independently hal or $OS(O)_pR'$, wherein p is 0, 1 or 2 and R' is alkyl or aryl;

each W is independently absent, $CH_2$, $CH_2CH_2$, $(CH_2)_3$, $(CH_2)_4$, O, S, or $NR_3$;

ring C is a 5-6 membered heterocyclic or heteroaryl having 1, 2, or 3 nitrogens;

m is 1, 2, or 3; and
n is 0, 1 or 2;

wherein if $R_A$ and $R_B$ together with the atoms to which each is attached, form a fused aryl, heteroaryl, carbocyclic or heterocyclic, then one of

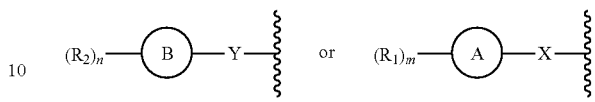

may be absent.

In certain embodiments, the invention provides a method as described above wherein the compound is a compound of formula II-a, II-b, II-c, III, IV, V, VI, or VII. In certain embodiments, the invention provides a method as described above wherein the compound is selected from the compounds in Tables 1-6. In certain embodiments, the invention provides a method as described above wherein the compound is WZ3146, WZ4002 or WZ8040.

In certain embodiments, the EGFR activation is selected from mutation of EGFR, amplification of EGFR, expression of EGFR, and ligand mediated activation of EGFR.

In a further embodiment, the mutation of EGFR is located at G719S, G719C, G719A, L858R, L861Q, an exon 19 deletion mutation or an exon 20 insertion mutation.

In certain embodiments, the disease is lung cancer, colon cancer, breast cancer, prostate cancer, liver cancer, pancreas cancer, brain cancer, kidney cancer, ovarian cancer, stomach cancer, skin cancer, bone cancer, gastric cancer, breast cancer, pancreatic cancer, glioma, glioblastoma, hepatocellular carcinoma, papillary renal carcinoma, head and neck squamous cell carcinoma, leukemias, lymphomas, myelomas, or solid tumors.

In another aspect, the invention provides a method of treating cancer in a subject, wherein the subject is identified as being in need of EGFR inhibition for the treatment of cancer, comprising administering to the subject a compound, pharmaceutically acceptable salt, ester or prodrug of formula I

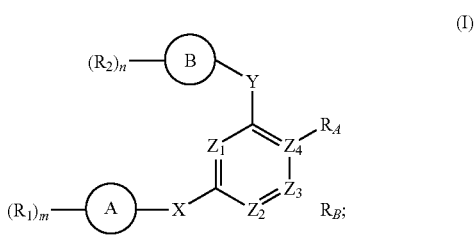

(I)

or a pharmaceutically acceptable salt, ester or prodrug thereof, wherein, $Z_1$ and $Z_2$ are each independently N or $CR_5$; $Z_3$ and $Z_4$ are each independently N or C, wherein $R_A$ and $R_B$ are absent when $Z_3$ or $Z_4$ is N; wherein at least one of $Z_1$, $Z_2$, $Z_3$ or $Z_4$ is N;

X is O, S, or $NR_6$;

Y is absent, CO, O, S, or $NR_6$;

each $R_6$ is independently H or alkyl;

ring A is aryl, heteroaryl, carbocyclic or heterocyclic; or a fused 8-14 membered bicyclic aryl, heteroaryl, carbocyclic or heterocyclic;

ring B is aryl, heteroaryl, carbocyclic or heterocyclic; or a fused 8-14 membered bicyclic aryl, heteroaryl, carbocyclic or heterocyclic;

$R_A$ is H, hal, OH, $NH_2$, $NHR_3$, $NR_3R_4$, $SR_3$, haloalkyl, CN, $N_3$, $NO_2$; alkyl, alkoxy, alkenyl, alkynyl, aryl, arylalkyl, heteroaryl, heterocyclic, or carbocyclic, each of which may be optionally substituted;

$R_B$ is H, hal, OH, $NH_2$, $NHR_3$, $NR_3R_4$, $SR_3$, haloalkyl, CN, $N_3$, $NO_2$; alkyl, alkoxy, alkenyl, alkynyl, aryl, arylalkyl, heteroaryl, heterocyclic, or carbocyclic, each of which may be optionally substituted;

or $R_A$ and $R_B$, together with the atoms to which each is attached, form a fused aryl, heteroaryl, carbocyclic or heterocyclic, each of which may be optionally substituted;

each $R_1$ is independently $NH(R_3)$, $N(R_3)(R_4)$, $N(R_3)CO(R_4)$, $N(R_3)SO_2(R_4)$, $N(R_3)SO(R_4)$, $N(R_3)SO(R_4)$, $CO_2H$, $C(O)R_3$, $C(O)OR_3$, $C(O)NH_2$, $C(O)NH(R_3)$, $C(O)N(R_3)(R_4)$, $SO_2R_3$, $SOR_3$, $SR_3$, $SO_2NR_3R_4$, $SONR_3R_4$, $OR_3$, cyano, nitro, hal, alkyl, alkenyl, alkynyl, haloalkyl, aryl, arylalkyl, alkoxy, heteroaryl, heterocyclic, or carbocyclic, each of which may be optionally substituted;

or if m is 2 or 3, then at least two of $R_1$ may together with the atoms to which each is attached, form a 5 or 6 membered carbocyclic, heterocyclic, aryl, or heteroaryl, each of which may be optionally substituted;

each $R_2$ is independently an optionally substituted alkyl, hal,

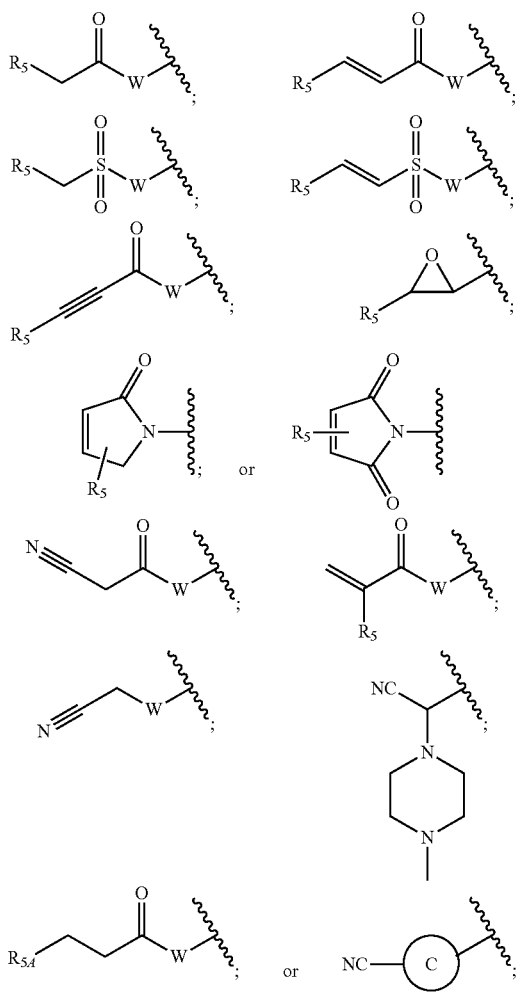

each $R_3$ and $R_4$ is independently H, alkyl, alkenyl, vinyl, heterocyclic, or carbocyclic, each of which may be optionally substituted;

each $R_5$ is independently H, alkyl, hal, or haloalkyl, each of which may be optionally substituted;

each $R_{5A}$ is independently hal or $OS(O)_pR'$, wherein p is 0, 1 or 2 and R' is alkyl or aryl;

each W is independently absent, $CH_2$, $CH_2CH_2$, $(CH_2)_3$, $(CH_2)_4$, O, S, or $NR_3$;

ring C is a 5-6 membered heterocyclic or heteroaryl having 1, 2, or 3 nitrogens;

m is 1, 2, or 3; and n is 0, 1 or 2;

wherein if $R_A$ and $R_B$ together with the atoms to which each is attached, form a fused aryl, heteroaryl, carbocyclic or heterocyclic, then one of

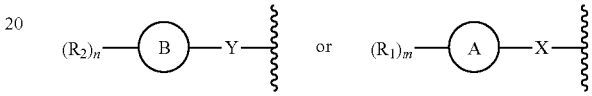

may be absent.

In certain embodiments, the invention provides a method as described above wherein the compound is a compound of formula II-a, II-b, II-c, III, IV, V, VI, or VII. In certain embodiments, the invention provides a method as described above wherein the compound is selected from the compounds in Tables 1-6. In certain embodiments, the invention provides a method as described above wherein the compound is WZ3146, WZ4002 or WZ8040.

In certain embodiments, the subject is identified as being in need of EGFR inhibition is resistant to gefitinib or erlotinib. In certain embodiments, a diagnostic test is performed to determine if the subject has an activating mutation in EGFR. In certain embodiments, a diagnostic test is performed to determine if the subject has an EGFR harboring an activating and a drug resistance mutation. Activating mutations comprise without limitation L858R, G719S, G719C, G719A, L861Q, a deletion in exon 19 and/or an insertion in exon 20. Drug-resistant EGFR mutants can have without limitation a drug resistance mutation comprising T790M, T854A or D761Y. The diagnostic test can comprise sequencing, pyrosequencing, PCR, RT-PCR, or similar analysis techniques known to those of skill in the art that can detect nucleotide sequences.

In other aspects, the invention provides a method of treating cancer in a subject, wherein the cancer comprises ERBB2 activated tumors, comprising administering to the subject a compound, pharmaceutically acceptable salt, ester or prodrug of formula I

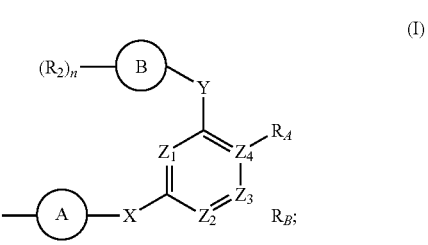

(I)

or a pharmaceutically acceptable salt, ester or prodrug thereof, wherein, $Z_1$ and $Z_2$ are each independently N or $CR_5$; $Z_3$ and $Z_4$ are each independently N or C, wherein $R_A$ and $R_B$ are absent when $Z_3$ or $Z_4$ is N; wherein at least one of $Z_1$, $Z_2$, $Z_3$ or $Z_4$ is N;

X is O, S, or $NR_6$;

Y is absent, CO, O, S, or $NR_6$;

each $R_6$ is independently H or alkyl;

ring A is aryl, heteroaryl, carbocyclic or heterocyclic; or a fused 8-14 membered bicyclic aryl, heteroaryl, carbocyclic or heterocyclic;

ring B is aryl, heteroaryl, carbocyclic or heterocyclic; or a fused 8-14 membered bicyclic aryl, heteroaryl, carbocyclic or heterocyclic;

$R_A$ is H, hal, OH, $NH_2$, $NHR_3$, $NR_3R_4$, $SR_3$, haloalkyl, CN, $N_3$, $NO_2$; alkyl, alkoxy, alkenyl, alkynyl, aryl, arylalkyl, heteroaryl, heterocyclic, or carbocyclic, each of which may be optionally substituted;

$R_B$ is H, hal, OH, $NH_2$, $NHR_3$, $NR_3R_4$, $SR_3$, haloalkyl, CN, $N_3$, $NO_2$; alkyl, alkoxy, alkenyl, alkynyl, aryl, arylalkyl, heteroaryl, heterocyclic, or carbocyclic, each of which may be optionally substituted;

or $R_A$ and $R_B$, together with the atoms to which each is attached, form a fused aryl, heteroaryl, carbocyclic or heterocyclic, each of which may be optionally substituted;

each $R_1$ is independently $NH(R_3)$, $N(R_3)(R_4)$, $N(R_3)CO(R_4)$, $N(R_3)SO_2(R_4)$, $N(R_3)SO(R_4)$, $N(R_3)SO(R_4)$, $CO_2H$, $C(O)R_3$, $C(O)OR_3$, $C(O)NH_2$, $C(O)NH(R_3)$, $C(O)N(R_3)(R_4)$, $SO_2R_3$, $SOR_3$, $SR_3$, $SO_2NR_3R_4$, $SONR_3R_4$, $OR_3$, cyano, nitro, hal, alkyl, alkenyl, alkynyl, haloalkyl, aryl, arylalkyl, alkoxy, heteroaryl, heterocyclic, or carbocyclic, each of which may be optionally substituted;

or if m is 2 or 3, then at least two of $R_1$ may together with the atoms to which each is attached, form a 5 or 6 membered carbocyclic, heterocyclic, aryl, or heteroaryl, each of which may be optionally substituted;

each $R_2$ is independently an optionally substituted alkyl, hal,

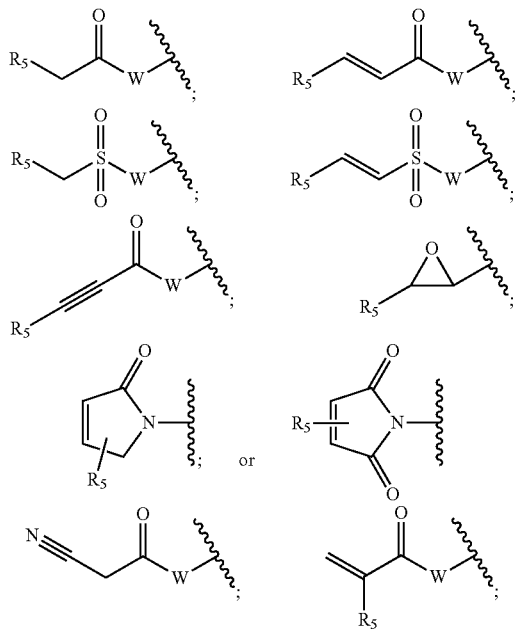

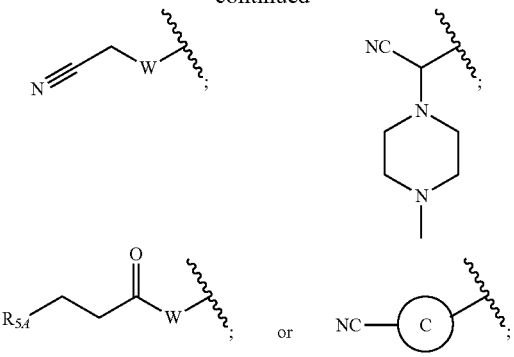

each $R_3$ and $R_4$ is independently H, alkyl, alkenyl, vinyl, heterocyclic, or carbocyclic, each of which may be optionally substituted;

each $R_5$ is independently H, alkyl, hal, or haloalkyl, each of which may be optionally substituted;

each $R_{5A}$ is independently hal or $OS(O)_pR'$, wherein p is 0, 1 or 2 and R' is alkyl or aryl;

each W is independently absent, $CH_2$, $CH_2CH_2$, $(CH_2)_3$, $(CH_2)_4$, O, S, or $NR_3$;

ring C is a 5-6 membered heterocyclic or heteroaryl having 1, 2, or 3 nitrogens;

m is 1, 2, or 3; and n is 0, 1 or 2;

wherein if $R_A$ and $R_B$ together with the atoms to which each is attached, form a fused aryl, heteroaryl, carbocyclic or heterocyclic, then one of

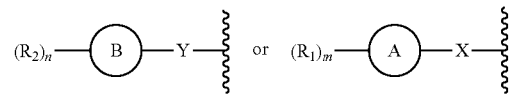

may be absent.

In certain embodiments, the invention provides a method as described above wherein the compound is a compound of formula II-a, II-b, II-c, III, IV, V, VI, or VII. In certain embodiments, the invention provides a method as described above wherein the compound is selected from the compounds in Tables 1-6. In certain embodiments, the invention provides a method as described above wherein the compound is WZ3146, WZ4002 or WZ8040.

In certain embodiments, the ERBB2 activation is selected from mutation of ERBB2, expression of ERBB2 and amplification of ERBB2.

In a further embodiment, the mutation is a mutation in exon 20 of ERBB2.

In further embodiments, the disease is lung cancer, colon cancer, breast cancer, prostate cancer, liver cancer, pancreas cancer, brain cancer, kidney cancer, ovarian cancer, stomach cancer, skin cancer, bone cancer, gastric cancer, breast cancer, pancreatic cancer, glioma, glioblastoma, hepatocellular carcinoma, papillary renal carcinoma, head and neck squamous cell carcinoma, leukemias, lymphomas, myelomas, or solid tumors.

In another aspect, the invention provides a method of treating cancer in a subject, wherein the subject is identified as being in need of ERBB2 inhibition for the treatment of cancer, comprising administering to the subject a compound, pharmaceutically acceptable salt, ester or prodrug of formula I

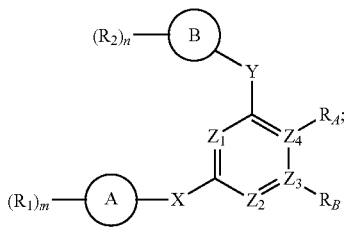

(I)

or a pharmaceutically acceptable salt, ester or prodrug thereof,
wherein, $Z_1$ and $Z_2$ are each independently N or $CR_5$; $Z_3$ and $Z_4$ are each independently N or C, wherein $R_A$ and $R_B$ are absent when $Z_3$ or $Z_4$ is N; wherein at least one of $Z_1$, $Z_2$, $Z_3$ or $Z_4$ is N;

X is O, S, or $NR_6$;

Y is absent, CO, O, S, or $NR_6$;

each $R_6$ is independently H or alkyl;

ring A is aryl, heteroaryl, carbocyclic or heterocyclic; or a fused 8-14 membered bicyclic aryl, heteroaryl, carbocyclic or heterocyclic;

ring B is aryl, heteroaryl, carbocyclic or heterocyclic; or a fused 8-14 membered bicyclic aryl, heteroaryl, carbocyclic or heterocyclic;

$R_A$ is H, hal, OH, $NH_2$, $NHR_3$, $NR_3R_4$, $SR_3$, haloalkyl, CN, $N_3$, $NO_2$; alkyl, alkoxy, alkenyl, alkynyl, aryl, arylalkyl, heteroaryl, heterocyclic, or carbocyclic, each of which may be optionally substituted;

$R_B$ is H, hal, OH, $NH_2$, $NHR_3$, $NR_3R_4$, $SR_3$, haloalkyl, CN, $N_3$, $NO_2$; alkyl, alkoxy, alkenyl, alkynyl, aryl, arylalkyl, heteroaryl, heterocyclic, or carbocyclic, each of which may be optionally substituted;

or $R_A$ and $R_B$, together with the atoms to which each is attached, form a fused aryl, heteroaryl, carbocyclic or heterocyclic, each of which may be optionally substituted;

each $R_1$ is independently $NH(R_3)$, $N(R_3)(R_4)$, $N(R_3)CO(R_4)$, $N(R_3)SO_2(R_4)$, $N(R_3)SO(R_4)$, $N(R_3)SO(R_4)$, $CO_2H$, $C(O)R_3$, $C(O)OR_3$, $C(O)NH_2$, $C(O)NH(R_3)$, $C(O)N(R_3)(R_4)$, $SO_2R_3$, $SOR_3$, $SR_3$, $SO_2NR_3R_4$, $SONR_3R_4$, $OR_3$, cyano, nitro, hal, alkyl, alkenyl, alkynyl, haloalkyl, aryl, arylalkyl, alkoxy, heteroaryl, heterocyclic, or carbocyclic, each of which may be optionally substituted;

or if m is 2 or 3, then at least two of $R_1$ may together with the atoms to which each is attached, form a 5 or 6 membered carbocyclic, heterocyclic, aryl, or heteroaryl, each of which may be optionally substituted;

each $R_2$ is independently an optionally substituted alkyl, hal,

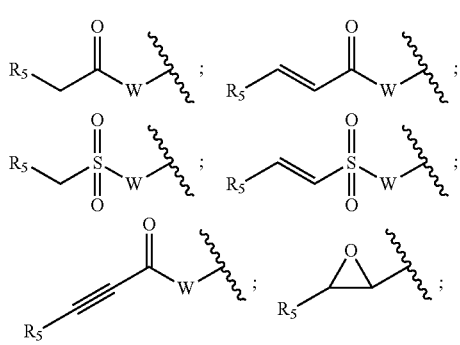

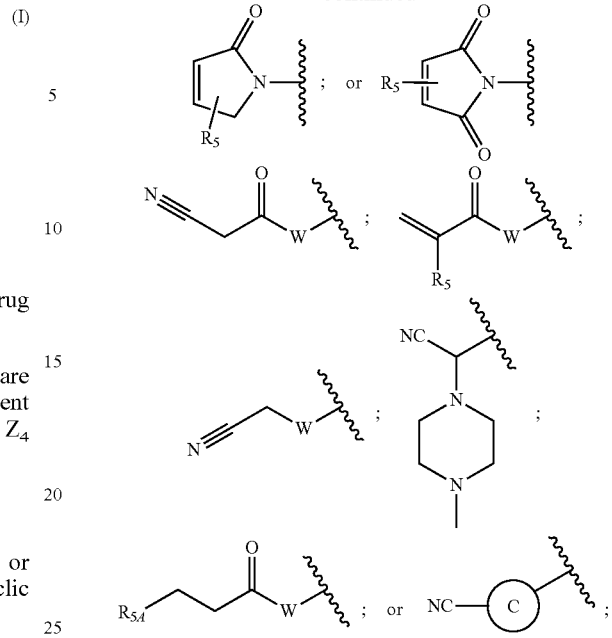

each $R_3$ and $R_4$ is independently H, alkyl, alkenyl, vinyl, heterocyclic, or carbocyclic, each of which may be optionally substituted;

each $R_5$ is independently H, alkyl, hal, or haloalkyl, each of which may be optionally substituted;

each $R_{5A}$ is independently hal or $OS(O)_pR'$, wherein p is 0, 1 or 2 and R' is alkyl or aryl;

each W is independently absent, $CH_2$, $CH_2CH_2$, $(CH_2)_3$, $(CH_2)_4$, O, S, or $NR_3$;

ring C is a 5-6 membered heterocyclic or heteroaryl having 1, 2, or 3 nitrogens;

m is 1, 2, or 3; and n is 0, 1 or 2;

wherein if $R_A$ and $R_B$ together with the atoms to which each is attached, form a fused aryl, heteroaryl, carbocyclic or heterocyclic, then one of

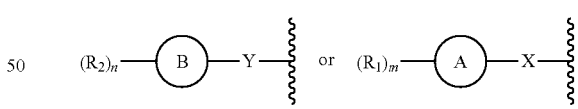

may be absent.

In certain embodiments, the invention provides a method as described above wherein the compound is a compound of formula II-a, II-b, II-c, III, IV, V, VI, or VII. In certain embodiments, the invention provides a method as described above wherein the compound is selected from the compounds in Tables 1-6. In certain embodiments, the invention provides a method as described above wherein the compound is WZ3146, WZ4002 or WZ8040.

The invention also provides a method of preventing resistance to gefitinib or erlotinib in a disease, comprising administering to a subject a compound, pharmaceutically acceptable salt, ester or prodrug of formula I

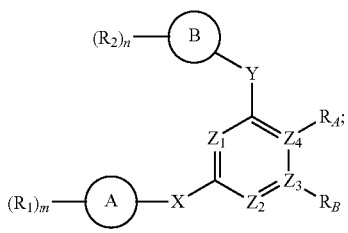

(I)

or a pharmaceutically acceptable salt, ester or prodrug thereof,
wherein,
$Z_1$ and $Z_2$ are each independently N or $CR_5$; $Z_3$ and $Z_4$ are each independently N or C, wherein $R_A$ and $R_B$ are absent when $Z_3$ or $Z_4$ is N; wherein at least one of $Z_1$, $Z_2$, $Z_3$ or $Z_4$ is N;
X is O, S, or $NR_6$;
Y is absent, CO, O, S, or $NR_6$;
each $R_6$ is independently H or alkyl;
ring A is aryl, heteroaryl, carbocyclic or heterocyclic; or a fused 8-14 membered bicyclic aryl, heteroaryl, carbocyclic or heterocyclic;
ring B is aryl, heteroaryl, carbocyclic or heterocyclic; or a fused 8-14 membered bicyclic aryl, heteroaryl, carbocyclic or heterocyclic;
$R_A$ is H, hal, OH, $NH_2$, $NHR_3$, $NR_3R_4$, $SR_3$, haloalkyl, CN, $N_3$, $NO_2$; alkyl, alkoxy, alkenyl, alkynyl, aryl, arylalkyl, heteroaryl, heterocyclic, or carbocyclic, each of which may be optionally substituted;
$R_B$ is H, hal, OH, $NH_2$, $NHR_3$, $NR_3R_4$, $SR_3$, haloalkyl, CN, $N_3$, $NO_2$; alkyl, alkoxy, alkenyl, alkynyl, aryl, arylalkyl, heteroaryl, heterocyclic, or carbocyclic, each of which may be optionally substituted;
or $R_A$ and $R_B$, together with the atoms to which each is attached, form a fused aryl, heteroaryl, carbocyclic or heterocyclic, each of which may be optionally substituted;
each $R_1$ is independently $NH(R_3)$, $N(R_3)(R_4)$, $N(R_3)CO(R_4)$, $N(R_3)SO_2(R_4)$, $N(R_3)SO(R_4)$, $N(R_3)SO(R_4)$, $CO_2H$, $C(O)R_3$, $C(O)OR_3$, $C(O)NH_2$, $C(O)NH(R_3)$, $C(O)N(R_3)(R_4)$, $SO_2R_3$, $SOR_3$, $SR_3$, $SO_2NR_3R_4$, $SONR_3R_4$, $OR_3$, cyano, nitro, hal, alkyl, alkenyl, alkynyl, haloalkyl, aryl, arylalkyl, alkoxy, heteroaryl, heterocyclic, or carbocyclic, each of which may be optionally substituted;
or if m is 2 or 3, then at least two of $R_1$ may together with the atoms to which each is attached, form a 5 or 6 membered carbocyclic, heterocyclic, aryl, or heteroaryl, each of which may be optionally substituted;
each $R_2$ is independently an optionally substituted alkyl, hal,

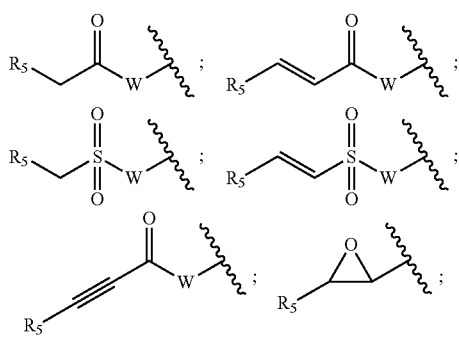

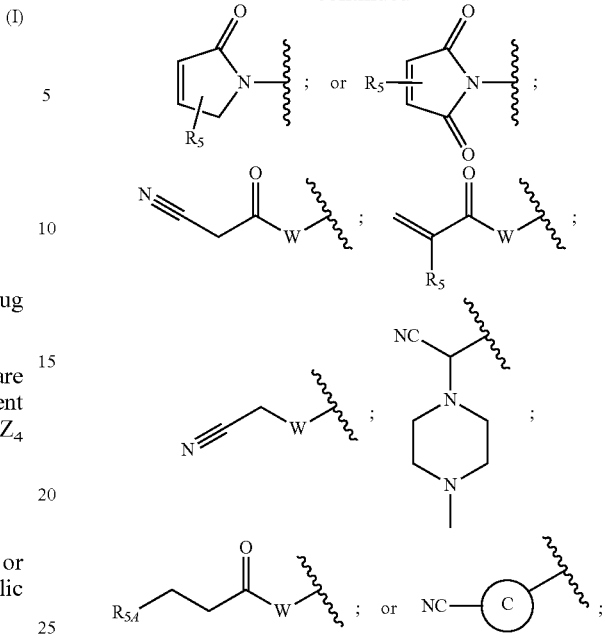

each $R_3$ and $R_4$ is independently H, alkyl, alkenyl, vinyl, heterocyclic, or carbocyclic, each of which may be optionally substituted;
each $R_5$ is independently H, alkyl, hal, or haloalkyl, each of which may be optionally substituted;
each $R_{5A}$ is independently hal or $OS(O)_pR'$, wherein p is 0, 1 or 2 and R' is alkyl or aryl;
each W is independently absent, $CH_2$, $CH_2CH_2$, $(CH_2)_3$, $(CH_2)_4$, O, S, or $NR_3$;
ring C is a 5-6 membered heterocyclic or heteroaryl having 1, 2, or 3 nitrogens;
m is 1, 2, or 3; and
n is 0, 1 or 2;
wherein if $R_A$ and $R_B$ together with the atoms to which each is attached, form a fused aryl, heteroaryl, carbocyclic or heterocyclic, then one of

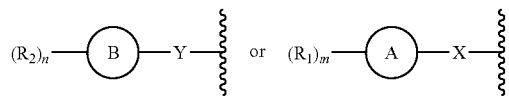

may be absent.

In certain embodiments, the invention provides a method as described above wherein the compound is a compound of formula II-a, II-b, II-c, III, IV, V, VI, or VII. In certain embodiments, the invention provides a method as described above wherein the compound is selected from the compounds in Tables 1-6. In certain embodiments, the invention provides a method as described above wherein the compound is WZ3146, WZ4002 or WZ8040.

In certain embodiments, the disease is cancer. In a further embodiment, the disease is lung cancer, colon cancer, breast cancer, prostate cancer, liver cancer, pancreas cancer, brain cancer, kidney cancer, ovarian cancer, stomach cancer, skin cancer, bone cancer, gastric cancer, breast cancer, pancreatic cancer, glioma, glioblastoma, hepatocellular carcinoma, papillary renal carcinoma, head and neck squamous cell carcinoma, leukemias, lymphomas, myelomas, or solid tumors.

In certain embodiments, the invention provides a method of treatment of any of the disorders described herein, wherein the subject is a human.

As inhibitors of Her kinases, the compounds and compositions of this invention are particularly useful for treating or lessening the severity of a disease, condition, or disorder where a protein kinase is implicated in the disease, condition, or disorder. In one aspect, the present invention provides a method for treating or lessening the severity of a disease, condition, or disorder where a protein kinase is implicated in the disease state. In another aspect, the present invention provides a method for treating or lessening the severity of a kinase disease, condition, or disorder where inhibition of enzymatic activity is implicated in the treatment of the disease. In another aspect, this invention provides a method for treating or lessening the severity of a disease, condition, or disorder with compounds that inhibit enzymatic activity by binding to the protein kinase. Another aspect provides a method for treating or lessening the severity of a kinase disease, condition, or disorder by inhibiting enzymatic activity of the kinase with a protein kinase inhibitor.

In some embodiments, said method is used to treat or prevent a condition selected from autoimmune diseases, inflammatory diseases, proliferative and hyperproliferative diseases, immunologically-mediated diseases, bone diseases, metabolic diseases, neurological and neurodegenerative diseases, cardiovascular diseases, hormone related diseases, allergies, asthma, and Alzheimer's disease. In other embodiments, said condition is selected from a proliferative disorder and a neurodegenerative disorder.

One aspect of this invention provides compounds that are useful for the treatment of diseases, disorders, and conditions characterized by excessive or abnormal cell proliferation. Such diseases include, a proliferative or hyperproliferative disease, and a neurodegenerative disease. Examples of proliferative and hyperproliferative diseases include, without limitation, cancer. The term "cancer" includes, but is not limited to, the following cancers: breast; ovary; cervix; prostate; testis, genitourinary tract; esophagus; larynx, glioblastoma; neuroblastoma; stomach; skin, keratoacanthoma; lung, epidermoid carcinoma, large cell carcinoma, small cell carcinoma, lung adenocarcinoma; bone; colon; colorectal; adenoma; pancreas, adenocarcinoma; thyroid, follicular carcinoma, undifferentiated carcinoma, papillary carcinoma; seminoma; melanoma; sarcoma; bladder carcinoma; liver carcinoma and biliary passages; kidney carcinoma; myeloid disorders; lymphoid disorders, Hodgkin's, hairy cells; buccal cavity and pharynx (oral), lip, tongue, mouth, pharynx; small intestine; colon-rectum, large intestine, rectum, brain and central nervous system; chronic myeloid leukemia (CML), and leukemia. The term "cancer" includes, but is not limited to, the following cancers: myeloma, lymphoma, or a cancer selected from gastric, renal, or and the following cancers: head and neck, oropharangeal, non-small cell lung cancer (NSCLC), endometrial, hepatocarcinoma, Non-Hodgkins lymphoma, and pulmonary.

The term "cancer" refers to any cancer caused by the proliferation of malignant neoplastic cells, such as tumors, neoplasms, carcinomas, sarcomas, leukemias, lymphomas and the like. For example, cancers include, but are not limited to, mesothelioma, leukemias and lymphomas such as cutaneous T-cell lymphomas (CTCL), noncutaneous peripheral T-cell lymphomas, lymphomas associated with human T-cell lymphotrophic virus (HTLV) such as adult T-cell leukemia/lymphoma (ATLL), B-cell lymphoma, acute non-lymphocytic leukemias, chronic lymphocytic leukemia, chronic myelogenous leukemia, acute myelogenous leukemia, lymphomas, and multiple myeloma, non-Hodgkin lymphoma, acute lymphatic leukemia (ALL), chronic lymphatic leukemia (CLL), Hodgkin's lymphoma, Burkitt lymphoma, adult T-cell leukemia lymphoma, acute-myeloid leukemia (AML), chronic myeloid leukemia (CML), or hepatocellular carcinoma. Further examples include myelodisplastic syndrome, childhood solid tumors such as brain tumors, neuroblastoma, retinoblastoma, Wilms' tumor, bone tumors, and soft-tissue sarcomas, common solid tumors of adults such as head and neck cancers (e.g., oral, laryngeal, nasopharyngeal and esophageal), genitourinary cancers (e.g., prostate, bladder, renal, uterine, ovarian, testicular), lung cancer (e.g., small-cell and non small cell), breast cancer, pancreatic cancer, melanoma and other skin cancers, stomach cancer, brain tumors, tumors related to Gorlin's syndrome (e.g., medulloblastoma, meningioma, etc.), and liver cancer. Additional exemplary forms of cancer which may be treated by the subject compounds include, but are not limited to, cancer of skeletal or smooth muscle, stomach cancer, cancer of the small intestine, rectum carcinoma, cancer of the salivary gland, endometrial cancer, adrenal cancer, anal cancer, rectal cancer, parathyroid cancer, and pituitary cancer.

Additional cancers that the compounds described herein may be useful in preventing, treating and studying are, for example, colon carcinoma, familiarly adenomatous polyposis carcinoma and hereditary non-polyposis colorectal cancer, or melanoma. Further, cancers include, but are not limited to, labial carcinoma, larynx carcinoma, hypopharynx carcinoma, tongue carcinoma, salivary gland carcinoma, gastric carcinoma, adenocarcinoma, thyroid cancer (medullary and papillary thyroid carcinoma), renal carcinoma, kidney parenchyma carcinoma, cervix carcinoma, uterine corpus carcinoma, endometrium carcinoma, chorion carcinoma, testis carcinoma, urinary carcinoma, melanoma, brain tumors such as glioblastoma, astrocytoma, meningioma, medulloblastoma and peripheral neuroectodermal tumors, gall bladder carcinoma, bronchial carcinoma, multiple myeloma, basalioma, teratoma, retinoblastoma, choroidea melanoma, seminoma, rhabdomyosarcoma, craniopharyngeoma, osteosarcoma, chondrosarcoma, myosarcoma, liposarcoma, fibrosarcoma, Ewing sarcoma, and plasmocytoma. In one aspect of the invention, the present invention provides for the use of one or more compounds of the invention in the manufacture of a medicament for the treatment of cancer, including without limitation the various types of cancer disclosed herein.

In some embodiments, the compounds of this invention are useful for treating cancer, such as colorectal, thyroid, breast, and lung cancer; and myeloproliferative disorders, such as polycythemia vera, thrombocythemia, myeloid metaplasia with myelofibrosis, chronic myelogenous leukemia, chronic myelomonocytic leukemia, hypereosinophilic syndrome, juvenile myelomonocytic leukemia, and systemic mast cell disease.

In some embodiments, the compounds of this invention are useful for treating hematopoietic disorders, in particular, acute-myelogenous leukemia (AMLi), chronic-myelogenous leukemia (CML), acute-promyelocytic leukemia, and acute lymphocytic leukemia (ALL).

This invention further embraces the treatment or prevention of cell proliferative disorders such as hyperplasias, dysplasias and pre-cancerous lesions. Dysplasia is the earliest form of pre-cancerous lesion recognizable in a biopsy by a pathologist. The subject compounds may be administered for the purpose of preventing said hyperplasias, dysplasias or pre-cancerous lesions from continuing to expand or from becoming cancerous. Examples of pre-cancerous lesions may occur in skin, esophageal tissue, breast and cervical intra-epithelial tissue.

Examples of neurodegenerative diseases include, without limitation, Adrenoleukodystrophy (ALD), Alexander's disease, Alper's disease, Alzheimer's disease, Amyotrophic lateral sclerosis (Lou Gehrig's Disease), Ataxia telangiectasia, Batten disease (also known as Spielmeyer-Vogt-Sjögren-Batten disease), Bovine spongiform encephalopathy (BSE), Canavan disease, Cockayne syndrome, Corticobasal degeneration, Creutzfeldt-Jakob disease, Familial fatal insomnia, Frontotemporal lobar degeneration, Huntington's disease, HIV-associated dementia, Kennedy's disease, Krabbe's disease, Lewy body dementia, Neuroborreliosis, Machado-Joseph disease (Spinocerebellar ataxia type 3), Multiple System Atrophy, Multiple sclerosis, Narcolepsy, Niemann Pick disease, Parkinson's disease, Pelizaeus-Merzbacher Disease, Pick's disease, Primary lateral sclerosis, Prion diseases, Progressive Supranuclear Palsy, Refsum's disease, Sandhoff disease, Schilder's disease, Subacute combined degeneration of spinal cord secondary to Pernicious Anaemia, Spielmeyer-Vogt-Sjogren-Batten disease (also known as Batten disease), Spinocerebellar ataxia (multiple types with varying characteristics), Spinal muscular atrophy, Steele-Richardson-Olszewski disease, Tabes dorsalis, and Toxic encephalopathy.

Another aspect of this invention provides a method for the treatment or lessening the severity of a disease selected from a proliferative or hyperproliferative disease, or a neurodegenerative disease, comprising administering an effective amount of a compound, or a pharmaceutically acceptable composition comprising a compound, to a subject in need thereof.

As inhibitors of Her kinases, the compounds and compositions of this invention are also useful in biological samples. One aspect of the invention relates to inhibiting protein kinase activity in a biological sample, which method comprises contacting said biological sample with a compound of the invention or a composition comprising said compound. The term "biological sample", as used herein, means an in vitro or an ex vivo sample, including, without limitation, cell cultures or extracts thereof; biopsied material obtained from a mammal or extracts thereof; and blood, saliva, urine, feces, semen, tears, or other body fluids or extracts thereof. Inhibition of protein kinase activity in a biological sample is useful for a variety of purposes that are known to one of skill in the art. Examples of such purposes include, but are not limited to, blood transfusion, organ-transplantation, and biological specimen storage.

Another aspect of this invention relates to the study of Her kinases in biological and pathological phenomena; the study of intracellular signal transduction pathways mediated by such protein kinases; and the comparative evaluation of new protein kinase inhibitors. Examples of such uses include, but are not limited to, biological assays such as enzyme assays and cell-based assays.

The activity of the compounds as Her kinase inhibitors may be assayed in vitro, in vivo or in a cell line. In vitro assays include assays that determine inhibition of either the kinase activity or ATPase activity of the activated kinase. Alternate in vitro assays quantitate the ability of the inhibitor to bind to the protein kinase and may be measured either by radiolabelling the inhibitor prior to binding, isolating the inhibitor/kinase complex and determining the amount of radiolabel bound, or by running a competition experiment where new inhibitors are incubated with the kinase bound to known radioligands. Detailed conditions for assaying a compound utilized in this invention as an inhibitor of various kinases are set forth in the Examples below.

In accordance with the foregoing, the present invention further provides a method for preventing or treating any of the diseases or disorders described above in a subject in need of such treatment, which method comprises administering to said subject a therapeutically effective amount of a compound of the invention or a pharmaceutically acceptable salt thereof. For any of the above uses, the required dosage will vary depending on the mode of administration, the particular condition to be treated and the effect desired.

Pharmaceutical Compositions

In another aspect, the invention provides a pharmaceutical composition comprising a compound of formula I, or a pharmaceutically acceptable ester, salt, or prodrug thereof, together with a pharmaceutically acceptable carrier.

Compounds of the invention can be administered as pharmaceutical compositions by any conventional route, in particular enterally, e.g., orally, e.g., in the form of tablets or capsules, or parenterally, e.g., in the form of injectable solutions or suspensions, topically, e.g., in the form of lotions, gels, ointments or creams, or in a nasal or suppository form. Pharmaceutical compositions comprising a compound of the present invention in free form or in a pharmaceutically acceptable salt form in association with at least one pharmaceutically acceptable carrier or diluent can be manufactured in a conventional manner by mixing, granulating or coating methods. For example, oral compositions can be tablets or gelatin capsules comprising the active ingredient together with a) diluents, e.g., lactose, dextrose, sucrose, mannitol, sorbitol, cellulose and/or glycine; b) lubricants, e.g., silica, talcum, stearic acid, its magnesium or calcium salt and/or polyethyleneglycol; for tablets also c) binders, e.g., magnesium aluminum silicate, starch paste, gelatin, tragacanth, methylcellulose, sodium carboxymethylcellulose and or polyvinylpyrrolidone; if desired d) disintegrants, e.g., starches, agar, alginic acid or its sodium salt, or effervescent mixtures; and/or e) absorbents, colorants, flavors and sweeteners. Injectable compositions can be aqueous isotonic solutions or suspensions, and suppositories can be prepared from fatty emulsions or suspensions. The compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances. Suitable formulations for transdermal applications include an effective amount of a compound of the present invention with a carrier. A carrier can include absorbable pharmacologically acceptable solvents to assist passage through the skin of the host. For example, transdermal devices are in the form of a bandage comprising a backing member, a reservoir containing the compound optionally with carriers, optionally a rate controlling barrier to deliver the compound to the skin of the host at a controlled and predetermined rate over a prolonged period of time, and means to secure the device to the skin. Matrix transdermal formulations may also be used. Suitable formulations for topical application, e.g., to the skin and eyes, are preferably aqueous solutions, ointments, creams or gels well-known in the art. Such may contain solubilizers, stabilizers, tonicity enhancing agents, buffers and preservatives.

Compounds of the invention can be administered in therapeutically effective amounts in combination with one or more therapeutic agents (pharmaceutical combinations). For example, synergistic effects can occur with other antiproliferative, anti-cancer, immunomodulatory or anti-inflammatory substances. Where the compounds of the invention are administered in conjunction with other therapies, dosages of the co-administered compounds will of course vary depending on the type of co-drug employed, on the specific drug employed, on the condition being treated and so forth.

Combination therapy includes the administration of the subject compounds in further combination with other biologically active ingredients (such as, but not limited to, a second and different antineoplastic agent) and non-drug therapies (such as, but not limited to, surgery or radiation treatment). For instance, the compounds of the invention can be used in combination with other pharmaceutically active compounds, preferably compounds that are able to enhance the effect of the compounds of the invention. The compounds of the invention can be administered simultaneously (as a single preparation or separate preparation) or sequentially to the other drug therapy. In general, a combination therapy envisions administration of two or more drugs during a single cycle or course of therapy.

In one aspect of the invention, the compounds may be administered in combination with one or more separate agents that modulate protein kinases involved in various disease states. Examples of such kinases may include, but are not limited to: serine/threonine specific kinases, receptor tyrosine specific kinases and non-receptor tyrosine specific kinases. Serine/threonine kinases include mitogen activated protein kinases (MAPK), meiosis specific kinase (MEK), RAF and aurora kinase. Examples of receptor kinase families include epidermal growth factor receptor (EGFR) (e.g. HER2/neu, HER3, HER4, ErbB, ErbB2, ErbB3, ErbB4, Xmrk, DER, Let23); fibroblast growth factor (FGF) receptor (e.g. FGF-R1, GFF-R2/BEK/CEK3, FGF-R3/CEK2, FGF-R4/TKF, KGF-R); hepatocyte growth/scatter factor receptor (HGFR) (e.g., MET, RON, SEA, SEX); insulin receptor (e.g. IGFI-R); Eph (e.g. CEK5, CEK8, EBK, ECK, EEK, EHK-1, EHK-2, ELK, EPH, ERK, HEK, MDK2, MDK5, SEK); Axl (e.g. Mer/Nyk, Rse); RET; and platelet-derived growth factor receptor (PDGFR) (e.g. PDGF.alpha.-R, PDG.beta.-R, CSF1-R/FMS, SCF-R/C-KIT, VEGF-R/FLT, NEK/FLK1, FLT3/FLK2/STK-1). Non-receptor tyrosine kinase families include, but are not limited to, BCR-ABL (e.g. p43.sup.abl, ARG); BTK (e.g. ITK/EMT, TEC); CSK, FAK, FPS, JAK, SRC, BMX, FER, CDK and SYK.

In another aspect of the invention, the subject compounds may be administered in combination with one or more agents that modulate non-kinase biological targets or processes. Such targets include histone deacetylases (HDAC), DNA methyltransferase (DNMT), heat shock proteins (e.g. HSP90), and proteosomes.

In a preferred embodiment, subject compounds may be combined with antineoplastic agents (e.g. small molecules, monoclonal antibodies, antisense RNA, and fusion proteins) that inhibit one or more biological targets such as Zolinza, Tarceva, Iressa, Tykerb, Gleevec, Sutent, Sprycel, Nexavar, Sorafinib, CNF2024, RG108, BMS387032, Affinitak, Avastin, Herceptin, Erbitux, AG24322, PD325901, ZD6474, PD184322, Obatodax, ABT737 and AEE788. Such combinations may enhance therapeutic efficacy over efficacy achieved by any of the agents alone and may prevent or delay the appearance of resistant mutational variants.

In certain preferred embodiments, the compounds of the invention are administered in combination with a chemotherapeutic agent. Chemotherapeutic agents encompass a wide range of therapeutic treatments in the field of oncology. These agents are administered at various stages of the disease for the purposes of shrinking tumors, destroying remaining cancer cells left over after surgery, inducing remission, maintaining remission and/or alleviating symptoms relating to the cancer or its treatment. Examples of such agents include, but are not limited to, alkylating agents such as mustard gas derivatives (Mechlorethamine, cylophosphamide, chlorambucil, melphalan, ifosfamide), ethylenimines (thiotepa, hexamethylmelanine), Alkylsulfonates (Busulfan), Hydrazines and Triazines (Altretamine, Procarbazine, Dacarbazine and Temozolomide), Nitrosoureas (Carmustine, Lomustine and Streptozocin), Ifosfamide and metal salts (Carboplatin, Cisplatin, and Oxaliplatin); plant alkaloids such as Podophyllotoxins (Etoposide and Tenisopide), Taxanes (Paclitaxel and Docetaxel), Vinca alkaloids (Vincristine, Vinblastine, Vindesine and Vinorelbine), and Camptothecan analogs (Irinotecan and Topotecan); anti-tumor antibiotics such as Chromomycins (Dactinomycin and Plicamycin), Anthracyclines (Doxorubicin, Daunorubicin, Epirubicin, Mitoxantrone, Valrubicin and Idarubicin), and miscellaneous antibiotics such as Mitomycin, Actinomycin and Bleomycin; anti-metabolites such as folic acid antagonists (Methotrexate, Pemetrexed, Raltitrexed, Aminopterin), pyrimidine antagonists (5-Fluorouracil, Floxuridine, Cytarabine, Capecitabine, and Gemcitabine), purine antagonists (6-Mercaptopurine and 6-Thioguanine) and adenosine deaminase inhibitors (Cladribine, Fludarabine, Mercaptopurine, Clofarabine, Thioguanine, Nelarabine and Pentostatin); topoisomerase inhibitors such as topoisomerase I inhibitors (Ironotecan, topotecan) and topoisomerase H inhibitors (Amsacrine, etoposide, etoposide phosphate, teniposide); monoclonal antibodies (Alemtuzumab, Gemtuzumab ozogamicin, Rituximab, Trastuzumab, Ibritumomab Tioxetan, Cetuximab, Panitumumab, Tositumomab, Bevacizumab); and miscellaneous anti-neoplastics such as ribonucleotide reductase inhibitors (Hydroxyurea); adrenocortical steroid inhibitor (Mitotane); enzymes (Asparaginase and Pegaspargase); anti-microtubule agents (Estramustine); and retinoids (Bexarotene, Isotretinoin, Tretinoin (ATRA).

In certain preferred embodiments, the compounds of the invention are administered in combination with a chemoprotective agent. Chemoprotective agents act to protect the body or minimize the side effects of chemotherapy. Examples of such agents include, but are not limited to, amfostine, mesna, and dexrazoxane.

In one aspect of the invention, the subject compounds are administered in combination with radiation therapy. Radiation is commonly delivered internally (implantation of radioactive material near cancer site) or externally from a machine that employs photon (x-ray or gamma-ray) or particle radiation. Where the combination therapy further comprises radiation treatment, the radiation treatment may be conducted at any suitable time so long as a beneficial effect from the co-action of the combination of the therapeutic agents and radiation treatment is achieved. For example, in appropriate cases, the beneficial effect is still achieved when the radiation treatment is temporally removed from the administration of the therapeutic agents, perhaps by days or even weeks.

It will be appreciated that compounds of the invention can be used in combination with an immunotherapeutic agent. One form of immunotherapy is the generation of an active systemic tumor-specific immune response of host origin by administering a vaccine composition at a site distant from the tumor. Various types of vaccines have been proposed, including isolated tumor-antigen vaccines and anti-idiotype vaccines. Another approach is to use tumor cells from the subject to be treated, or a derivative of such cells (reviewed by Schirrmacher et al. (1995) J. Cancer Res. Clin. Oncol. 121:487). In U.S. Pat. No. 5,484,596, Hanna Jr. et al. claim a method for treating a respectable carcinoma to prevent recurrence or metastases, comprising surgically removing the tumor, dispersing the cells with collagenase, irradiating the cells, and vaccinating the patient with at least three consecutive doses of about $10^7$ cells.

It will be appreciated that the compounds of the invention may advantageously be used in conjunction with one or more adjunctive therapeutic agents. Examples of suitable agents for adjunctive therapy include a $5HT_1$ agonist, such as a triptan (e.g. sumatriptan or naratriptan); an adenosine A1 agonist; an EP ligand; an NMDA modulator, such as a glycine antagonist; a sodium channel blocker (e.g. lamotrigine); a substance P antagonist (e.g. an $NK_1$ antagonist); a cannabinoid; acetaminophen or phenacetin; a 5-lipoxygenase inhibitor; a leukotriene receptor antagonist; a DMARD (e.g. methotrexate); gabapentin and related compounds; a tricyclic antidepressant (e.g. amitryptilline); a neurone stabilising antiepileptic drug; a mono-aminergic uptake inhibitor (e.g. venlafaxine); a matrix metalloproteinase inhibitor; a nitric oxide synthase (NOS) inhibitor, such as an iNOS or an nNOS inhibitor; an inhibitor of the release, or action, of tumour necrosis factor a; an antibody therapy, such as a monoclonal antibody therapy; an antiviral agent, such as a nucleoside inhibitor (e.g. lamivudine) or an immune system modulator (e.g. interferon); an opioid analgesic; a local anaesthetic; a stimulant, including caffeine; an $H_2$-antagonist (e.g. ranitidine); a proton pump inhibitor (e.g. omeprazole); an antacid (e.g. aluminium or magnesium hydroxide); an antiflatulent (e.g. simethicone); a decongestant (e.g. phenylephrine, phenylpropanolamine, pseudoephedrine, oxymetazoline, epinephrine, naphazoline, xylometazoline, propylhexedrine, or levo-desoxyephedrine); an antitussive (e.g. codeine, hydrocodone, carmiphen, carbetapentane, or dextramethorphan); a diuretic; or a sedating or non-sedating antihistamine.

The pharmaceutical compositions of the present invention comprise a therapeutically effective amount of a compound of the present invention formulated together with one or more pharmaceutically acceptable carriers. As used herein, the term "pharmaceutically acceptable carrier" means a non-toxic, inert solid, semi-solid or liquid filler, diluent, encapsulating material or formulation auxiliary of any type. The pharmaceutical compositions of this invention can be administered to humans and other animals orally, rectally, parenterally, intracisternally, intravaginally, intraperitoneally, topically (as by powders, ointments, or drops), buccally, or as an oral or nasal spray.

Liquid dosage forms for oral administration include pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

In order to prolong the effect of a drug, it is often desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid compositions of a similar type may also be employed as fillers in soft and hard-filled gelatin capsules using such excipients as lactose or milk sugar as well as high molecular weight polyethylene glycols and the like.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, eye ointments, powders and solutions are also contemplated as being within the scope of this invention.

The ointments, pastes, creams and gels may contain, in addition to an active compound of this invention, excipients such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to the compounds of this invention, excipients such as lactose, talc, silicic acid, aluminum hydroxide, calcium silicates and polyamide powder, or mixtures of these substances. Sprays can additionally contain customary propellants such as chlorofluorohydrocarbons.

Transdermal patches have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

According to the methods of treatment of the present invention, disorders are treated or prevented in a subject, such as a human or other animal, by administering to the subject a therapeutically effective amount of a compound of the invention, in such amounts and for such time as is necessary to achieve the desired result. The term "therapeutically effective amount" of a compound of the invention, as used herein, means a sufficient amount of the compound so as to decrease the symptoms of a disorder in a subject. As is well understood in the medical arts a therapeutically effective amount of a compound of this invention will be at a reasonable benefit/risk ratio applicable to any medical treatment.

In general, compounds of the invention will be administered in therapeutically effective amounts via any of the usual and acceptable modes known in the art, either singly or in combination with one or more therapeutic agents. A therapeutically effective amount may vary widely depending on the severity of the disease, the age and relative health of the subject, the potency of the compound used and other factors. In general, satisfactory results are indicated to be obtained systemically at daily dosages of from about 0.03 to 2.5 mg/kg per body weight. An indicated daily dosage in the larger mammal, e.g. humans, is in the range from about 0.5 mg to about 100 mg, conveniently administered, e.g. in divided doses up to four times a day or in retard form. Suitable unit dosage forms for oral administration comprise from ca. 1 to 50 mg active ingredient.

In certain embodiments, a therapeutic amount or dose of the compounds of the present invention may range from about 0.1 mg/Kg to about 500 mg/Kg, alternatively from about 1 to about 50 mg/Kg. In general, treatment regimens according to the present invention comprise administration to a patient in need of such treatment from about 10 mg to about 1000 mg of the compound(s) of this invention per day in single or multiple doses. Therapeutic amounts or doses will also vary depending on route of administration, as well as the possibility of co-usage with other agents.

Upon improvement of a subject's condition, a maintenance dose of a compound, composition or combination of this invention may be administered, if necessary. Subsequently, the dosage or frequency of administration, or both, may be reduced, as a function of the symptoms, to a level at which the improved condition is retained when the symptoms have been alleviated to the desired level, treatment should cease. The subject may, however, require intermittent treatment on a long-term basis upon any recurrence of disease symptoms.

It will be understood, however, that the total daily usage of the compounds and compositions of the present invention will be decided by the attending physician within the scope of sound medical judgment. The specific inhibitory dose for any particular patient will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts.

The invention also provides for a pharmaceutical combinations, e.g. a kit, comprising a) a first agent which is a compound of the invention as disclosed herein, in free form or in pharmaceutically acceptable salt form, and b) at least one co-agent. The kit can comprise instructions for its administration.

The terms "co-administration" or "combined administration" or the like as utilized herein are meant to encompass administration of the selected therapeutic agents to a single patient, and are intended to include treatment regimens in which the agents are not necessarily administered by the same route of administration or at the same time.

The term "pharmaceutical combination" as used herein means a product that results from the mixing or combining of more than one active ingredient and includes both fixed and non-fixed combinations of the active ingredients. The term "fixed combination" means that the active ingredients, e.g. a compound of the invention and a co-agent, are both administered to a patient simultaneously in the form of a single entity or dosage. The term "non-fixed combination" means that the active ingredients, e.g. a compound of the invention and a co-agent, are both administered to a patient as separate entities either simultaneously, concurrently or sequentially with no specific time limits, wherein such administration provides therapeutically effective levels of the two compounds in the body of the patient. The latter also applies to cocktail therapy, e.g. the administration of three or more active ingredients.

In certain embodiments, these compositions optionally further comprise one or more additional therapeutic agents. For example, chemotherapeutic agents or other antiproliferative agents may be combined with the compounds of this invention to treat proliferative diseases and cancer. Examples of known chemotherapeutic agents include, but are not limited to, Gleevec™, adriamycin, dexamethasone, vincristine, cyclophosphamide, fluorouracil, topotecan, taxol, interferons, and platinum derivatives.

Other examples of agents the compounds of this invention may also be combined with include, without limitation: treatments for Alzheimer's Disease such as Aricept18 and Excelon(R); treatments for Parkinson's Disease such as L-DOPA/carbidopa, entacapone, ropinrole, pramipexole, bromocriptine, pergolide, trihexephendyl, and amantadine; agents for treating Multiple Sclerosis (MS) such as beta interferon (e.g., Avonex(R) and Rebif(R)), Copaxone(R), and mitoxantrone; treatments for asthma such as albuterol and Singulair(R); agents for treating schizophrenia such as zyprexa, risperdal, seroquel, and haloperidol; anti-inflammatory agents such as corticosteroids, TNF blockers, IL-1 RA, azathioprine, cyclophosphamide, and sulfasalazine; immunomodulatory and immunosuppressive agents such as cyclosporin, tacrolimus, rapamycin, mycophenolate mofetil, interferons, corticosteroids, cyclophophamide, azathioprine, and sulfasalazine; neurotrophic factors such as acetylcholinesterase inhibitors, MAO inhibitors, interferons, anti-convulsants, ion channel blockers, riluzole, and antiparkinsonian agents; agents for treating cardiovascular disease such as beta-blockers, ACE inhibitors, diuretics, nitrates, calcium channel blockers, and statins; agents for treating liver disease such as corticosteroids, cholestyramine, interferons, and anti-viral agents; agents for treating blood disorders such as corticosteroids, antileukemic agents, and growth factors; and agents for treating immunodeficiency disorders such as gamma globulin. Some examples of materials which can serve as pharmaceutically acceptable carriers include, but are not limited to, ion exchangers, alumina, aluminum stearate, lecithin, serum proteins, such as human serum albumin, buffer substances such as phosphates, glycine, sorbic acid, or potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, polyacrylates, waxes, polyethylene-polyoxypropylene-block polymers, wool fat, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes, oils such as peanut oil, cottonseed oil; safflower oil; sesame oil; olive oil; corn oil and soybean oil; glycols; such a propylene glycol or polyethylene glycol; esters such as ethyl oleate and ethyl laurate, agar; buffering agents such as magnesium hydroxide and aluminum hydroxide; alginic acid; pyrogen-free water, isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator. The protein kinase inhibitors or pharmaceutical salts thereof may be formulated into pharmaceutical compositions for administration to animals or humans. These pharmaceutical compositions, which comprise an amount of the protein inhibitor effective to treat or prevent a protein kinase-mediated condition and a pharmaceutically acceptable carrier, are another embodiment of the present invention.

In another aspect, the invention provides a kit comprising a compound capable of inhibiting kinase activity selected from one or more compounds of formula I, and instructions for use in treating cancer. In certain embodiments, the kit further comprises components for performing a test to determine whether a subject has activating and/or drug resistance mutations in EGFR.

EXAMPLES

The compounds and processes of the present invention will be better understood in connection with the following examples, which are intended as an illustration only and not to limit the scope of the invention. Various changes and modifications to the disclosed embodiments will be apparent to those skilled in the art and such changes and modifications including, without limitation, those relating to the chemical structures, substituents, derivatives, formulations and/or methods of the invention may be made without departing from the spirit of the invention and the scope of the appended claims.

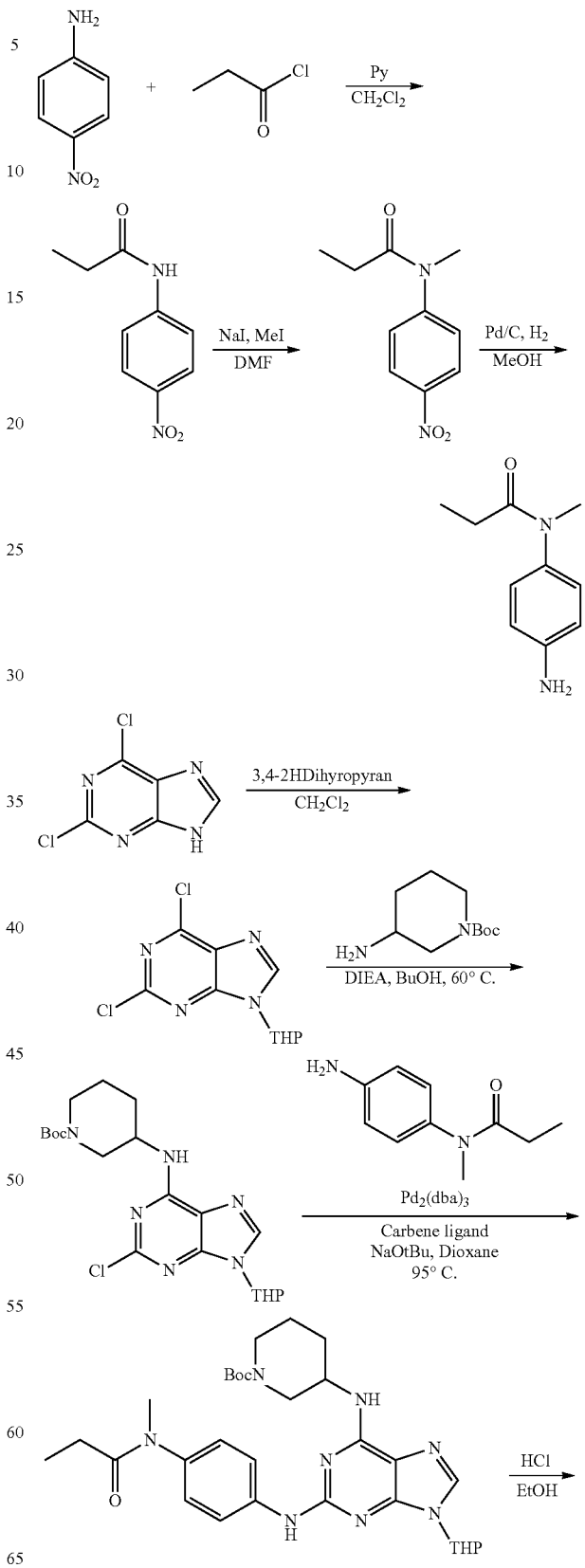

Scheme 1

127

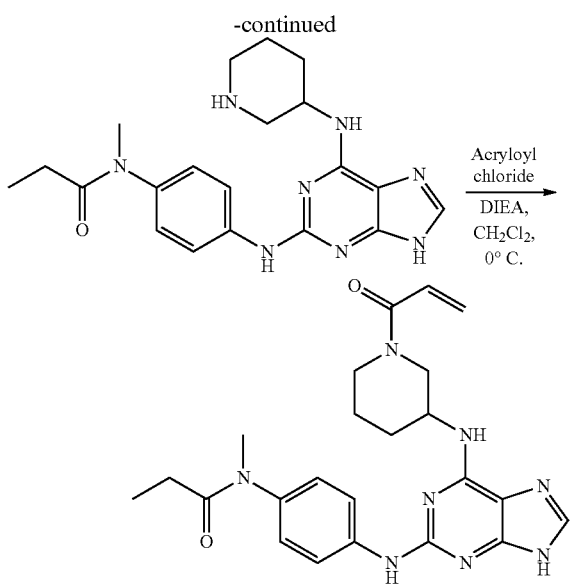

Example 1

Synthesis of N-(4-(6-(1-acryloylpiperidin-3-ylamino)-9H-purin-2-ylamino)phenyl)-N-methylpropionamide

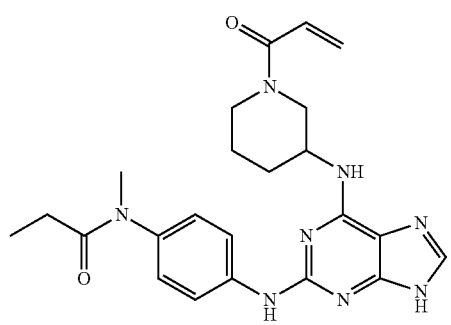 [SMILES: C=CC(=O)N1CCCC(Nc2nc(Nc3ccc(N(C)C(=O)CC)cc3)nc3[nH]cnc23)C1]

Step 1: Synthesis of N-(4-nitrophenyl)propionamide

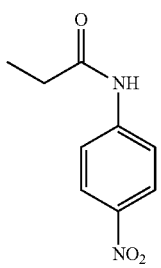

Propionyl chloride was added to the solution of 4-nitroaniline (1.0 g, 7.25 mmol), DMAP (40 mg), and pyridine (0.70 mL) in CH$_2$Cl$_2$ (30 ml) at 0° C. The reaction was stirred for 4 hours. The solution was washed with an aqueous 0.1N HCl, H$_2$O, dried with Na$_2$SO$_4$, concentrated to afford yellow solid 1.37 g. $^1$H NMR 600 MHz (DMSO-d$_6$) δ 10.21

128

(s, 1H), 8.10 (d, J=9.0 Hz, 2H), 7.90 (d, J=9.0 Hz, 2H), 2.38 (t, J=7.2 Hz, 2H), 1.04 (q, J=7.8 Hz, 7.2 Hz, 3H).

Step 2: Synthesis of N-methyl-N-(4-nitrophenyl)propionamide

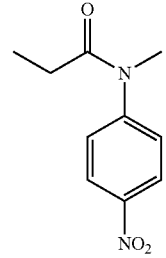

N-(4-nitrophenyl)propionamide (1.37 g) was dissolved in DMF (20 mL) and cooled to 0° C. Sodium hydride (0.84 g) and methyliodide (1.32 mL) were added sequentially. The reaction was stirred for 1 h. After it was quenched by water, the crude product was extracted with ethyl acetate and then purified by flash chromatography with 3:1 hexane-ethyl acetate to afford the title compound (1.17 g). $^1$H NMR 600 MHz (DMSO-d$_6$) δ 8.24 (d, J=9.0 Hz, 2H), 7.40 (d, J=9.0 Hz, 2H), 3.31 (s, 3H), 2.20 (t, J=7.2 Hz, 2H), 1.10 (q, J=7.8 Hz, 7.2 Hz, 3H).

Step 3: Synthesis of N-(4-aminophenyl)-N-methylpropionamide

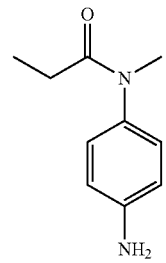

Palladium and carbon (10%) was added to the solution of N-methyl-N-(4-nitrophenyl) propionamide (1.17 g) in methanol (30 mL). The reaction was stirred under hydrogen for 4 hours. The solution was filtered through celite and used for next step without purification.
MS m/z: 179.23 (M+1).

Step 4: Synthesis of 2,6-dichloro-9-(tetrahydro-2H-pyran-2-yl)-9H-purine

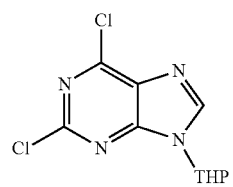

To a solution of 2,6-dichloropurine (2.0 g) in CH$_2$Cl$_2$ (30 mL) was added para-toluenesulfonic acid (0.22 g) and 3,4-dihydro-2H-pyran. The reaction was stirred for 4 h. The solution was washed with an aqueous sodium carbonate solution and water, dried and concentrated to afford to afford 2.7 g white solid. $^1$H NMR 600 MHz (DMSO-d6) δ 8.98 (s, 1H), 5.72 (m, 1H), 4.00 (m, 1H), 3.72 (m, 1H), 2.24 (m, 1H), 1.96 (m, 2H), 1.74 (m, 1H). 1.56 (m, 3H).

MS m/z: 274.12 (M+1).

Step 5: Synthesis of tert-butyl-3-(2-chloro-9-(tetrahydro-2H-pyran-2-yl)-9H-purin-6-ylamino)piperidine-1-carboxylate

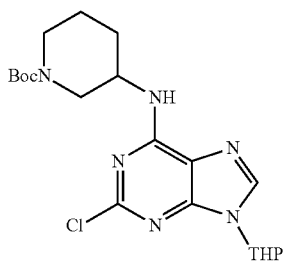

A flask was charged with 2,6-dichloro-9-(tetrahydro-2H-pyran-2-yl)-9H-purine (0.27 g), N-Boc-3-aminopiperidine (0.21 g), diisopropylethylamine (0.20 mL) in n-BuOH (5 mL). The reaction was heated to 90° C. and stirred for 4 h. After removal of solvent, the residue was purified by flash chromatography with 30:1 CH$_2$Cl$_2$-MeOH to afford 0.36 g white solid. $^1$H NMR 600 MHz (DMSO-d6) δ 8.40 (s, 1H), 5.60 (m, 1H), 4.00 (d, J=8.4 Hz, 2H), 3.65 (m, 2H), 3.4 (m, 2H), 2.75 (m, 1H), 2.20 (m, 2H), 1.98 (m, 2H), 1.70 (m, 2H), 1.58 (m, 2H), 1.39 (m, 11H).

MS m/z: 437.93 (M+1).

Step 6: tert-butyl-3-(2-(4-(N-methylpropionamido)phenylamino)-9-(tetrahydro-2H-pyran-2-yl)-9H-purin-6-ylamino)piperidine-1-carboxylate

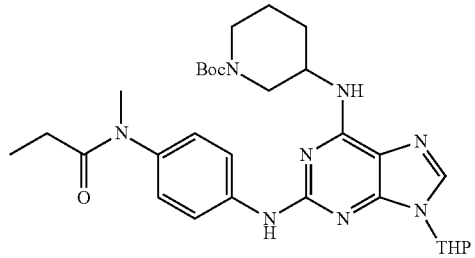

A sealed tube was charged with N-(4-aminophenyl)-N-methylpropionamide (62 mg), Pd$_2$(dba)$_3$ (12 mg), and tert-butyl 3-(2-chloro-9-(tetrahydro-2H-pyran-2-yl)-9H-purin-6-ylamino)piperidine-1-carboxylate (110 mg), 1,3-Bis(2,6-diisopropyphenyl)imidazonium chloride (10 mg), potassium tert-butoxide (120 mg) in dioxane (4.0 mL). The reaction was heated to 90° C. and stirred for 2 h. The reaction was diluted with ethyl acetate and then filtered through celite. The crude residue was purified by flash chromatography with 40:1 CH$_2$Cl$_2$-MeOH to afford light yellow solid (115 mg). $^1$H NMR 600 MHz (CDCl$_3$) δ 7.78 (s, 1H), 7.70 (d, J=Hz, 2H), 7.10 (d, J=Hz, 2H), 7.0 (s, 1H), 5.60 (m, 1H), 4.11 (m, 2H), 3.24 (s, 3H), 2.11 (m, 6H), 1.80 (m, 4H), 1.62 (m, 3H), 1.46 (s, 9H), 1.27 (m, 6H), 1.04 (t, J=Hz, 3H). MS m/z: 579.72 (M+1).

Step 7: Synthesis of N-methyl-N-(4-(6-(piperidin-3-ylamino)-9H-purin-2-ylamino)phenyl)propionamide

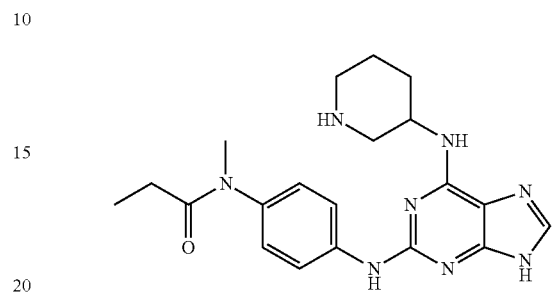

tert-butyl-3-(2-(4-(N-methylacetamido)phenylamino)-9-(tetrahydro-2H-pyran-2-yl)-9H-purin-6-ylamino)piperidine-1-carboxylate (115 mg) was dissolved in EtOH (2 mL) of 4N HCl in dioxane (2 mL) was added. The reaction was stirred for 1 h. After removal of solvent, the residue was dried under vacuum and used for next step without purification. MS m/z: 395.47 (M+1).

Step 8: Synthesis of N-(4-(6-(1-acryloylpiperidin-3-ylamino)-9H-purin-2-ylamino)phenyl)-N-methylpropionamide

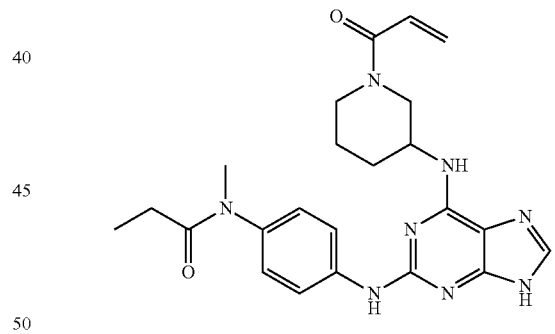

N-methyl-N-(4-(6-(piperidin-3-ylamino)-9H-purin-2-ylamino)phenyl)acetamide was dissolved in DMF (2 mL) and CH$_2$Cl$_2$ (6 mL). Diisopropylethylamine (0.17 mL) and acryloyl chloride (16 uL) were added sequentially at 0° C. The reaction was stirred for 1 h. After removal of solvents, the residue was dissolved in DMSO (3 mL) and purified by Prep-HPLC to give 45 mg of title compound as TFA salt. $^1$H NMR 600 MHz (MeOD) δ 7.86 (s, 1H), 7.82 (d, J=9.6 Hz, 2H), 7.12 (d, J=9.6 Hz, 2H), 6.25 (d, J=16.2 Hz, 1H), 6.04 (d, J=16.2 Hz, 1H), 5.78 (d, J=9.6 Hz, 1H), 3.92 (m, 1H), 3.41 (m, 2H), 3.21 (m, 5H), 2.15 (m, 4H), 1.94 (m, 2H), 1.02 (t, J=7.8 Hz, 3H). MS m/z: 449.51 (M+1).

The compounds of Table 1 were made according to the process described in Example 1.

Scheme 2

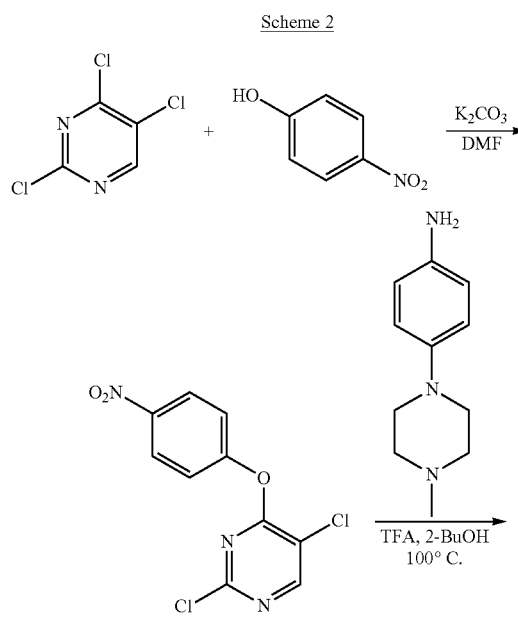

Example 2

Synthesis of N-(4-(5-chloro-2-(4-(4-methylpiperazin-1-yl)phenylamino)pyrimidin-4-yloxy)phenyl)acrylamide

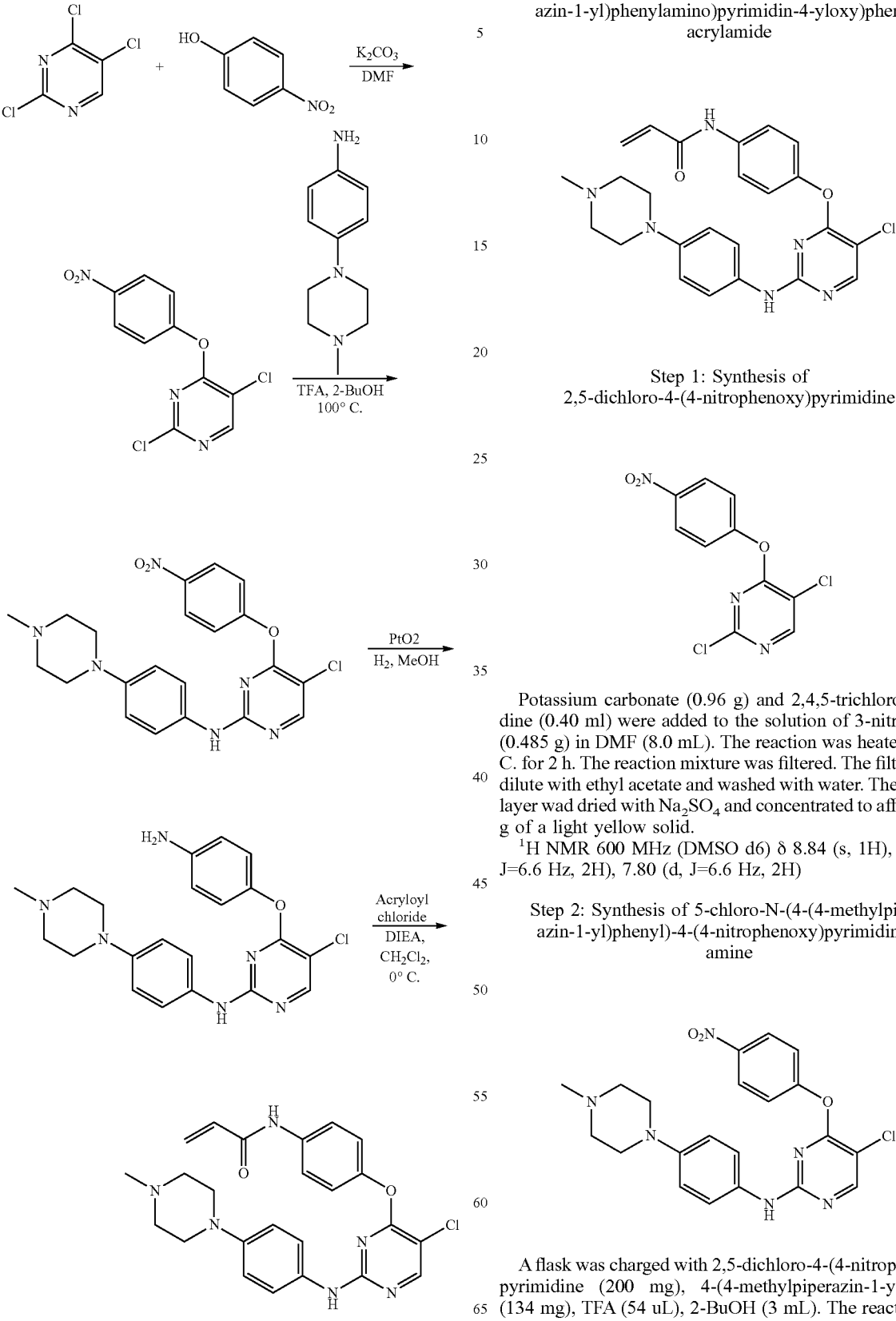

Step 1: Synthesis of 2,5-dichloro-4-(4-nitrophenoxy)pyrimidine

Potassium carbonate (0.96 g) and 2,4,5-trichloropyrimidine (0.40 ml) were added to the solution of 3-nitrophenol (0.485 g) in DMF (8.0 mL). The reaction was heated to 60° C. for 2 h. The reaction mixture was filtered. The filtrate was dilute with ethyl acetate and washed with water. The organic layer wad dried with $Na_2SO_4$ and concentrated to afford 0.80 g of a light yellow solid.

$^1$H NMR 600 MHz (DMSO d6) δ 8.84 (s, 1H), 8.38 (d, J=6.6 Hz, 2H), 7.80 (d, J=6.6 Hz, 2H)

Step 2: Synthesis of 5-chloro-N-(4-(4-methylpiperazin-1-yl)phenyl)-4-(4-nitrophenoxy)pyrimidin-2-amine A flask was charged with 2,5-dichloro-4-(4-nitrophenoxy)pyrimidine (200 mg), 4-(4-methylpiperazin-1-yl)aniline (134 mg), TFA (54 uL), 2-BuOH (3 mL). The reaction was heated to 100° C. for 2 h. The reaction mixture was basified with a saturated aqueous sodium bicarbonate solution and then was extracted with ethyl acetate. The crude product was purified with flash chromatography with 30:1:0.3 CH$_2$Cl$_2$-MeOH-Triethylamine to afford 0.17 g brown solid.

$^1$H NMR 600 MHz (CDCl$_3$) δ 8.28 (s, 1H), 8.30 (s, J=7.2 Hz, 2H), 7.39 (d, J=7.2 Hz, 2H), 7.14 (m, 2H), 6.84 (m, 2H), 3.10 (m, 4H), 2.62 (m, 2H), 2.38 (s, 3H). MS m/z: 441.88 (M+1).

Step 3: Synthesis of 4-(4-aminophenoxy)-5-chloro-N-(4-(4-methylpiperazin-1-yl)phenyl)pyrimidin-2-amine

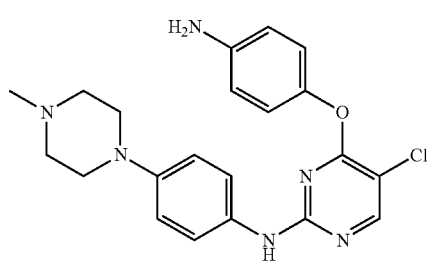 [SMILES: CN1CCN(c2ccc(Nc3ncc(Cl)c(Oc4ccc(N)cc4)n3)cc2)CC1]

Platinum(IV) oxide (50 mg) was added to the solution of 5-chloro-N-(4-(4-methylpiperazin-1-yl)phenyl)-4-(4-nitrophenoxy)pyrimidin-2-amine in methanol (10 mL). The reaction was stirred under hydrogen for 1 h. The reaction mixture was filtrated through celite to afford 100 mg oil. MS m/z: 411.9 (M+1).

Step 4: Synthesis of N-(4-(5-chloro-2-(4-(4-methylpiperazin-1-yl)phenylamino)pyrimidin-4-yloxy)phenyl)acrylamide

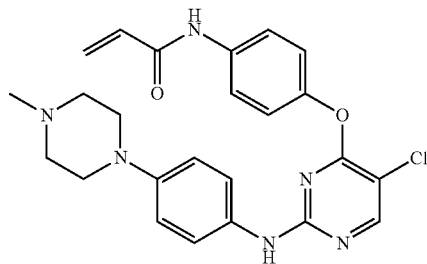 [SMILES: C=CC(=O)Nc1ccc(Oc2nc(Nc3ccc(N4CCN(C)CC4)cc3)ncc2Cl)cc1]

Acryloyl chloride (9.2 uL) was added to the solution of 4-(4-aminophenoxy)-5-chloro-N-(4-(4-methylpiperazin-1-yl)phenyl)pyrimidin-2-amine (50 mg) and diisopropyethylamine (25 uL) at 0° C. The reaction was stirred for 1 h. The title compound was obtained after purification by reverse-phase HPLC (10 mgs). $^1$H NMR 600 MHz (DMSO-d6) δ 10.18 (s, 1H), 8.53 (dd, J=1.2, J=8.4 Hz, 1H), 7.92 (dd, J=1.2 Hz, J=8.4 Hz, 1H), 7.38 (dt, J=1.8 Hz, J=8.4 Hz, 1H), 7.35 (dt, J=1.2 Hz, J=7.2 Hz, 1H), 3.21 (m, 1H), 1.31 (d, J=6.6 Hz, 6H).

MS m/z: 465.94 (M+1).

The compounds of Table 2 were made according to the process described in Example 2.

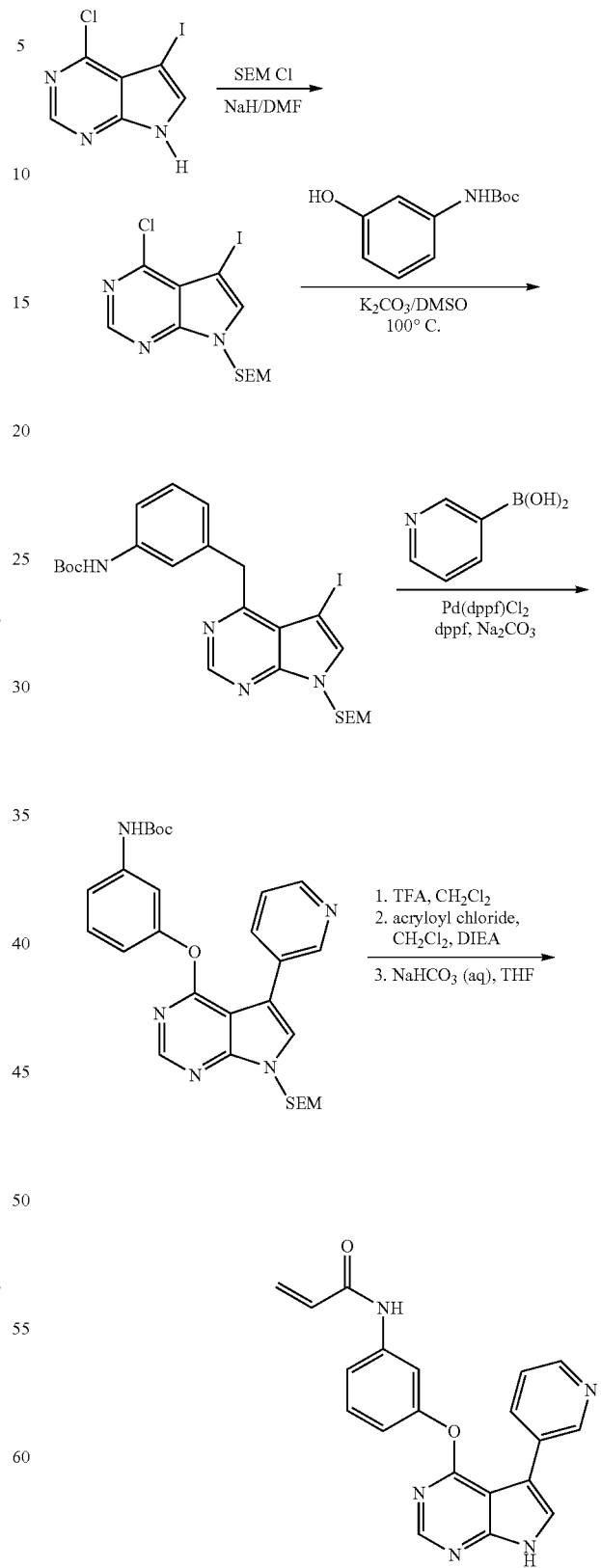

Scheme 3

Example 3

Synthesis of 4-chloro-5-iodo-7-((2-(trimethylsilyl)ethoxy)methyl)-7H-pyrrolo[2,3-d]pyrimidine

Step 1

4-chloro-5-iodo-7H-pyrrolo[2,3-d]pyrimidine (0.90 g) was dissolved in DMF (10 mL). Sodium hydride (0.13 g) was added at 0° C. The mixture was stirred for 5 min. SEM Cl was added dropwise to the reaction and the resulting brown mixture was stirred for 15 min. The reaction was diluted with ethyl acetate (50 mL) and quenched with water. After separation of organic layer, the crude product was purified by flash chromatograph with 5% ethyl acetate in methylene chloride to afford 1.20 g of gray solid. $^1$H NMR 600 MHz (CDCl$_3$) δ 8.68 (s, 1H), 7.58 (s, 1H), 5.66 (s, 2H), 3.57 (t, J=7.8 Hz, 2H), 0.96 (J=7.8 Hz, 2H), 0 (s, 6H). MS m/z: 410.72 (M+1).

Step 2: Synthesis of tert-butyl-3-(5-iodo-7-((2-(trimethylsilyl)ethoxy)methyl)-7H-pyrrolo[2,3-d]pyrimidin-4-yloxy)phenylcarbamate

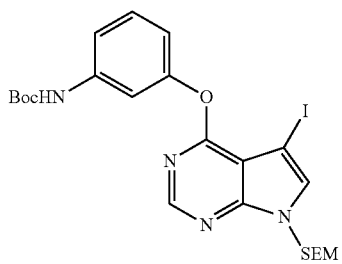 [SMILES: CC(C)(C)OC(=O)Nc1cccc(Oc2ncnc3c2c(I)cn3COCC[Si](C)(C)C)c1]

4-chloro-5-iodo-7-((2-(trimethylsilyl)ethoxy)methyl)-7H-pyrrolo[2,3-d]pyrimidine (0.30 g) was dissolved in DMSO (3.0 mL). K$_2$CO$_3$ (0.202 g) and tert-butyl 3-hydroxyphenylcarbamate (0.175 g) were added and the resulted mixture was heated to 100° C. overnight. The reaction was diluted with ethyl acetate (20 mL) and washed with water for 3 times. The crude product was purified by flash chromatograph with 5% ethyl acetate in methylene chloride to afford 0.38 g of white solid. $^1$H NMR 600 MHz (CDCl$_3$) δ 8.45 (s, 1H), 7.54 (s, 1H), 7.42 (s, 1H), 7.38 (t, J=7.8 Hz, 1H), 7.17-7.15 (dd, J=7.8 Hz, J=1.2 Hz, 1H), 6.98 (dd, J=7.8 Hz, J=1.2 Hz, 1H), 6.59 (s, 1H), 5.63 (s, 2H), 3.57 (t, J=7.8 Hz, 2H), 0.96 (t, J=7.8 Hz, 2H), 0 (s, 6H). MS m/z: 583.50 (M+1).

Step 3: Synthesis of tert-butyl-3-(5-(pyridin-3-yl)-7-((2-(trimethylsilyl)ethoxy)methyl)-7H-pyrrolo[2,3-d]pyrimidin-4-yloxy)phenylcarbamate

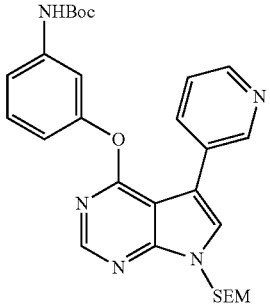 [SMILES: CC(C)(C)OC(=O)Nc1cccc(Oc2ncnc3c2c(-c2cccnc2)cn3COCC[Si](C)(C)C)c1]

The mixture of tert-butyl 3-(5-iodo-7-((2-(trimethylsilyl)ethoxy)methyl)-7H-pyrrolo[2,3-d]pyrimidin-4-yloxy)phenylcarbamate (0.136 g), Na$_2$CO$_3$ (1N, 1.2 mL), Dioxane (0.4 mL) was degassed for 10 min. Pd(dppf)Cl$_2$ (19 mg) was added to the above mixture and was heated to 100° C. for 1 hour. The mixture was diluted with ethyl acetate (10 mL) and filtered through celite. After separation of organic layer, the crude product was purified by flash chromatograph with 20:1 methylene chloride-methanol to afford 0.10 g of light yellow oil $^1$H NMR 600 MHz (CDCl$_3$) δ 8.97 (s, 1H), 8.55 (d, J=4.8 Hz, 1H), 8.51 (s, 1H), 8.10 (m, 1H), 7.49 (s, 1H), 7.46 (, s, 1H), 7.37 (m, 2H), 7.10 (dd, J=7.8 Hz, J=2.4 Hz, 1H), 6.90 (dd, J=7.8 Hz, J=2.4 Hz, 1H), 6.58 (s, 1H), 5.73 (s, 2H), 3.64 (t, J=7.8 Hz, 2H), 1.50 (s, 9H), 0.98 (t, J=7.8 Hz, 2H), 0 (s, 6H).

MS m/z: 534.69 (M+1).

Step 4: Synthesis of (4-(3-aminophenoxy)-5-(pyridin-3-yl)-7H-pyrrolo[2,3-d]pyrimidin-7-yl)methanol

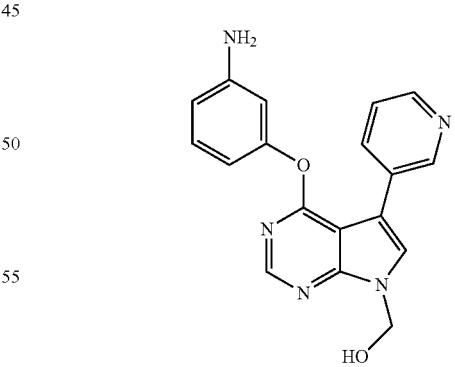

To the solution of tert-butyl 3-(5-(pyridin-3-yl)-7-((2-(trimethylsilyl)ethoxy)methyl)-7H-1-pyrrolo[2,3-d]pyrimidin-4-yloxy)phenylcarbamate (0.12 g) in methylene chloride (10 mL) was added TFA (5 mL). The solution was stirred for 1 hour. The solvent was evaporated. The resulting residue was dried under vacuum and used without further purification. MS m/z: 334.34 (M+1).

137

Step 5: Synthesis of N-(3-(7-(hydroxymethyl)-5-(pyridin-3-yl)-7H-pyrrolo[2,3-d]pyrimidin-4-yloxy)phenyl)acrylamide

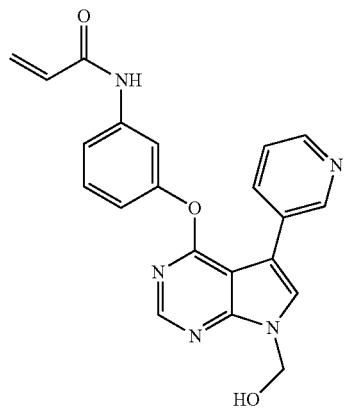 [SMILES: C=CC(=O)Nc1cccc(Oc2ncnc3c2c(-c2cccnc2)cn3CO)c1]

(4-(3-aminophenoxy)-5-(pyridin-3-yl)-7H-pyrrolo[2,3-d]pyrimidin-7-yl)methanol was dissolved in methylene chloride (4 mL). DIEA (0.20 mL) and acryloyl chloride (20 uL) was added sequentially. After stirring for 1 hour, the solution was diluted with methylene chloride (20 mL) and washed with a saturated aqueous sodium bicarbonate solution. The organic layer was dried, concentrated and used without further purification. MS m/z: 388.39 (M+1).

Step 6: Synthesis of N-(3-(5-(pyridin-3-yl)-7H-pyrrolo[2,3-d]pyrimidin-4-yloxy)phenyl)acrylamide

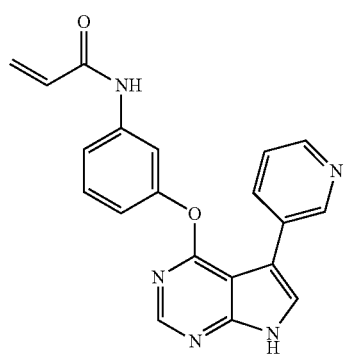 [SMILES: C=CC(=O)Nc1cccc(Oc2ncnc3[nH]cc(-c4cccnc4)c23)c1]

N-(3-(7-(hydroxymethyl)-5-(pyridin-3-yl)-7H-pyrrolo[2,3-d]pyrimidin-4-yloxy)phenyl)acrylamide was dissolved in THF (3 mL). NaHCO$_3$ (1N, 3 mL) was added and stirred for 2 hours. After removing the THF, the residue was purified by preparative reverse phase HPLC to afford 40 mg of white solid. $^1$H NMR 600 MHz (CH$_3$OD) δ 8.85 (s, 1H), 8.43 (m, 1H), 8.30 (d, J=13.8 Hz, 1H), 8.20 (m, 1H), 7.68 (m, 2H), 7.47 (m, 2H), 7.38 (m, 1H), 6.97 (m, 1H), 6.40 (m, 2H), 5.77 (m, 1H). MS m/z: 358.36 (M+1).

The compounds of Table 3 were made according to the process described in Example 3.

138

Example 4

Synthetic Scheme for Halogenated Compounds

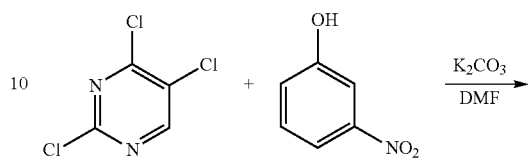

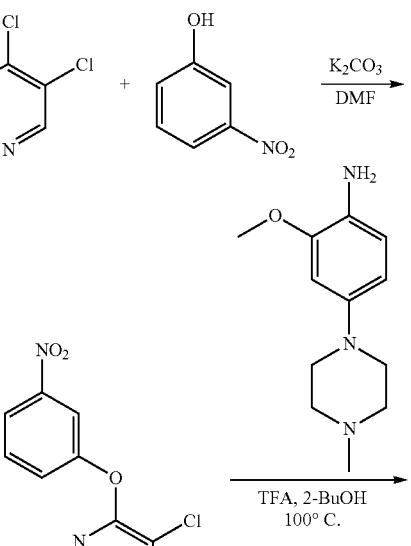

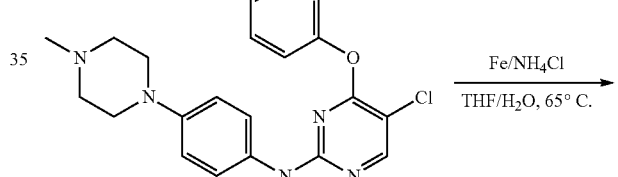

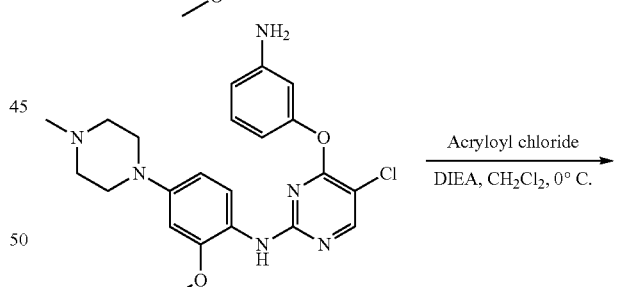

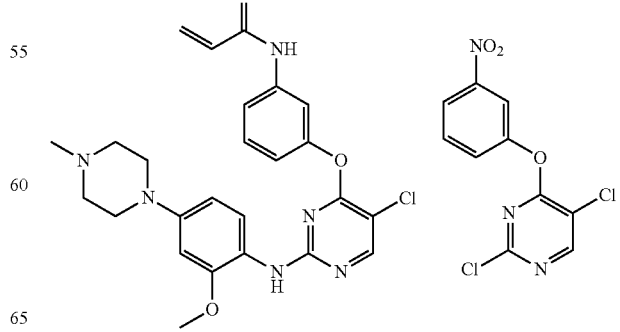

2,5-dichloro-4-(3-nitrophenoxy)pyrimidine

Potassium carbonate (2.42 g, 17.5 mmol) and 2,4,5-trichloropyrimidine (1.0 mL, 8.72 mmol) were added to the solution of 3-nitrophenol (1.21 g, 8.72 mmol) in DMF (20 mL). The reaction was heated to 60° C. for 2 h. The reaction mixture was filtered, the filtrate was dilute with ethyl acetate and washed with water (20 mL) three times. The organic layer wad dried over anhydrous sodium sulfate and concentrated to afford 2.24 g (90%) of a light yellow solid, which was used without further purification. $^1$H NMR 600 MHz (DMSO d6) δ 8.87 (s, 1H), 8.28 (m, 1H), 8.21 (m, 1H), 7.84 (m, 2H); MS m/z: 287.07 (M+1)

5-chloro-N-(2-methoxy-4-(4-methylpiperazin-1-yl)phenyl)-4-(3-nitrophenoxy)pyrimidin-2-amine A flask was charged with 2,5-dichloro-4-(3-nitrophenoxy)pyrimidine (1.56 g, 5.45 mmol), 2-methoxy-4-(4-methylpiperazin-1-yl)benzenamine (1.21 g, 5.45 mmol), TFA (0.42 mL, 5.45 mmol uL), 2-BuOH (30 mL). The slurry was heated to 100° C. for 2 h. The reaction mixture was allowed to cool to room temperature and, was neutralized with a saturated aqueous sodium bicarbonate solution. The aqueous mixture was then extracted with ethyl acetate (50 mL) three times. The crude product was purified using flash chromatography with 30:1:0.3 (v/v/v) dichloromethane-methanol-triethylamine to afford 2.07 g brown solid (81%). $^1$H NMR 600 MHz (DMSO d6) δ 8.38 (s, 1H), 8.28 (s, 1H), 8.16 (m, 2H), 7.76 (m, 2H), 7.08 (s, 1H), 6.46 (m, 1H), 6.14 (m, 1H), 3.72 (s, 3H), 3.33 (m, 4H), 3.05 (m, 4H), 2.28 (s, 3H); MS m/z: 471.91 (M+1)

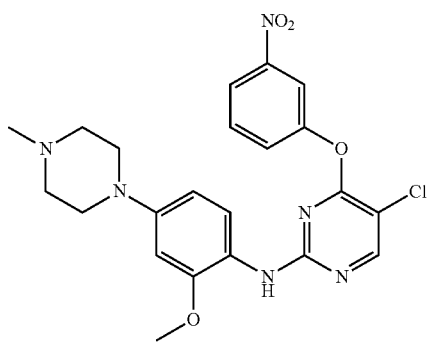 [SMILES: COc1cc(N2CCN(C)CC2)ccc1Nc1ncc(Cl)c(Oc2cccc([N+](=O)[O-])c2)n1]

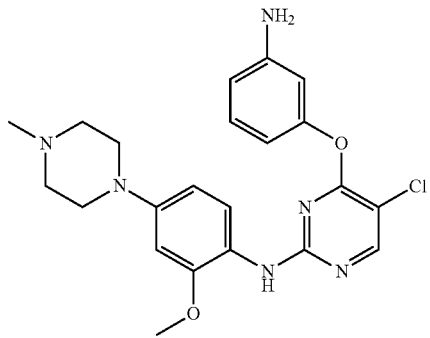

4-(3-aminophenoxy)-5-chloro-N-(2-methoxy-4-(4-methylpiperazin-1-yl)phenyl)pyrimidin-2-amine 5-chloro-N-(2-methoxy-4-(4-methylpiperazin-1-yl)phenyl)-4-(3-nitrophenoxy)pyrimidin-2-amine (2.00 g, 4.25 mmol) was dissolved in THF (50 mL) and water (50 mL) was added. Iron powder (1.19 g, 21.25 mmol) and ammonium chloride (1.18 g, 21.25 mmol) were then added, and the resulting mixture was heated to 65° C. for 4 hours. The reaction mixture was cooled to room temperature and filtered through celite. The THF was removed in vacuo, and the resulting residue was basified with sodium bicarbonate and extracted with ethyl acetate (50 mL) three times. The organic layer was separated and dried using anhydrous sodium sulfate, concentrated, and purified by flash chromatography with 20:1 dichloromethane-methanol to afford 1.42 g of light yellow solid (76%); MS m/z: 441.93 (M+1)

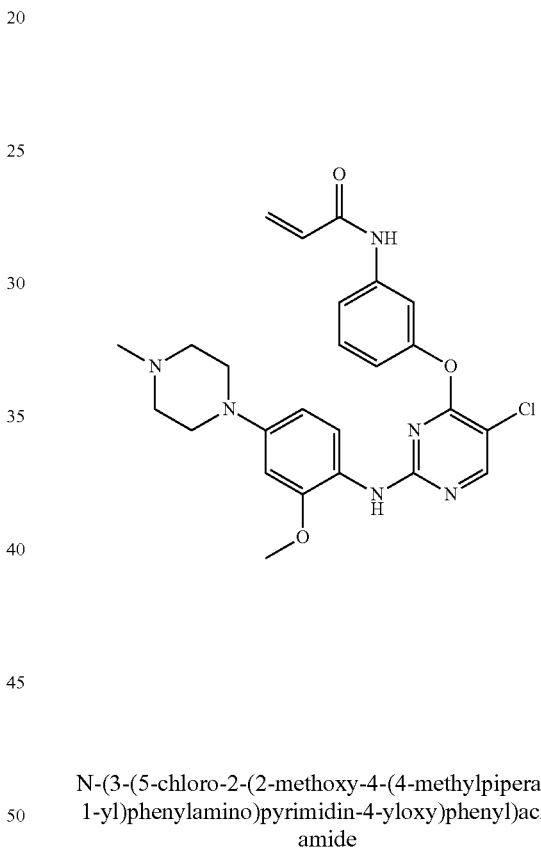

N-(3-(5-chloro-2-(2-methoxy-4-(4-methylpiperazin-1-yl)phenylamino)pyrimidin-4-yloxy)phenyl)acrylamide Acryloyl chloride (0.257 mL, 3.18 mmol) was added dropwise to a solution of 4-(3-aminophenoxy)-5-chloro-N-(2-methoxy-4-(4-methylpiperazin-1-yl)phenyl)-pyrimidin-2-amine (1.40 g, 3.18 mmol) and diisopropylethylamine (0.56 mL, 3.18 mmol) in methylene chloride (30 mL) at 0° C. The reaction was stirred for 1 h. 1.10 g of the title compound was obtained after purification by flash chromatography with 20:1 (v/v) dichloromethane-methanol. $^1$H NMR 600 MHz (DMSO-d$_6$) δ 8.32 (s, 1H), 7.38 (m, 2H), 7.26 (m, 2H), 6.96 (m, 1H), 6.48 (m, 2H), 6.35 (dd, J=10.2 Hz, 17.4 Hz, 1H), 6.21 (m, 1H), 5.75 (d, J=9.6 Hz, 1H), 3.80 (s, 3H), 3.61 (m, 4H), 3.11 (m, 4H), 2.38 (s, 3H); MS m/z: 495.97 (M+1)

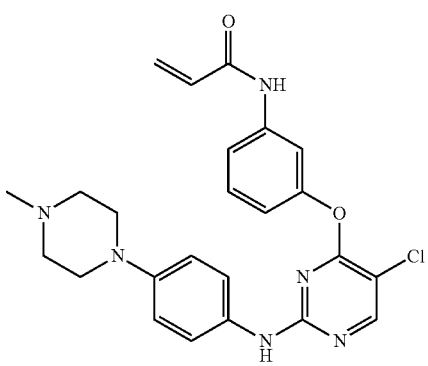 [SMILES: C=CC(=O)Nc1cccc(Oc2nc(Nc3ccc(N4CCN(C)CC4)cc3)ncc2Cl)c1]

N-(3-(5-chloro-2-(4-(4-methylpiperazin-1-yl)phenylamino)pyrimidin-4-yloxy)phenyl)acrylamide The title compound was prepared analogously as described above, using 4-(4-methylpiperazin-1-yl)benzenamine for the amination at pyrimidine C2. $^1$H NMR 600 MHz (DMSO-d6) δ10.35 (s, 1H), 9.60 (s, 1H), 8.40 (s, 1H), 7.62 (s, 1H), 7.50 (m, 1H), 7.42 (t, J=7.8 Hz, 17.4 Hz, 1H), 7.28 (s, 2H), 6.95 (m, 1H), 6.70 (s, 2H). 6.42 (dd, J=10.2 Hz, 16.8 Hz, 1H), 6.26 (dd, J=1.8 Hz, 16.8 Hz, 1H), 5.77 (dd, J=1.8 Hz, 10.2 Hz, 1H), 3.49 (m, 4H), 3.11 (m, 4H), 2.84 (s, 3H); MS m/z: 465.95 (M+1)

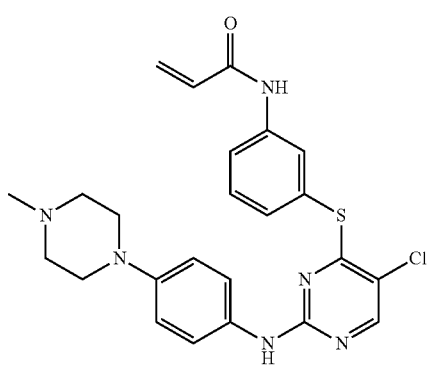

N-(3-(5-chloro-2-(4-(4-methylpiperazin-1-yl)phenylamino)pyrimidin-4-ylthio)phenyl)acrylamide The title compound was prepared analogously as described above, starting from 3-nitrobenzenethiol and 4-(4-methylpiperazin-1-yl)benzenamine. $^1$H NMR 600 MHz (DMSO-d6) δ 10.50 (s, 1H), 10.08 (s, 1H), 9.59 (s, 1H), 8.26 (s, 1H), 8.19 (d, J=6.6 Hz, 1H), 7.50 (t, J=7.8 Hz, 1H), 7.32 (d, J=7.8 Hz, 1H), 7.00 (s, 2H), 6.58 (s, 1H), 6.45 (m, 1H), 6.29 (dd, J=1.8 Hz, 17.4 Hz, 1H), 5.76 (dd, J=1.8 Hz, 17.4 Hz, 1H), 3.50 (m, 4H), 3.12 (m, 4H), 2.83 (s, 3H); MS m/z: 482.01 (M+1)

Example 5

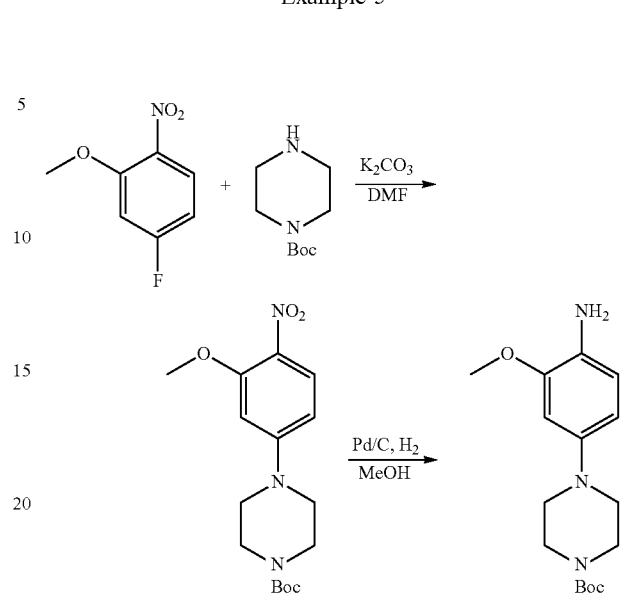

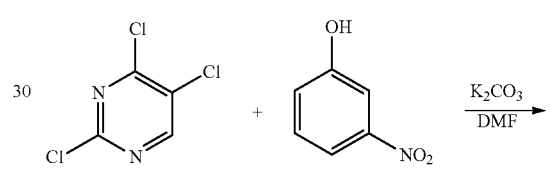

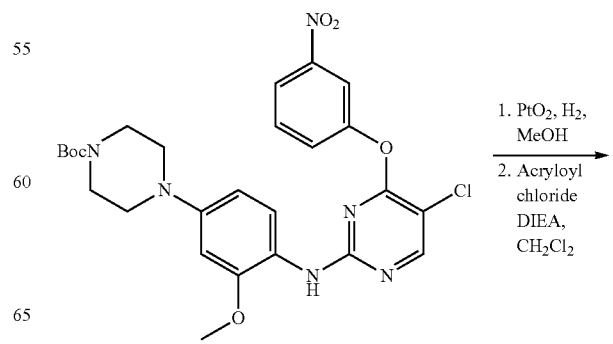

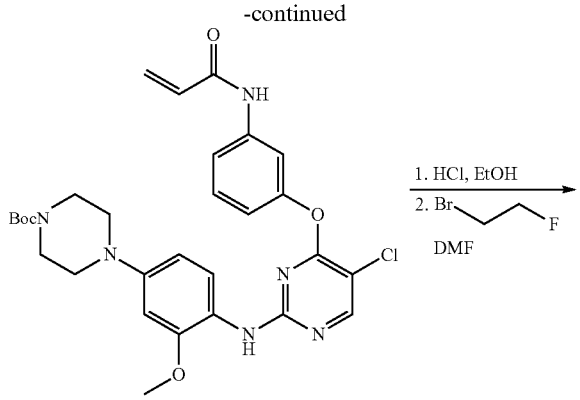

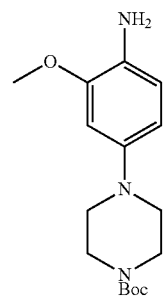 [SMILES: COc1cc(N2CCN(C(=O)OC(C)(C)C)CC2)ccc1N]

tert-butyl 4-(4-amino-3-methoxyphenyl)piperazine-1-carboxylate

To a solution of tert-butyl 4-(3-methoxy-4-nitrophenyl) piperazine-1-carboxylate (3.90 g, 11.6 mmol) in MeOH (100 mL) was added Pd/C (40 mg). The suspension was stirred under hydrogen for 2 hours. The mixture was filtrated through celite. The solution was concentrated to afford the title compound. MS (M+1): 308.3

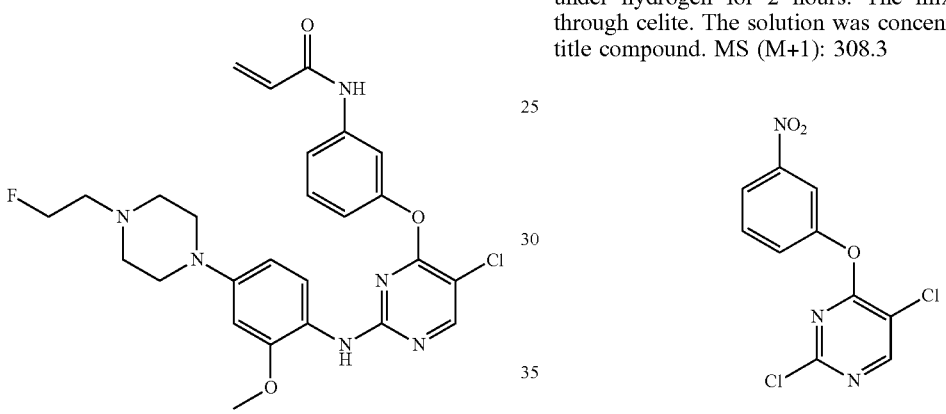

2,5-dichloro-4-(3-nitrophenoxy)pyrimidine

Potassium carbonate (2.42 g, 17.5 mmol) and 2,4,5-trichloropyrimidine (1.0 mL, 8.72 mmol) were added to the solution of 3-nitrophenol (1.21 g, 8.72 mmol) in DMF (20 mL). The reaction was heated to 60° C. for 2 h. The reaction mixture was filtered; the filtrate was dilute with ethyl acetate and washed with water (20 mL) three times. The organic layer wad dried over anhydrous sodium sulfate and concentrated to afford 2.24 g (90%) of light yellow solid, which was used without further purification. $^1$H NMR 600 MHz (DMSO d6) δ 8.87 (s, 1H), 8.28 (m, 1H), 8.21 (m, 1H), 7.84 (m, 2H); MS m/z: 287.07 (M+1)

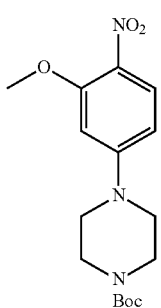

tert-butyl 4-(3-methoxy-4-nitrophenyl)piperazine-1-carboxylate

The mixture of 2-nitro-5-fluoroanisole (2.0 g, 11.7 mmol), N-Bocpiperazine (2.18 g, 11.7 mmol), potassium carbonate (3.2 g, 23.4 mmol) in DMF (30 mL) was heated to 70° C. for 12 hours. The solution was diluted with ethyl acetate (100 mL) and washed with water three times. The organic layer was dried over sodium sulfate and concentrated to afford the title compound. MS (M+1): 338.3

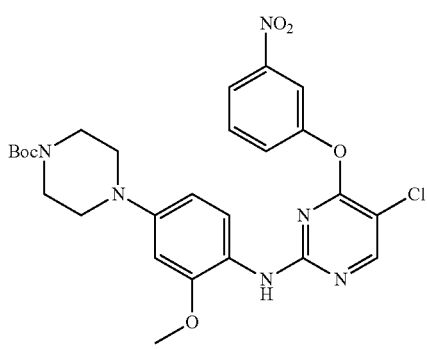 [SMILES: COc1cc(N2CCN(C(=O)OC(C)(C)C)CC2)ccc1Nc1ncc(Cl)c(Oc2cccc([N+](=O)[O-])c2)n1]

tert-butyl 4-(4-(5-chloro-4-(3-nitrophenoxy)pyrimidin-2-ylamino)-3-methoxyphenyl)piperazine-1-carboxylate A flask was charged with 2,5-dichloro-4-(3-nitrophenoxy) pyrimidine (200 mg, 0.7 mmol), tert-butyl 4-(4-amino-3-methoxyphenyl)piperazine-1-carboxylate (215 mg, 0.7 mmol), $Pd_2(dba)_3$ (64 mg, 0.07 mmol)), X-Phos (33 mg, 0.07 mmol), potassium carbonate (200 mg, 1.4 mmol) in 2-BuOH (10 mL). The mixture was degassed and heated to 90° C. for 2 hours. The slurry was filtrated through celite and washed with ethyl acetate. The concentrated residue was purified by flash chromatography to afford the title compound. MS (M+1): 558.0

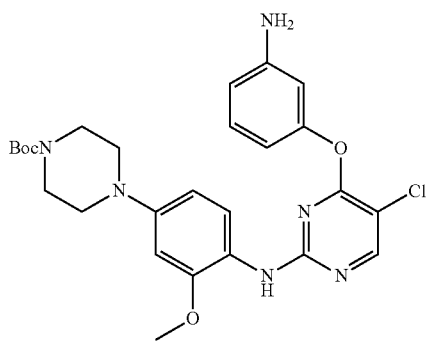 [SMILES: COc1cc(N2CCN(C(=O)OC(C)(C)C)CC2)ccc1Nc1ncc(Cl)c(Oc2cccc(N)c2)n1]

tert-butyl 4-(4-(4-(3-aminophenoxy)-5-chloropyrimidin-2-ylamino)-3-methoxyphenyl)piperazine-1-carboxylate A flask was charged with tert-butyl 4-(4-(5-chloro-4-(3-nitrophenoxy)pyrimidin-2-ylamino)-3-methoxyphenyl)piperazine-1-carboxylate (200 mg, 0.36 mmol), $PtO_2$ (20 mg) in MeOH. The mixture was stirred under hydrogen for 2 hours and then filtrated through celite. The solution was concentrated to afford the title compound.

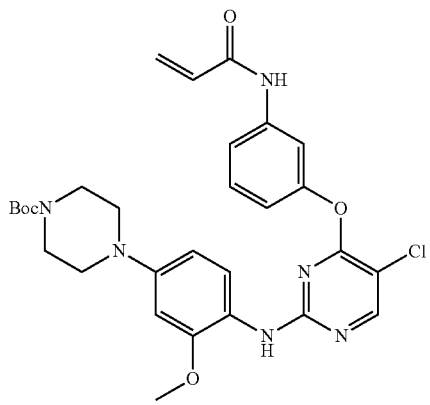 [SMILES: C=CC(=O)Nc1cccc(Oc2nc(Nc3ccc(N4CCN(C(=O)OC(C)(C)C)CC4)cc3OC)ncc2Cl)c1]

tert-butyl 4-(4-(4-(3-acrylamidophenoxy)-5-chloropyrimidin-2-ylamino)-3-methoxyphenyl)piperazine-1-carboxylate tert-butyl 4-(4-(4-(3-aminophenoxy)-5-chloropyrimidin-2-ylamino)-3-methoxyphenyl)piperazine-1-carboxylate (180 mg, 0.34 mmol) was dissolved in $CH_2Cl_2$ (10 mL). The solution was cooled down in ice-water bath. DIEA (60 uL, 0.34 mmol) and acryloyl chloride (30 uL, 0.34 mmol) were added sequentially. The reaction was stirred for 1 hour. The mixture was purified by flash chromatography to afford the title compound.

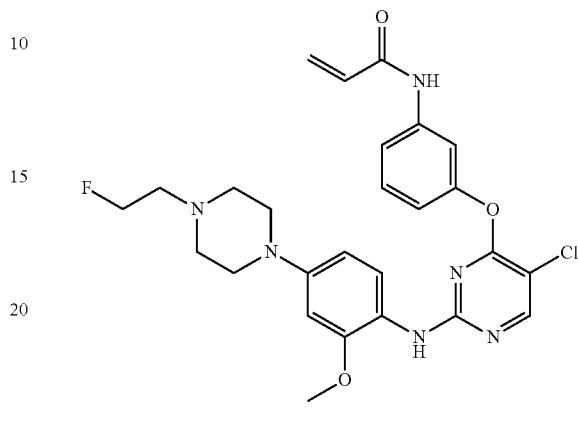

N-(3-(5-chloro-2-(4-(4-(2-fluoroethyl)piperazin-1-yl)-2-methoxyphenylamino)pyrimidin-4-yloxy)phenyl)acrylamide To a solution of tert-butyl 4-(4-(4-(3-acrylamidophenoxy)-5-chloropyrimidin-2-ylamino)-3-methoxyphenyl) piperazine-1-carboxylate (20 mg, 0.034 mmol) in EtOH (2 mL) was added HCl (4M in Dioxane, 2 mL). The reaction was stirred for 1 hour. The solvent was removed. The resulting residue was dissolved in DMF (2 mL). $Cs_2CO_3$ (27 mg, 0.068 mmol) and 2-fluorobromoethane (5.3 mg, 0.034 mmol) were added to the above solution. The reaction was heated to 70° C. for 4 hours. The mixture was purified by PREP HPLC to afford the title compound.

Example 6

Biological Studies

Cell Culture and Reagents

The EGFR mutant NSCLC cell lines HCC827 (del E746_A750), H3255 (L858R), HCC827 GR (del E746_A750/MET amplified), H1975 (L858R/T790M) and PC9 (del E746_A750) have been previously characterized (Amann, J. et al. Cancer Res 65, 226-35 (2005); Engelman, J. A. et al. Science 316, 1039-43 (2007); Ono, M. et al. Mol Cancer Ther 3, 465-72 (2004); Ogino, A. et al. Cancer Res 67, 7807-14 (2007)). The PC9 GR (del E746_A750/T790M) cells were generated and verified to contain del E746_A750 in cis with T790M. The ERBB2 amplified (Calu-3 and H1819) and mutant (H1781) were obtained from ATCC. All cell lines were maintained in RPMI 1640 (Cellgro; Mediatech Inc., Herndon, Calif.) supplemented with 10% FBS 100 units/mL penicillin, 100 units/mL streptomycin, and 2 mM glutamine. H3255 were maintained in ACL-4 media (Invitrogen, Carlsbad, Calif.) supplemented with 5% FBS, 100 units/mL penicillin, 100 units/mL streptomycin, and 2 mM glutamine.

The EGFR and ERBB2 mutant Ba/F3 cells and the NIH-3T3 cells have been previously characterized (Engelman, J. A. et al. Cancer Res 67, 11924-32 (2007); Yuza, Y.

et al. Cancer Biol Ther 6 (2007)). The EGFR C797S and the ERBB2 T798I mutations were introduced using site directed mutagenesis using the Quick Change Site-Directed Mutagenesis kit (Stratagene; La Jolla, Calif.) according to the manufacturer's instructions (Mukohara, T. et al. J Natl Cancer Inst 97, 1185-94 (2005)). The oligonucleotide sequences are available upon request. All constructs were confirmed by DNA sequencing. The constructs were shuttled into the retroviral vector JP1540 using the BD Creator™ System (BD Biosciences). Ba/F3 of NIH-3T3 cells were infected with retrovirus according to standard protocols, as described previously (Engelman, J. A. et al. Proc Natl Acad Sci USA 102, 3788-93 (2005); Zhao, J. J. et al. Cancer Cell 3, 483-95 (2003)). Stable populations were obtained by selection in puromycin (2 µg/ml).

Kinase Inhibitors

Gefitinib was obtained from commercial sources and was purified through an ethyl acetate extraction. The resulting product was verified by liquid chromatography-electrospray mass spectrometry (LC-MS). CL-387,785 was obtained from EMD (Gibbstown, N.J.). HKI-272 was obtained from Medicilon Inc. (Shanghai, China). The structure of HKI-272 was confirmed LC-MS and $^1$H and $^{13}$C nuclear magnetic resonance (NMR). HKI-272 was determined to be >95% pure by LC-MS. Stock solutions of all drugs were prepared in DMSO. and stored at −20° C.

Cell Proliferation and Growth Assays

Growth and inhibition of growth was assessed by MTS assay. This assay, a colorimetric method for determining the number of viable cells, is based on the bioreduction of 3-(4,5-dimethylthiazol-2-yl)-5-(3-carboxymethoxyphenyl)-2-(4-sulfophenyl)-2H-tetrazolium (MTS) by cells to a formazan product that is soluble in cell culture medium, can be detected spectrophotometrically and was performed according to previously established methods (Mukohara, T. et al. J Natl Cancer Inst 97, 1185-94 (2005); Paez, J. G. et al. Science 304, 1497-500 (2004); Engelman, J. A. et al. J Clin Invest 116, 2695-2706 (2006). NSCLC or Ba/F3 cells were exposed to treatment for 72 hours and the number of cells used per experiment determined empirically and has been previously established. All experimental points were set up in six to twelve wells and all experiments were repeated at least three times. The data was graphically displayed using GraphPad Prism version 5.0 for Windows, (GraphPad Software; www.graphpad.com). The curves were fitted using a non-linear regression model with a sigmoidal dose response.

Antibodies and Western Blotting

Cells grown under the previously specified conditions were lysed in the following lysis buffer: 20 mM Tris, pH 7.4/150 mM NaCl/1% Nonidet P-40/10% glycerol/1 mM EDTA/1 mM EGTA/5 mM sodium pyrophosphate/50 mM NaF/10 nM β-glycerophosphate/1 mM sodium vanadate/0.5 mM DTT/4 µg/ml leupeptin/4 µg/ml pepstatin/4 µg/ml apoprotein/1 mM PMSF. After cell lysis, lysates were centrifuged at 16,000×g for 5 min at 4° C. The supernatant was used for subsequent procedures. Western blot analyses were conducted after separation by SDS/PAGE electrophoresis and transfer to nitrocellulose membranes. Immunoblotting was performed according to the antibody manufacturers' recommendations. Antibody binding was detected using an enhanced chemiluminescence system (New England Nuclear Life Science Products Inc.). Anti-phospho-Akt (Ser-473), anti-total Akt, and anti-EGFR antibodies were obtained from Cell Signaling Technology. The phospho-specific EGFR (pY1068), total ERK1/2, phospho-ERK1/2 (pT185/pY187) antibodies were purchased from Biosource International Inc.

Mass Spectrometry

For intact protein mass spectral analysis, the proteins T790M alone and with small molecules bound were injected onto a POROS 20 R2 protein trap and desalted with 0.05% trifluoroacetic acid (TFA) at a flow rate of 100 µL/min. The proteins were eluted into the mass spectrometer using a linear 15%-75% (v/v) acetonitrile gradient over 4 min at 50 µL/min using a Shimadzu HPLC system (LC-10ADvp). Intact protein analyses were performed on an LCT-Premier instrument (Waters Corp., Milford, Mass., USA) equipped with a standard electrospray source. The capillary voltage was 3.2 kV and the cone voltage of 35 V. Nitrogen was used as desolvation gas. A source temperature of 175° C. and a desolvation temperature of 80° C. were applied. The instrument was calibrated by infusing a solution of 500 fmol/µL myoglobin and the mass accuracy was less than 10 ppm.

Pepsin Digestion and Peptide Analysis

For the elucidation of the modification site, all three proteins (50 pmol each) were digested offline with pepsin in an enzyme: substrate ratio of 1:1. The pepsin digestion was performed in a potassium phosphate buffer (75 mM $KH_2PO_4$/75 mM $K_2HPO_4$) pH 2.5. The reaction was carried out for 5 minutes on ice. The resulting peptides were injected into a Waters nanoAcquity HPLC system (Waters, Milford, Mass.) and trapped and desalted for 3 min at 100 µL/min and then separated in 60 min by an 8%-40% acetonitrile:water gradient at 40 µL/min. The separation column was a 1.0× 100.0 mm ACQUITY HPLC C18 BEH (Waters) containing 1.7 µm particles.

Mass spectra were obtained with a Waters QTOF Premier equipped with standard ESI source (Waters Corp., Milford, Mass., USA). The instrument configuration was the following: capillary was 3.5 kV, trap collision energy at 6V, sampling cone at 37 V, source temperature of 100° C. and desolvation temperature of 250° C. Mass spectra were acquired over an m/z range of 100 to 2000. Mass accuracy was ensured by calibration with 100 fmol/µL GFP, and was less than 10 ppm throughout all experiments. Identification of the peptic fragments was accomplished through a combination of exact mass analysis and $MS^{E12}$ using custom Identity Software from the Waters Corporation. $MS^E$ was performed by a series of low-high collision energies ramping from 5-25 V, therefore ensuring proper fragmentation of all the peptic peptides eluting from the LC system.

Generation of Mouse Cohorts and Treatment with WZ-4002

EGFR-TL (T790M/L858R) mice were generated as previously described (Li, D. et al. Cancer Cell 12, 81-93 (2007)). EGFR exon19 Deleletion-T790M (TD) inducible bitransgenic mice were similarly generated and characterized. Briefly, exon 19 deletion was introduced in the human EGFR gene through site directed mutagenesis in the pTRE2-hyg-EGFR-T790M. The constructs were then digested with XhoI to release the entire allele containing Tet-op-EGFR TD-beta-globin PolyA. Transgenic mice were then generated by injection of the construct into FVB/N fertilized eggs. Progeny were genotyped through PCR exactly the same as reported. Founders were crossed with CCSP-rtTA mice and inducible bitransgenic mice with high and inducible expression of the mutant hEGFR transgene were identified and expanded for subsequent analyses and experiments. All mice were housed in a pathogen-free environment at the Harvard School of Public Health and were handled in strict accordance with Good Animal Practice as defined by the Office of Laboratory Animal Welfare, and all animal work was done with Dana-Farber Cancer Institute IACUC approval.

Cohorts of EGFR TL/CCSP-rtTA and EGFR TD/CCSP-rtTA were put on doxycycline diet at 5 weeks of age to induce the expression of mutant EGFR. These mice undergo MRI after 6 to 8 weeks of doxycycline diet to document and quantify the lung cancer burden before being assigned to various treatment study cohorts. There is a minimum of 3 mice per treatment group. Mice are then treated either with vehicle (NMP (10% 1-methyl-2-pyrrolidinone: 90% PEG-300) alone or WZ4002 at 25 mg/kg gavage daily. After 2 weeks of treatment, these mice undergo a second round of MRI to document their response to the treatment. MRIs and tumor burden measurement were performed as described previously (Li, D. et al. Cancer Cell 12, 81-93 (2007); Ji, H. et al. Cancer Cell 9, 485-95 (2006)).

MRI Scanning and Tumor Volume Measurement

Mice were anesthetized with 1% isoflurane in an oxygen/air mixture. The respiratory and cardiac rates of anesthetized mice were monitored using Biotrig Software. The animals were imaged with a rapid acquisition with relaxation enhancement (RARE) sequence (TR=2000 ms, TE effect=25 ms) in the coronal and axial planes with a 1 mm slice thickness and with sufficient number of slices to cover the entire lung. Matrix size of 128×128 and a field of view (FOV) of 2.5 cm×2.5 $cm^2$ were used for all imaging. With same geometry and described above, the mice were also imaged with a gradient echo fast imaging (GEFI) sequence (TR=180 ms, TE effect=2.2 ms) with respiratory and cardiac gating, in both coronal and axial planes. The detailed procedure for MRI scanning has been previously described (Li, D. et al. Cancer Cell 12, 81-93 (2007); Ji, H. et al. Cancer Cell 9, 485-95 (2006)).

Immunohistochemical Analyses

Hematoxylin and eosin (H&E) staining of tumor sections was performed at the Department of Pathology at the Brigham and Women's Hospital. Immunohistochemistry was performed on formal fixed paraffin embedded tumor sections. The antibodies used were: total EGFR and phospho-EGFR Y1068 (Cell Signaling Technology) and Ki67. Apoptosis was measured by counting nuclear bodies in H&E stained sections and by a terminal deoxynucleotidyl-transferase mediated dUTP-biotin nick end labeling (TUNEL) assay.

Pharmacokinetic Analyses

Dose administration: All mice are weighed before dose administration and randomized. For intravenous administration, freshly prepared solution of WZ-4002 is administered at a dose level of 1 mg/kg via tail vein at a slow and steady rate. The dosing volume for intravenous administration is 5 mL/kg. Freshly prepared suspension of WZ-4002 is administered at an oral dose of 10 mg/kg, by stomach intubation using a 16 gauge oral feeding needle. The dosing volume for oral dose group is 10 mL/kg.

Blood samples: Blood samples (0.06 mL) are collected from saphenous vein of each mouse at regular intervals. During each sampling point, blood samples are collected in labeled micro-tubes containing K2EDTA as an anticoagulant. Samples are centrifuged at 4000 rpm for 10 min at 4±2° C. (Centrifuge Model: Kubota 3500). The recovered quantity of plasma from each sample is transferred to labeled micro-tubes. The plasma samples are stored at −70° C. until bioanalysis.

Bioanalysis of samples: Bioanalytical method for the determination of WZ-4002 in mouse plasma is developed using LC-MS/MS equipment. The method is partially validated prior to sample analysis.

Pharmacokinetic analysis: The pharmacokinetic parameters of WZ-4002 such as $T_{max}$, $C_{max}$, AUC, CL, $V_d$, $T_{1/2}$, and bioavailability in mouse plasma are determined from the concentration-time data using non-compartmental analysis (WinNonlin Enterprise version 5.2, Pharsight Corporation, USA).

Serum Creatinine and White Blood Cell Count Analyses

Blood was collected from vehicle and WZ-4002 treated mice into appropriate tubes and analyzed at the clinical laboratory at the Boston Children's Hospital.

Statistical Analyses

Statistical analyses were performed using an unpaired two tailed Student's t-test. A p value of less than 0.05 was considered significant.

The selectivity between wild-type EGFR and the L858R/T790M or Exon19 deletion/T790M EGFR mutants was measured using cellular proliferation assays where cell proliferation is completely dependent on kinase activity. For example, murine Ba/F3 cells transfected with a suitable version of wild-type EGFR (such as VIII; containing a WT EGFR kinase domain), or Ba/F3 cells transfected with L858R/T790M or Exon19 deletion/T790M were used. Proliferation assays were preformed at a range of inhibitor concentrations (10 uM, 3 uM, 1.1 uM, 330 nM, 110 nM, 33 nM, 11 nM, 3 nM, 1 nM) and an EC50 was calculated. For example, compound 2-2 (WZ4002) exhibited approximately 20-fold selectivity for inhibiting Ba/F3 proliferation dependent on the L858R/T790M mutant (IC50=8 nM) relative to wild type EGFR (EC50=157 nM) and 80-fold for Exon-19 deletion/T790M mutant (EC50=2 nM) relative to wild type EGFR (EC50=157 nM).

An alternative method to measure effects on EGFR activity is to assay EGFR phosphorylation. Wild type or mutant (L858R/T790M or Del19/T790M) EGFR was transfected into NIH-3T3 cells (which do not normally express endogenous EGFR) and the ability of the inhibitor (using concentrations as above) to inhibit EGFR phosphorylation was assayed. Cells were exposed to increasing concentrations of inhibitor for 6 hours and stimulated with EGF for 10 minutes. The effects on EGFR phosphorylation were assayed by Western Blotting using phospho-specific (Y1068) EGFR antibodies. For example, approximately a 10-100 nM concentration of compound 2-2 (WZ4002) was required to completely inhibit L858R/T790M EGFR phosphorylation in 3T3 cells while 1-10 uM was required to inhibit wild-type EGFR. Selectivity ratio here is 10-100 fold.

INCORPORATION BY REFERENCE

The contents of all references (including literature references, issued patents, published patent applications, and co-pending patent applications) cited throughout this application are hereby expressly incorporated herein in their entireties by reference. Unless otherwise defined, all technical and scientific terms used herein are accorded the meaning commonly known to one with ordinary skill in the art.

EQUIVALENTS

Those skilled in the art will recognize, or be able to ascertain using no more than routine experimentation, many equivalents of the specific embodiments of the invention described herein. Such equivalents are intended with be encompassed by the following claims.

What is claimed:

1. A method for treating a non-small cell lung cancer in a subject comprising administering a compound that covalently bonds to Cysteine 797 in epidermal growth factor receptor (EGFR), wherein said compound is WZ-3146, WZ-4002, WZ-8040, or a pharmaceutically acceptable salt, or prodrug thereof,

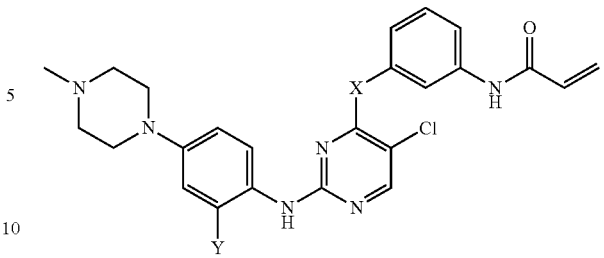

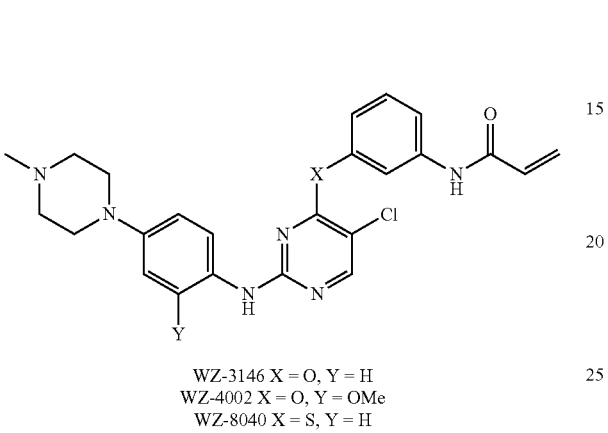

WZ-3146 X = O, Y = H
WZ-4002 X = O, Y = OMe
WZ-8040 X = S, Y = H wherein said compound exhibits at least 2-fold greater inhibition of a drug-resistant EGFR mutant relative to wild-type EGFR, and wherein the drug-resistant EGFR mutant is selected from L858R/T790M EGFR and Exon-19 deletion/T790M EGFR.

2. The method of claim 1 wherein the cancer in said subject harbors an EGFR mutation.

3. The method of claim 2 wherein said EGFR mutation is selected from T790M, L858R, G719S, G719C, G719A, L861Q, a deletion in exon 19, or an insertion in exon 20.

4. A method for modulating epidermal growth factor receptor (EGFR) in a subject comprising administering a compound that covalently bonds to Cysteine 797 in EGFR, wherein said compound is WZ-3146, WZ-4002, WZ-8040, or a pharmaceutically acceptable salt, or prodrug thereof, WZ-3146 X = O, Y = H
WZ-4002 X = O, Y = OMe
WZ-8040 X = S, Y = H wherein said compound exhibits at least 2-fold greater inhibition of a drug-resistant EGFR mutant relative to wild-type EGFR, and wherein the drug-resistant EGFR mutant is selected from L858R/T790M EGFR and Exon-19 deletion/T790M EGFR.

5. A method for inhibiting epidermal growth factor receptor (EGFR) in a subject comprising administering a compound that covalently bonds to Cysteine 797 in EGFR, wherein said compound is WZ-3146, WZ-4002, WZ-8040, or a pharmaceutically acceptable salt, or prodrug thereof,

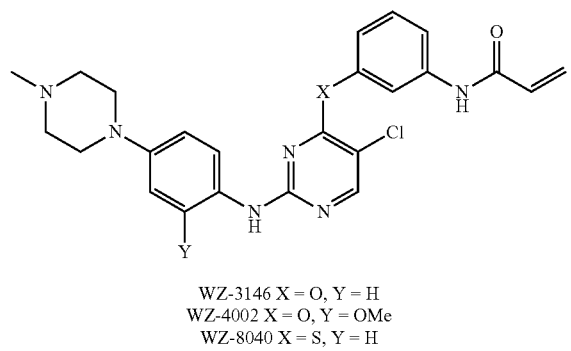

WZ-3146 X = O, Y = H
WZ-4002 X = O, Y = OMe
WZ-8040 X = S, Y = H wherein said compound exhibits at least 2-fold greater inhibition of a drug-resistant EGFR mutant relative to wild-type EGFR, and wherein the drug-resistant EGFR mutant is selected from L858R/T790M EGFR and Exon-19 deletion/T790M EGFR.

* * * * *